United States Patent
Wu et al.

(10) Patent No.: US 10,693,077 B2
(45) Date of Patent: Jun. 23, 2020

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Hui-Ling Wu, Jhubei (TW); Liang-Di Liao, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 304 days.

(21) Appl. No.: 15/828,752

(22) Filed: Dec. 1, 2017

(65) Prior Publication Data
US 2018/0155312 A1 Jun. 7, 2018

Related U.S. Application Data

(60) Provisional application No. 62/430,982, filed on Dec. 7, 2016, provisional application No. 62/433,371, filed on Dec. 13, 2016.

(51) Int. Cl.
*H01L 51/50* (2006.01)
*H01L 51/00* (2006.01)
(Continued)

(52) U.S. Cl.
CPC ........ *H01L 51/0058* (2013.01); *C07D 311/82* (2013.01); *C07D 335/12* (2013.01);
(Continued)

(58) Field of Classification Search
None
See application file for complete search history.

(56) References Cited

U.S. PATENT DOCUMENTS

2017/0317283 A1* 11/2017 Mujica-Fernaud .........................
H01L 51/006

FOREIGN PATENT DOCUMENTS

WO WO 2016/087017 A1 6/2016

* cited by examiner

*Primary Examiner* — Gregory D Clark
(74) *Attorney, Agent, or Firm* — Birch, Stewart, Kolasch & Birch, LLP

(57) ABSTRACT

Provided are a novel compound and an organic electronic device using the same. The novel corn pound is represented by the following Formula (I):

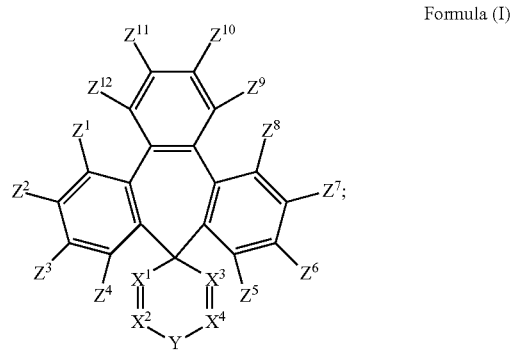

Formula (I)

wherein Y is an oxygen atom, a sulfur atom, or a sulfur dioxide group; $X^1$ and $X^2$ are each independently $C(R^a)$, multiple $(R^a)$s are the same or different, and the two $(R^a)$s are joined together to form a first aryl ring; $X^3$ and $X^4$ are each independently $C(R^b)$, multiple $(R^b)$s are the same or different, and the two $(R^b)$s are joined to form a second aryl ring or a heteroaryl ring.

17 Claims, 27 Drawing Sheets

(51) Int. Cl.
*C07D 311/82* (2006.01)
*C07D 335/12* (2006.01)
*C07D 405/04* (2006.01)
*C07D 405/14* (2006.01)
*C07D 409/04* (2006.01)
*C07D 409/14* (2006.01)
*C09K 11/06* (2006.01)
*G01R 33/46* (2006.01)

(52) U.S. Cl.
CPC ......... *C07D 405/04* (2013.01); *C07D 405/14* (2013.01); *C07D 409/04* (2013.01); *C07D 409/14* (2013.01); *C09K 11/06* (2013.01); *H01L 51/0054* (2013.01); *H01L 51/0057* (2013.01); *H01L 51/0067* (2013.01); *H01L 51/0068* (2013.01); *H01L 51/0071* (2013.01); *H01L 51/0072* (2013.01); *H01L 51/0073* (2013.01); *H01L 51/0074* (2013.01); *H01L 51/5072* (2013.01); *C09K 2211/1088* (2013.01); *C09K 2211/1092* (2013.01); *G01R 33/46* (2013.01); *H01L 51/5076* (2013.01)

COMPOUND AND ORGANIC ELECTRONIC DEVICE USING THE SAME

CROSS-REFERENCE TO RELATED APPLICATIONS

Pursuant to 35 U.S.C. § 119(e), this application claims the benefits of the priority to U.S. Provisional Patent Application No. 62/430,982, filed Dec. 7, 2016 and of the priority to U.S. Provisional Patent Application No. 62/433,371, filed Dec. 13, 2016. The contents of the prior applications are incorporated herein by their entirety.

BACKGROUND OF THE INVENTION

1. Field of the Invention

The present invention relates to a novel compound and an organic electronic device using the same, more particularly to a novel compound as electron-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching Tang and Steven VanSlyke of Kodak Company deposited an electron transport material such as tris(8-hydroxyquinoline)aluminum(III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting light when the excitons decay from excited state to ground state.

Another approach is to modify the materials of ETL for OLEDs to render the electron transport materials to exhibit hole-blocking ability. Examples of conventional electron transport materials include 3,3'-[5'-[3-(3-Pyridinyl)phenyl][1,1':3',1''-terphenyl]-3,3''-diyl]bispyridine (TmPyPb), 1,3,5-tris(1-phenyl-1H-benzimidazol-2-yl)benzene(TPBi), tris(2,4,6-trimethyl-3-(pyridin-3-yl)phenyl)borane(3TPYMB), 1,3-bis(3,5-dipyrid-3-yl-phenyl)benzene(BmPyPb), and 9,10-bis(3-(pyridin-3-yl)phenyl)anthracene(DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

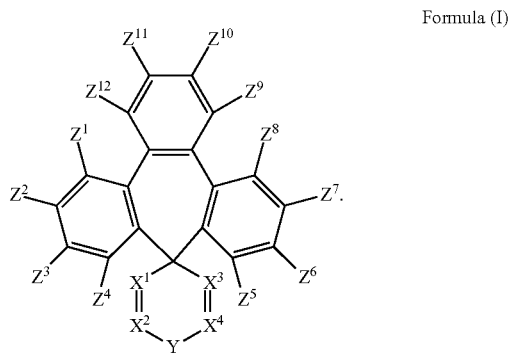

Formula (I)

In formula (I), Y is an oxygen atom, a sulfur atom, or a sulfur dioxide group.

In formula (I), $X^1$ and $X^2$ are each independently $C(R^a)$, the two ($R^a$)s are the same or different, and the two ($R^a$)s are joined together to form a first aryl ring.

In formula (I), $X^3$ and $X^4$ are each independently $C(R^b)$, the two ($R^b$)s are the same or different, and the two ($R^b$)s are joined together to form a second aryl ring or a heteroaryl ring.

In formula (I), $Z^1$ to $Z^{12}$ are each independently selected from the group consisting of: a hydrogen atom, a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atom, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atom, a phosphine group having 1 to 40 carbon atoms, and a phosphine oxide group having 1 to 40 carbon atoms.

In accordance with the present invention, the double bond between X¹ and X² in Formula (I) and the bonds between the two joined (Rᵃ)s are conjugated and commonly construct the first aryl ring. Likely, the double bond between X³ and X⁴ in Formula (I) and the bonds between the two joined (Rᵇ)s are conjugated and commonly construct the second aryl ring or the heteroaryl ring.

Preferably, the first aryl ring extended from X¹ and X² in Formula (I) and the second aryl ring extended from X³ and X⁴ in Formula (I) are each independently a substituted or unsubstituted 6 to 60-membered carbon ring, more preferably a substituted or unsubstituted 6 to 20-membered carbon ring. For example, the substituted or unsubstituted 6 to 60-membered carbon ring may be selected from the group consisting of: a substituted or unsubstituted benzene ring, a substituted or unsubstituted naphthalene ring, a substituted or unsubstituted anthracene ring, a substituted or unsubstituted phenanthrene ring, a substituted or unsubstituted pyrene ring, a substituted or unsubstituted fluoranthene ring, a substituted or unsubstituted benzofluoranthene ring, and a substituted or unsubstituted fluorene ring, but is not limited thereto. More preferably, the substituted or unsubstituted 6 to 60-membered carbon ring is a substituted or unsubstituted benzene structure, a substituted or unsubstituted naphthalene ring or a substituted or unsubstituted fluorene ring. The substitution group on the 6 to 20-membered carbon ring may be, but not limited to, a halogen group, a cyano group, a nitro group, an alkyl group having 1 to 12 carbon atoms, an alkenyl group having 2 to 12 carbon atoms, an alkynyl group having 2 to 12 carbon atoms.

Preferably, the heteroaryl ring extended from X³ and X⁴ in Formula (I) may contain at least one furan group or at least one thiophene group. For example, the heteroaryl ring may be, but not limited to, a substituted or unsubstituted dibenzofuran ring, a substituted or unsubstituted dibenzothiophene ring, a substituted or unsubstituted dibenzothiophene sulfone ring, a substituted or unsubstituted benzofuran ring, a substituted or unsubstituted isobenzofuran ring, a substituted or unsubstituted benzothiophene ring, a substituted or unsubstituted isobenzothiophene ring.

Preferably, Z¹ to Z¹² are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 30 carbon atoms, an alkoxy group having 1 to 12 carbon atoms, an aryloxy group having 6 to 30 ring carbon atoms, an alkylsilyl group having 1 to 12 carbon atoms, an arylsilyl group having 6 to 30 ring carbon atoms, an alkylboron group having 1 to 12 carbon atoms, an arylboron group having 6 to 30 ring carbon atoms, a phosphine group having 1 to 12 carbon atoms, and a phosphine oxide group having 1 to 12 carbon atoms.

In a case that Y is an oxygen atom, the compound may be, for example, represented by any one of the following Formulae:

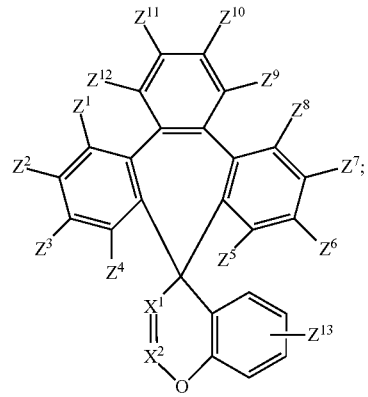

Formula (I-I)

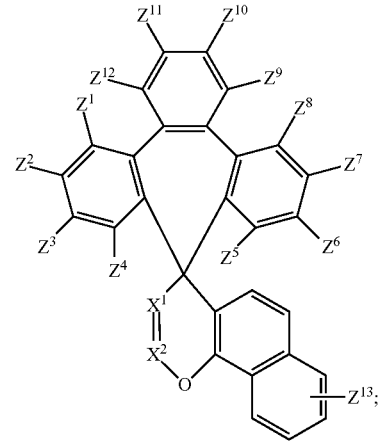

Formula (I-IV)

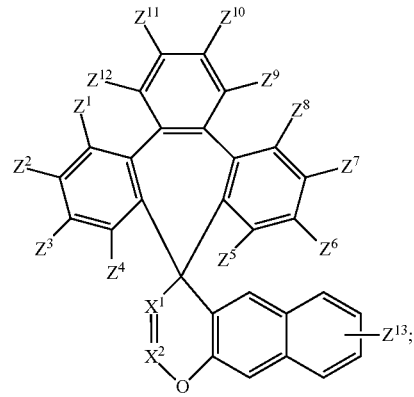

Formula (I-VII)

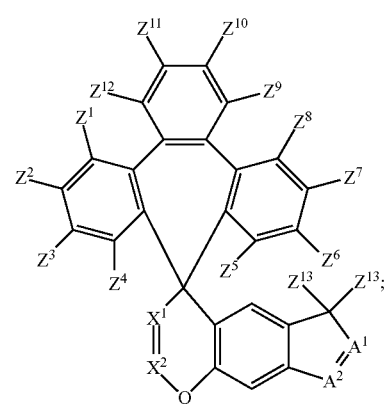

Formula (I-X)

Formula (I-XIII)
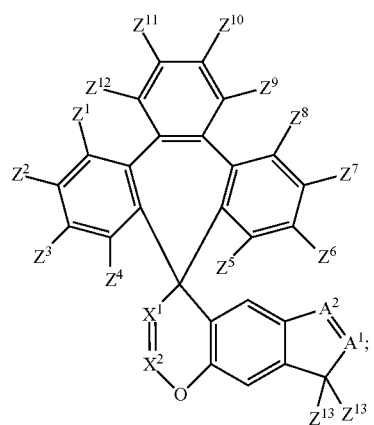
Formula (I-XVI)
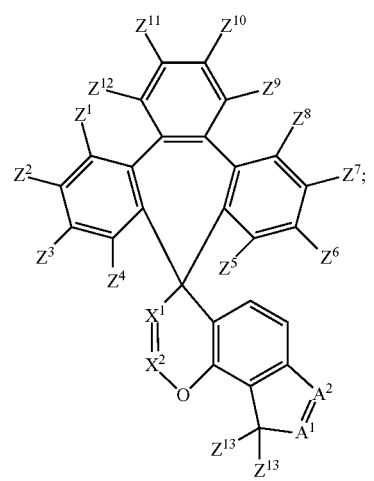
Formula (I-XIX)
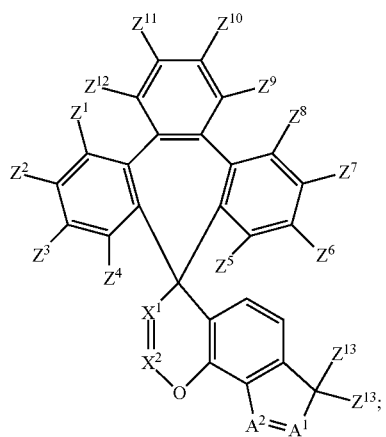
Formula (I-XXII)
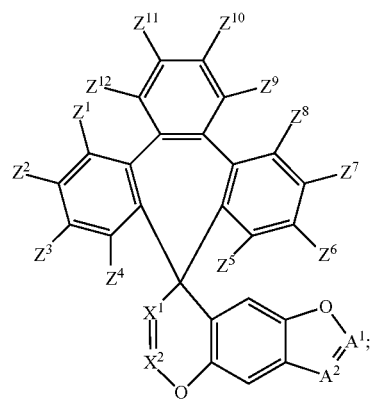
Formula (I-XXV)
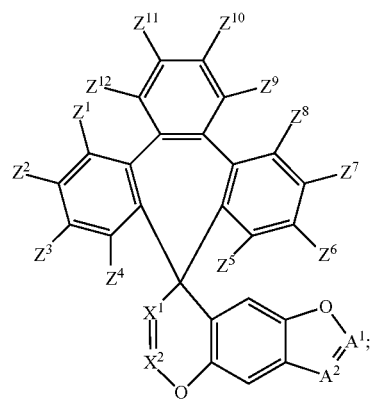
Formula (I-XXVIII)
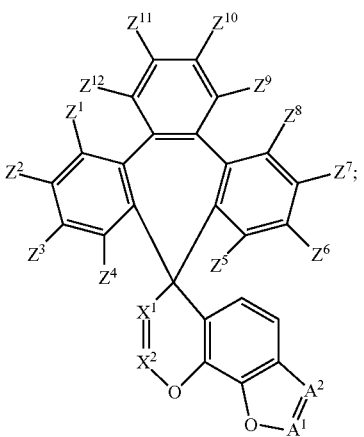

Formula (I-XXXI)
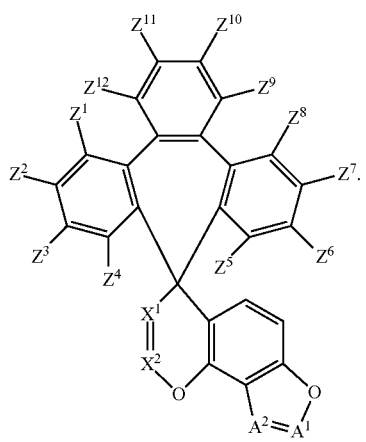
In a case that Y is a sulfur atom, the compound may be, for example, represented by any one of the following Formulae:
Formula (I-II)
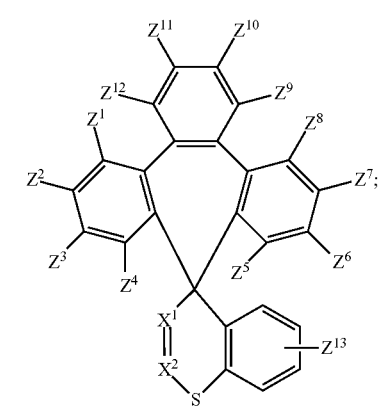
Formula (I-V)
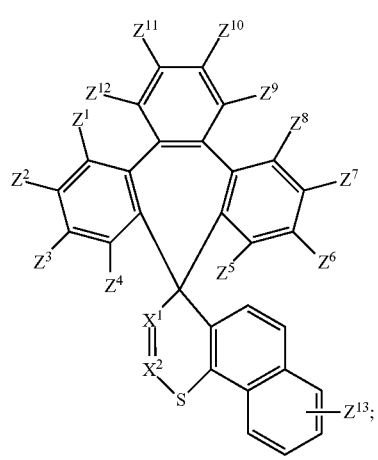
Formula (I-VIII)
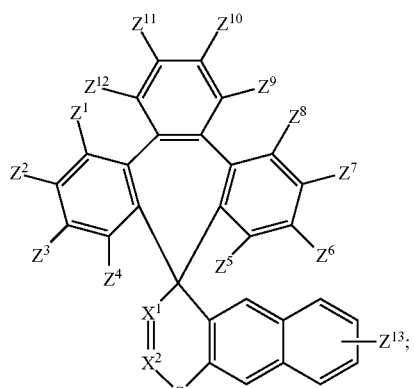
Formula (I-XI)
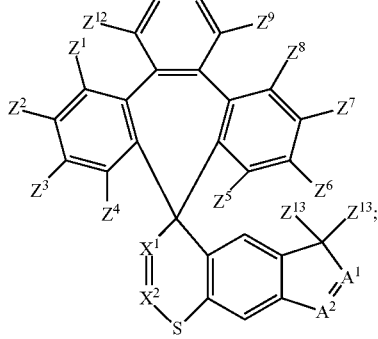
Formula (I-XIV)
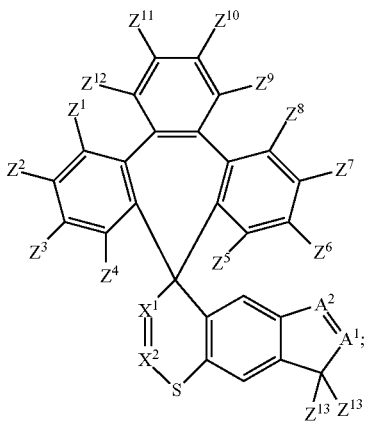
Formula (I-XVII)
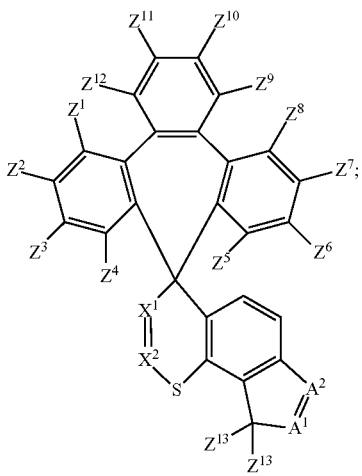

Formula (I-XX)
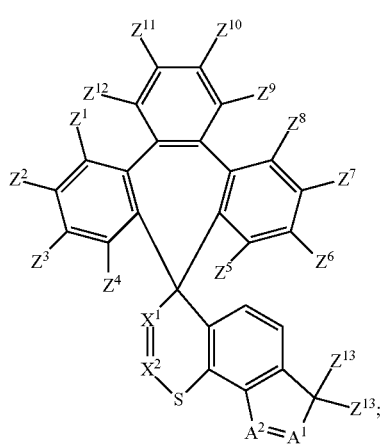
Formula (I-XXIII)
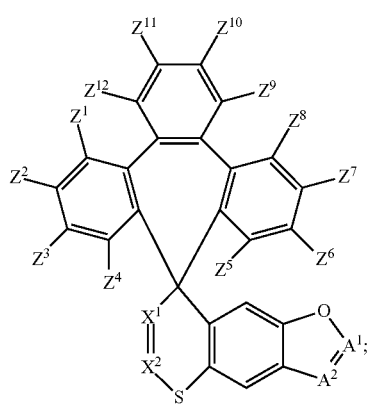
Formula (I-XXVI)
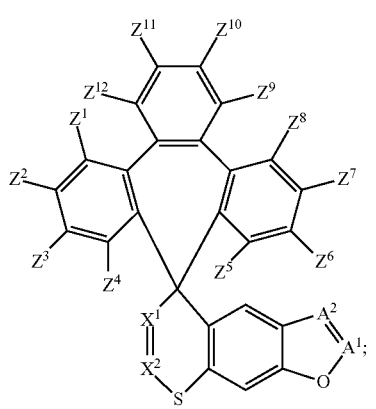
Formula (I-XXIX)
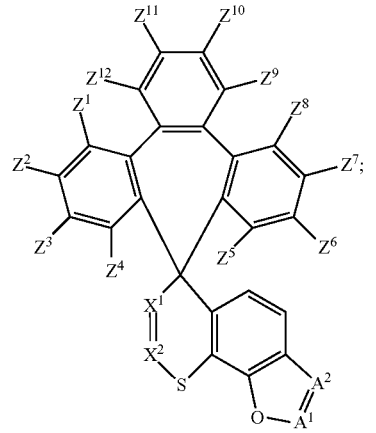
Formula (I-XXXII)
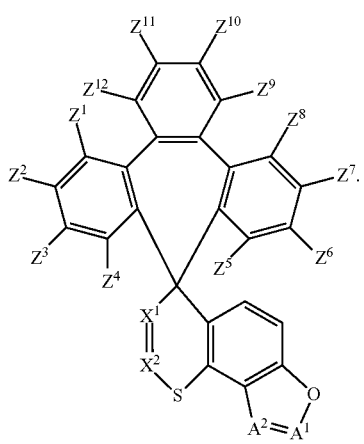
In a case that Y is a sulfur dioxide group, the compound is represented by any one of the following Formulae:
Formula (I-III)
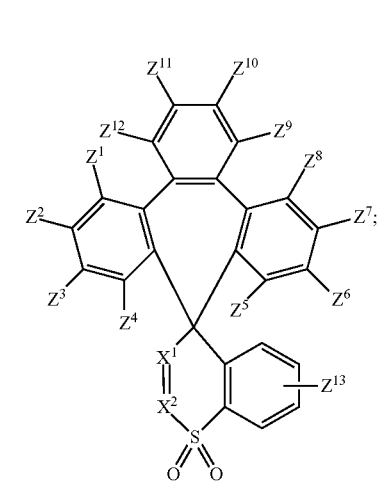
Formula (I-VI)
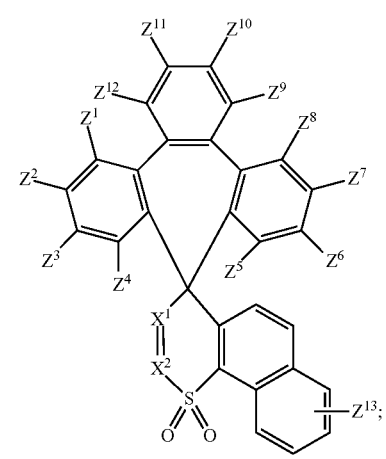

Formula (I-IX)
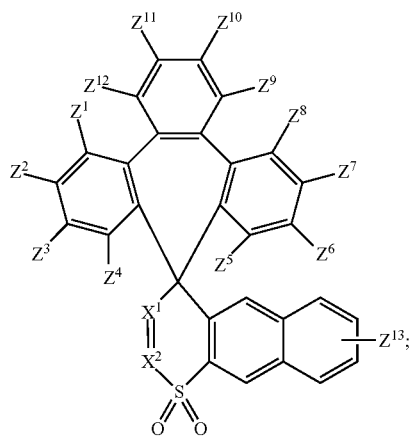
Formula (I-XII)
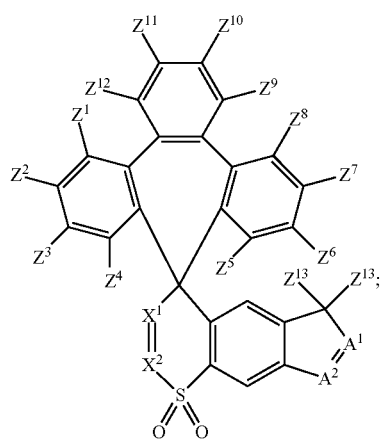
Formula (I-XV)
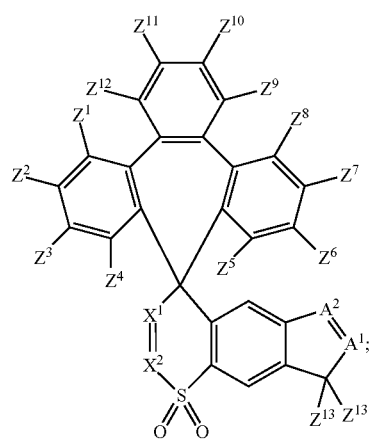
Formula (I-XVIII)
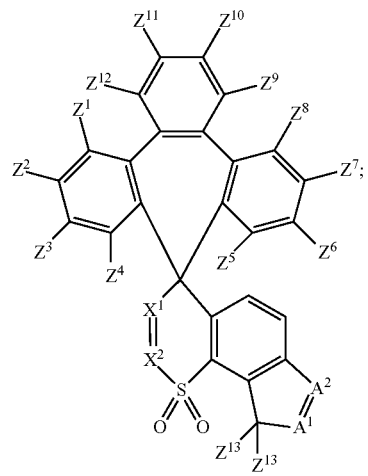
Formula (I-XXI)
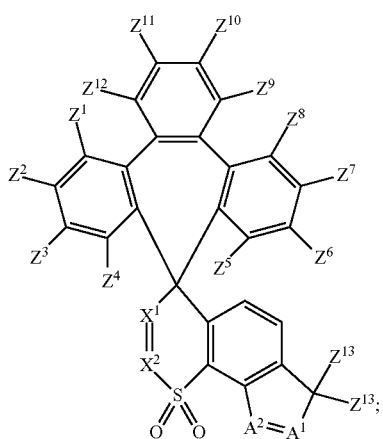
Formula (I-XXIV)
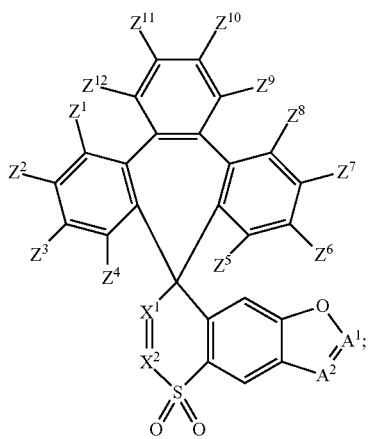

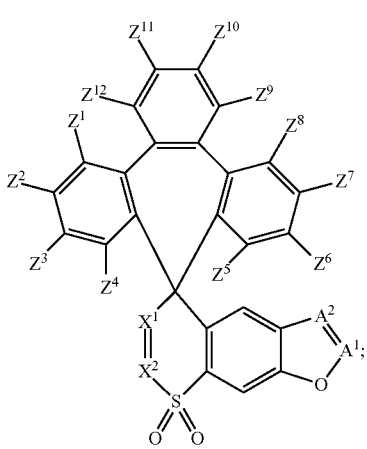

Formula (I-XXVII)

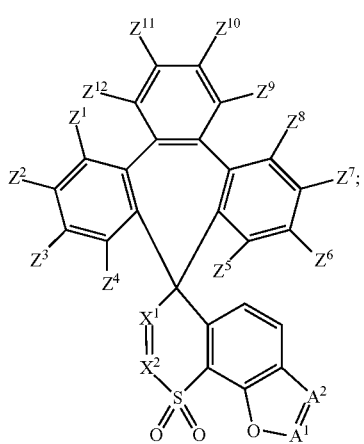

Formula (I-XXX)

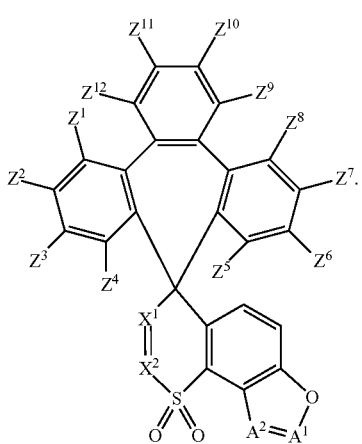

Formula (I-XXXIII)

In accordance with the present invention, the foresaid $A^1$ and $A^2$ are each independently $C(R^c)$, the two $(R^c)$s are the same or different. The two $(R^c)$s are joined together to form an aromatic structure contained in the second aryl ring or the heteroaryl ring.

In accordance with the present invention, each of the foresaid $Z^{13}$ is selected from the group consisting of: a methyl group, an ethyl group, a propyl group, a butyl group, a pentyl group, a hexyl group, and a phenyl group.

Preferably, the aromatic structure formed by the two $(R^c)$s may be a substituted or unsubstituted 6 to 20-membered carbon aromatic cyclic structure, for example, but not limited to, a substituted or unsubstituted benzene structure, a substituted or unsubstituted naphthalene structure, a substituted or unsubstituted anthracene structure, a substituted or unsubstituted phenanthrene structure, a substituted or unsubstituted pyrene structure, a substituted or unsubstituted fluoranthene structure, a substituted or unsubstituted benzofluoranthene structure, or a substituted or unsubstituted fluorene structure. The substitution group on the 6 to 20-membered carbon aromatic cyclic structure may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, at least one of $Z^1$ to $Z^8$ in any one of formulae may be selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 carbon atoms and substituted with at least one functional group, and a phosphine oxide group having 1 to 40 carbon atoms and substituted with at least one functional group; and the other of $Z^1$ to $Z^8$ in any one of foresaid formulae may be a hydrogen atom, a deuterium atom, or any other substitution groups as mentioned in the specification. Said functional group is selected from the group consisting of: a cyano group, a nitro group, a fluoro group, and a chloro group.

More specifically, at least one of $Z^1$ to $Z^8$ in any one of foresaid formulae may be a specific aromatic substitution. The specific aromatic substitution may be selected from the group consisting of:

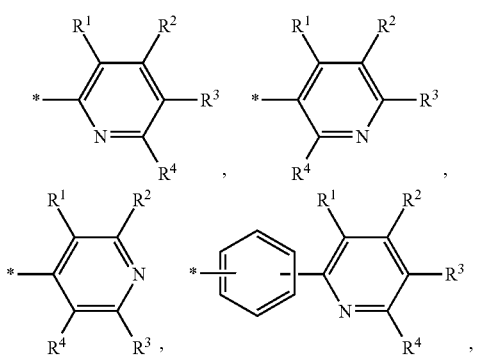

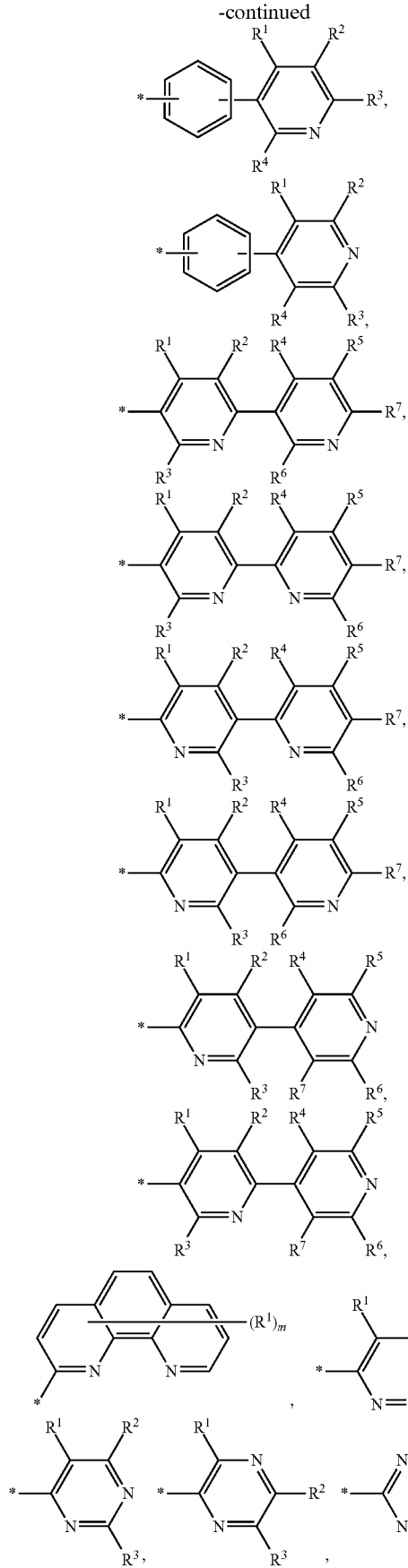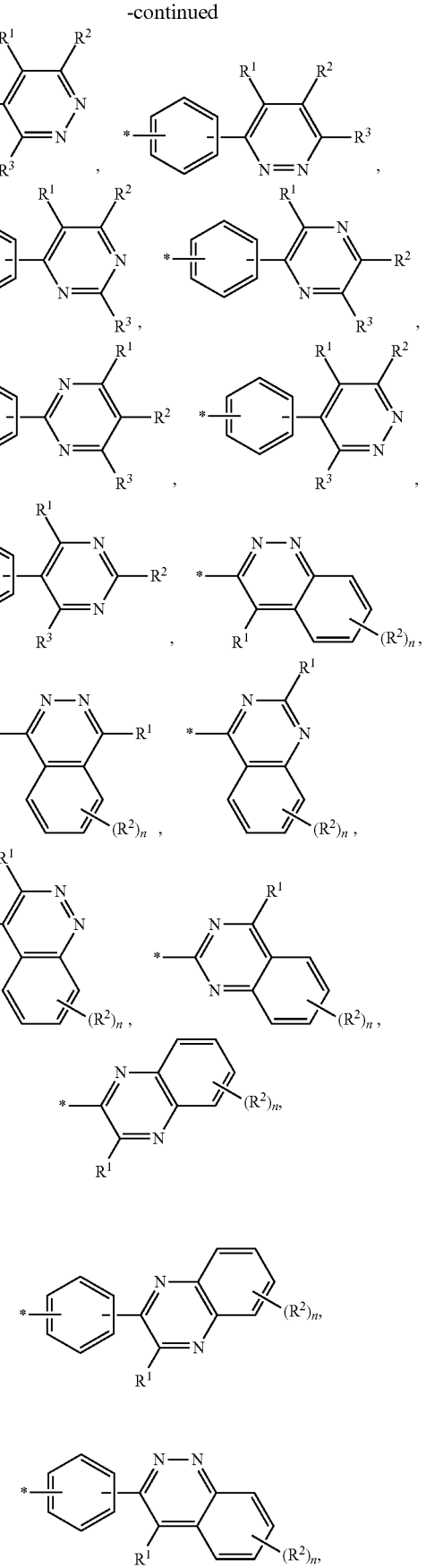

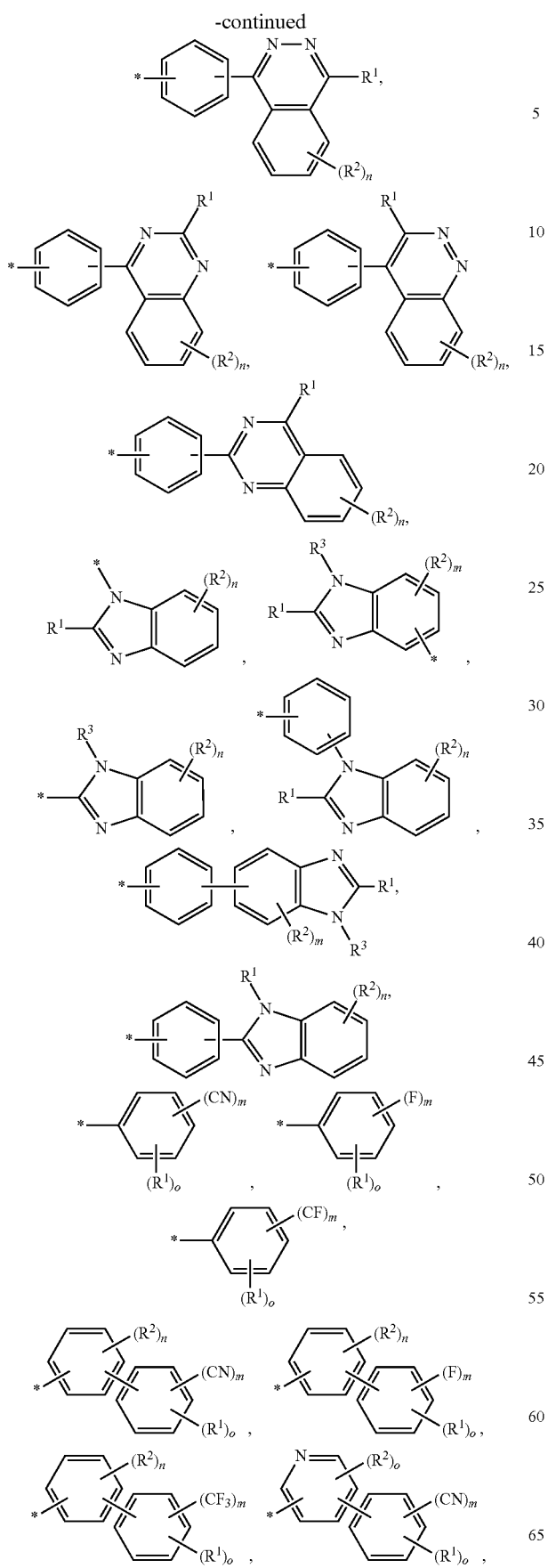

-continued

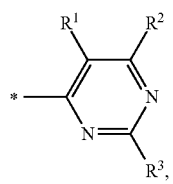

and

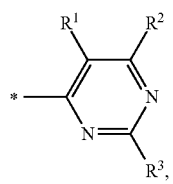

wherein R¹ to R⁷ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is a positive integral from 0 to 4, m is a positive integral from 0 to 3, o is a positive integral from 0 to 3, and the total of m and o is not more than 5.

Preferably, R¹ to R³ each may independently be, for example, but not limited to, phenyl group, pyridine group, pyrimidine group, pyrazine group, pyridazine group, phenylpyridine group, phenylpyrimidine group, phenylpyrazine group, or phenylpyridazine group.

In an embodiment, at least one of $Z^1$ to $Z^8$ in any one of foresaid formulae may preferably be

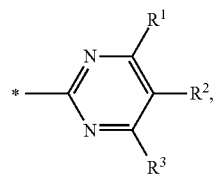

wherein R¹ may be pyridinyl group or cyanophenyl group, and R² and R³ may be any substitution group as stated above.

In another embodiment, at least one of $Z^1$ to $Z^8$ in any one of foresaid formulae may preferably be

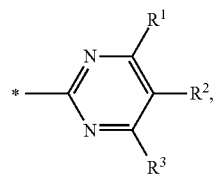

wherein R² may be pyridinyl group or cyanophenyl group, and R¹ and R³ may be any substitution group as stated above.

In further another embodiment, at least one of $Z^1$, $Z^2$, $Z^3$, $Z^6$, $Z^7$, and $Z^8$ in any one of foresaid formulae may be a substituted triazine group with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

Preferably, at least one of $Z^1$, $Z^2$, $Z^3$, $Z^6$, $Z^7$, and $Z^8$ in any one of foresaid formulae may be the specific aromatic substitution as stated above, and $Z^4$ and $Z^5$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms. Or, at least one of $Z^2$, $Z^3$, $Z^6$, and $Z^7$ in any one of foresaid formulae may be the specific aromatic substitution as stated above, and $Z^1$, $Z^4$, $Z^5$, $Z^8$ are each independently selected from the group consisting of: a hydrogen atom, a deuterium atom, an alkyl group having 1 to 12 carbon atoms, an alkenyl group having 2 to 12 carbon atoms, and an alkynyl group having 2 to 12 carbon atoms.

Preferably, at least one of $Z^2$, $Z^3$, $Z^6$, and $Z^7$ in any one of foresaid formulae is selected from the group consisting of:

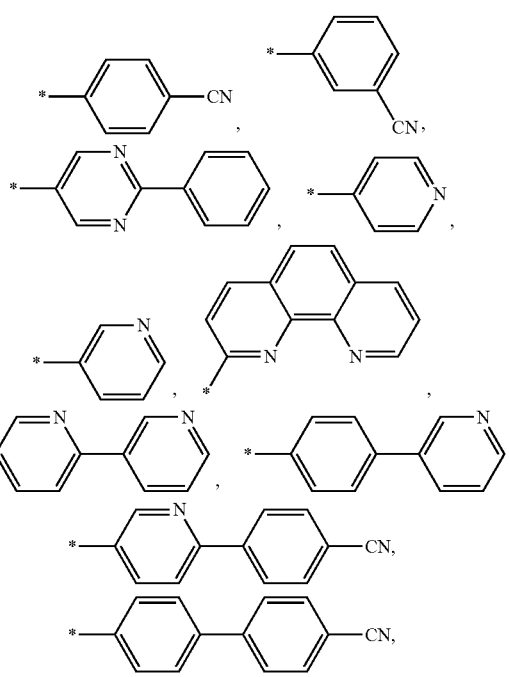

-continued
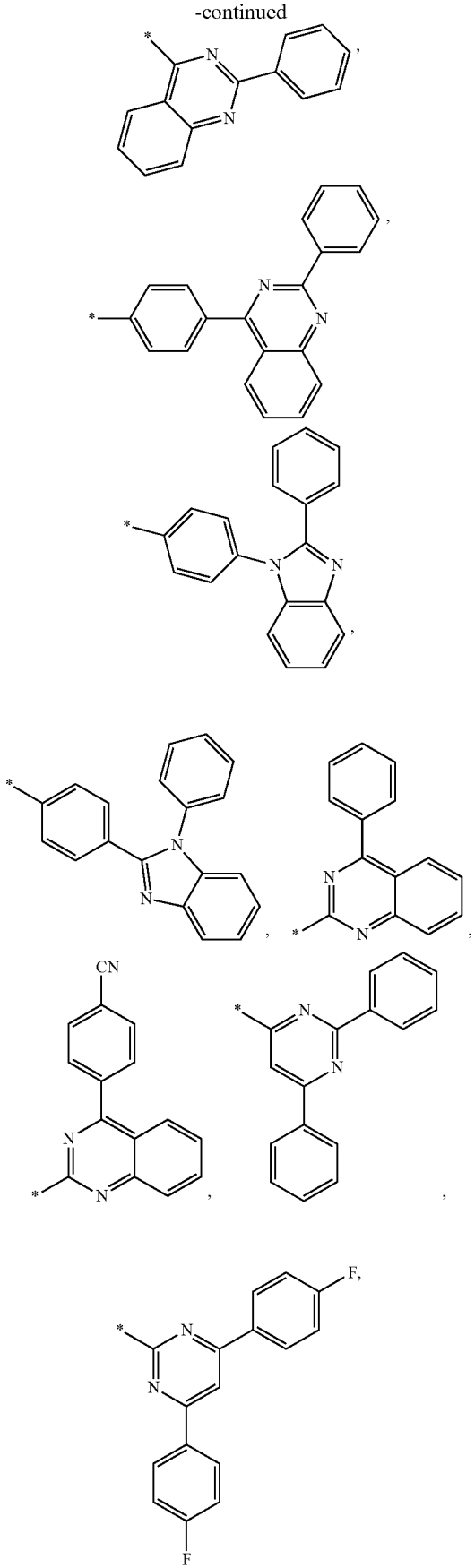
-continued
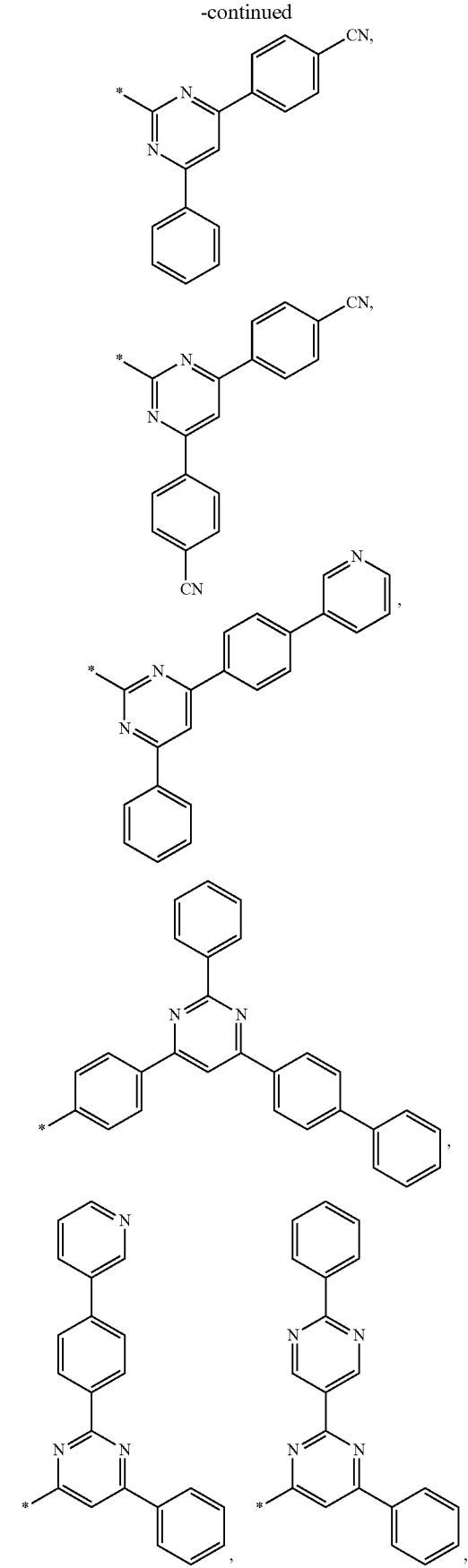

-continued

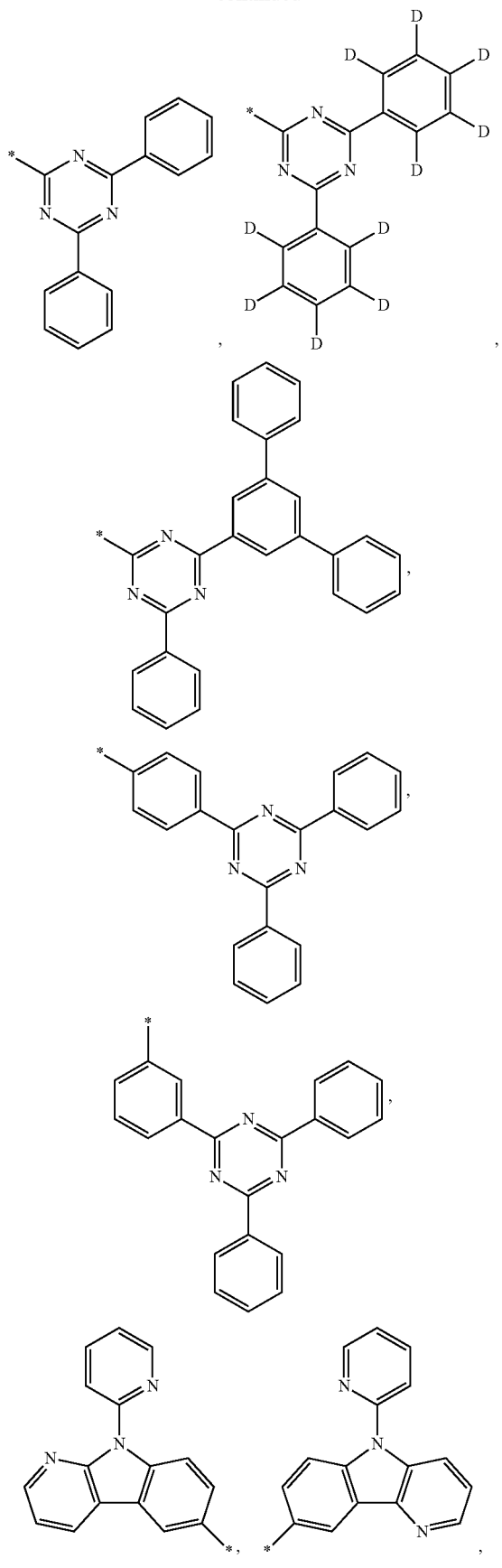

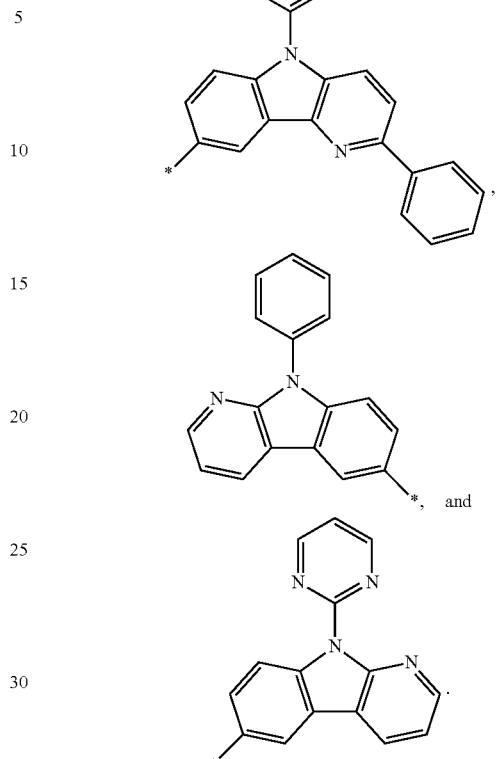

Preferably, at least one of $Z^1$, $Z^2$, $Z^3$, $Z^6$, $Z^7$, and $Z^8$ in any one of foresaid formulae may be the specific aromatic substitution as stated above, and $Z^4$ and $Z^5$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

Preferably, $Z^9$ to $Z^{12}$ in Formula (I) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

In accordance with the present invention, $Z^1$ and $Z^8$ may be the same or different. In accordance with the present invention, $Z^2$ and $Z^7$ may be the same or different. In accordance with the present invention, $Z^3$ and $Z^6$ may be the same or different. In one embodiment, any two of $Z^1$, $Z^2$, $Z^3$, $Z^6$, $Z^7$, and $Z^8$ may be the same substitution as stated above, and the others of $Z^1$, $Z^2$, $Z^3$, $Z^6$, $Z^7$, and $Z^8$ may be a hydrogen atom, a deuterium atom, a halogen group, a cyano group, a nitro group, an alkyl group having 1 to 12 carbon atoms, an alkenyl group having 2 to 12 carbon atoms, or an alkynyl group having 2 to 12 carbon atoms.

For example, $Z^1$, $Z^4$ to $Z^8$ are each independently a hydrogen atom or a deuterium atom, and $Z^2$ and/or $Z^3$ may be a specific aromatic substitution. Or, $Z^1$, $Z^2$, $Z^4$, $Z^5$, $Z^7$, and $Z^8$ are each independently a hydrogen atom or a deuterium atom, and $Z^3$ and $Z^6$ are both the above specific aromatic substitutions.

For example, the compound may be selected from the group consisting of:

Compound I
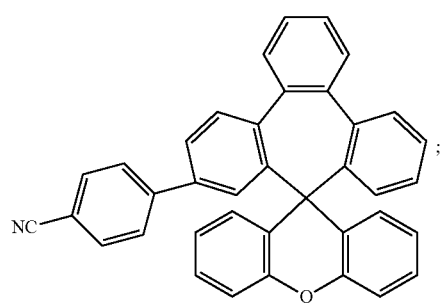
Compound II
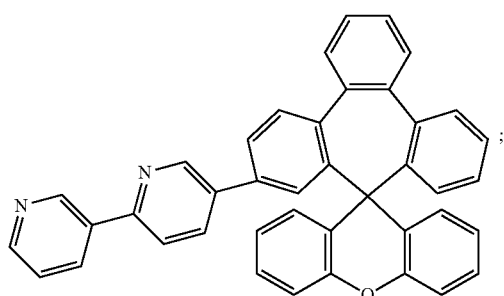
Compound III
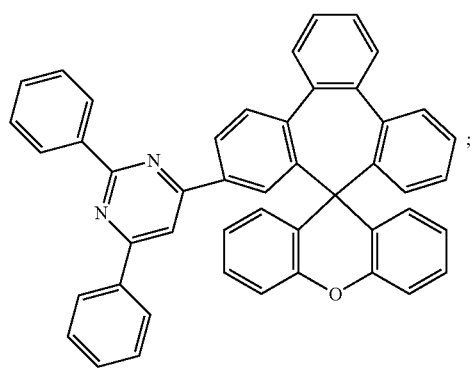
Compound IV
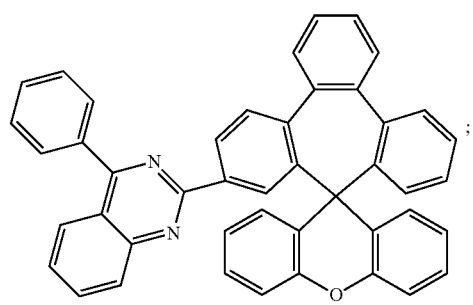
Compound V
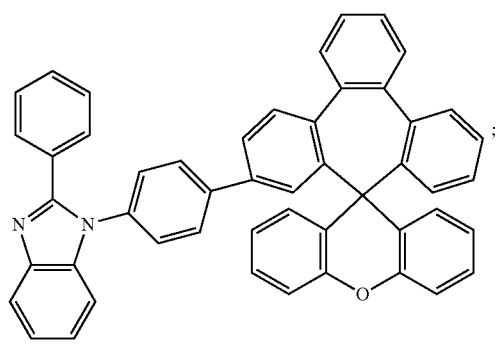
Compound VI
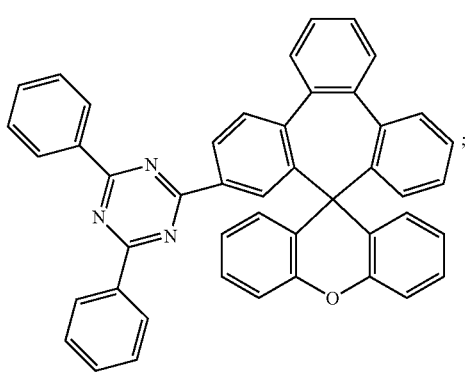
Compound VII
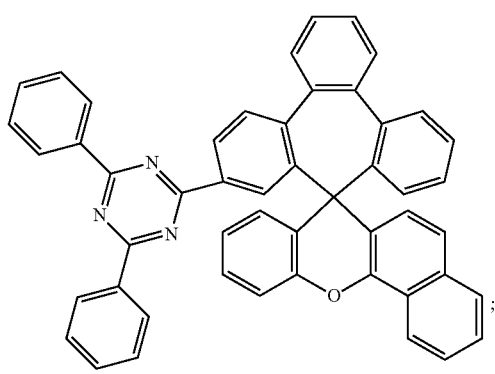
Compound VIII
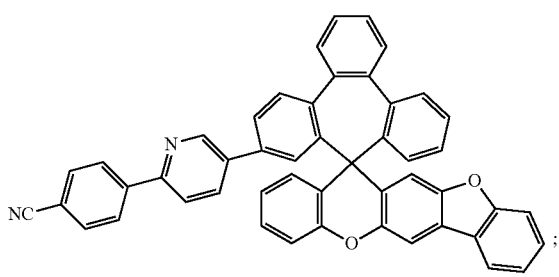

Compound IX
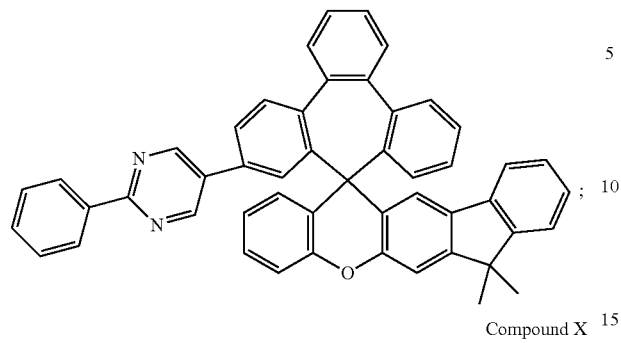
Compound X
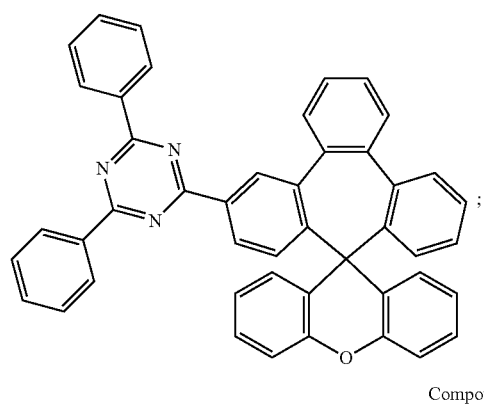
Compound XI
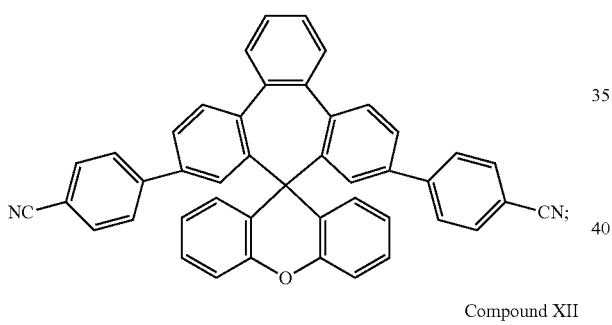
Compound XII
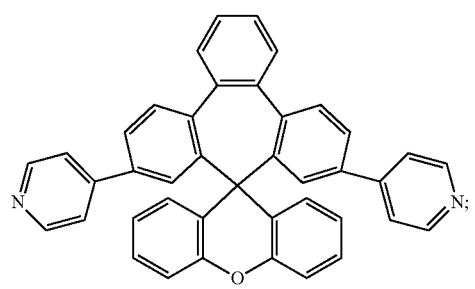
Compound XIII
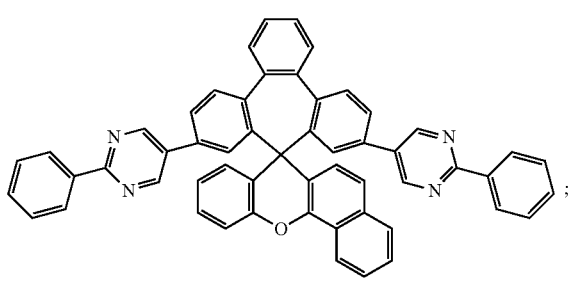
Compound XIV
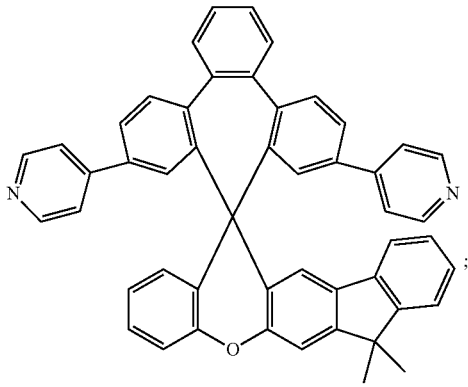
Compound XV
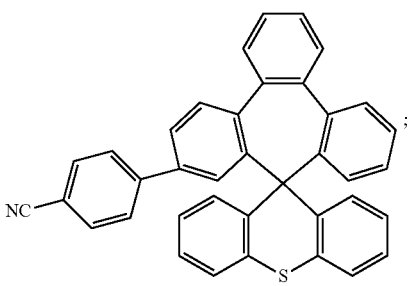
Compound XVI
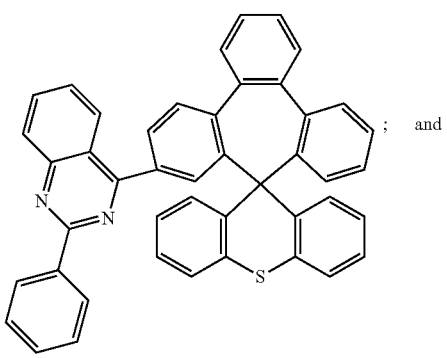
; and
Compound XVII
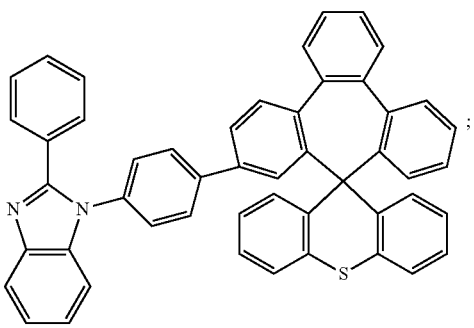
;

Compound XVIII
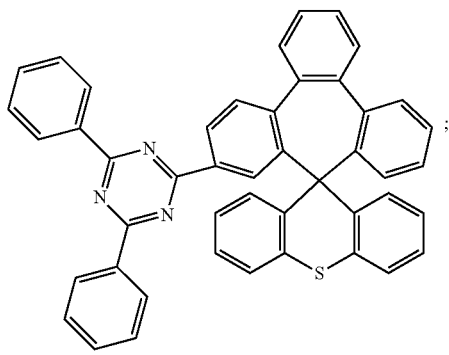
Compound XIX
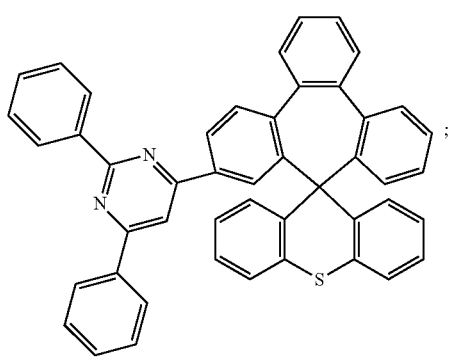
Compound XX
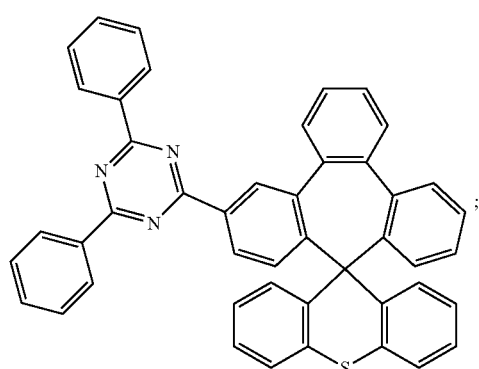
Compound XXI
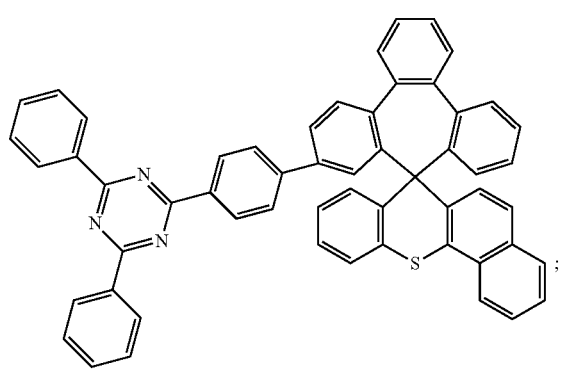
Compound XXII
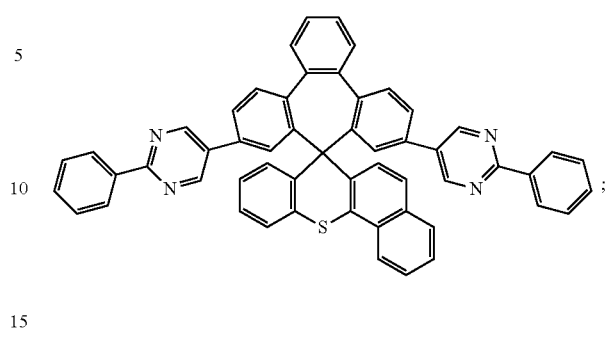
Compound XXIII
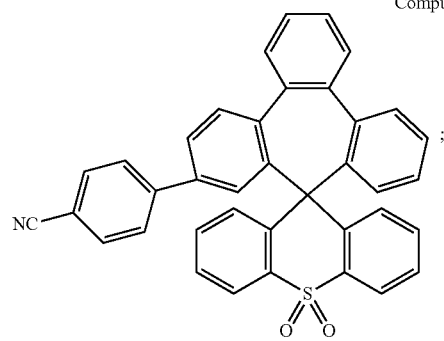
Compound XXIV
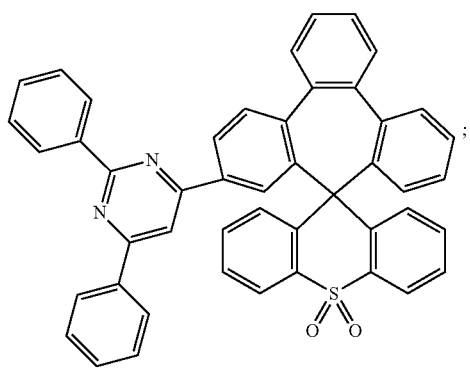
Compound XXV
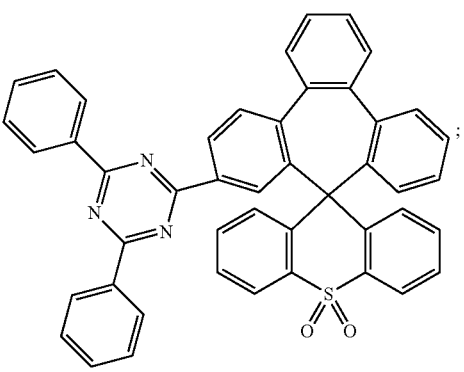

Compound XXVI
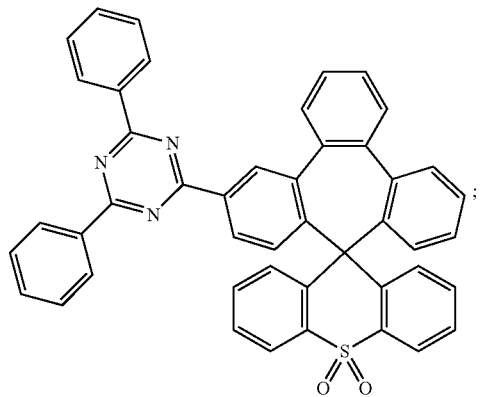
Compound XXVII
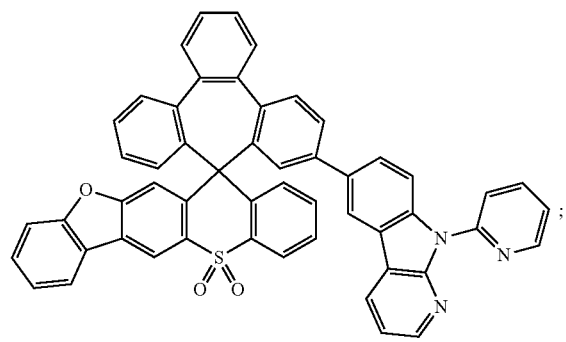
Compound XXVIII
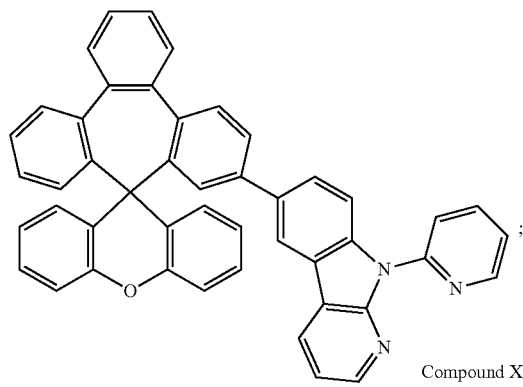
Compound XXIX
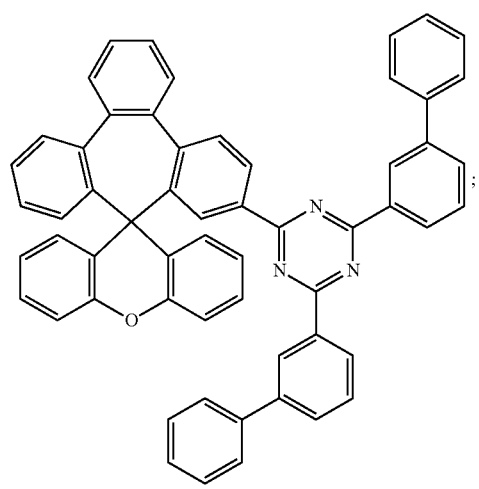
Compound XXX
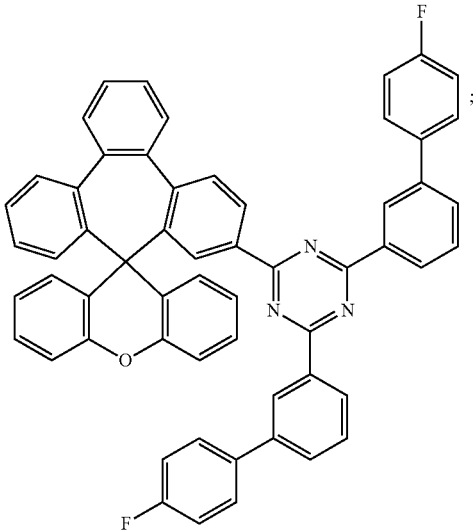
Compound XXXI
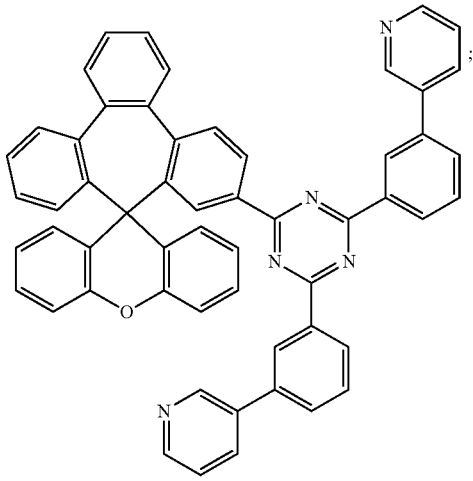
Compound XXXII
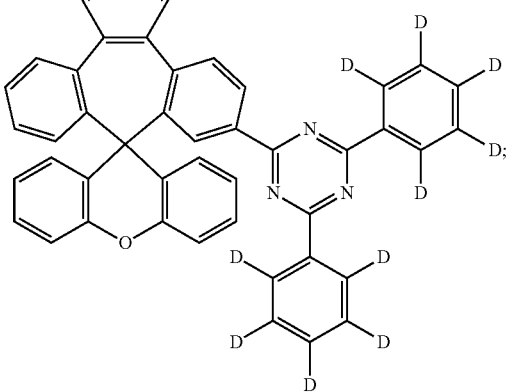

Compound XXXIII
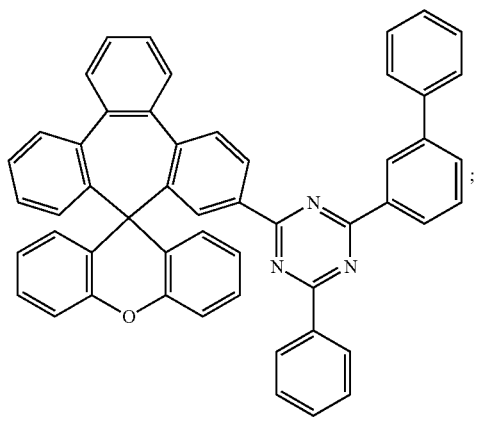
Compound XXXIV
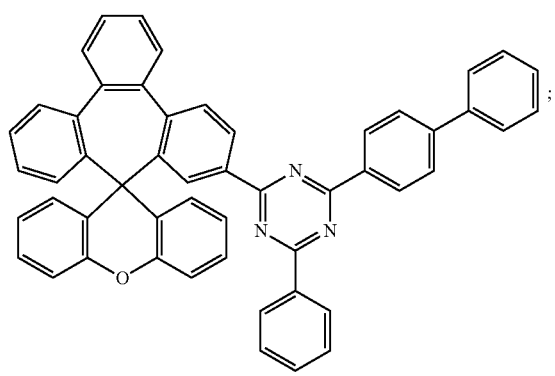
Compound XXXV
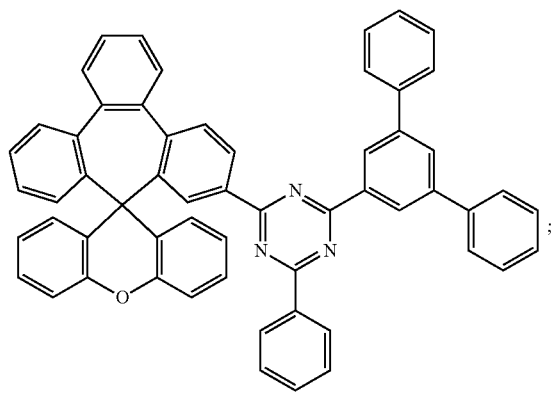
Compound XXXVI
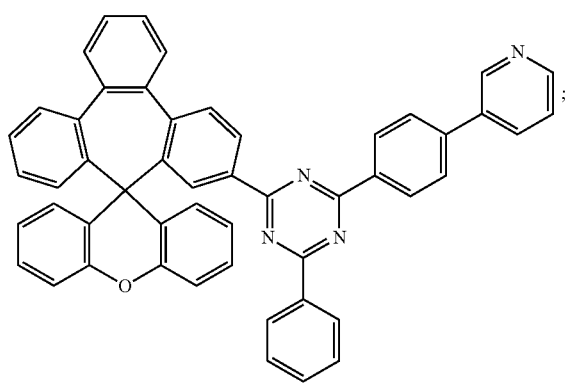
Compound XXXVII
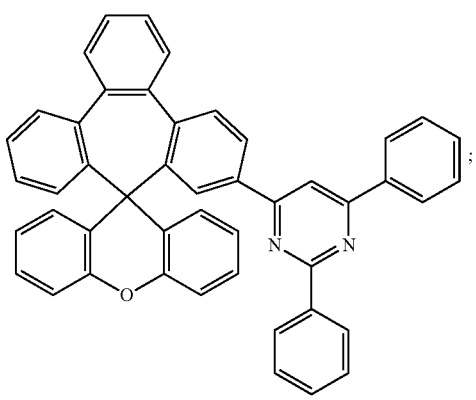
Compound XXXVIII
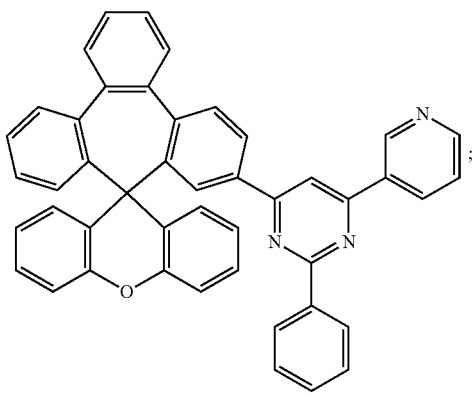
Compound XXXIX
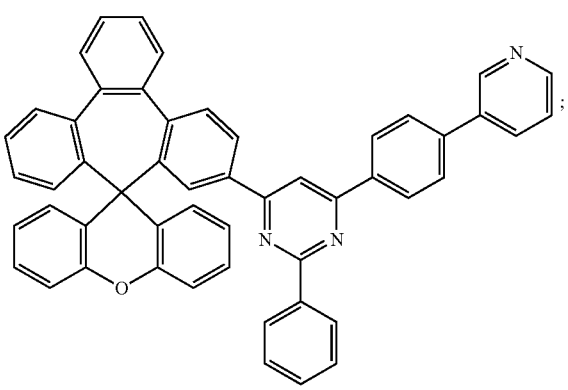
Compound XL
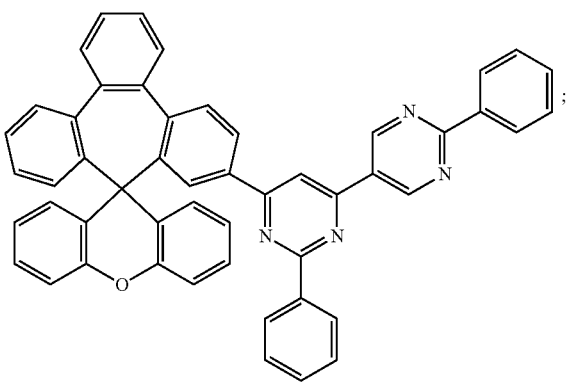

-continued
Compound XLI
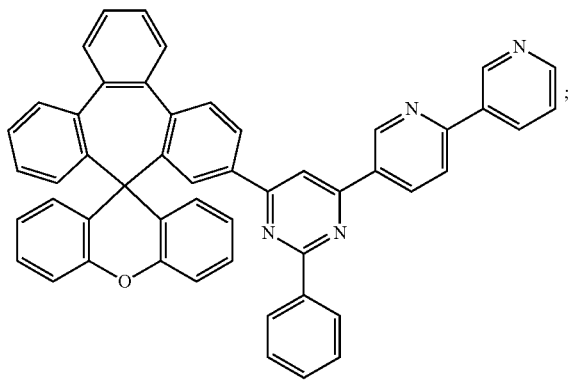
Compound XLII
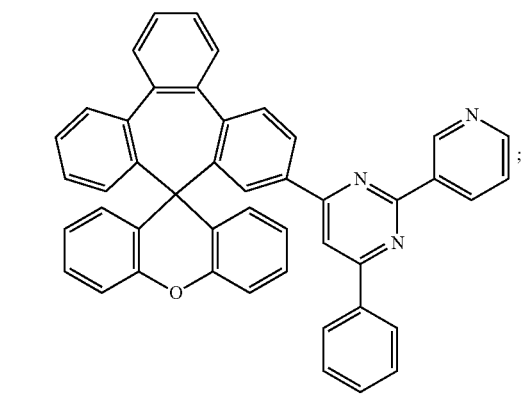
Compound LIII
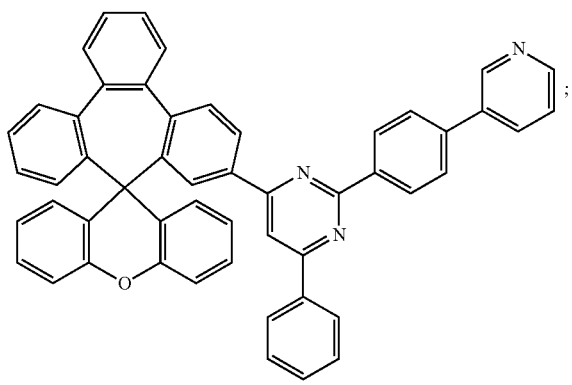
Compound XLIV
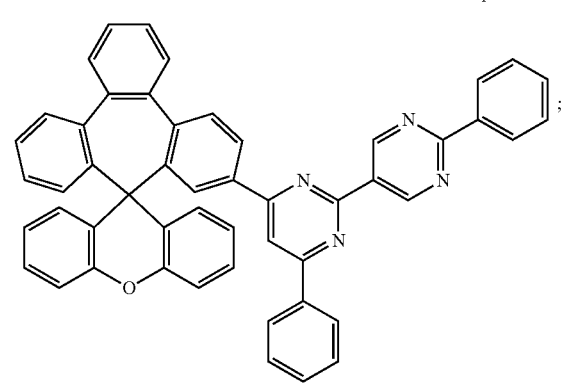
Compound XLV
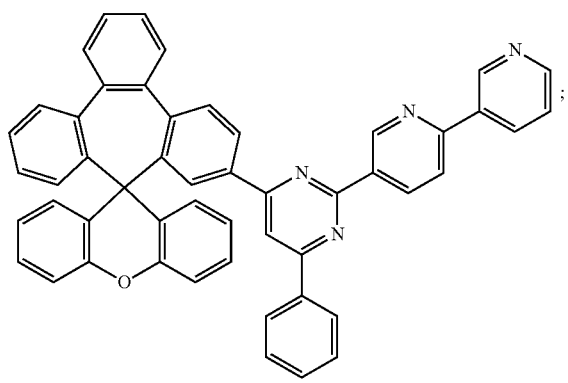
Compound LVI
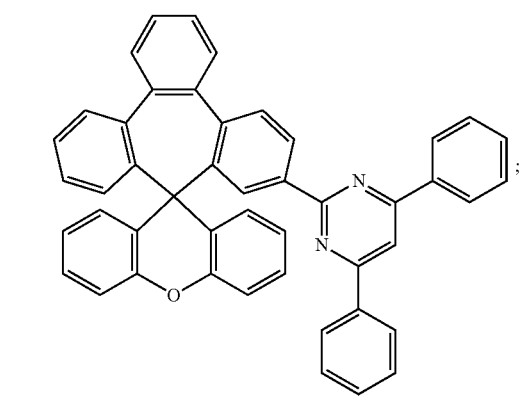
Compound LVII
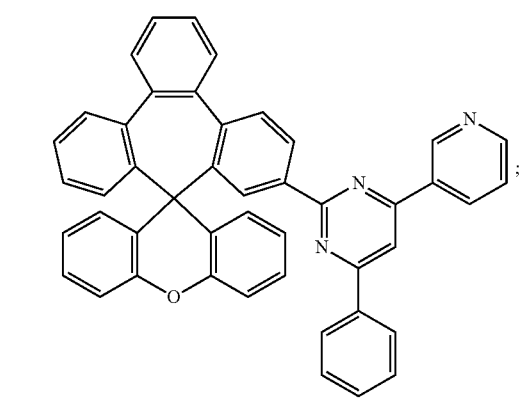
Compound XLVIII
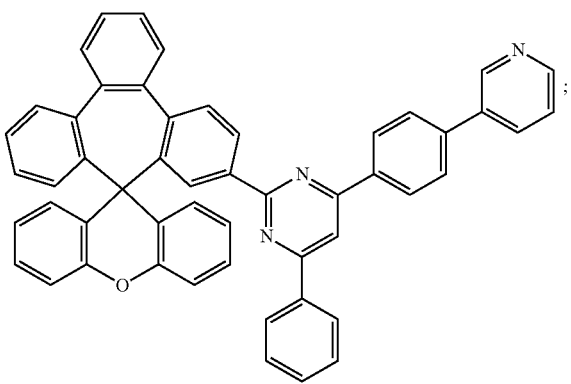

Compound IL
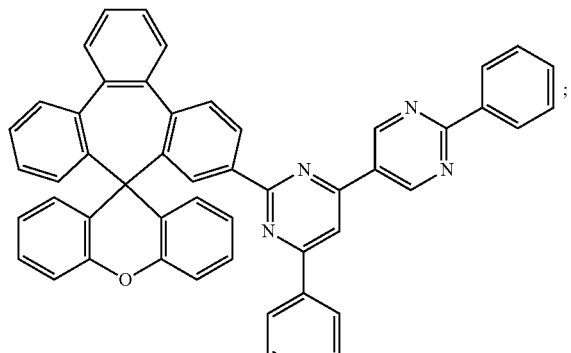
Compound L
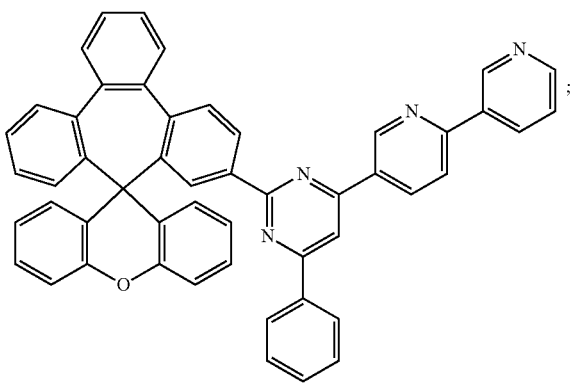
Compound LI
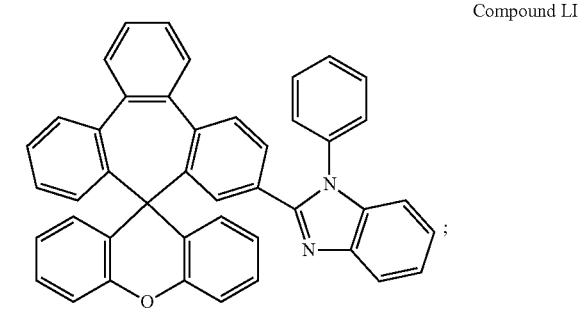
Compound LII
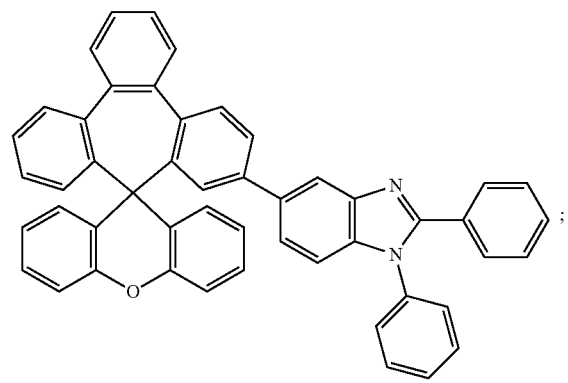
Compound LIII
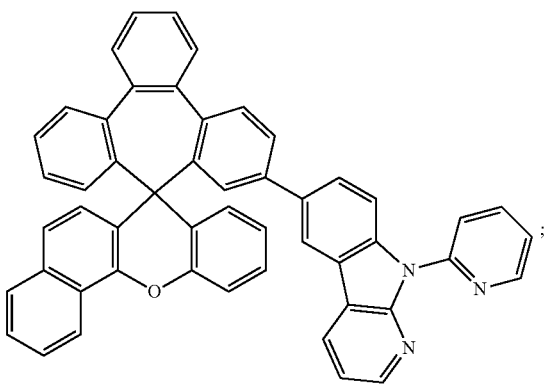
Compound LIV
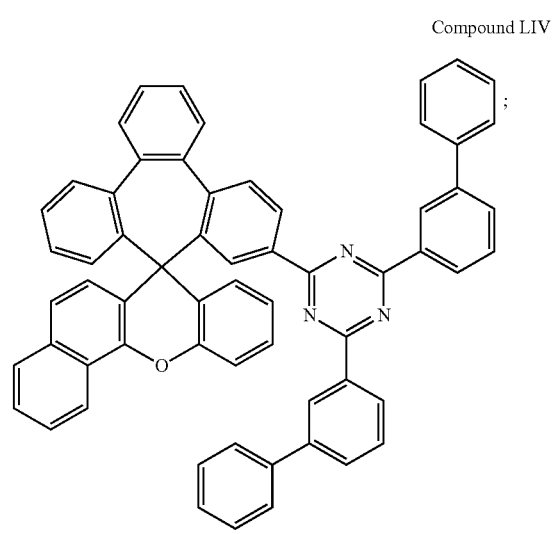
Compound LV
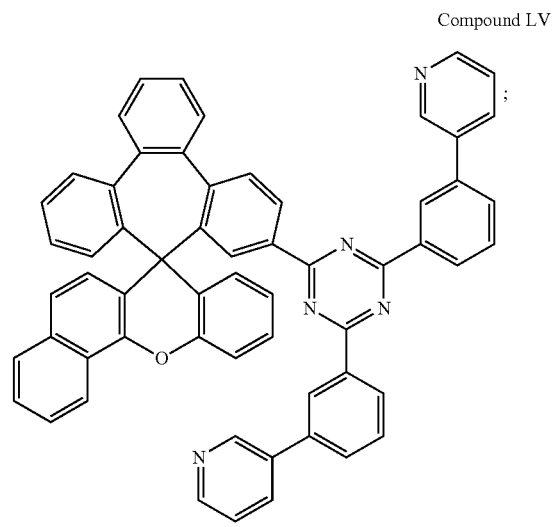

Compound LVI
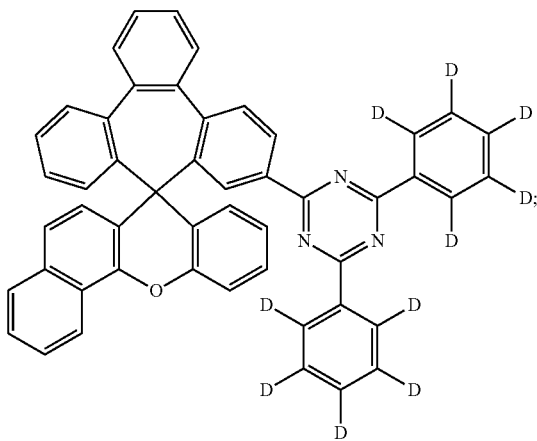
Compound LVII
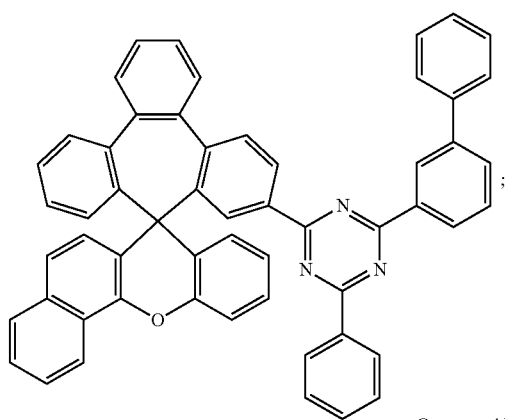
Compound LVIII
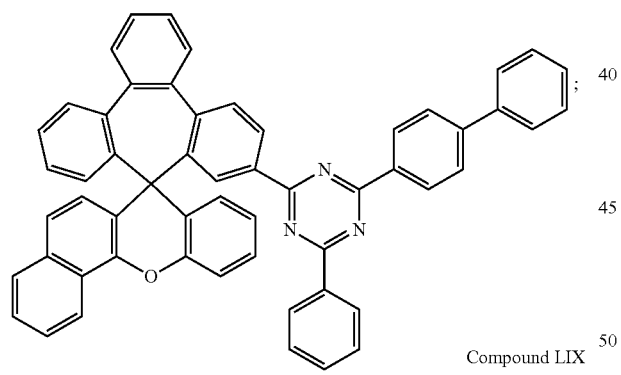
Compound LIX
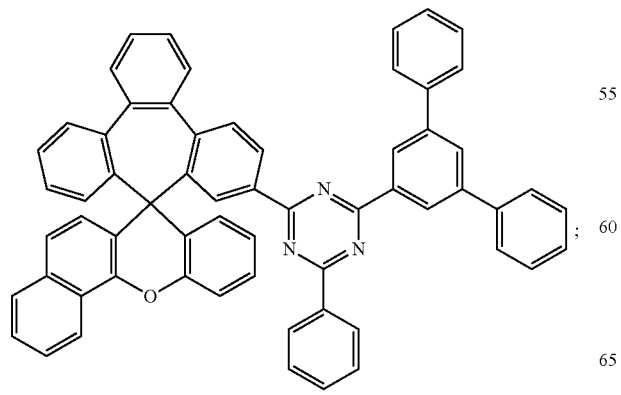
Compound LX
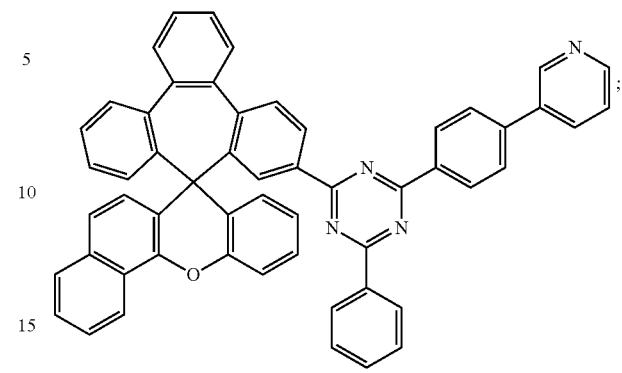
Compound LXI
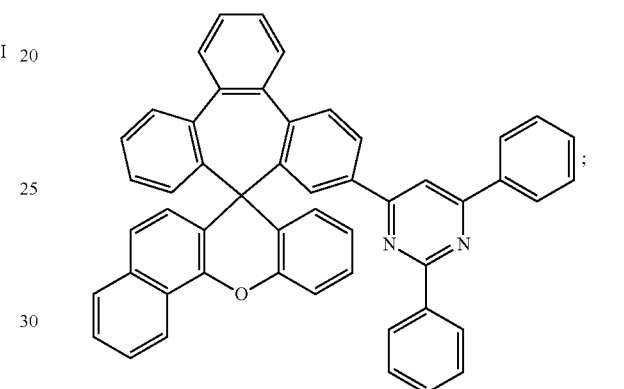
Compound LXII
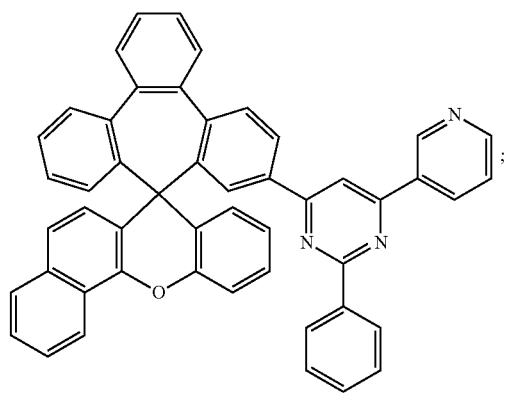
Compound LXIII Compound LXIV
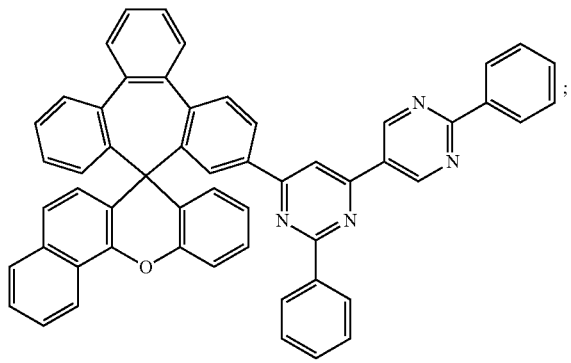
Compound LXV
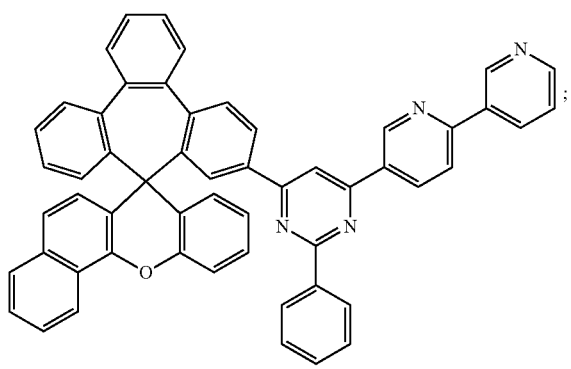
Compound LXVI
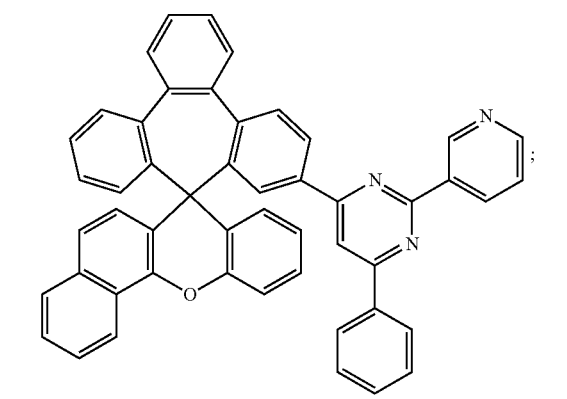
Compound LXVII
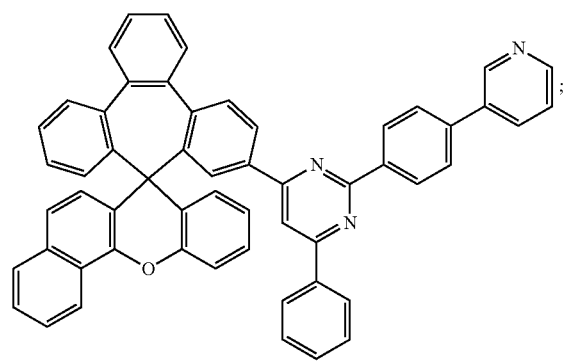
Compound LXVIII
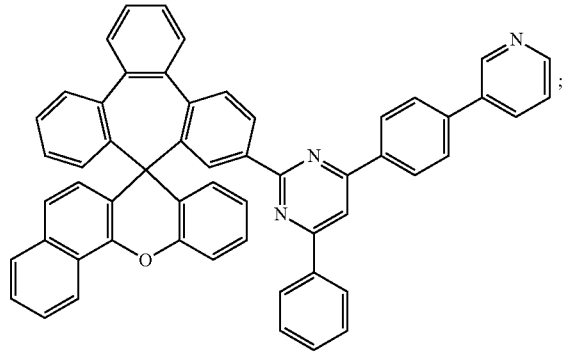
Compound LXIX
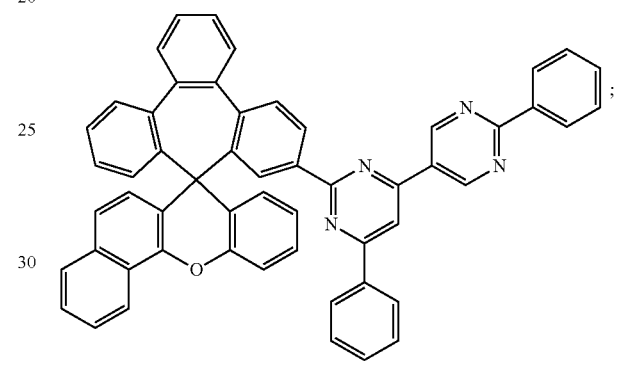
Compound LXX
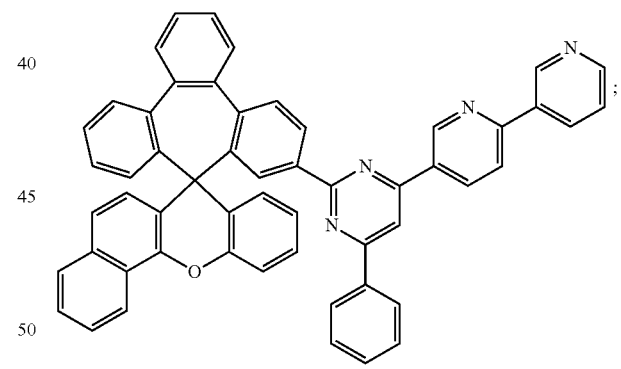
Compound LXXI
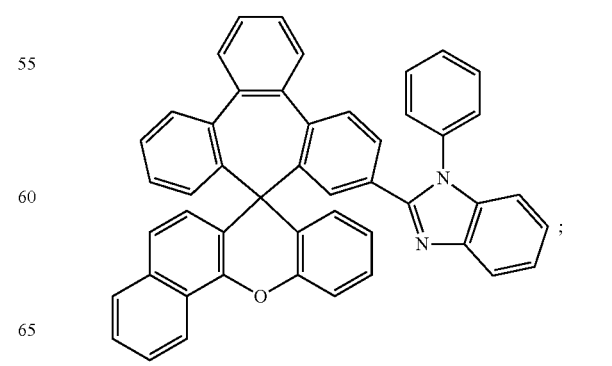

Compound LXXII
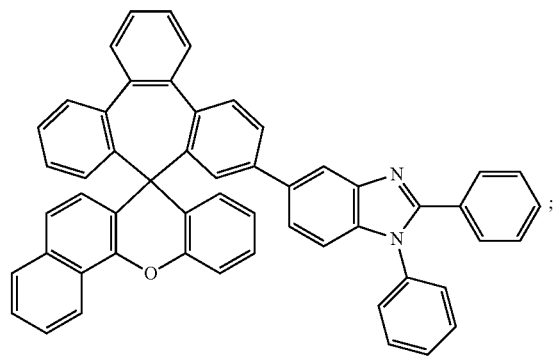
Compound LXXIII
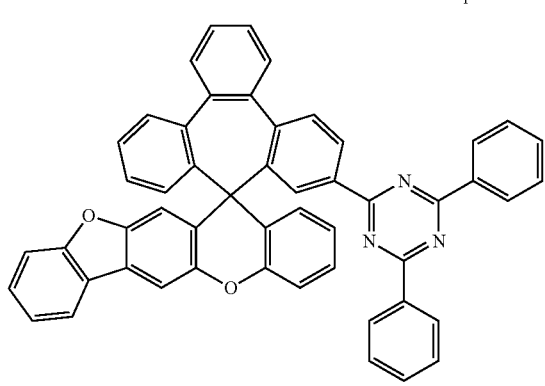
Compound LXXIV
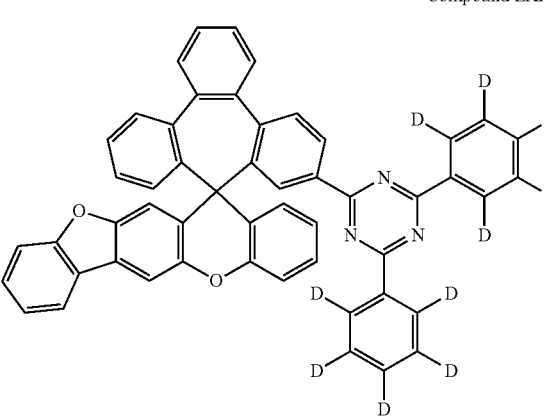
Compound LXXV
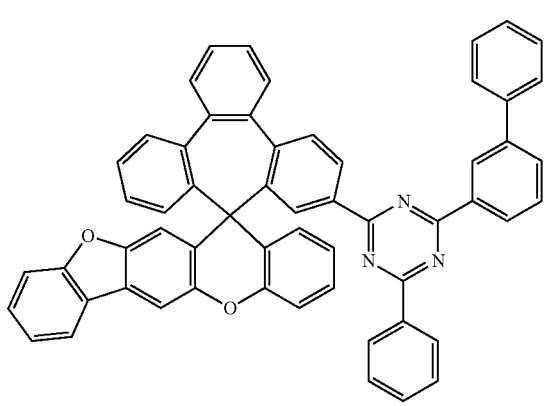
Compound LXXVI
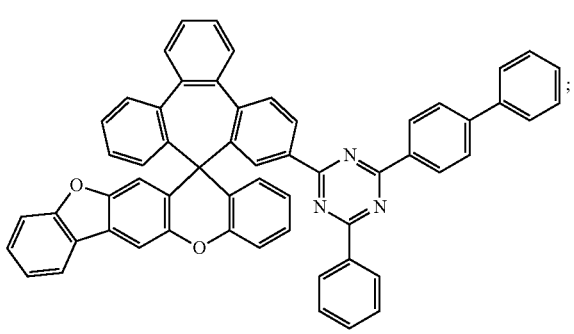
Compound LXXVII
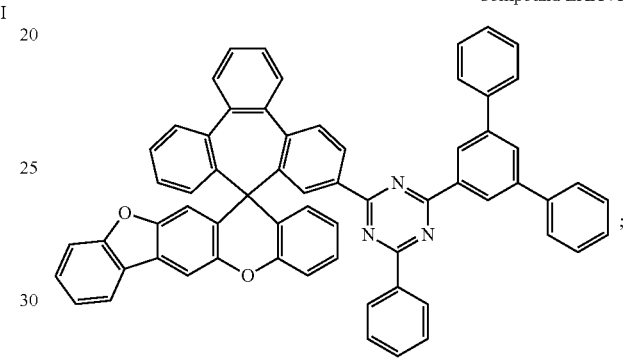
Compound LXXVIII
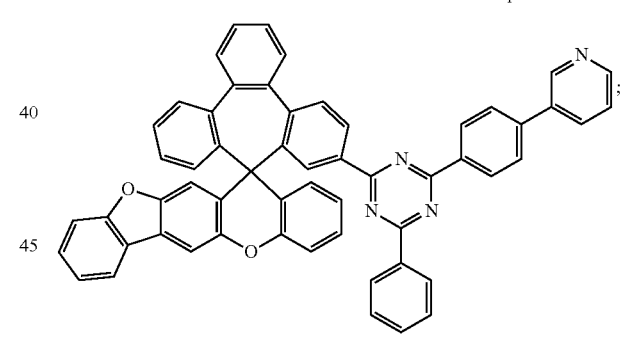
Compound LXXIX
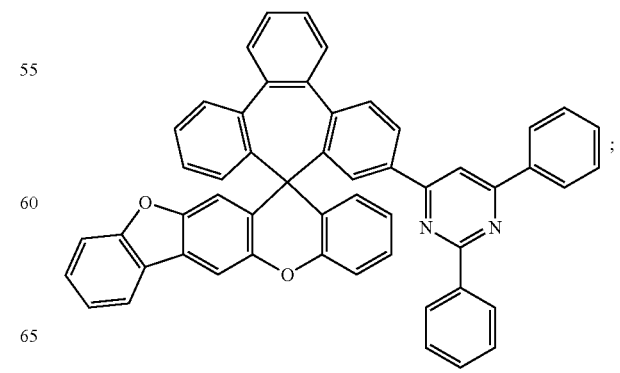

Compound LXXX
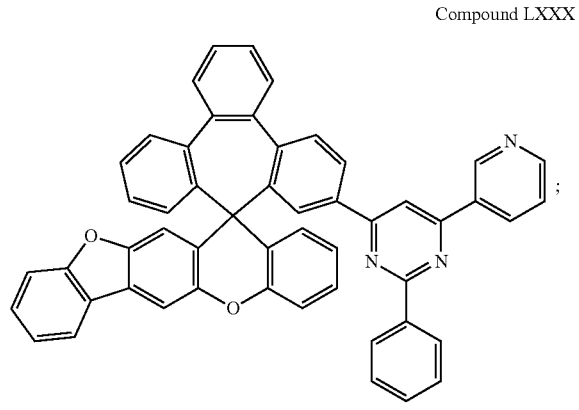
Compound LXXXI
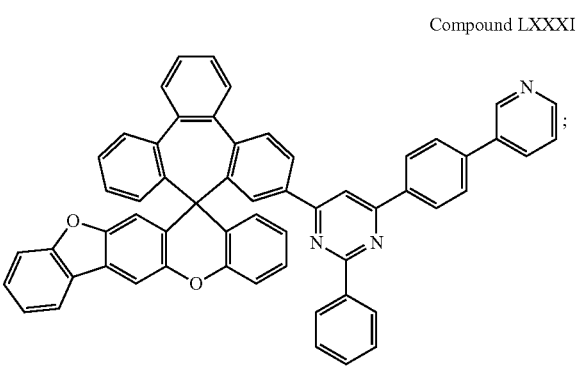
Compound LXXXII
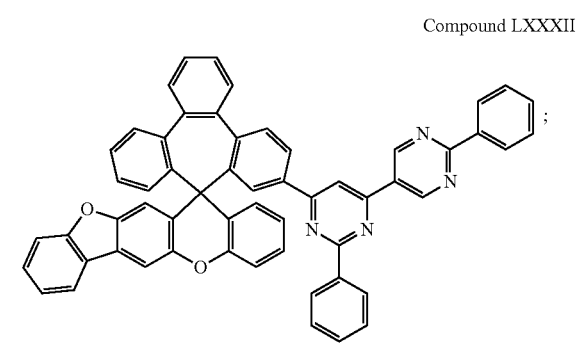
Compound LXXXIII
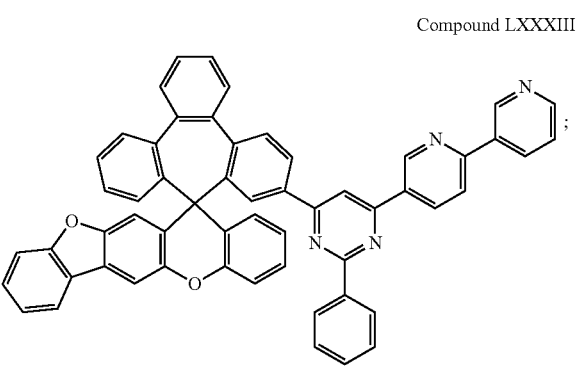
Compound LXXXIV
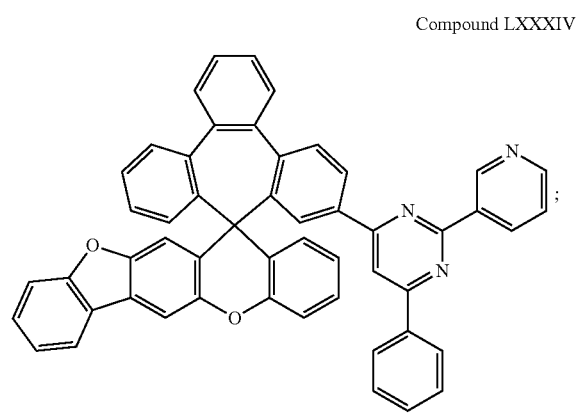
Compound LXXXV
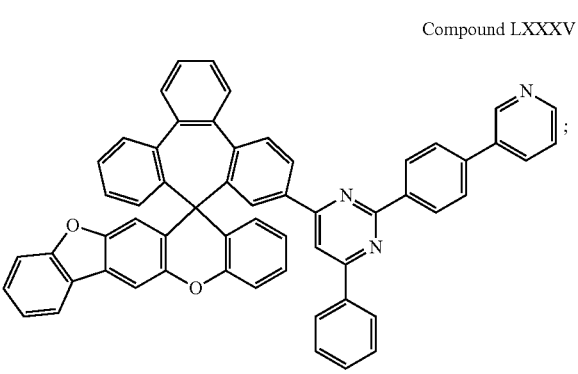
Compound LXXXVI
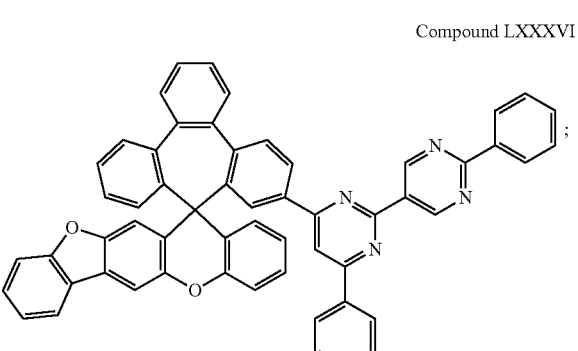
Compound LXXXVII
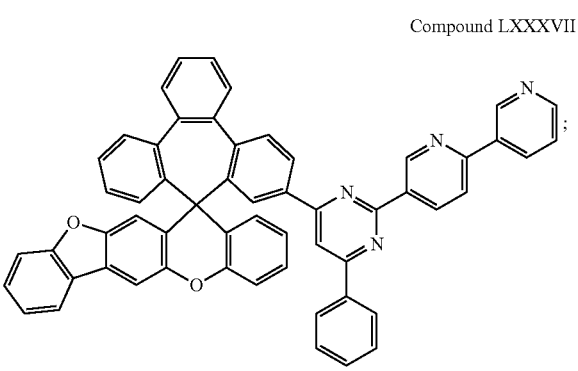

Compound LXXXVIII
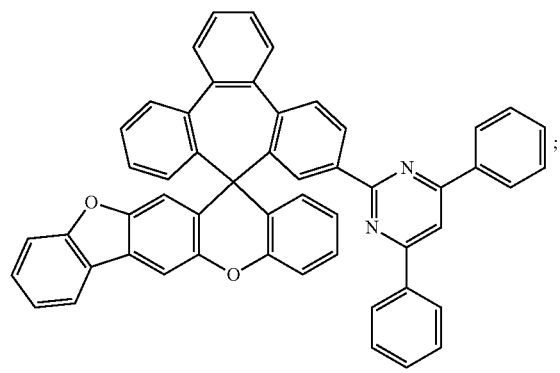
Compound LXXXIX
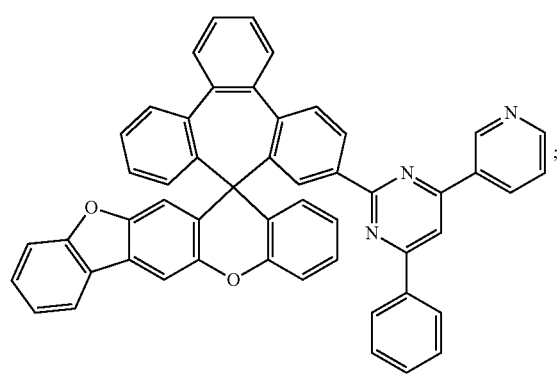
Compound XC
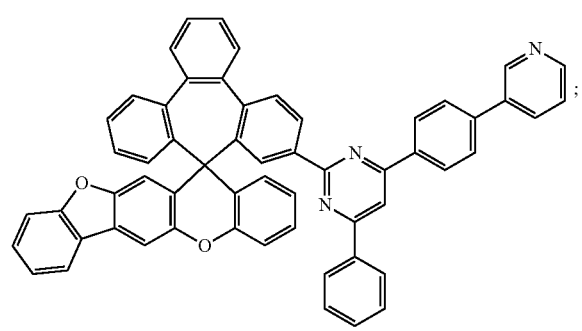
Compound XCI
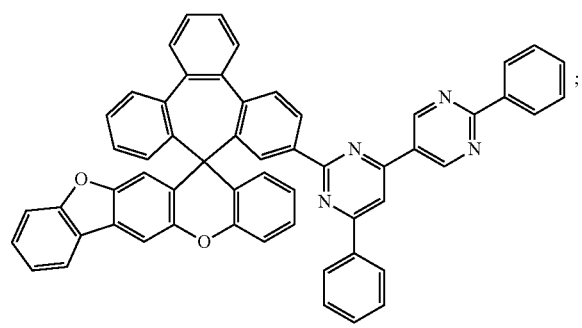
Compound XCII
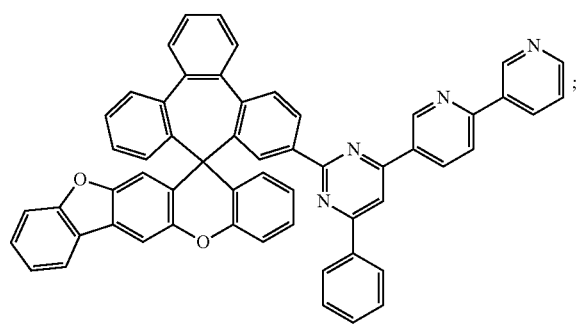
Compound XCIII
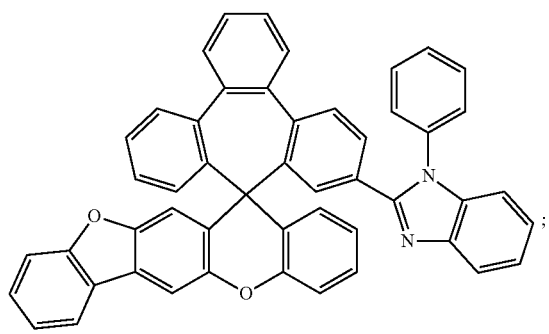
Compound XCIV
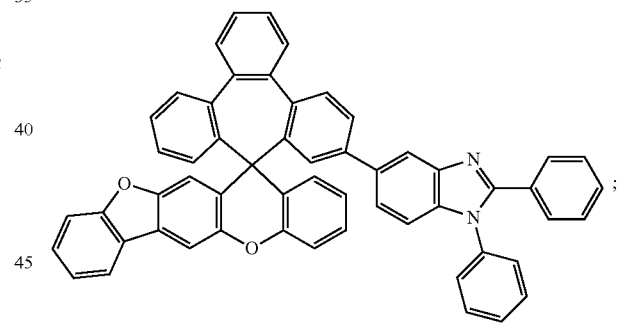
Compound XCV
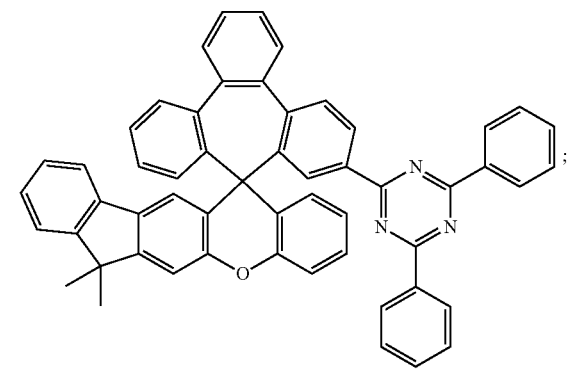

Compound XCVI
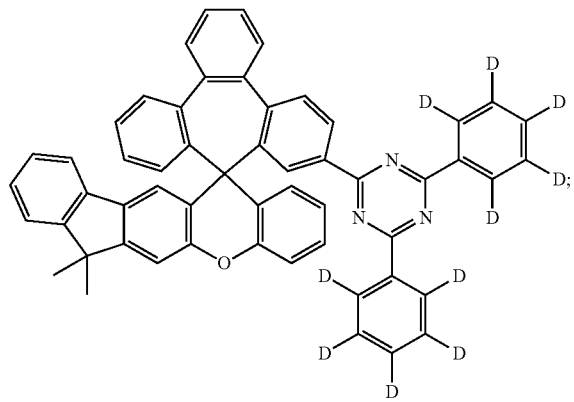
Compound C
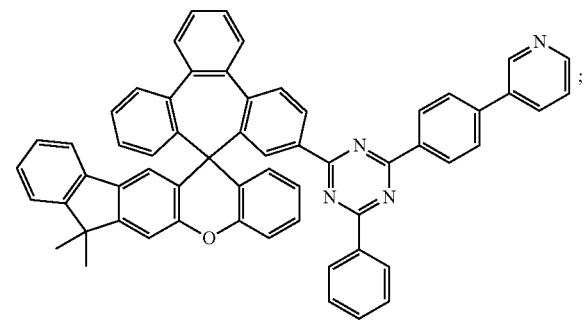
Compound XCVII
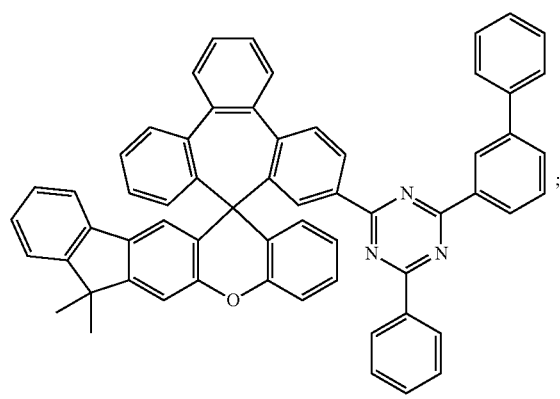
Compound CI
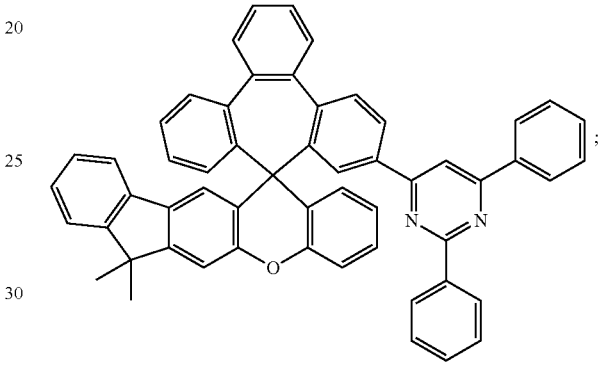
Compound XCVIII
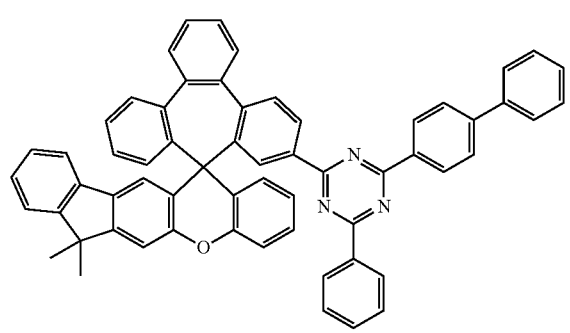
Compound CII
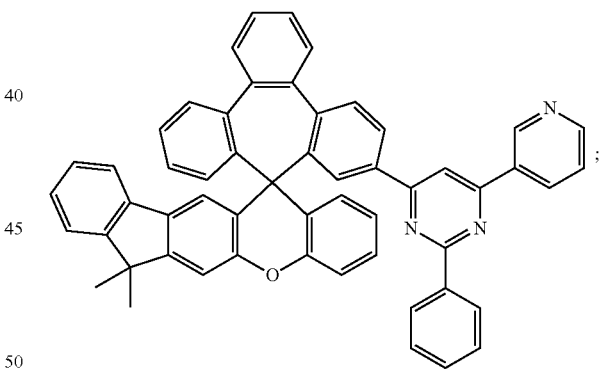
Compound IC
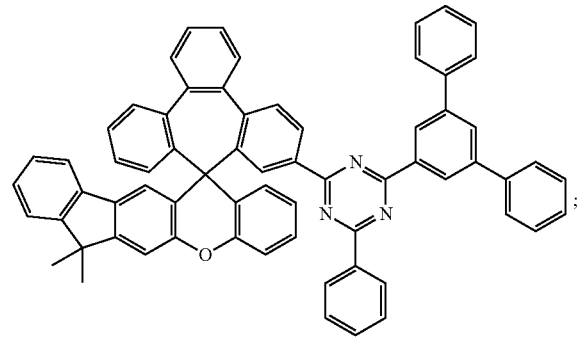
Compound CIII

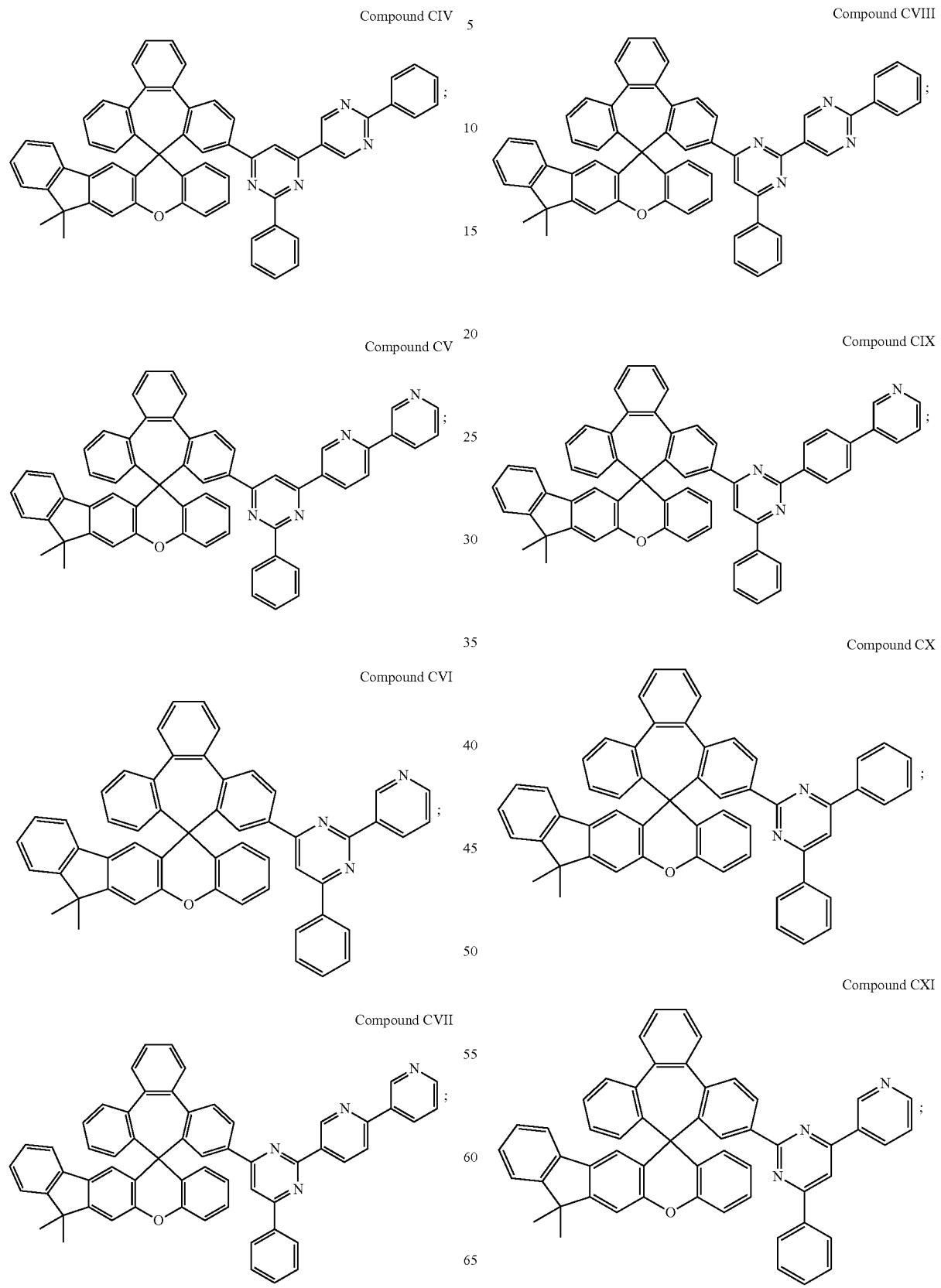

Compound CXII
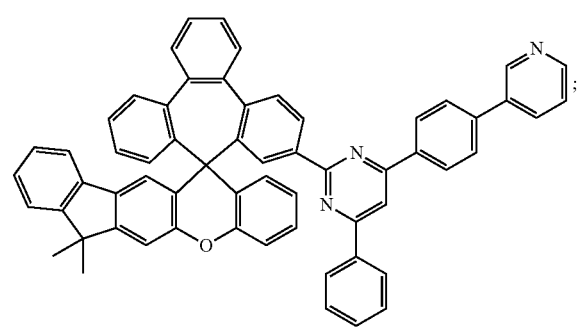
Compound CXIII
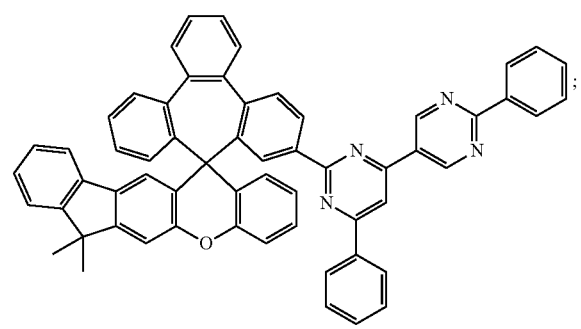
Compound CXIV
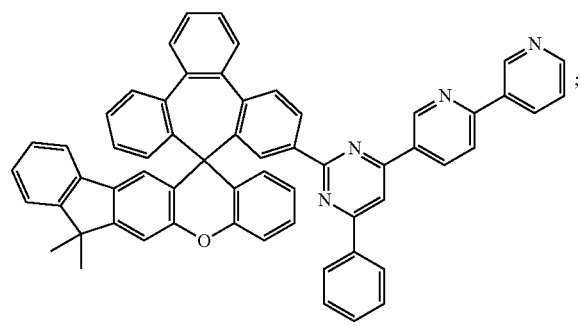
Compound CXV
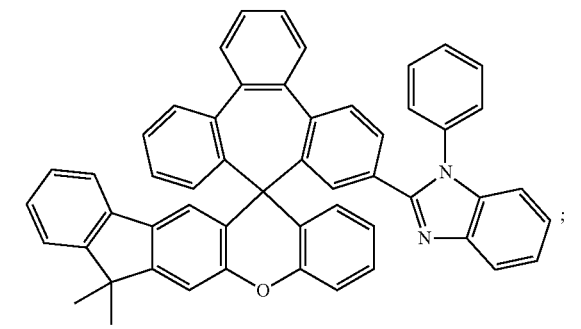
Compound CXVI
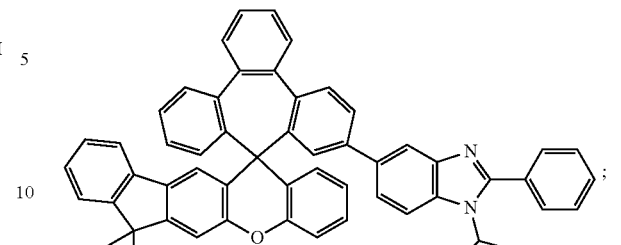
Compound CXVII
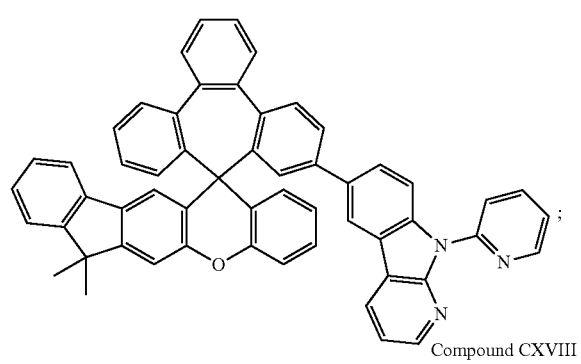
Compound CXVIII
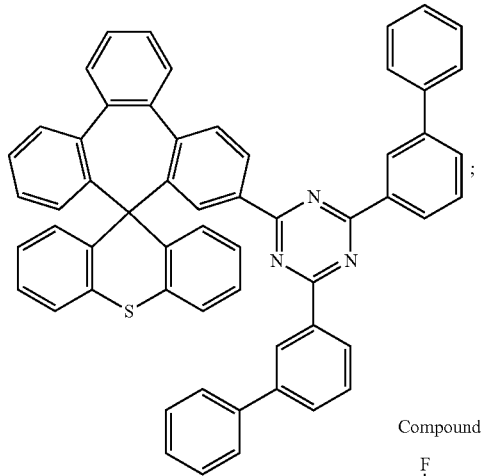
Compound CXIX
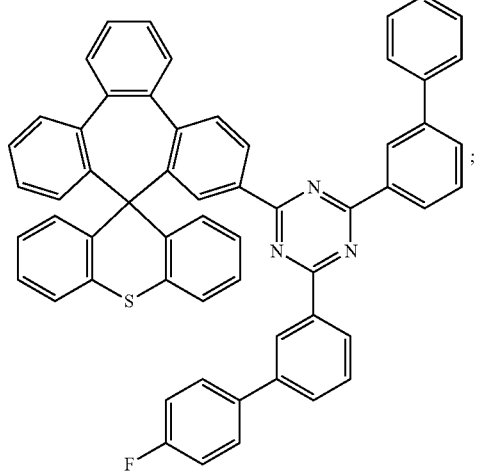

Compound CXX
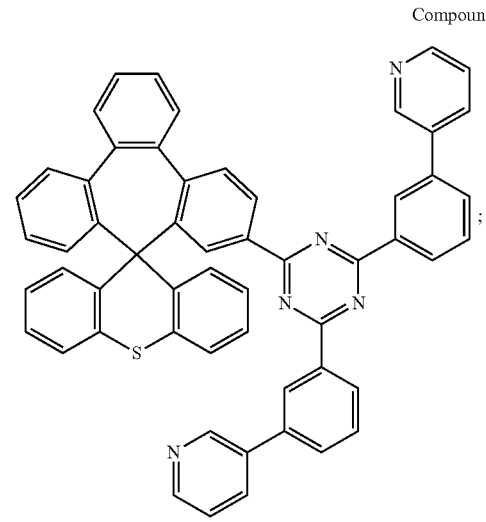
Compound CXXI
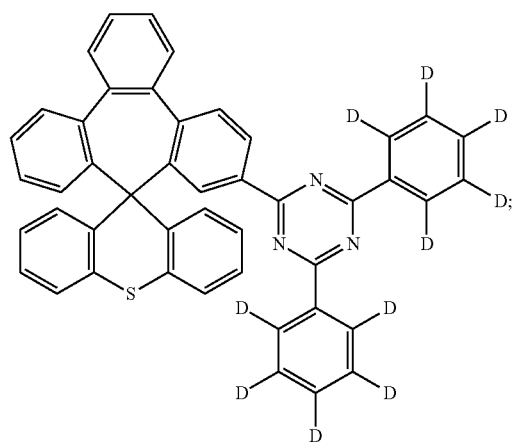
Compound CXXII
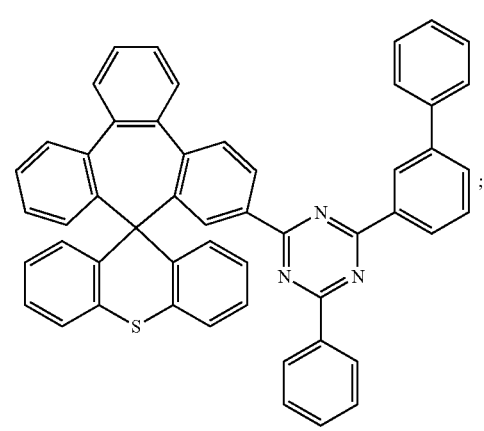
Compound CXXIII
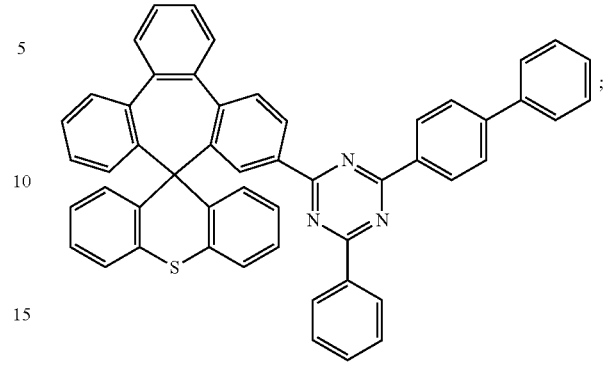
Compound CXXIV
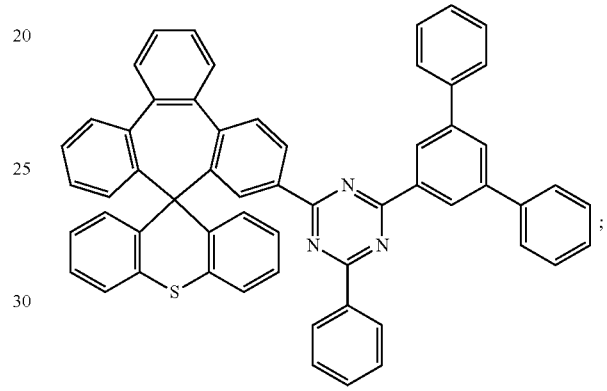
Compound CXXV
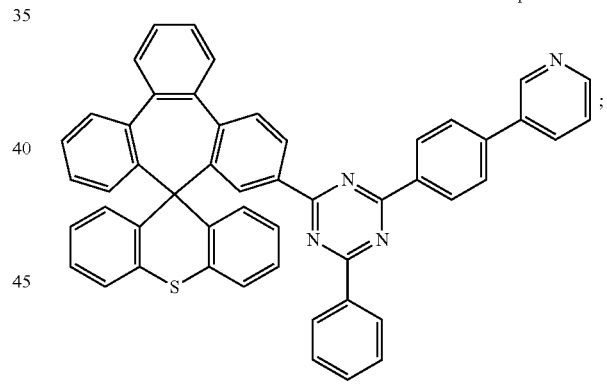
Compound CXXVI
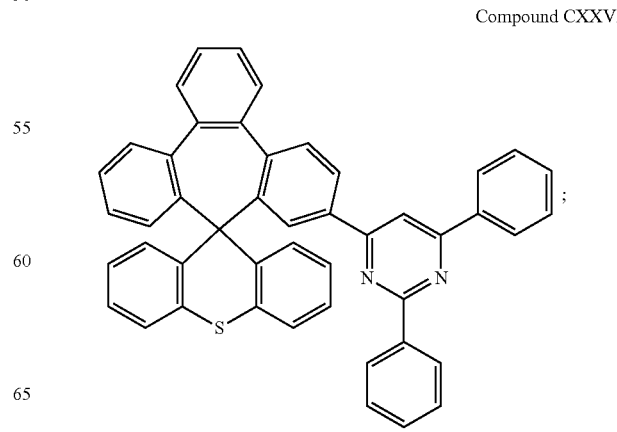

Compound CXXVII
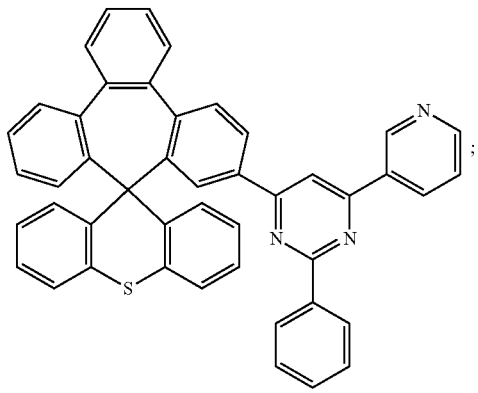
Compound CXXVIII
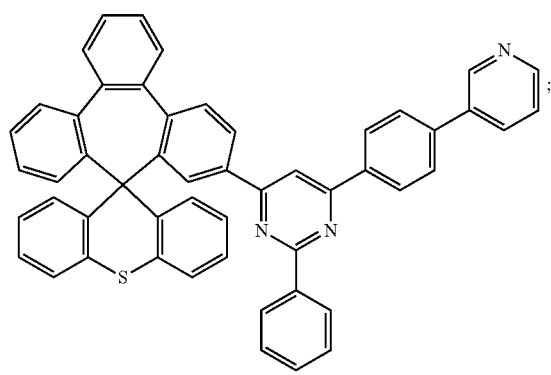
Compound CXXIX
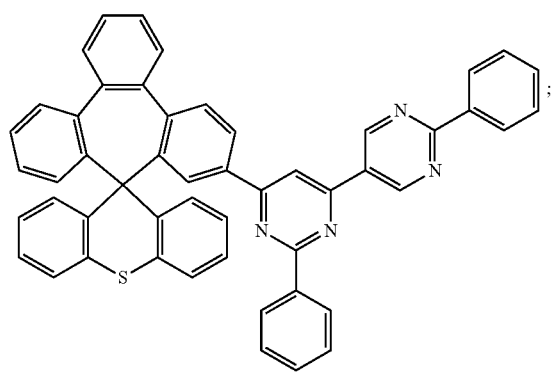
Compound CXXX
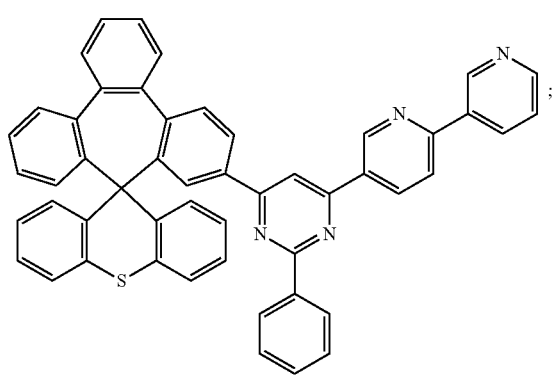
Compound CXXXI
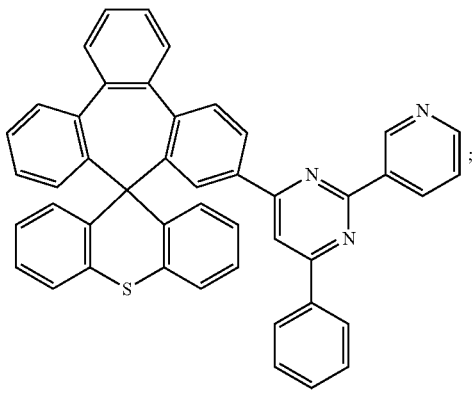
Compound CXXXII
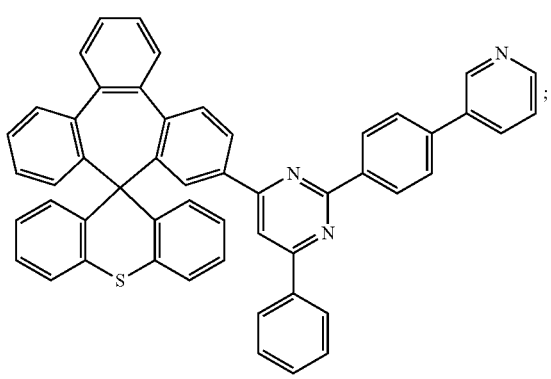
Compound CXXXIII
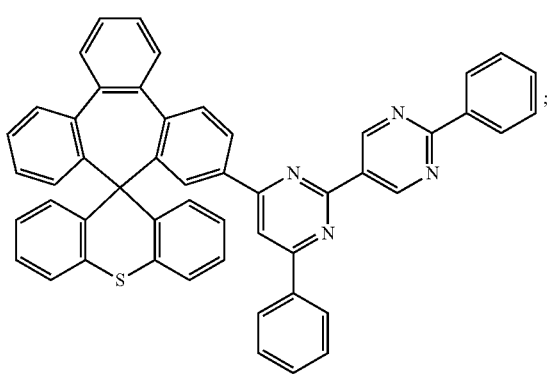
Compound CXXXIV
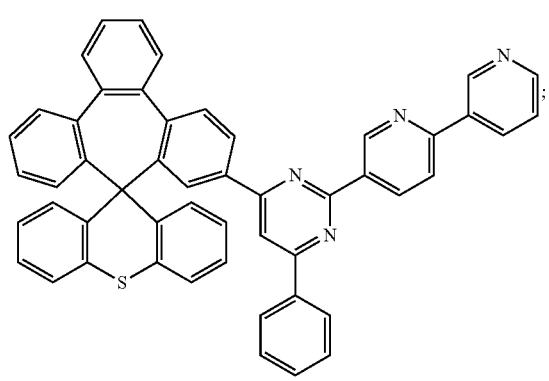

Compound CXXXV
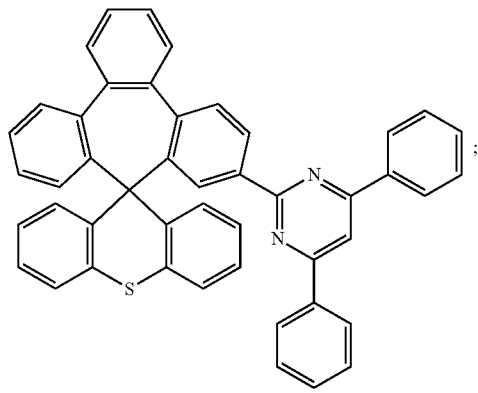
Compound CXXXVI
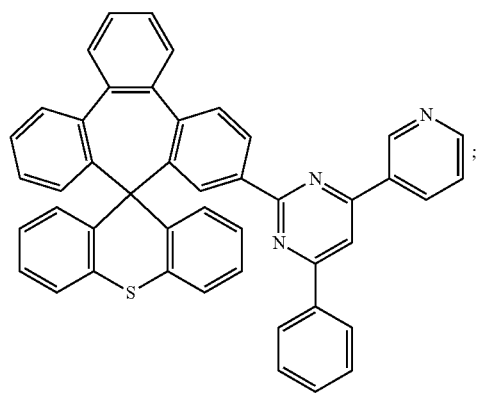
Compound CXXXVII
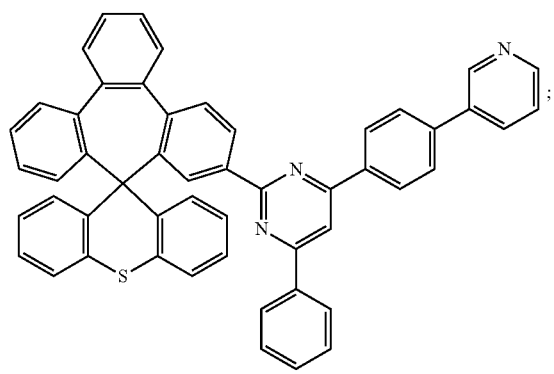
Compound CXXXVIII
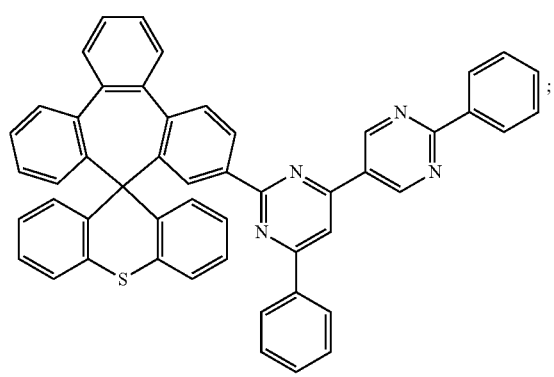
Compound CXXXIX
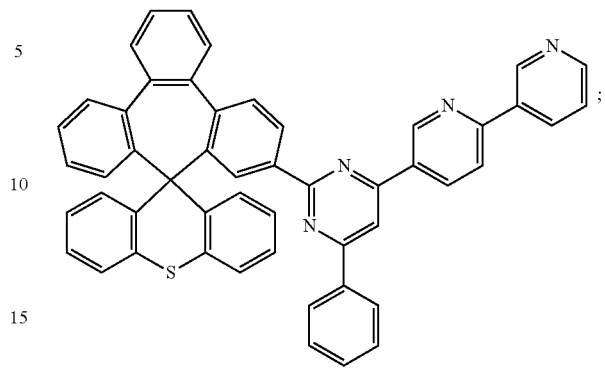
Compound CXL
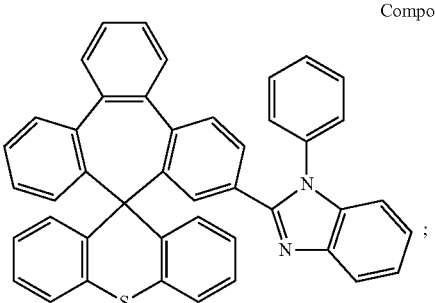
Compound CXLI
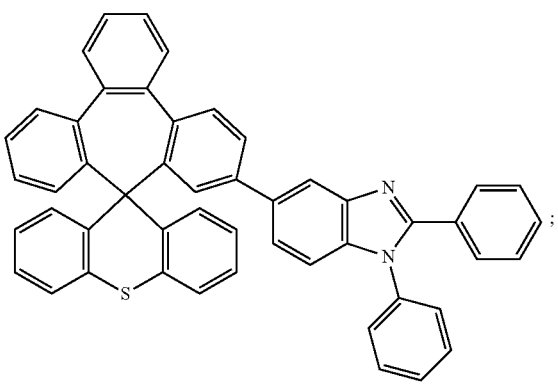
Compound CXLII
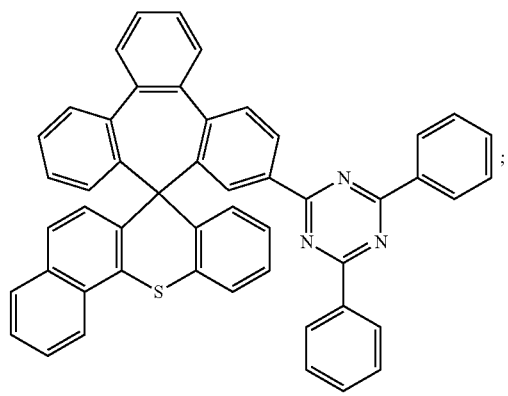

Compound CXLIII
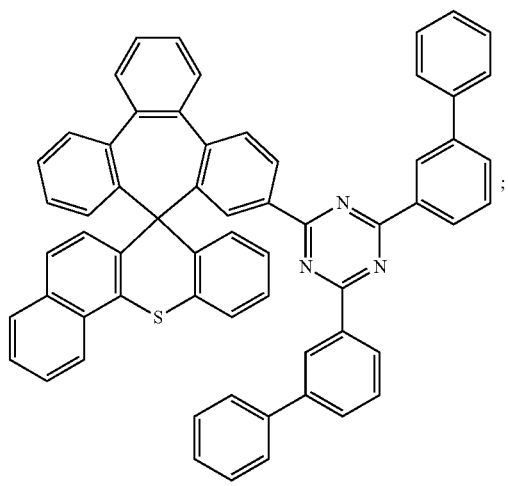
Compound CXLIV
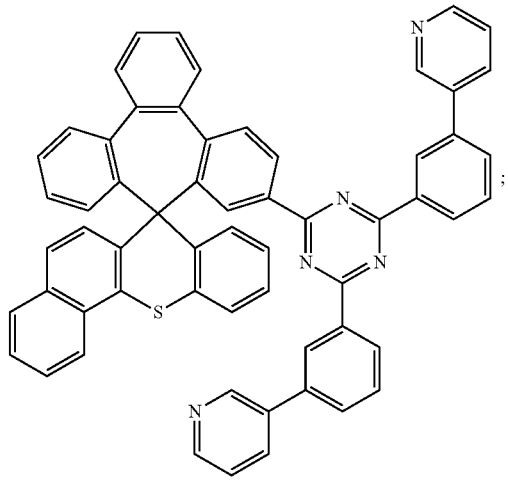
Compound CXLV
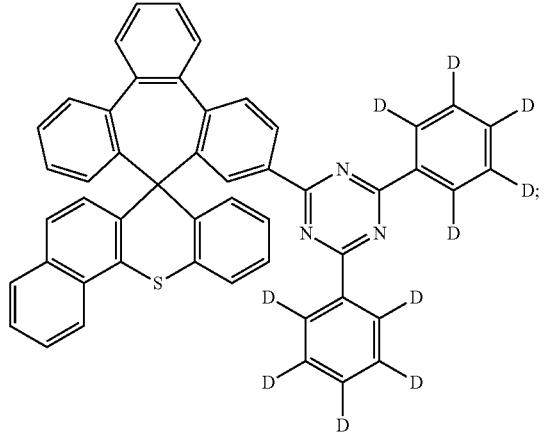
Compound CXLVI
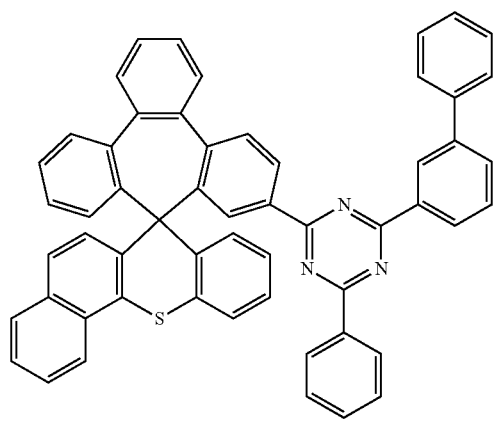
Compound CXLVII
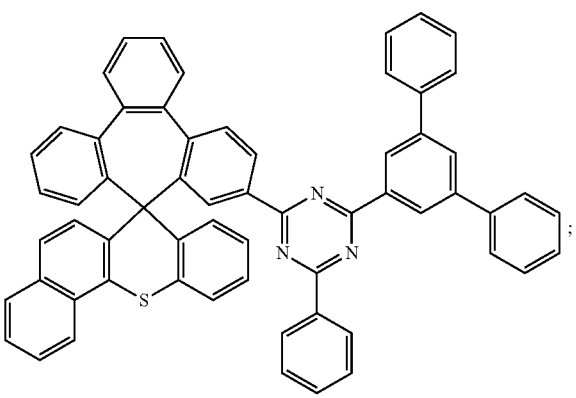
Compound CXLVIII
Compound CIL
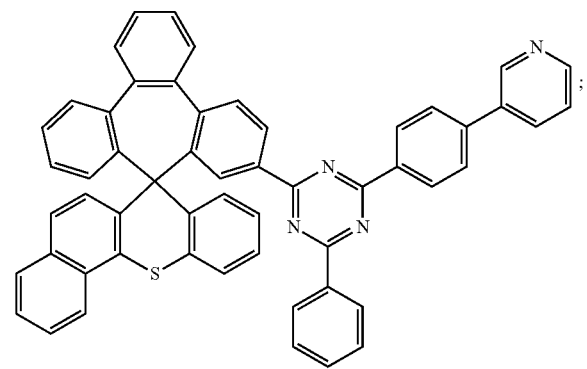

Compound CL
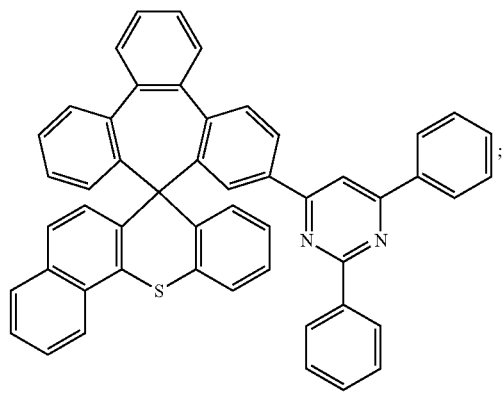
Compound CLIV
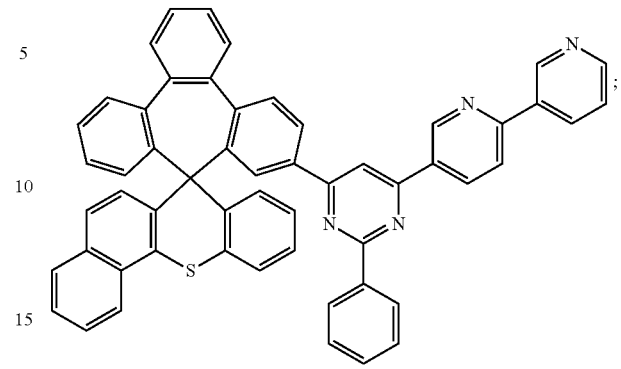
Compound CLI
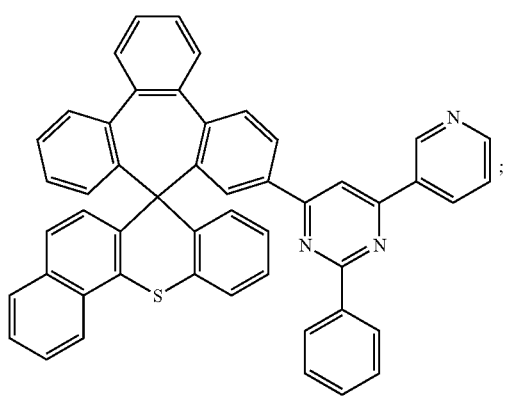
Compound CLV
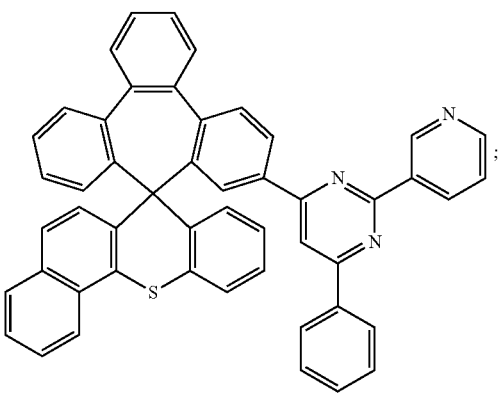
Compound CLII
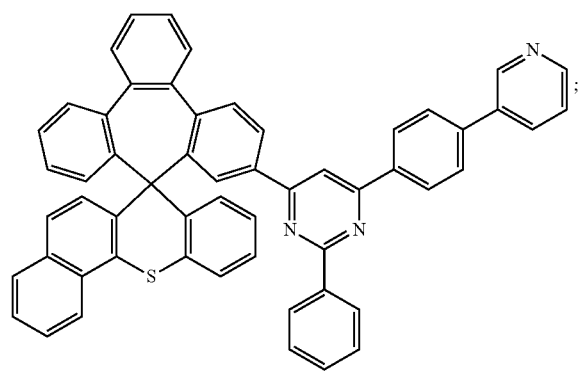
Compound CLVI
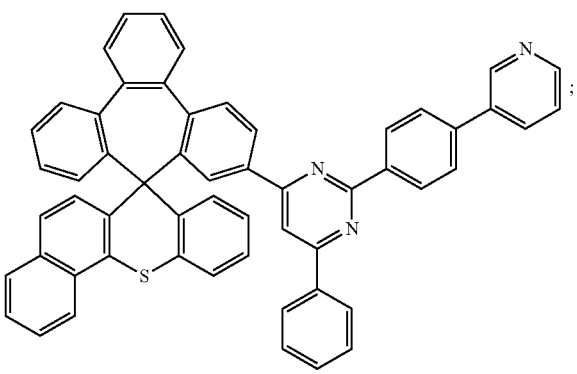
Compound CLIII
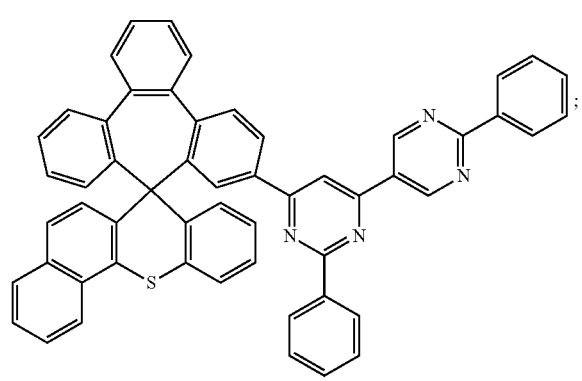
Compound CLVII
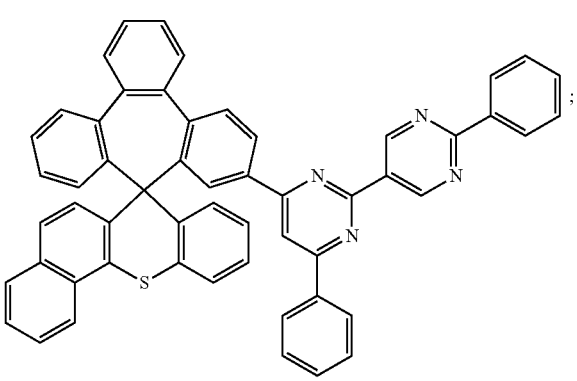

Compound CLVIII
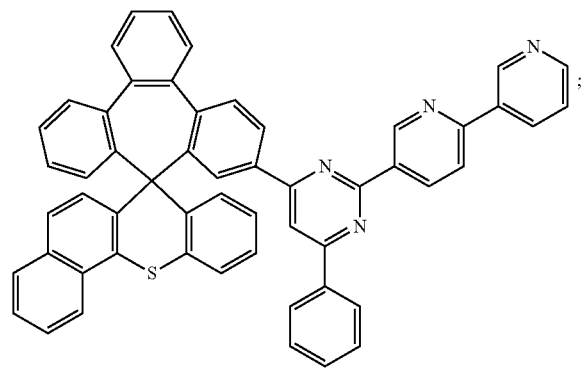
Compound CLIX
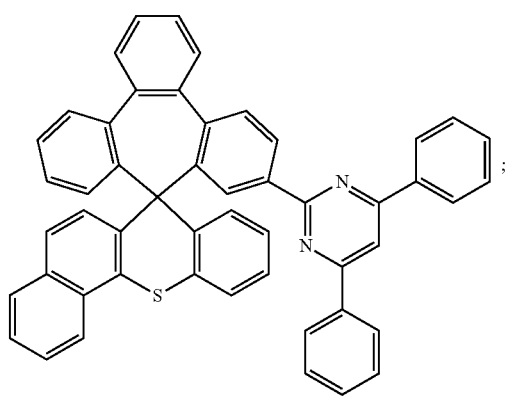
Compound CLX
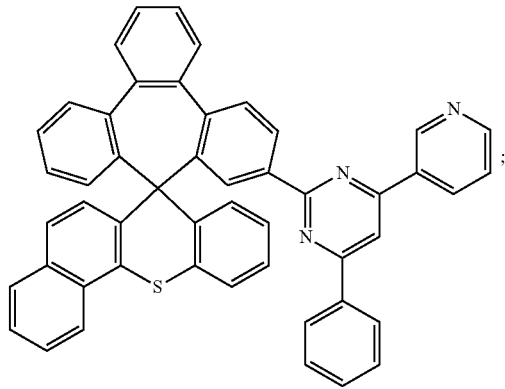
Compound CLXI
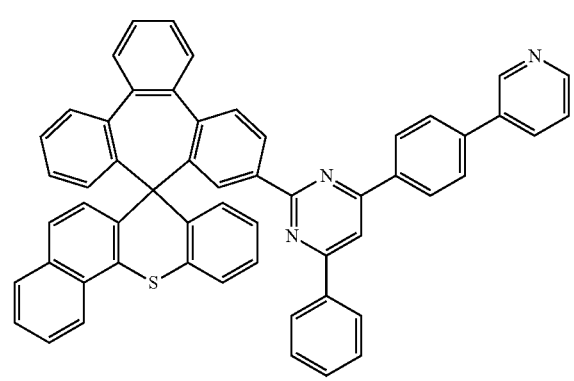
Compound CLXII
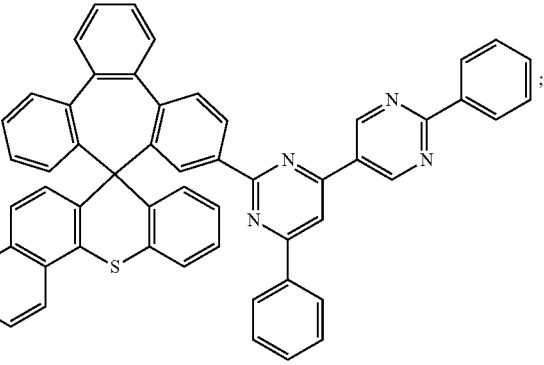
Compound CLXIII
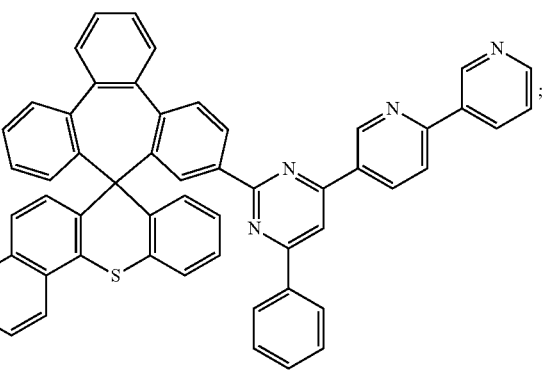
Compound CLXIV
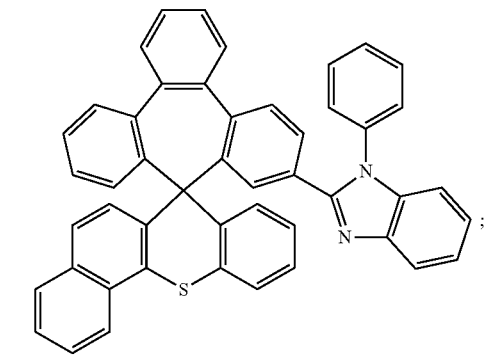
Compound CLXV
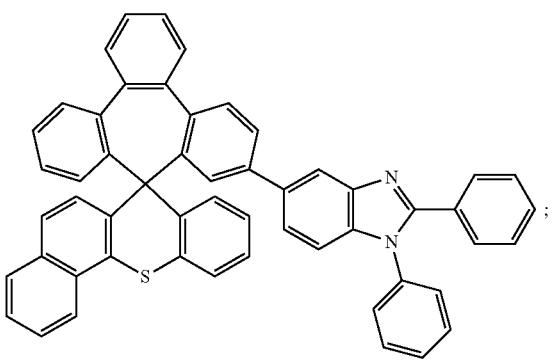

Compound CLXVI
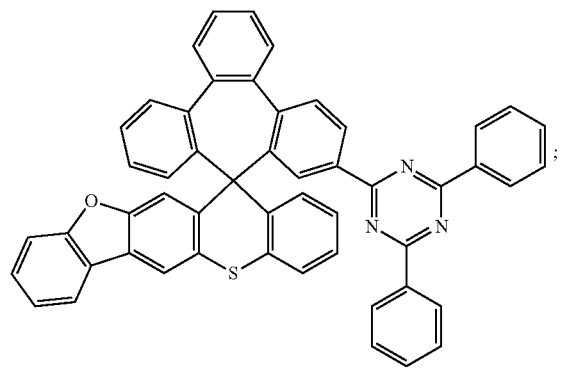
Compound CLXVII
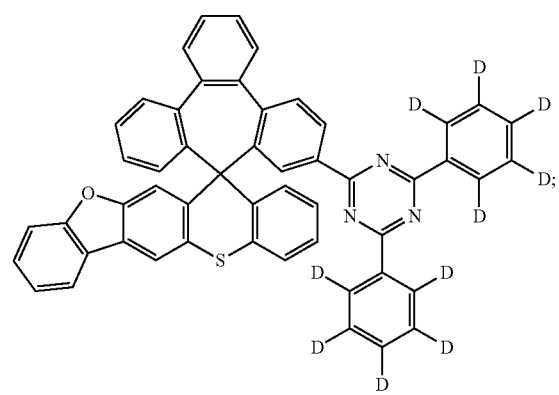
Compound CLXVIII
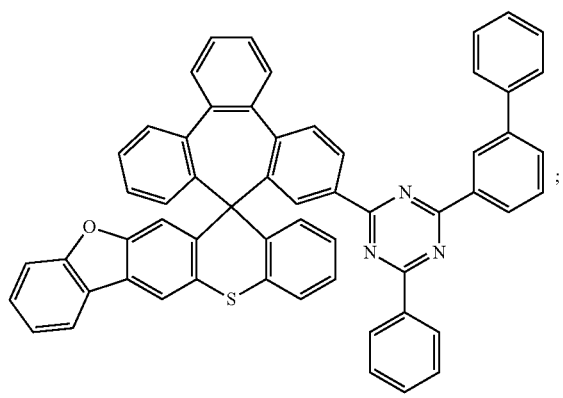
Compound CLXIX
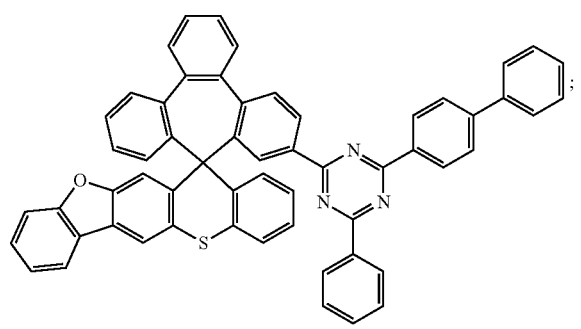
Compound CLXX
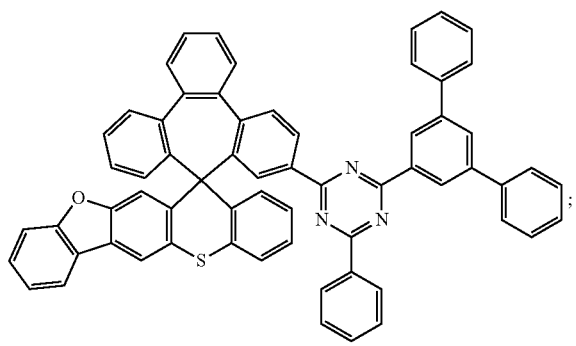
Compound CLXXI
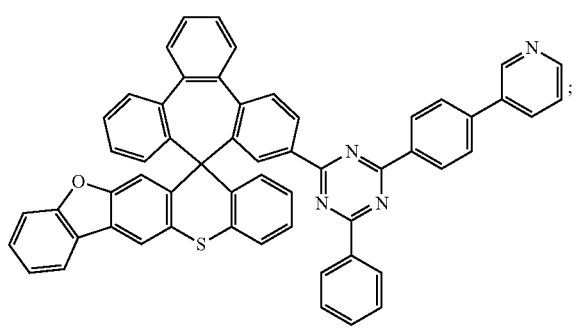
Compound CLXXII
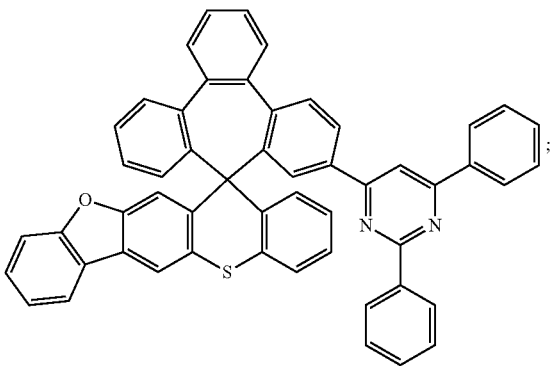
Compound CLXXIII
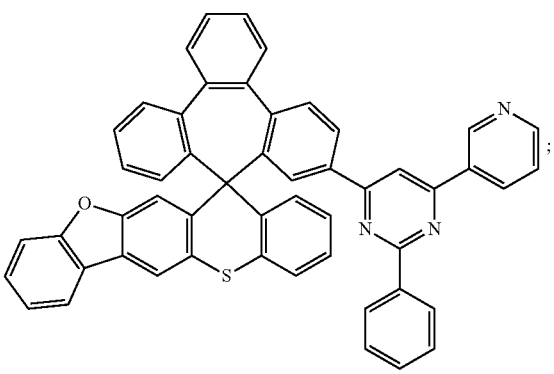

Compound CLXXIV
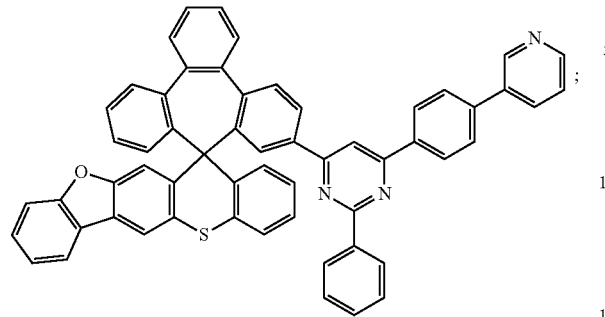
Compound CLXXV
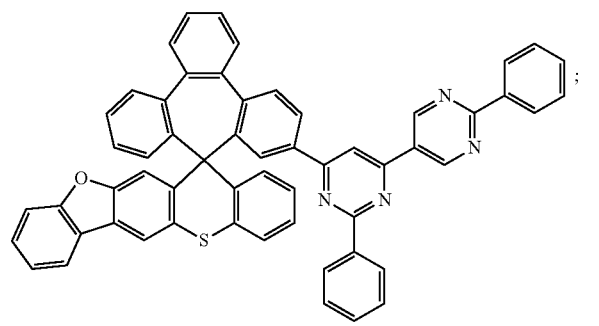
Compound CLXXVI
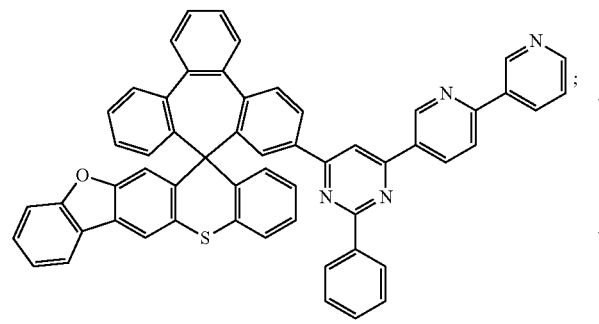
Compound CLXXVII
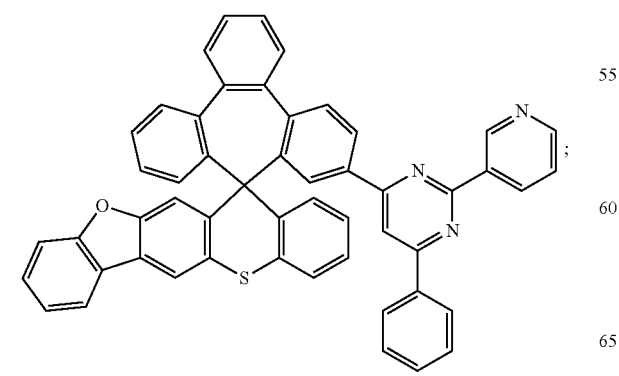
Compound CLXXVIII
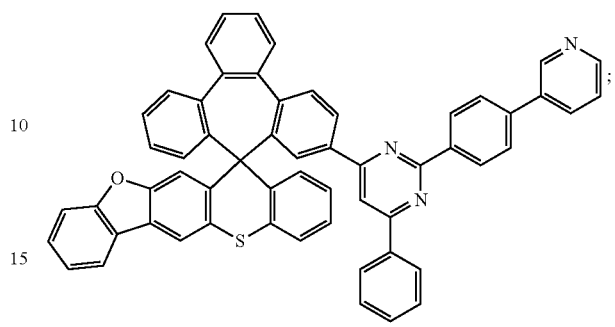
Compound CLXXIX
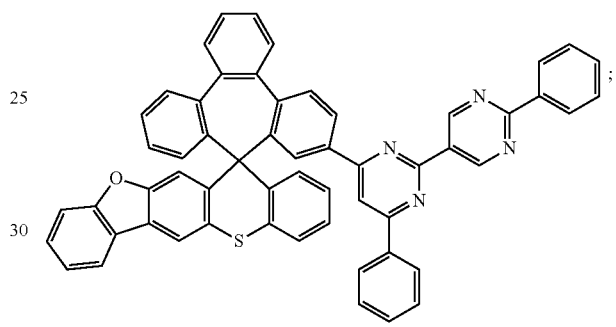
Compound CLXXX
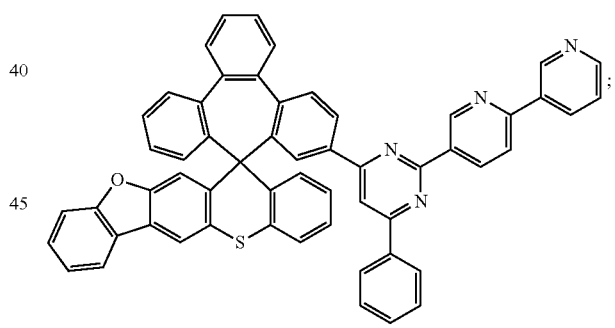
Compound CLXXXI Compound CLXXXII
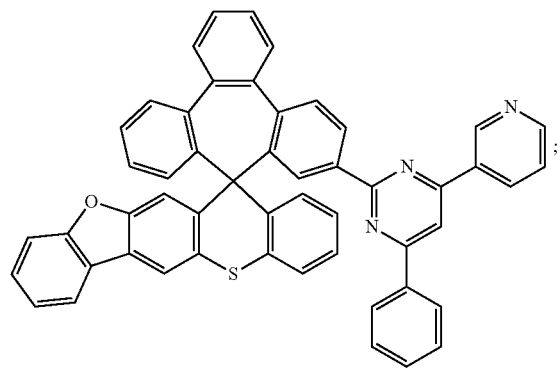
Compound CLXXXVI
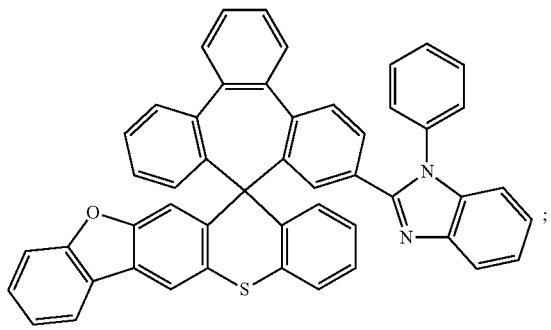
Compound CLXXXIII
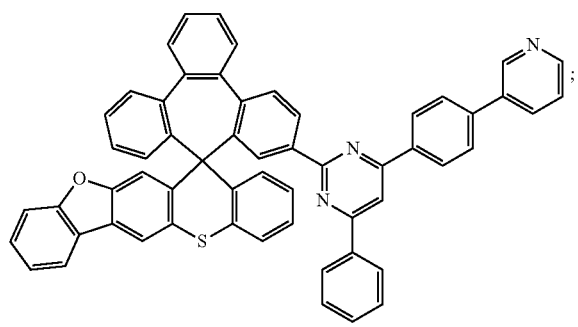
Compound CLXXXVII
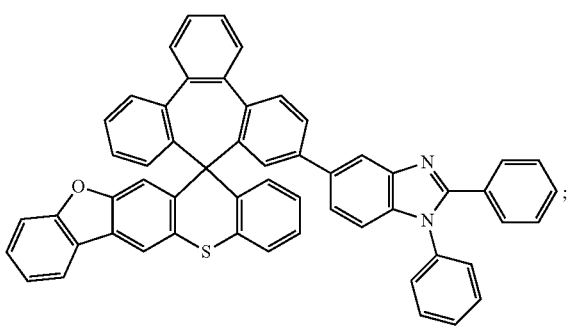
Compound CLXXXIV
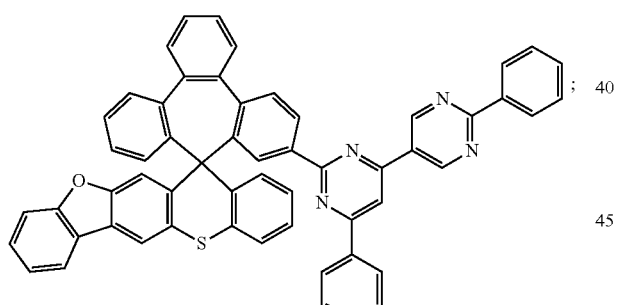
Compound CLXXXVIII
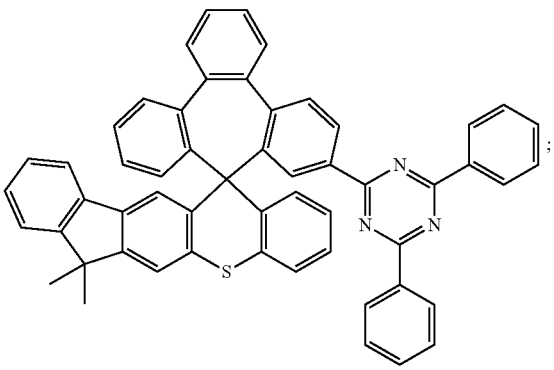
Compound CLXXXV
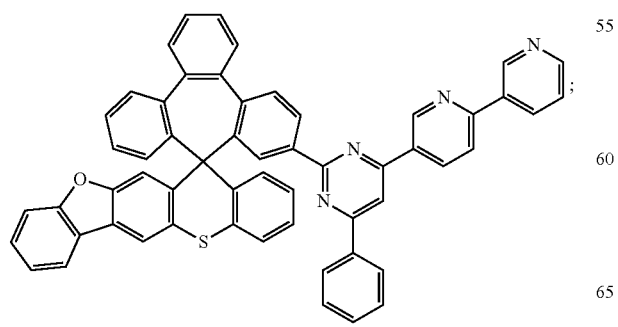
Compound CLXXXIX
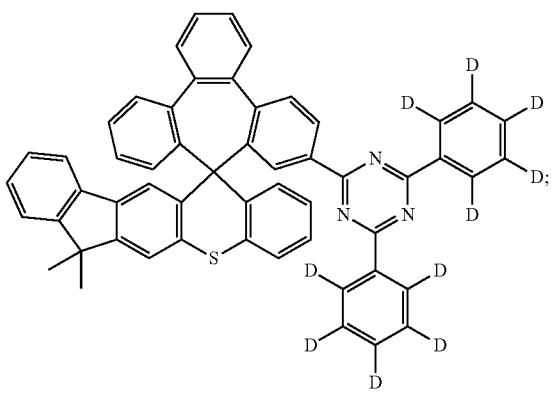

-continued
Compound CXC
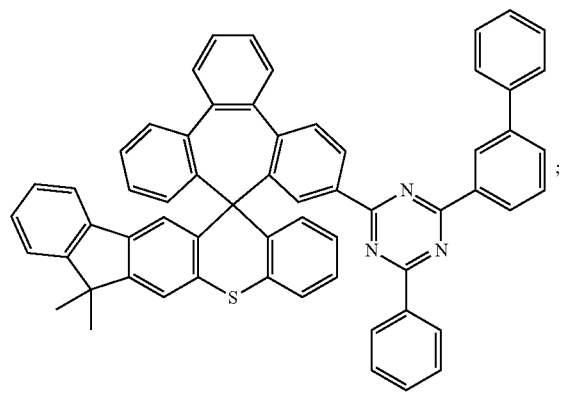
Compound CXCI
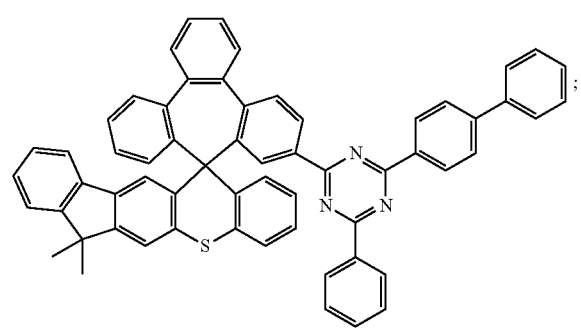
Compound CXCII
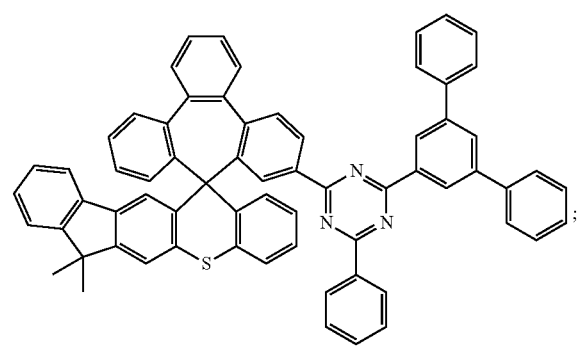
Compound CXCIII
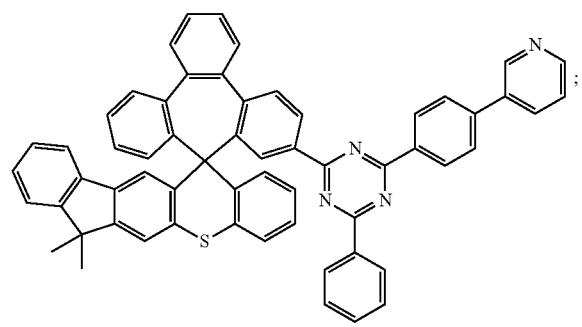
-continued
Compound CXCIV
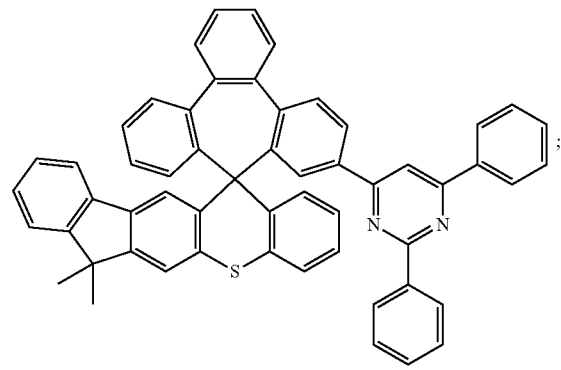
Compound CXCV
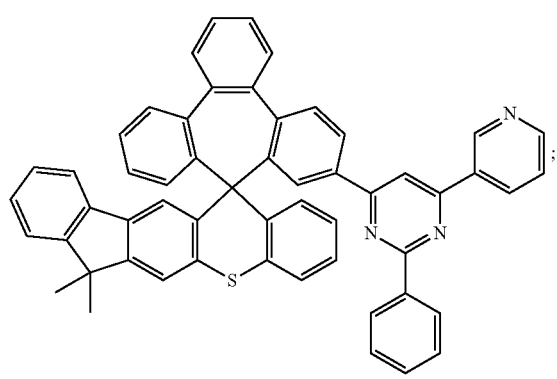
Compound CXCVI
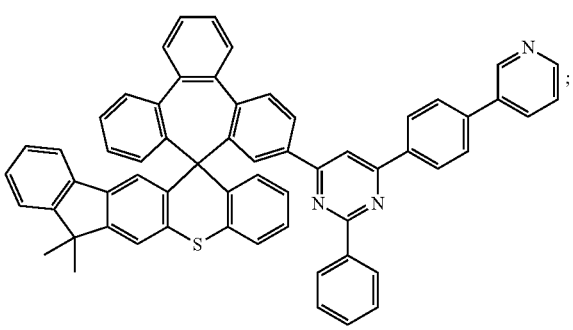
Compound CXCVII
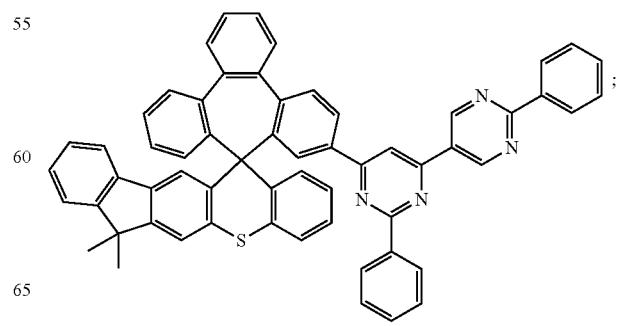

Compound CXCVIII
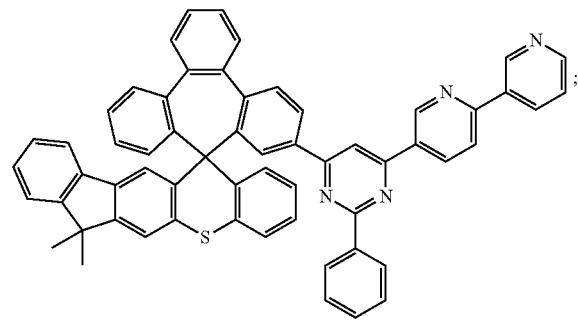
Compound CCII
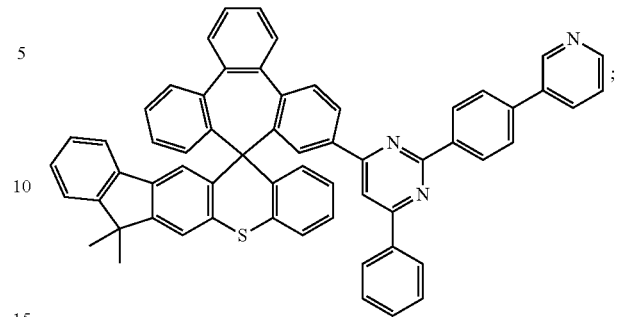
Compound CIC
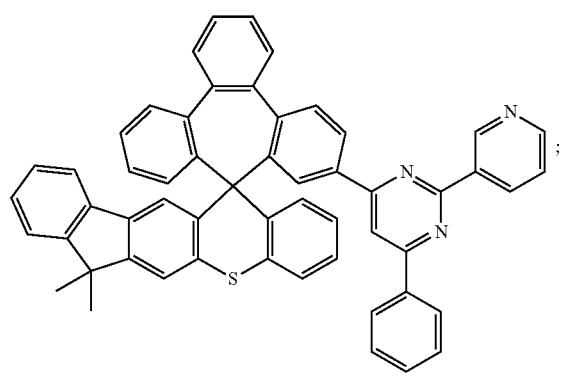
Compound CCIII
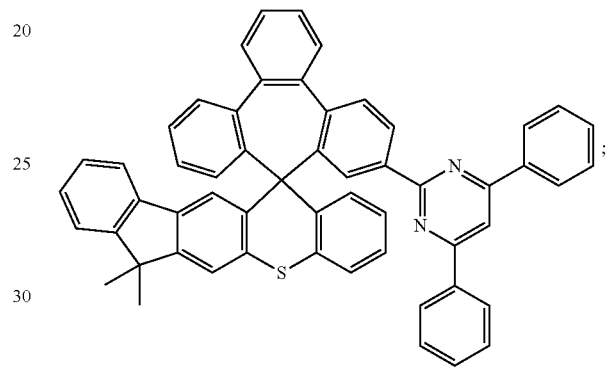
Compound CC
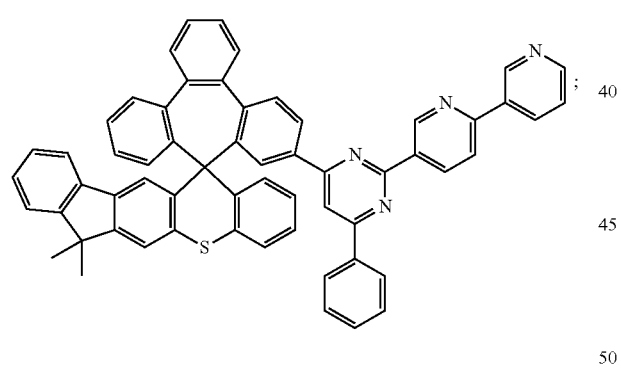
Compound CCIV
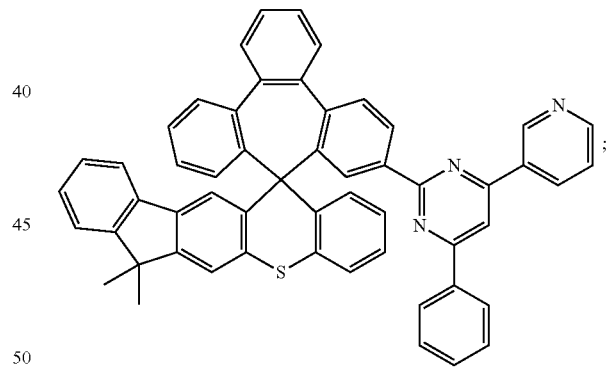
Compound CCI
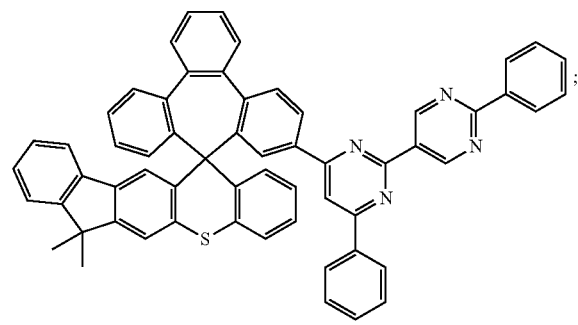
Compound CCV
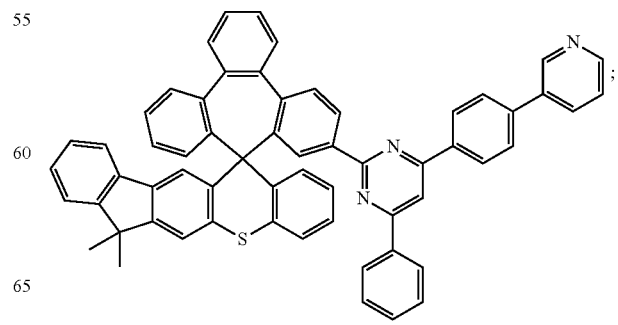

Compound CCVI
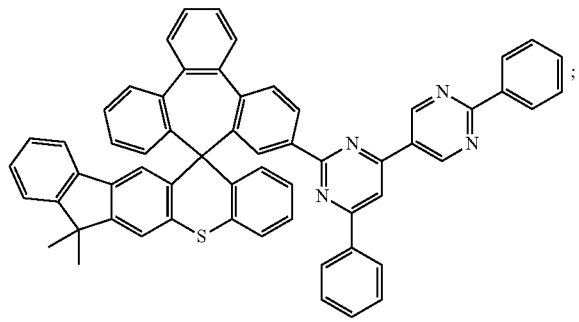
Compound CCX
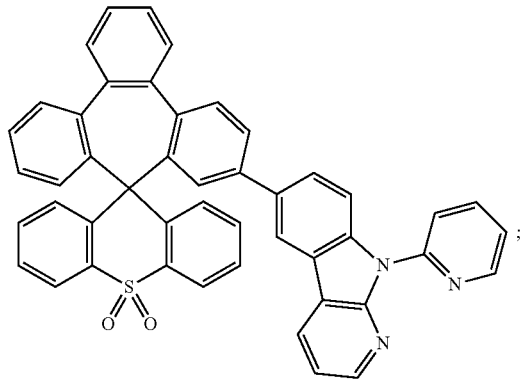
Compound CCVII
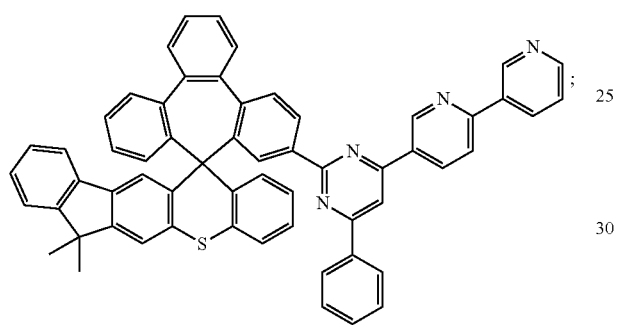
Compound CCXI
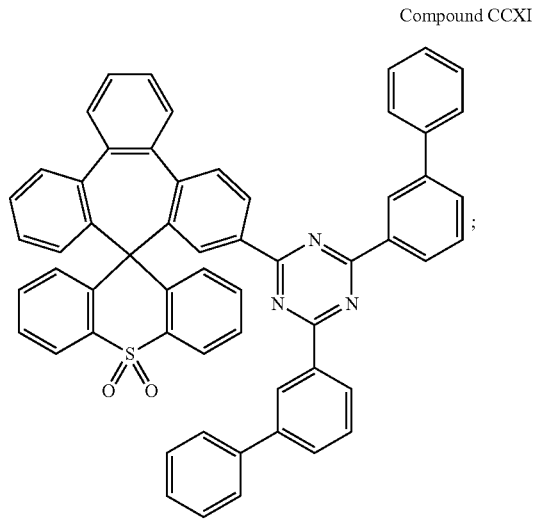
Compound CCVIII
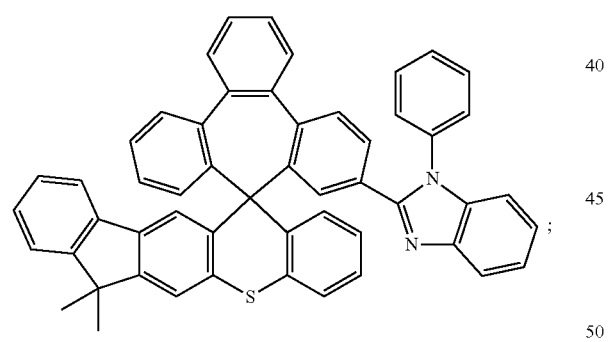
Compound CCIX
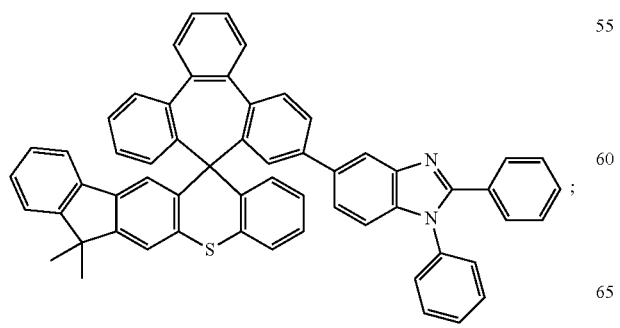
Compound CCXII
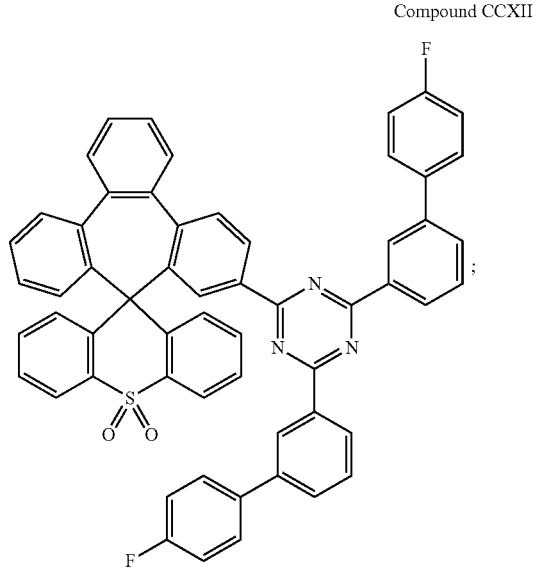

Compound CCXIII
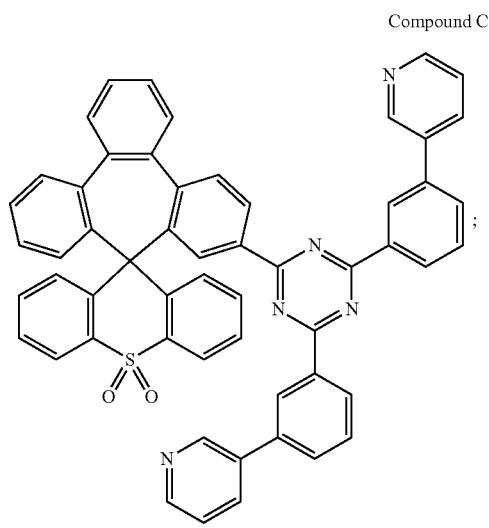
Compound CCXIV
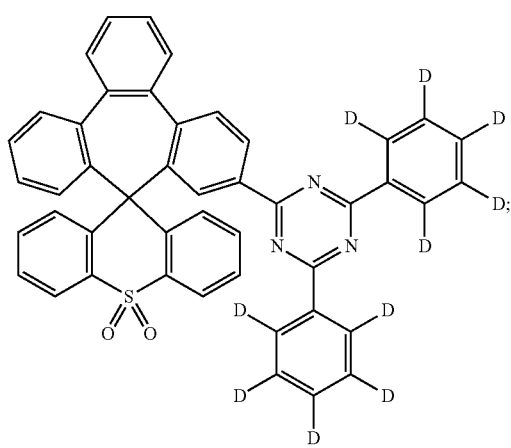
Compound CCXV
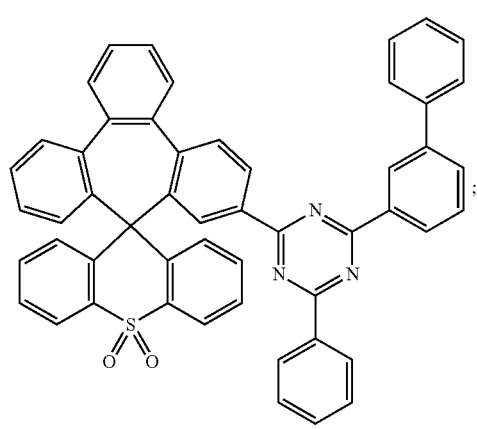
Compound CCXVI
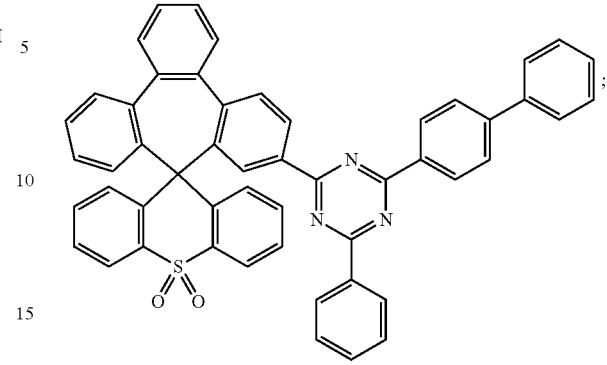
Compound CCXVII
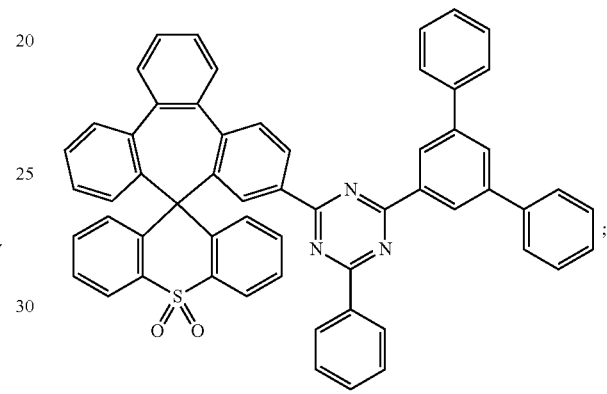
Compound CVXIII
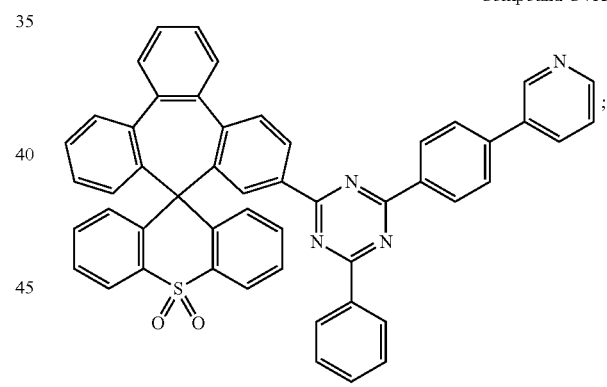
Compound CCXIX
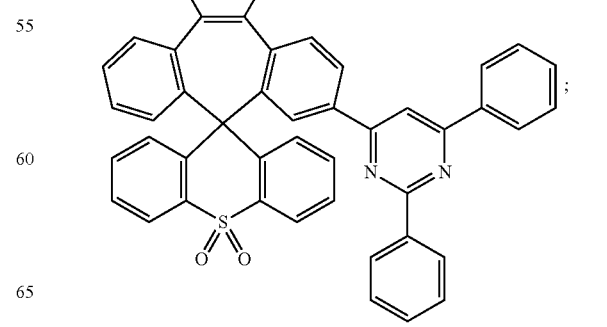

-continued
Compound CCXX
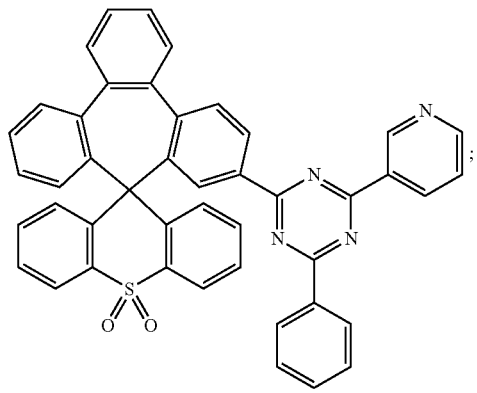
Compound CCXXI
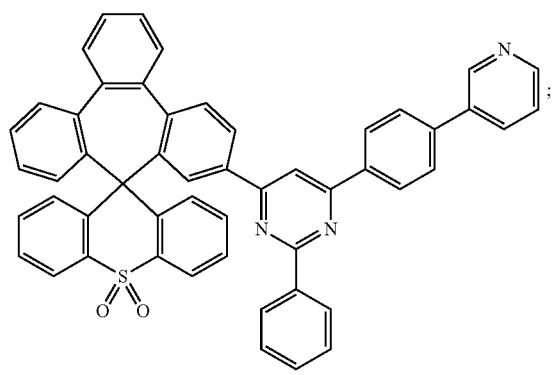
Compound CCXXII
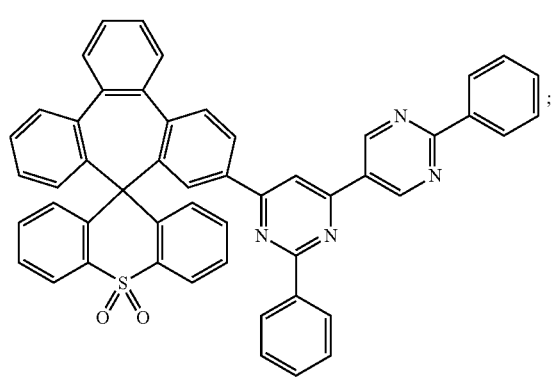
Compound CCXXIII
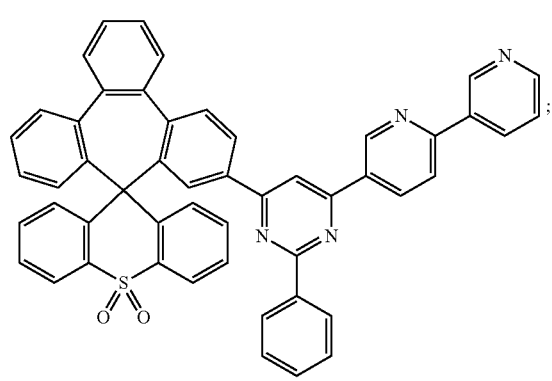
-continued
Compound CCXXIV
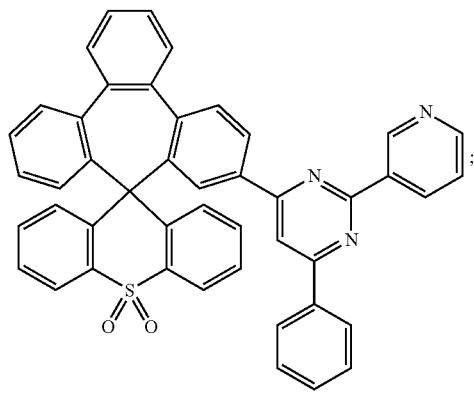
Compound CCXXV
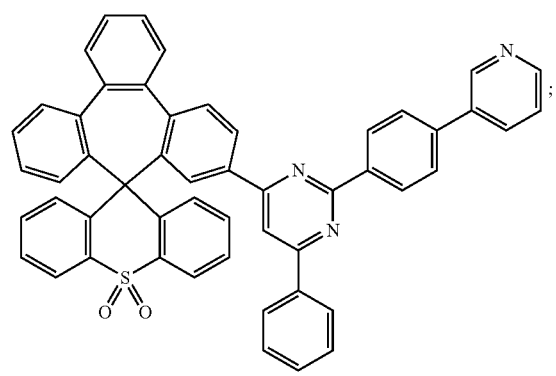
Compound CCXXVI
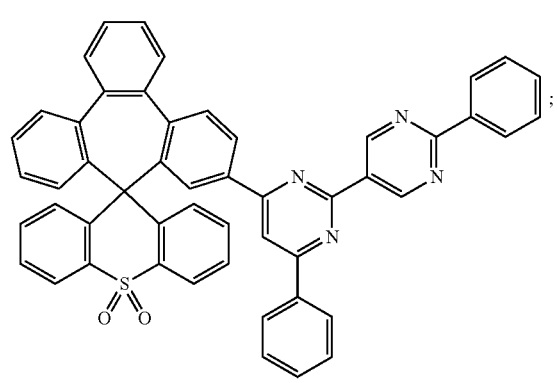
Compound CCXXVII
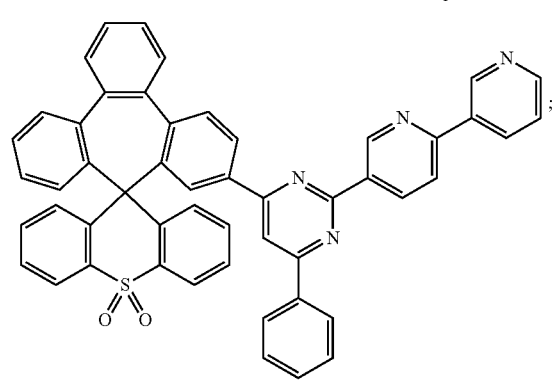

Compound CCXXVIII
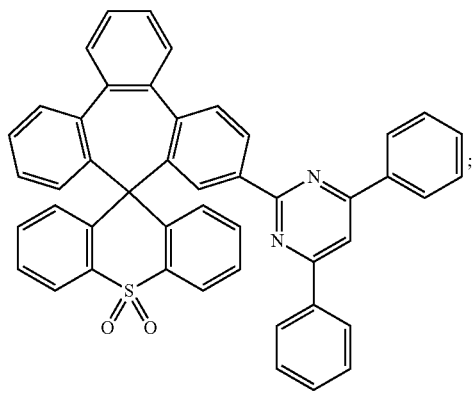
Compound CCXXIX
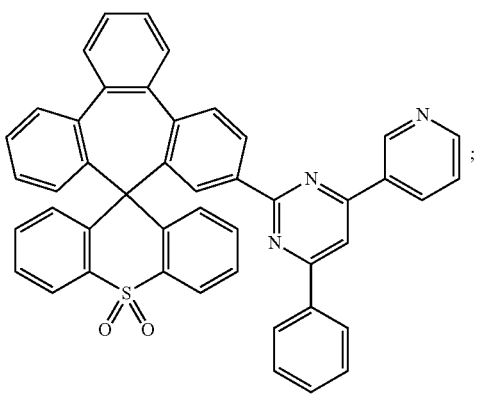
Compound CCXXX
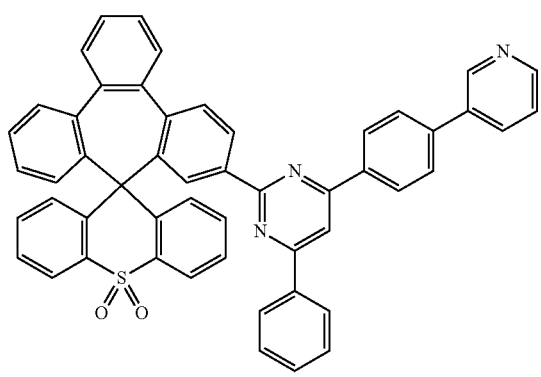
Compound CCXXXI
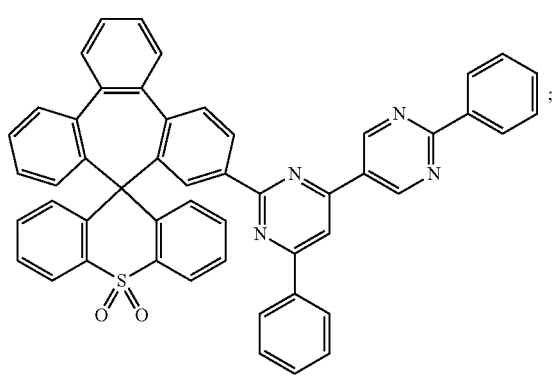
Compound CCXXXII
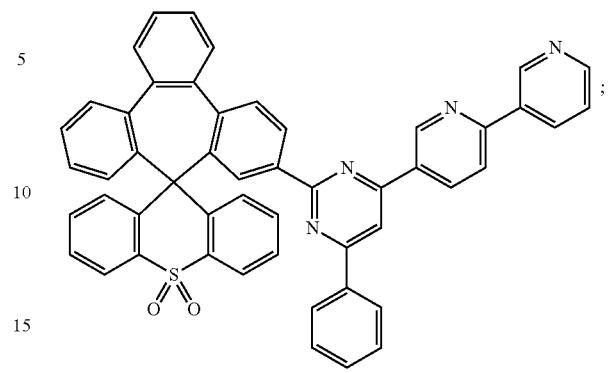
Compound CCXXXIII
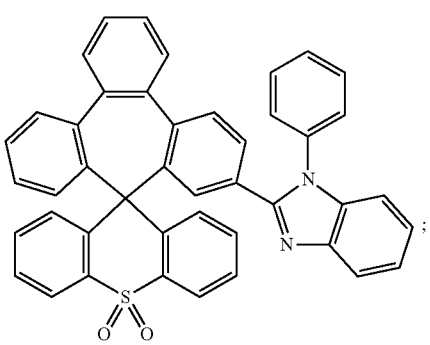
Compound CCXXXIV
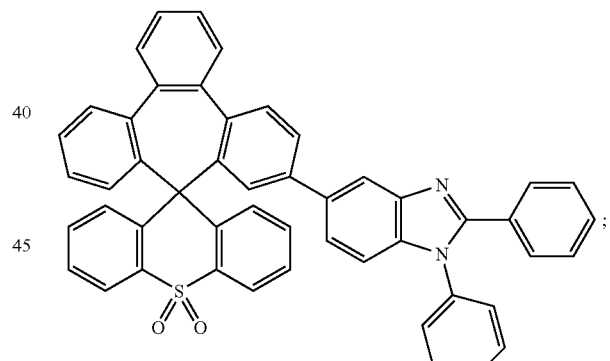
Compound CCXXXV
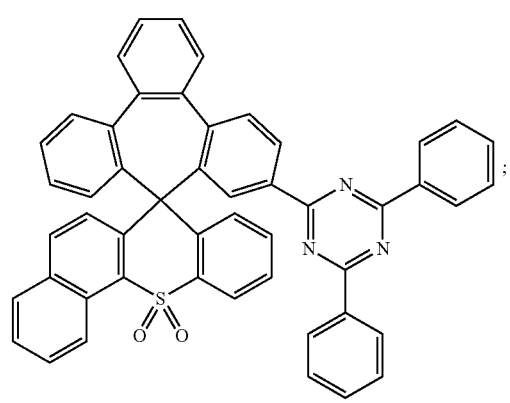

-continued
Compound CCXXXVI
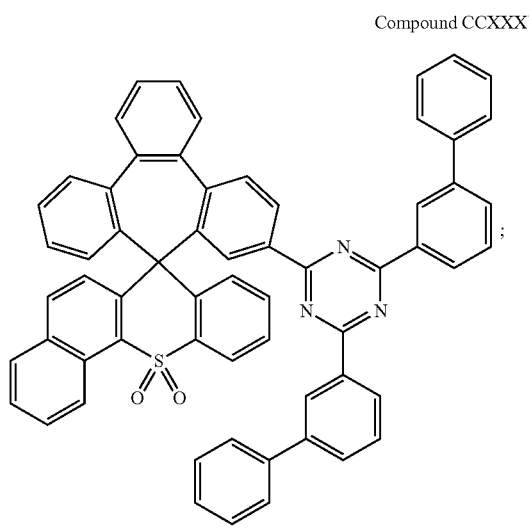
Compound CCXXXVII
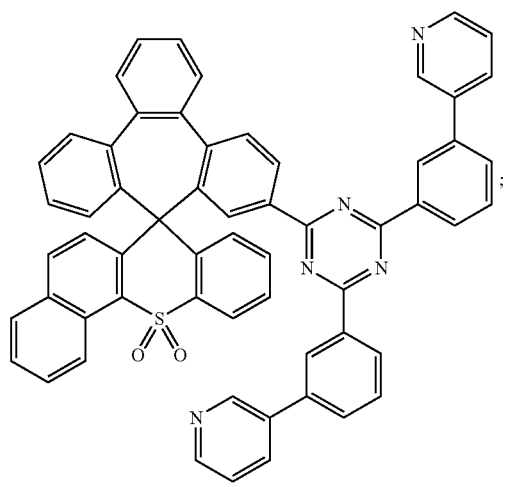
Compound CCXXXVIII
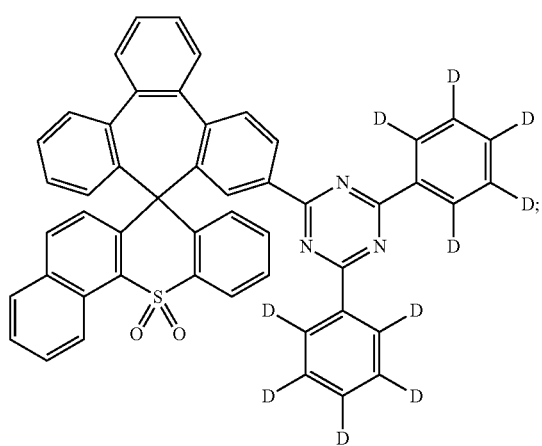
Compound CCXXXIX
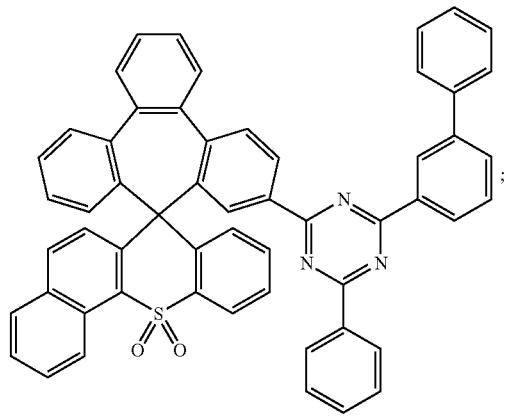
Compound CCXL
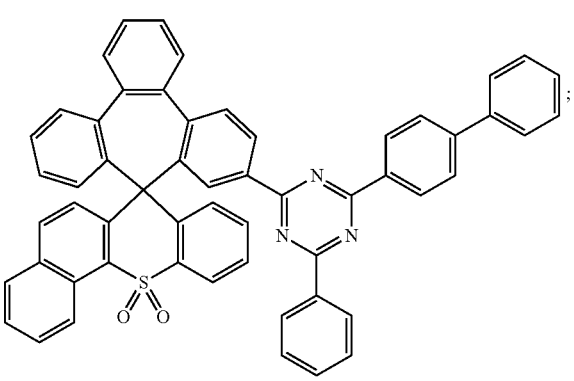
Compound CCXLI
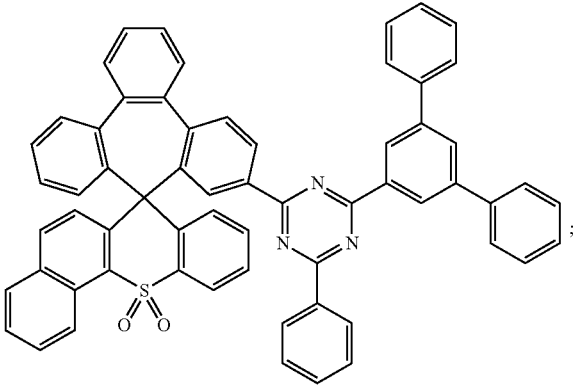
Compound CCXLII
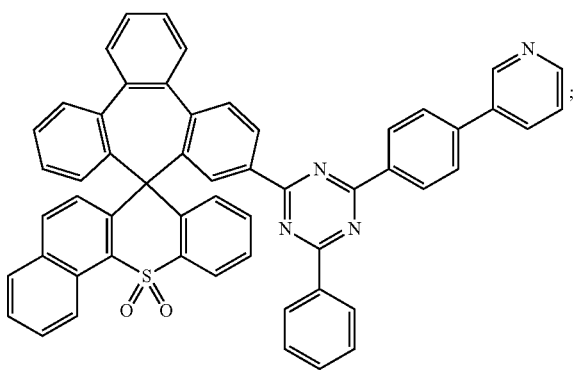

Compound CCXLIII
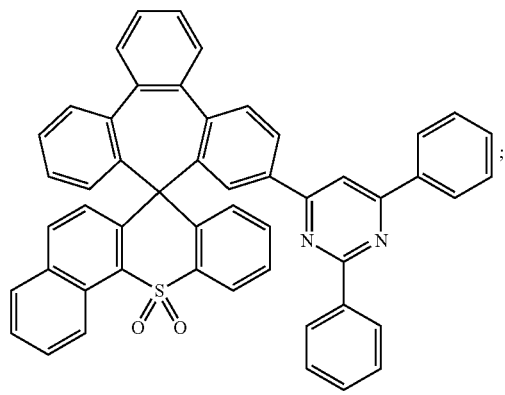
Compound CCXLIV
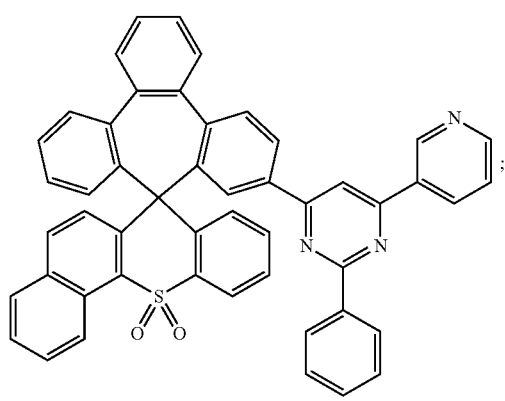
Compound CCXLV
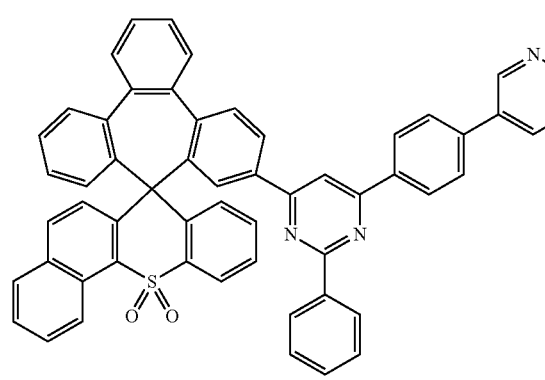
Compound CCXLVI
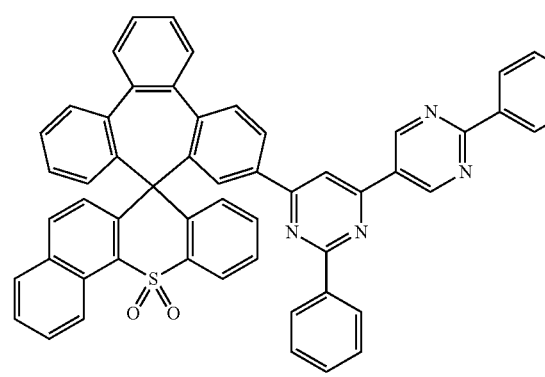
Compound CCXLVII
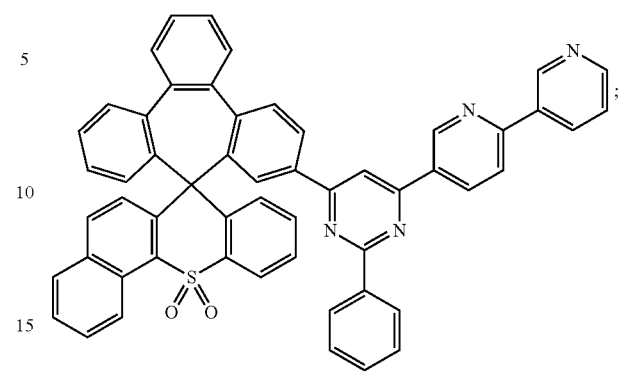
Compound CCXLVIII
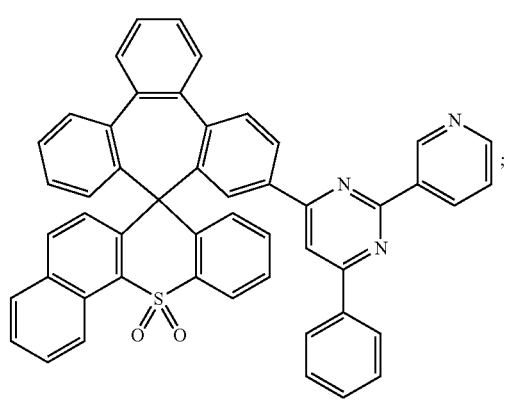
Compound CCIL
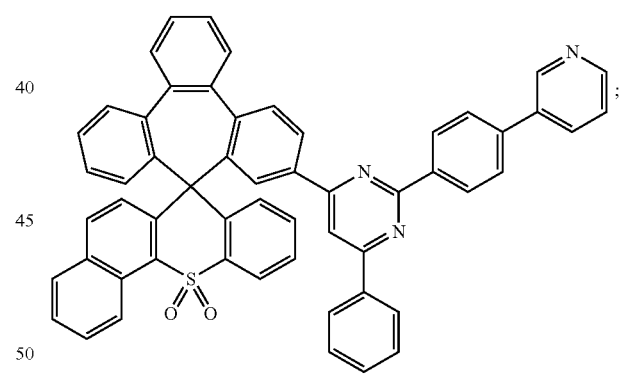
Compound CCL
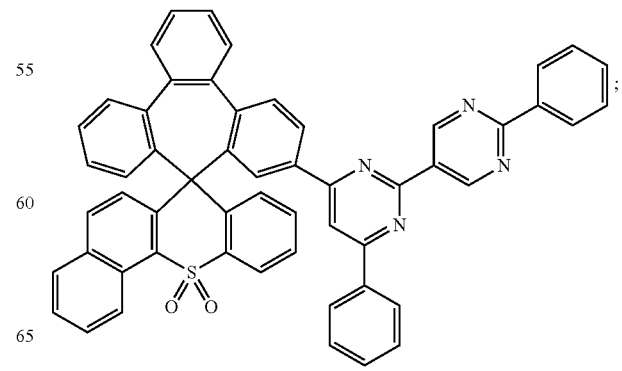

Compound CCLI
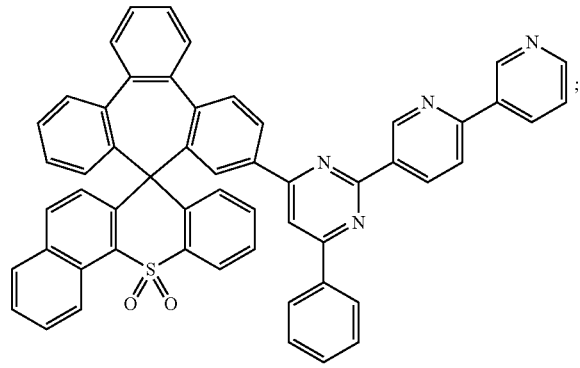
Compound CCLII
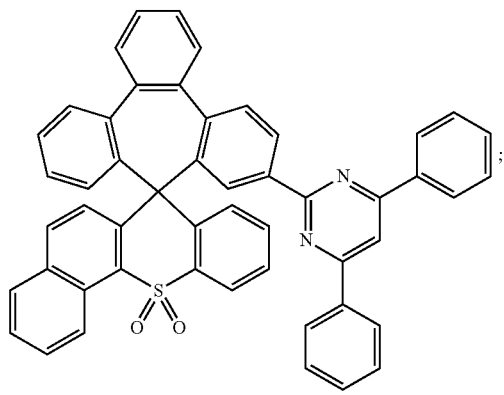
Compound CCLIII
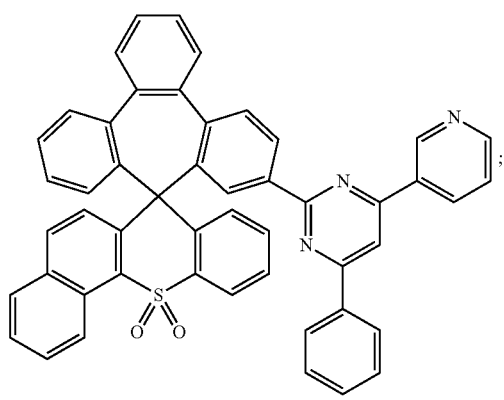
Compound CCLIV
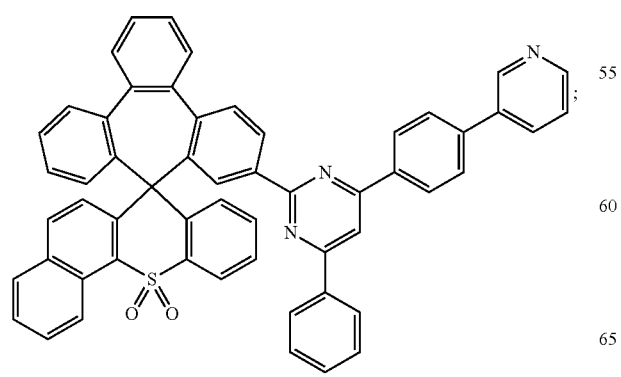
Compound CCLV
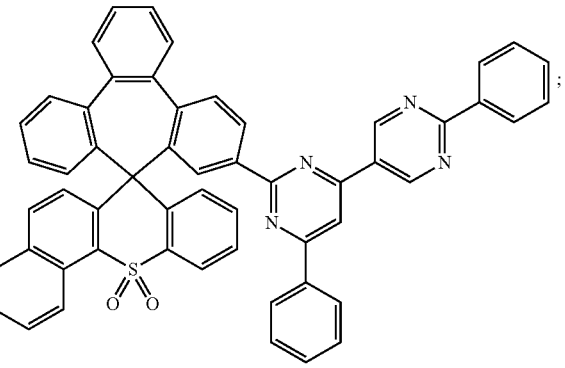
Compound CCLVI
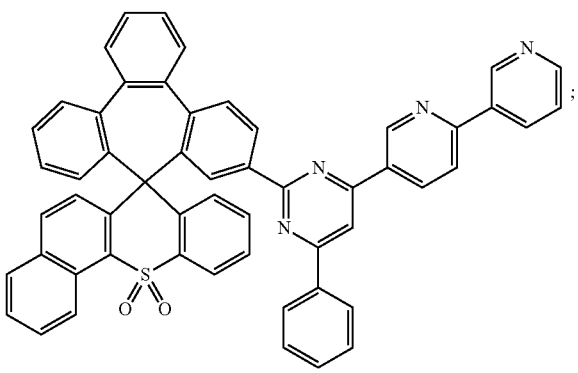
Compound CCLVII
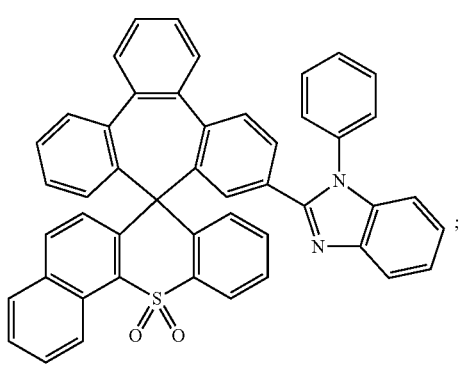
Compound CCLVIII
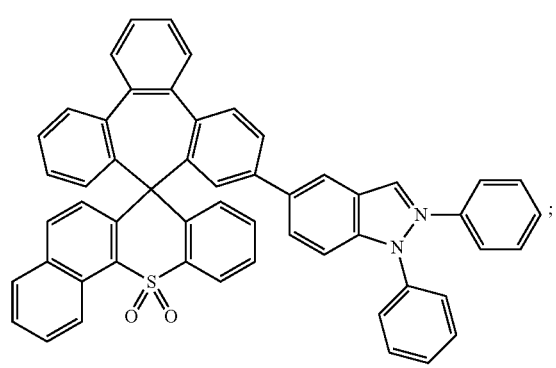

Compound CCLIX
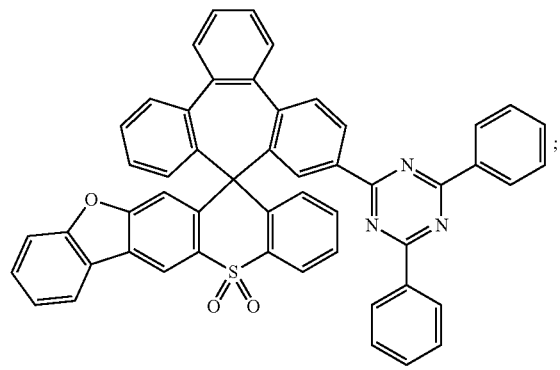
Compound CCLX
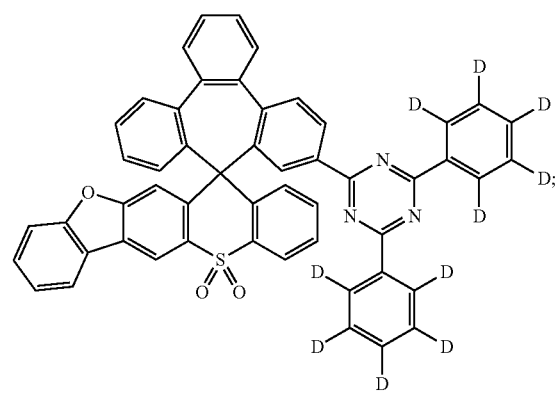
Compound CCLXI
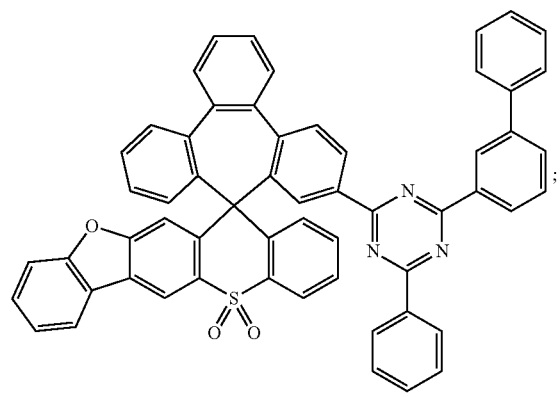
Compound CCLXII
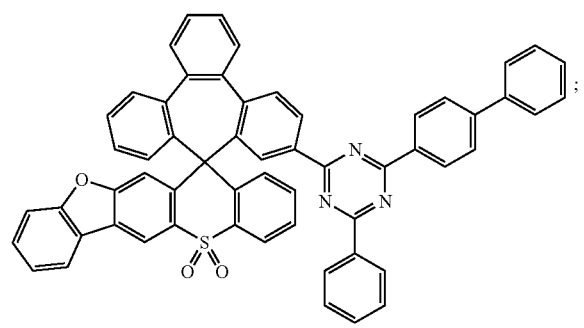
Compound CCLXIII
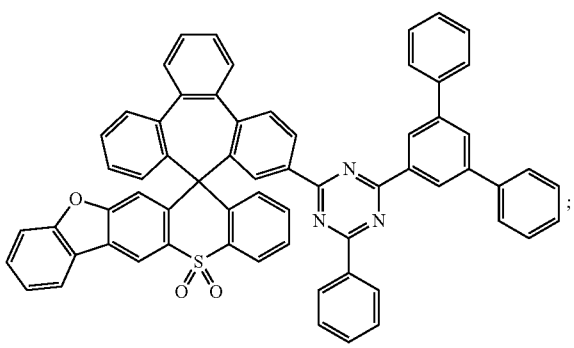
Compound CCLXIV
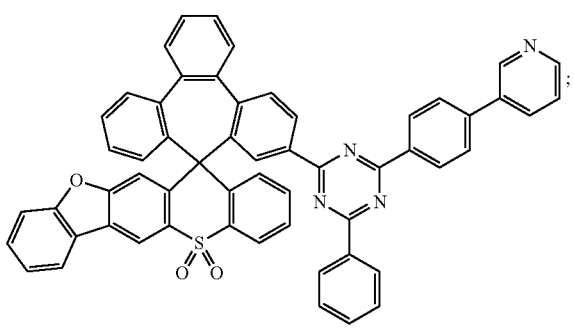
Compound CCLXV
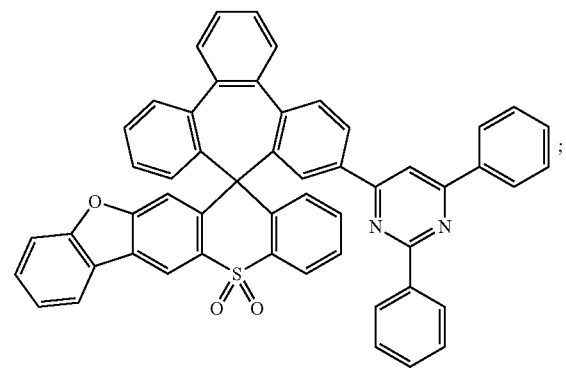
Compound CCLXVI
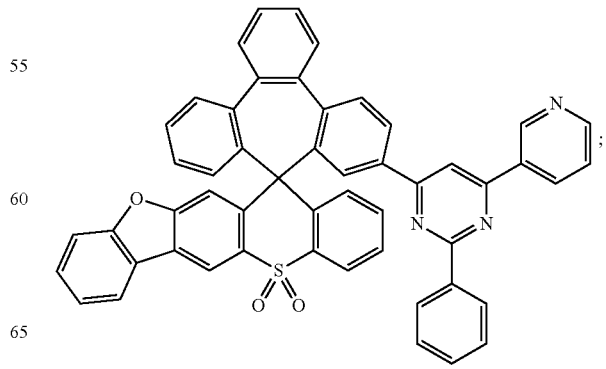

Compound CCLXVII
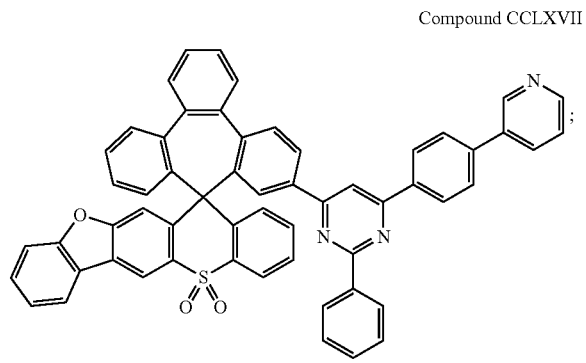
Compound CCLXVIII
Compound CCLXIX
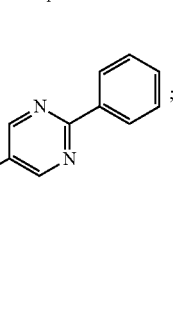
Compound CCLXX
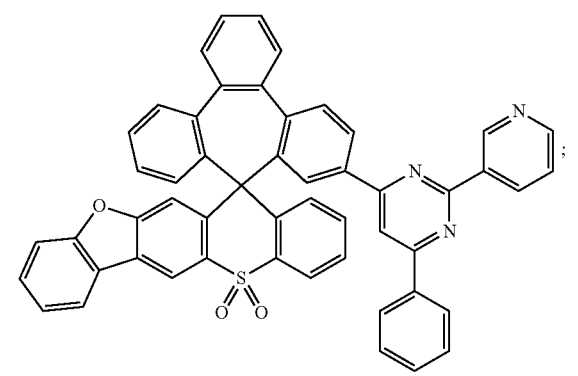
Compound CCLXXI
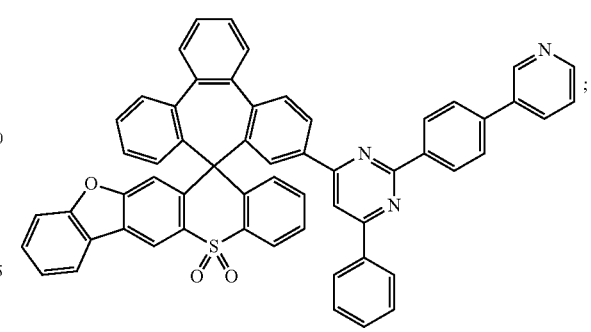
Compound CCLXXII
Compound CCLXXIII
Compound CCLXXIV
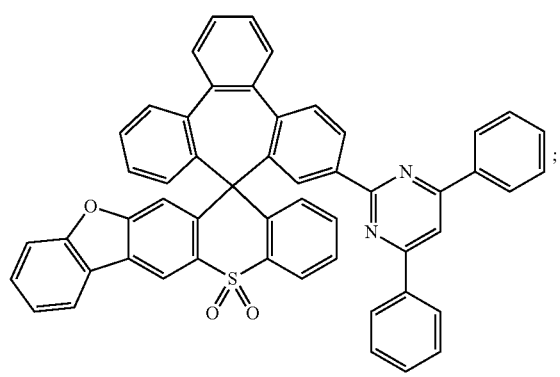

Compound CCLXXV
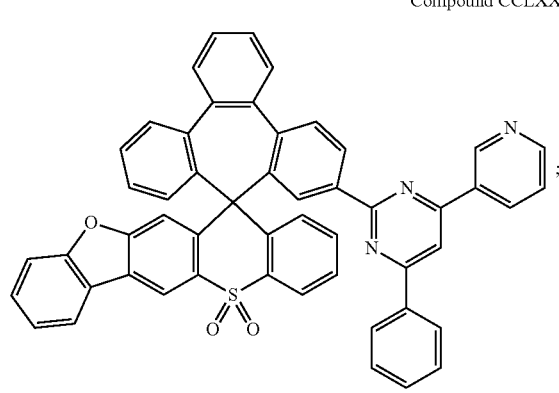
Compound CCLXXVI
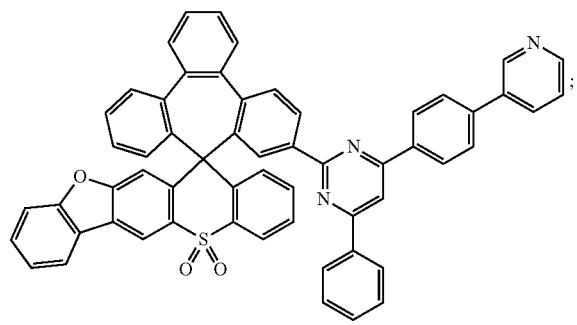
Compound CCLXXVII
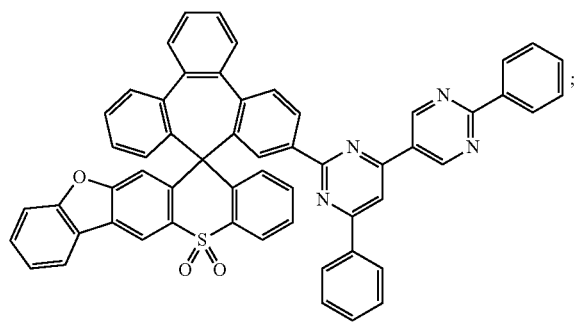
Compound CCLXXVIII
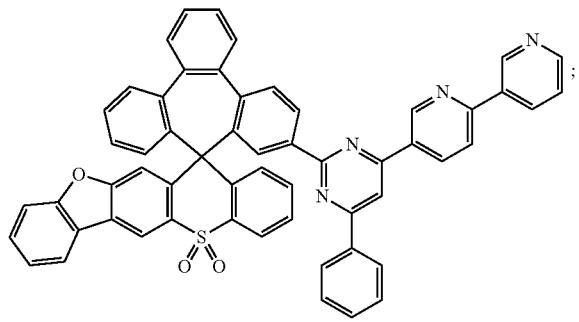
Compound CCLXXIX
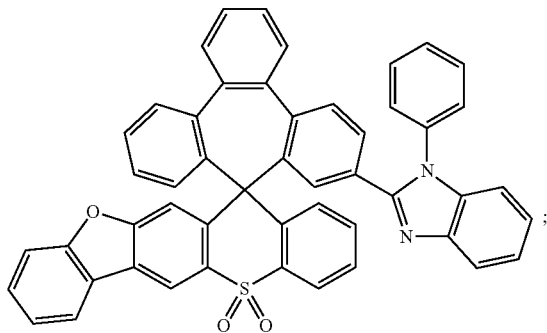
Compound CCLXXX
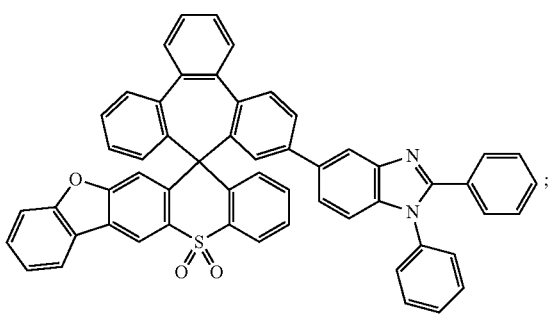
Compound CCLXXXI
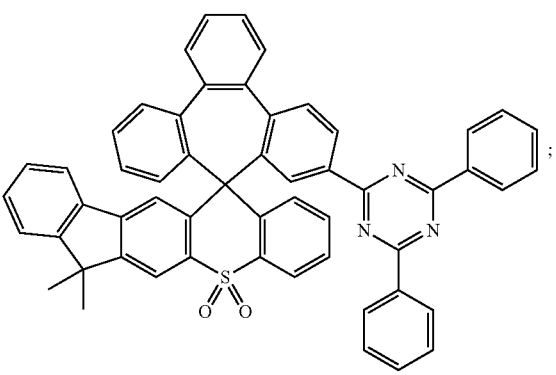
Compound CCLXXXII
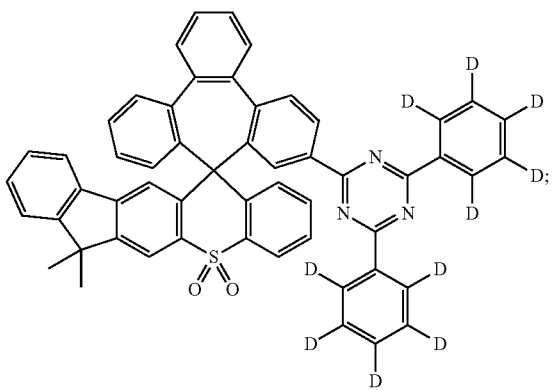

Compound CCLXXXIII
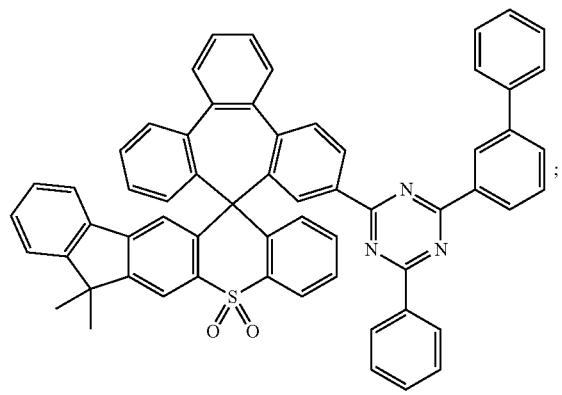
Compound CCLXXXIV
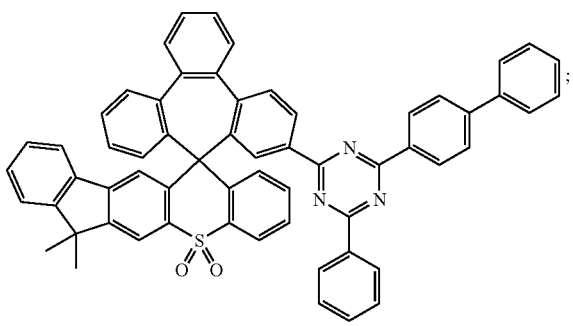
Compound CCLXXXV
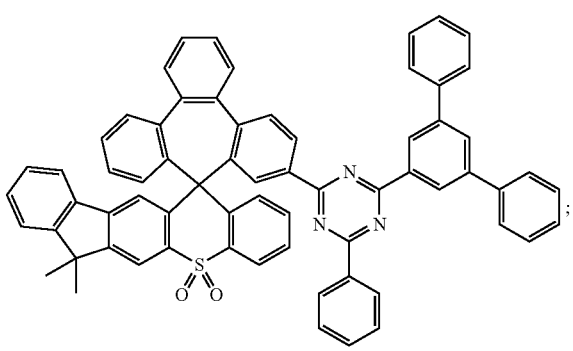
Compound CCLXXXVI
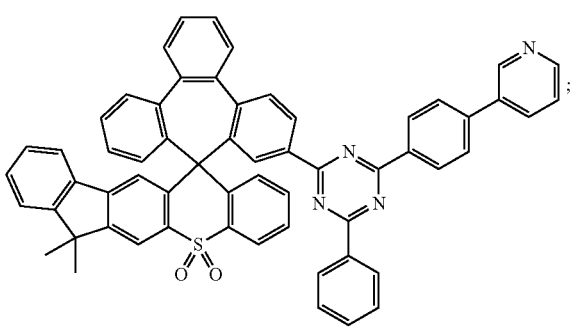
Compound CCLXXXVII
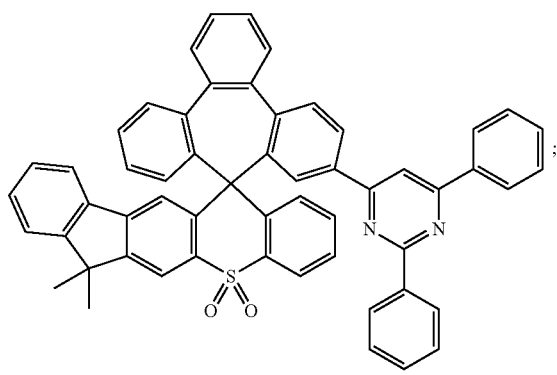
Compound CCLXXXVIII
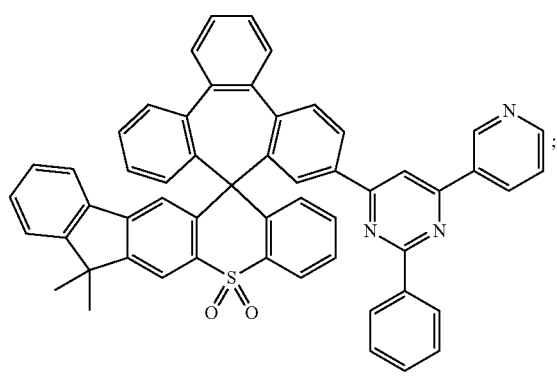
Compound CCLXXXIX
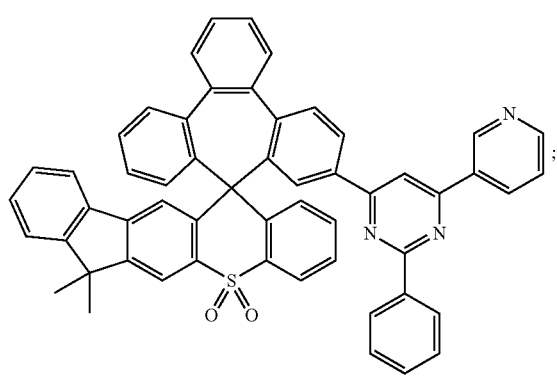
Compound CCXC
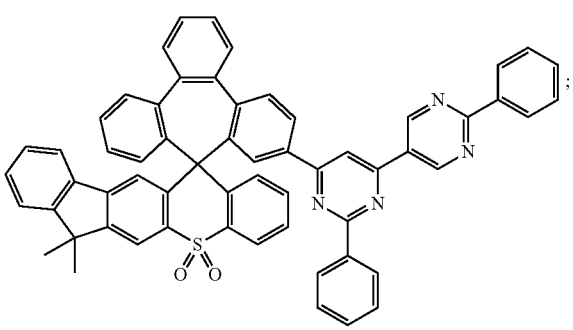

Compound CCXCI
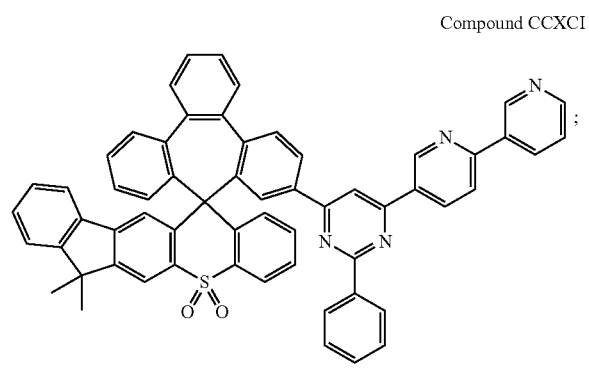
Compound CCXCII
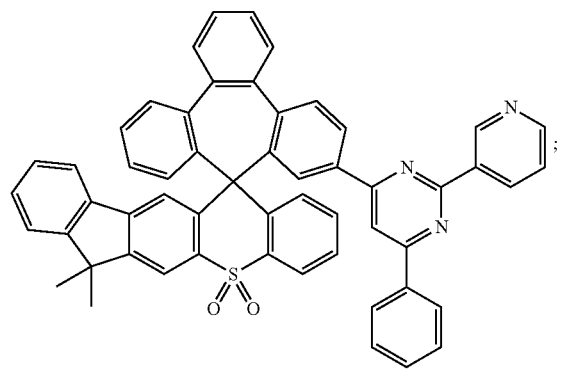
Compound CCXCIII
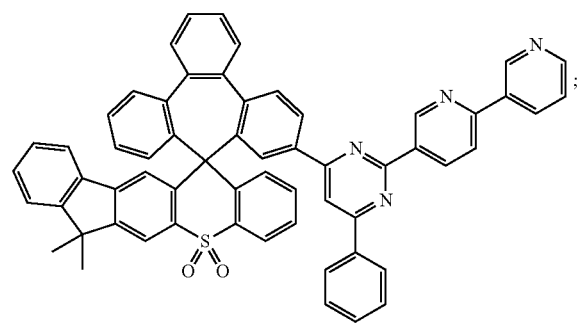
Compound CCXCIV
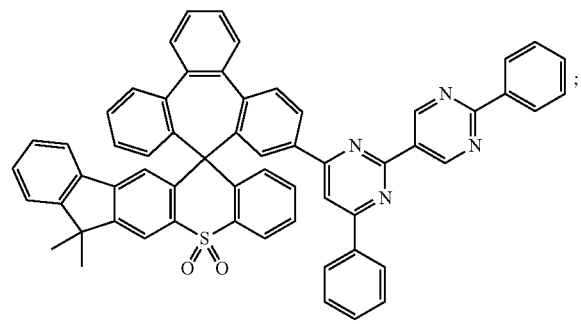
Compound CCXCV
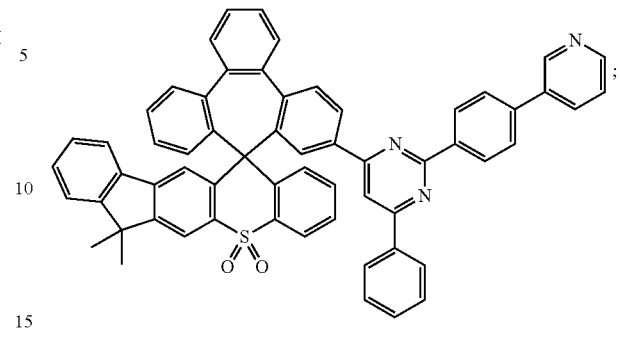
Compound CCXCVI
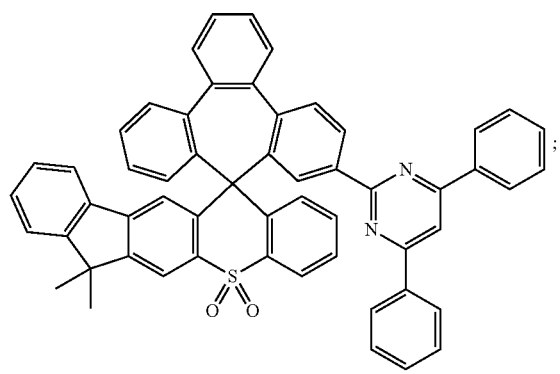
Compound CCXCVII
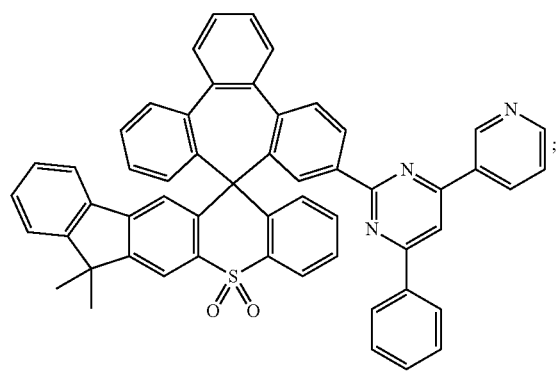
Compound CCXCVIII
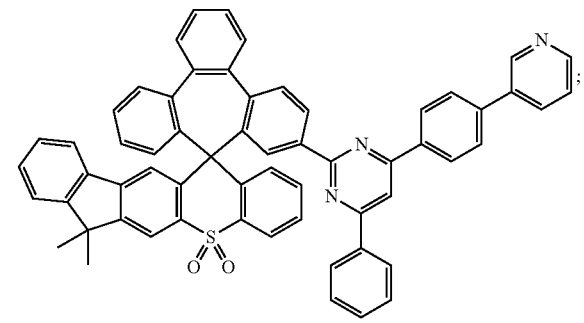

Compound CCIC
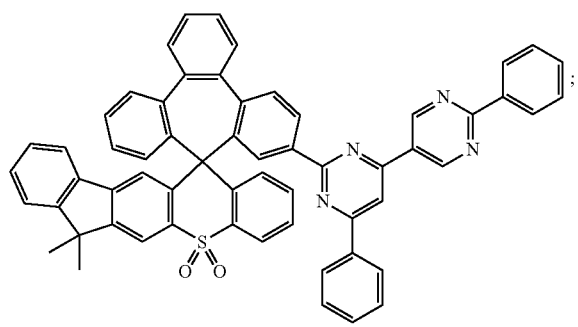
Compound CCC
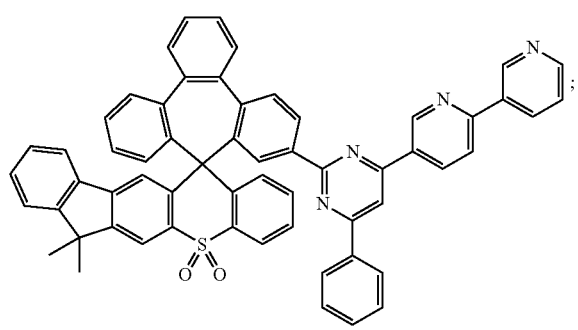
Compound CCCI
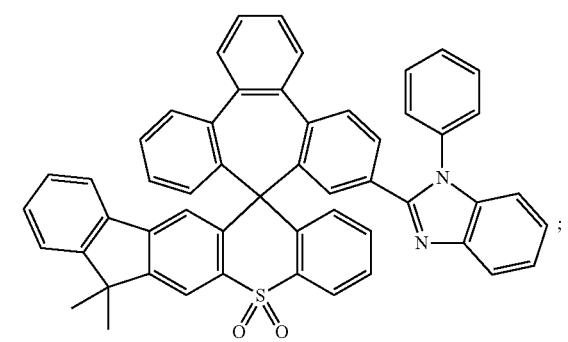
Compound CCCII
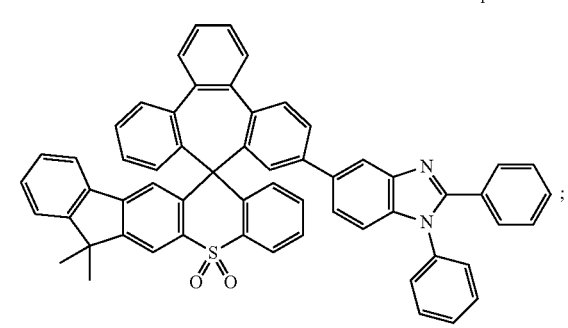
Compound CCCIII
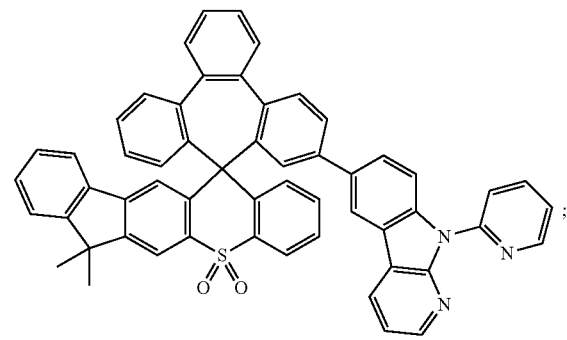
Compound CCCIV
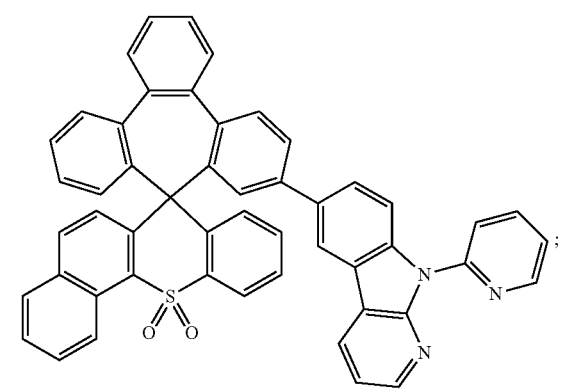
Compound CCCV
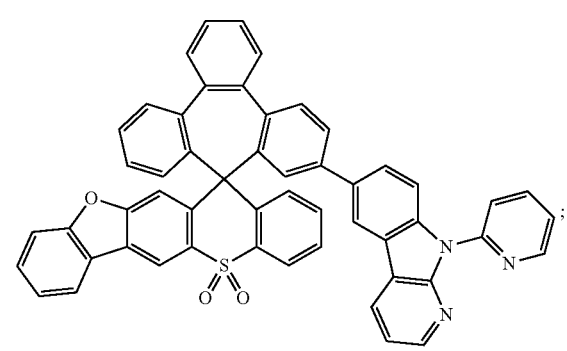
Compound CCCVI
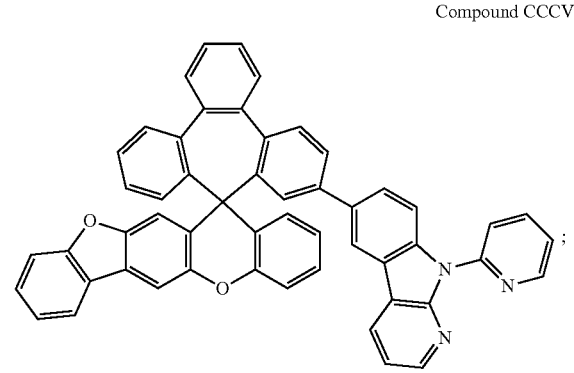

Compound CCCVII

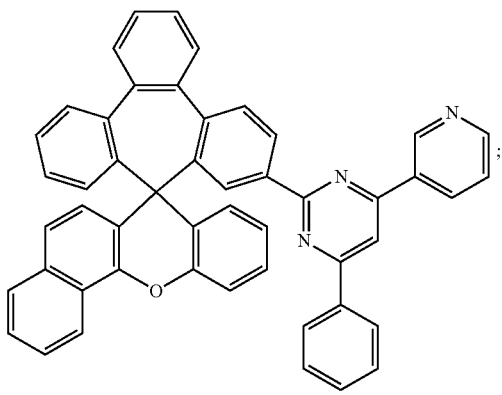

Compound CCCVIII

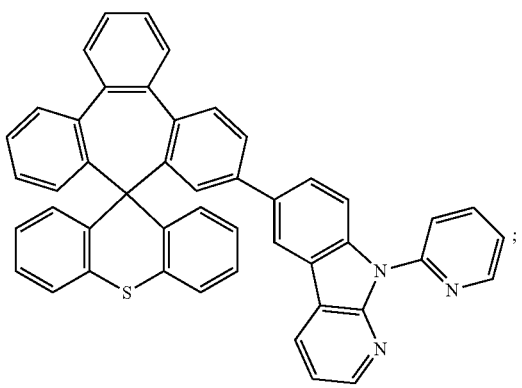

Compound CCCIX

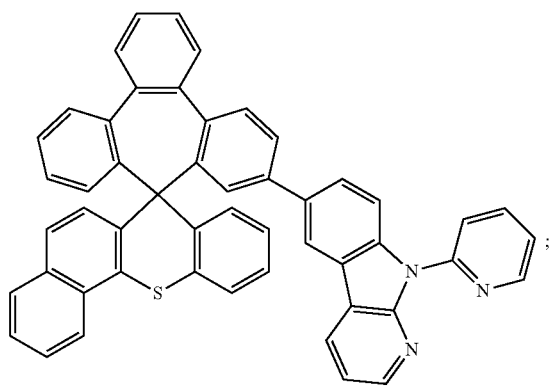

Compound CCCX

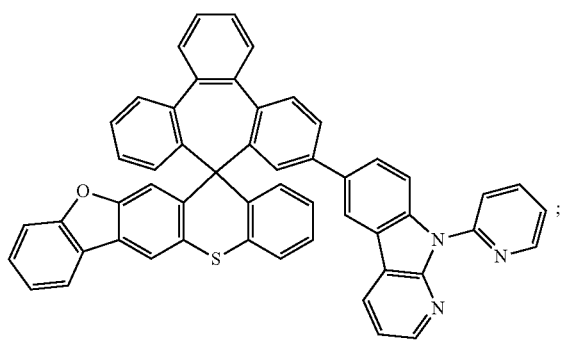

Compound CCCXI

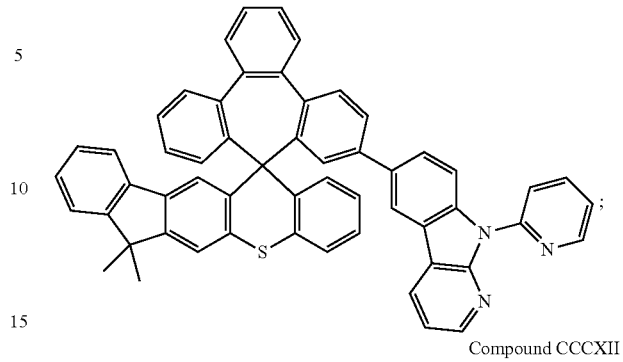

Compound CCCXII

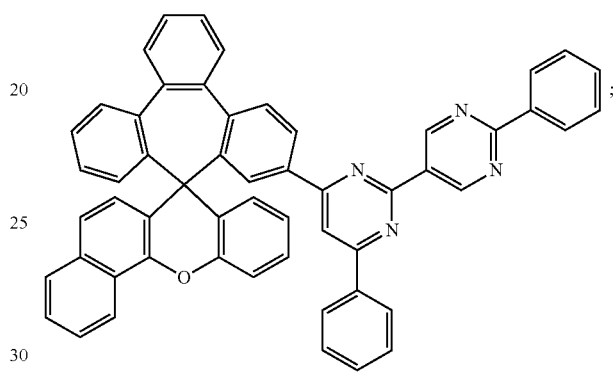

Compound CCCXIII

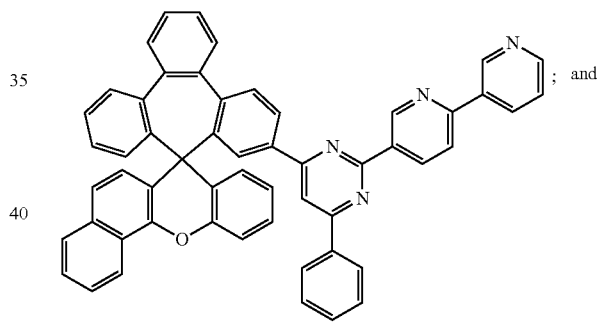

; and

Compound CCCXIV

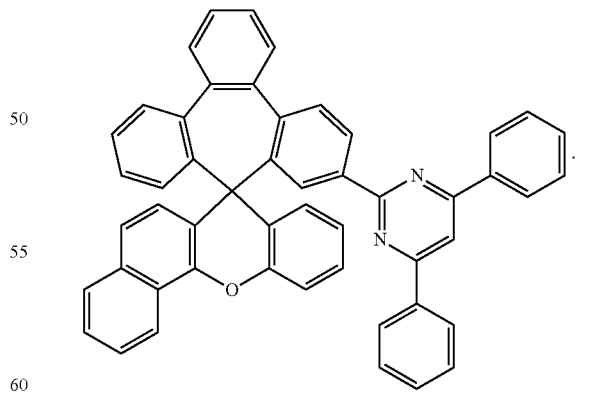

.

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material or a hole blocking layer.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the electron transport layer, i.e., the electron transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound such as Compounds I to CCCXIV. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]imidazole; bis(2-methyl-8quinolinolato)(p-phenylphenolato) aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of the foresaid novel compound, 2,9-dimethyl-4,7-diphenyl-1,10-phenanthroline (BCP) or 2,3,5,6-tetramethyl-phenyl-1,4-(bis-phthalimide) (TMPP), but not limited thereto. In another embodiment, the organic layer may be the hole blocking layer, i.e., the hole blocking layer comprises the novel compound as stated above.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4''-tri(N-carbazolyl)-triphenylamine (TCTA), but not limited thereto.

In the presence of such a hole blocking layer and/or an electron blocking layer in an OLED, the OLED has a higher luminous efficiency compared to a typical OLED.

Said first and second hole transport layers may be made of, for example, but not limited to: $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

Said first and second hole injection layers may be made of, for example, but not limited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having perylene ligands, fluoranthene ligands or periflanthene ligands. For green OLEDs, the dopant of the emission material is, for example, but not limited to: diaminofluorenes; diaminoanthracenes; or organometallic compounds of iridium (II) having phenylpyridine ligands. For blue OLEDs, the dopant of the emission material is, for example, but not limited to: diaminofluorenes; diaminoanthracenes; diaminopyrenes; or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
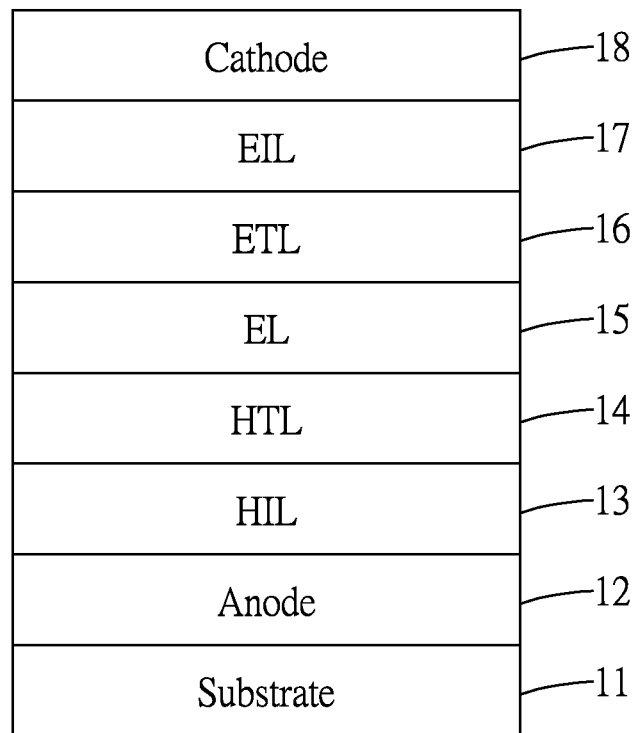
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

Scheme A1

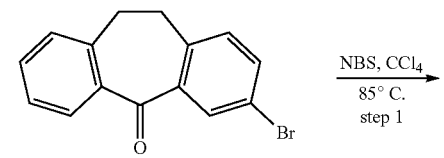

3-bromodibenzo[a,d]cyclohepten-5-one
[3973-53-3]

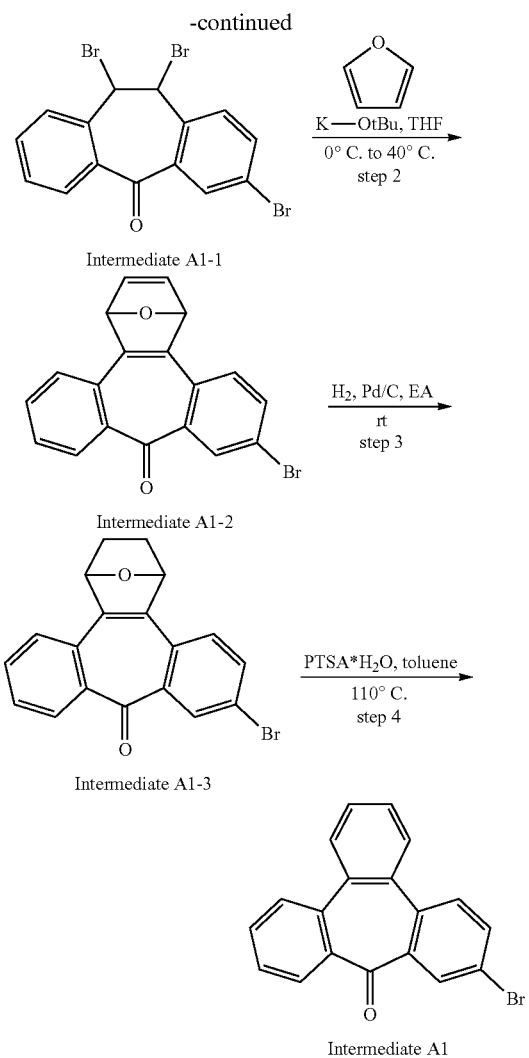

Intermediate A1-1

Intermediate A1-2

Intermediate A1-3

Intermediate A1

Step 1: Synthesis of Intermediate A1-1

A mixture of 3-bromodibenzo[a,d]cyclohepten-5-one (86 g, 1.0 eq), N-bromosuccinimide (NBS) (106 g, 2 eq), benzyl peroxide (0.7 g, 0.01 eq) in carbon tetrachloride ($CCl_4$) (5 times of starting material) was heated to 85° C. The reaction progress was monitored by high performance liquid chromatography (HPLC). After completion of the reaction, the precipitate was separated by filtration and washed with $CH_3OH$, which was then purified by recrystallization. The purified product was concentrated to dryness, whereby white solid products were obtained in an amount of 123 g and a yield of 92.3%.

The solid product was identified as Intermediate A1-1 by a field desorption mass spectroscopy (FD-MS) analysis. FD-MS analysis: $C_{15}H_9Br_3O$: theoretical value of 444.94 and observed value of 444.94.

Step 2: Synthesis of Intermediate A1-2

The obtained Intermediate A1-1 (116.0 g, 1.0 eq) was dissolved in 960 ml of THF (1.0 M), and the reaction was cooled to 0° C. and then treated with potassium tert-butoxide (K-OtBu) (87.8 g, 3.0 eq). The reaction was allowed to stir at 0° C. for 1 hour, and then stirred at room temperature for additional 12 hours. After completion of the reaction, the reaction was quenched by DI water and the organic layer was recovered by solvent extraction operation and dried over sodium sulfate. The solvent was removed from the organic layer by distillation under reduced pressure, and the resulting residue was purified by silica gel column chromatography. The purified product was concentrated to dryness, whereby a light yellow solid product was obtained in a yield of 60.3%.

The solid product was identified as Intermediate A1-2 by FD-MS analysis. FD-MS analysis $C_{19}H_{11}BrO_2$: theoretical value of 351.19 and observed value of 351.19.

Step 3: Synthesis of Intermediate A1-3

A suspension of Intermediate A1-2 (1.0 eq) and 5% Pd/C (0.025 eq) in ethyl acetate (EA, 2.0 M) was stirred for 3 hours to 6 hours under a hydrogen atmosphere ($H_2$) provided by a balloon of hydrogen. The resulting mixture was filtered through a pad of celite and washed with EA, and the filtrate was concentrated under reduced pressure to obtain 100 g (100%) of a yellow solid product.

The solid product was identified as Intermediate A1-3 by FD-MS analysis. FD-MS analysis $C_{19}H_{13}BrO_2$: theoretical value of 353.21 and observed value of 353.21. The intermediate A1-3 can be directly used in the following step without further purification.

Step 4: Synthesis of Intermediate A1-4

Intermediate A1-3 (53 g, 1.0 eq) and p-toluenesulfonic acid (PTSA) (2.0 eq) in 530 ml of toluene was heated to reflux for 12 hours. The reaction mixture was cooled to room temperature and then quenched with a saturated aqueous solution of $NaHCO_3$ and extracted with $CH_2Cl_2$. The organic layer was washed with water, brine and dried with anhydrous $Na_2SO_4$ subsequently. Then the resulting solution was concentrated under reduced pressure and purified by column chromatography on silica gel with $CH_2Cl_2$/hexane 1/1 (v/v) as eluent, whereby a light yellow solid product was obtained in an amount of 46.0 g and a yield of 91.5%.

The solid product was identified as Intermediate A1 by FD-MS analysis. FD-MS analysis $C_{19}H_{11}BrO$: theoretical value of 335.19 and observed value of 335.19.

Synthesis of Intermediate A2

Intermediate A2 used for preparing a novel compound was synthesized in a similar manner as Intermediate A1 through steps 1 to 4, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

Scheme A2

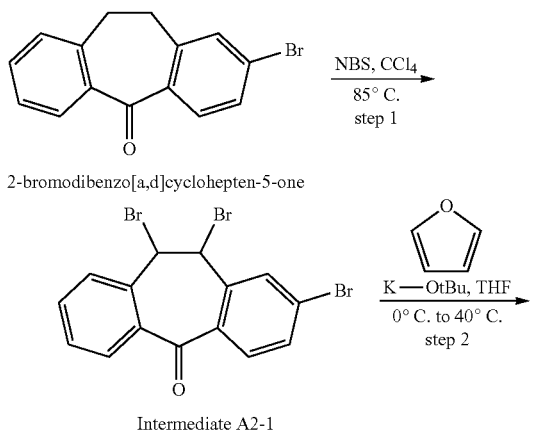

2-bromodibenzo[a,d]cyclohepten-5-one

Intermediate A2-1

Scheme A3

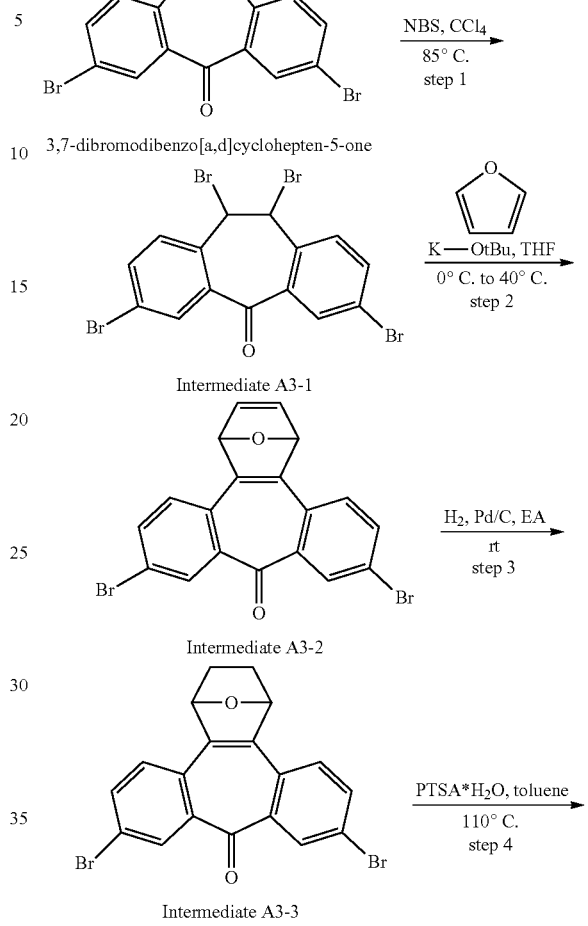

Synthesis of Intermediate A3

Intermediate A3 used for preparing a novel compound was synthesized in a similar manner as Intermediate A1 through steps 1 to 4, except that the starting material 3-bromodibenzo[a,d]cyclohepten-5-one was replaced by 3,7-dibromodibenzo[a,d]cyclohepten-5-one (CAS No. 226946-20-9). The synthesis pathway of Intermediate A3 was summarized in Scheme A3. All intermediates were analyzed as described above, and the results were listed in Table 1.

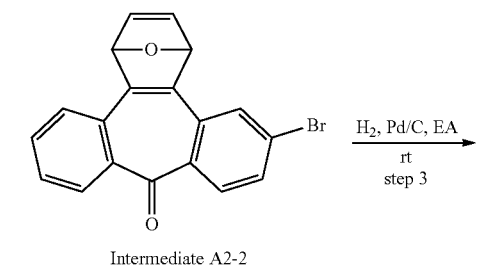

Intermediate A2-2

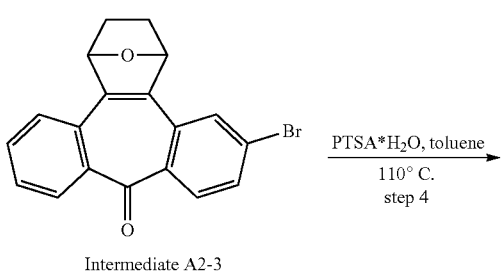

Intermediate A2-3

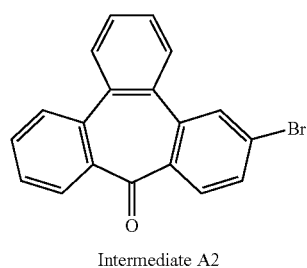

Intermediate A2

TABLE 1 chemical structures, yields, formulae, and mass (M+) analyzed by FD-MS of intermediates.

| Intermediate | A1-1 | A1-2 | A1-3 | A1 |
|---|---|---|---|---|
| Chemical Structure | (structure) | (structure) | (structure) | (structure) |
| Yield | 92.3% | 60.3% | NA | 91.5% |
| Formula | $C_{15}H_9Br_3O$ | $C_{19}H_{11}BrO_2$ | $C_{19}H_{13}BrO_2$ | $C_{19}H_{11}BrO$ |

TABLE 1-continued chemical structures, yields, formulae, and mass (M⁺) analyzed by FD-MS of intermediates.

| Mass(M⁺) | 444.94 | 351.19 | 353.21 | 335.19 |
|---|---|---|---|---|
| Intermediate | A2-1 | A2-2 | A2-3 | A2 |
| Chemical Structure | | | | |
| Yield | 91.5% | 58.2% | NA | 93.5% |
| Formula | $C_{15}H_9Br_3O$ | $C_{19}H_{11}BrO_2$ | $C_{19}H_{13}BrO_2$ | $C_{19}H_{11}BrO$ |
| Mass(M⁺) | 444.94 | 351.19 | 353.21 | 335.19 |
| Intermediate | A3-1 | A3-2 | A3-3 | A3 |
| Chemical Structure | | | | |
| Yield | 93.7% | 75.8% | NA | 93.0% |
| Formula | $C_{15}H_9Br_3O$ | $C_{19}H_{11}BrO_2$ | $C_{19}H_{13}BrO_2$ | $C_{19}H_{11}BrO$ |
| Mass(M⁺) | 523.84 | 430.09 | 432.11 | 414.09 |

Modifications of Intermediates A1 to A3

In addition to the Intermediates A1 to A3, one person skilled in the art can adopt other starting materials and successfully synthesize other desired intermediates through a reaction mechanism similar to Schemes A1 to A3. Applicable modifications of Intermediates A1 to A3 may be, for example, but not limited to, Intermediates A4 to A15 as follows.

Intermediate A4

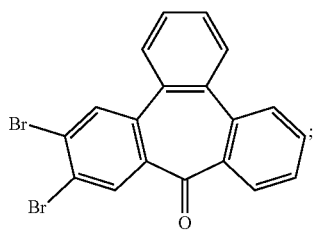

Intermediate A5

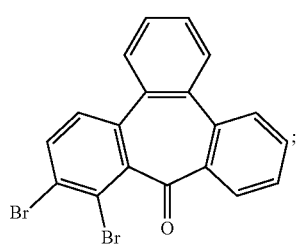

Intermediate A6

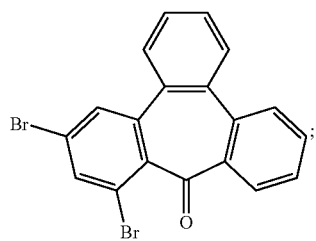

Intermediate A7

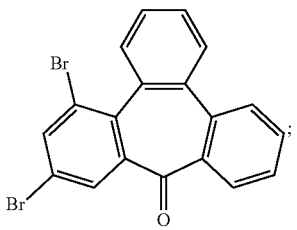

Intermediate A8

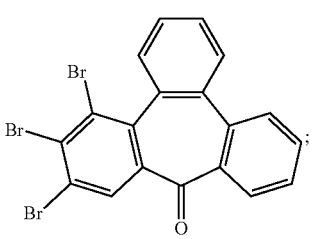

-continued

Intermediate A9

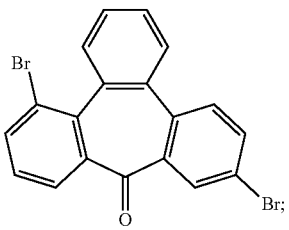 [SMILES: O=c1c2ccccc2c2ccccc2c2ccc(Br)cc12]

Intermediate A10

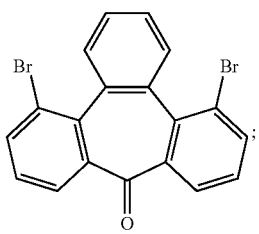

Intermediate A11

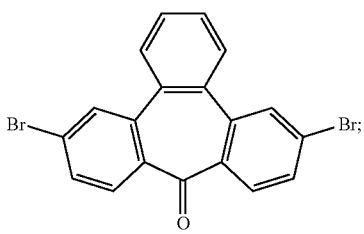

Intermediate A12

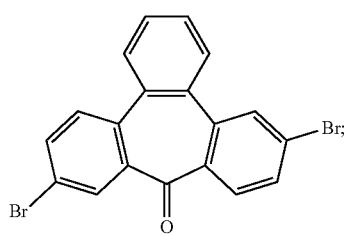

Intermediate A13

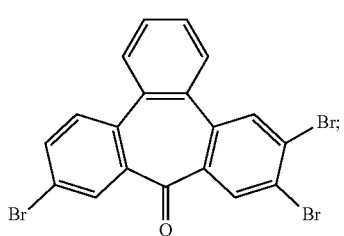

Intermediate A14

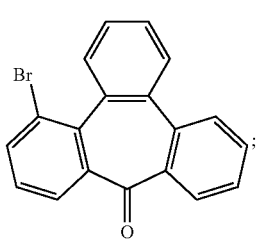

-continued

Intermediate A15

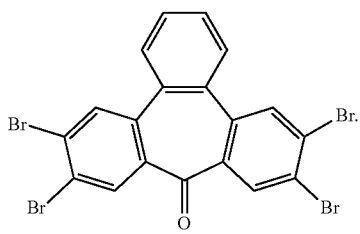

Synthesis of Intermediates B1 to B4

Intermediates B1 to B4 were synthesized by reacting 1-fluoro-2-nitrobenzene and phenol derivative. A general synthesis pathway for Intermediate Bn was summarized in Scheme B-1. In the following Scheme B-1, "Reactant An" may be any one of Reactants A1 to A4 as listed in Table 2-1, and "Intermediate Bn" may be any one of Intermediates B1 to B4.

Scheme B-1

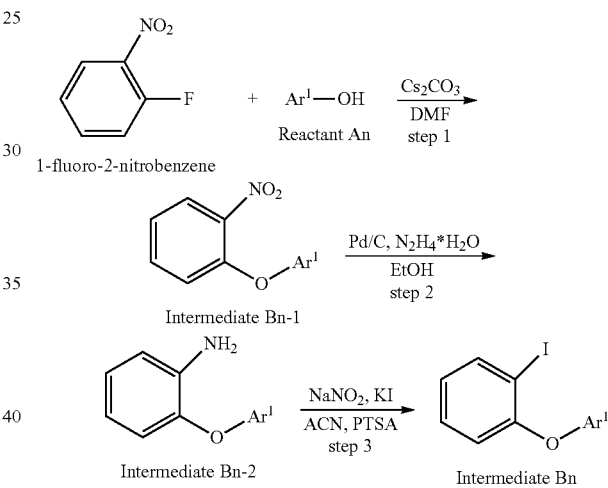

According to the Scheme B-1, each of Intermediates B1 to B4 was synthesized by the steps 1 to 3 as follows.

Step 1: Synthesis of Intermediate Bn-1

The mixture of $Ar^1$—OH (referred Reactant An, 1 eq.), 1-fluoro-2-nitrobenzene (50 g, 1 eq.), and $Cs_2CO_3$ (230.9 g, 2 eq.) in DMF (2080 ml, 0.17M) was stirred at 90° C. under an argon atmosphere. After the completion of the reaction, DMF was distilled out. The residue was quenched with water, extracted with EA and dried over magnesium sulfate, followed by concentration under reduced pressure after filtration. The crude mixture was purified by silica-gel column chromatography, and then identified as Intermediate Bn-1 by FD-MS analysis. Take Intermediate B1-1 as an example, FD-MS analysis: $C_{12}H_9NO_3$: theoretical value of 215.2 and observed value of 215.2.

Step 2: Synthesis of Intermediate Bn-2

The mixture of intermediate Bn-1 (1 eq.), 5% Pd/C (10 g, 0.015 eq) in EtOH (680 ml, 0.5M) was stirred at 70° C. Hydrazine monohydrate (31.6 g, 2 eq.) was then slowly added to the mixture. After the completion of the reaction, the solution was filtered through a pad of Celite, followed by concentration under reduced pressure to obtain intermediate Bn-2. The product was identified as intermediate B1-2 by FD-MS analysis. Take Intermediate B1-2 as an example, FD-MS analysis: $C_{12}H_{11}NO$: theoretical value of 185.22 and observed value of 185.22.

Step 3: Synthesis of Intermediate Bn

The mixture of intermediate Bn-2 (1 eq.), PTSA*$H_2O$ (172.5 g, 3 eq) in Acetonitrile (224 ml, 1.3 M) was cooled to 5° C. using a ice bath. $NaNO_2$ (41.7 g, 2 eq.) in 240 ml water was added dropwise. After the addition was finished, the mixture was kept at 5° C. for 1 hr. The resulting diazonium salt was treated slowly with KI (100 g, 2 eq.) in 300 ml water. After the completion of the reaction, the residue was extracted with EtOAc and the combined organic layer was washed with a 10% $Na_2SO_{3(aq)}$ and then dried over $Na_2SO_4$. The organic layer was concentrated under reduced pressure after filtration. The crude mixture was purified by silica-gel column chromatography to obtain intermediate Bn.

The chemical structure of $Ar^1$—OH used for synthesizing Intermediate B1 n, i.e., Intermediates B1 to B4, the yield, and the chemical structures of the products obtained in steps 1 to 3 were listed in Table 2-1. All Intermediate Bn, including Intermediates B1 to B4, were analyzed by FD-MS, and the results were listed in Table 2-1.

TABLE 2-1

Reactant An used for preparing Intermediates B1 to B4, and the chemical structures, yields, formulae, and mass analyzed by FD-MS of Intermediates B1 to B4.

| Reactant An Chemical Structure | Intermediate Bn-1 Chemical Structure | Yield (%) | Intermediate Bn-2 Chemical Structure | Yield (%) | Intermediate Bn Chemical Structure | Yield (%)/ Formula/ Mass (M+) |
|---|---|---|---|---|---|---|
| 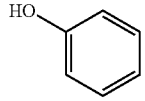 Reactant A1 | 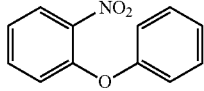 [SMILES: O=[N+]([O-])c1ccccc1Oc1ccccc1] Intermediate B1-1 | 89.2% | 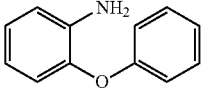 [SMILES: Nc1ccccc1Oc1ccccc1] Intermediate B1-2 | 95.7% | 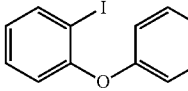 Intermediate B1 | 78.2%/ $C_{12}H_9IO$/ 296.1 |
| 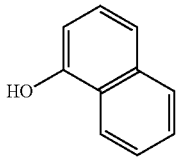 Reactant A2 | 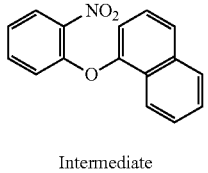 Intermediate B2-1 | 92% | 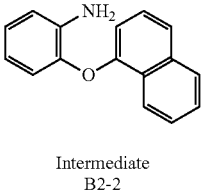 Intermediate B2-2 | 95.3% | 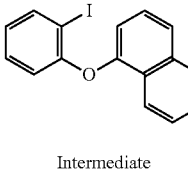 Intermediate B2 | 83%/ $C_{16}H_{11}IO$/ 346.16 |
| 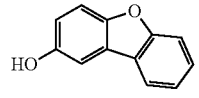 Reactant A3 | 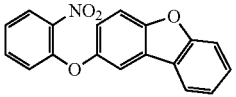 [SMILES: O=[N+]([O-])c1ccccc1Oc1ccc2oc3ccccc3c2c1] Intermediate B3-1 | 91.6% | 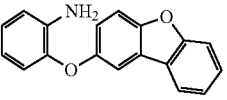 [SMILES: Nc1ccccc1Oc1ccc2oc3ccccc3c2c1] Intermediate B3-2 | 94.6% | 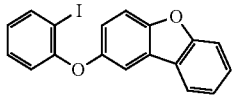 [SMILES: Ic1ccccc1Oc1ccc2oc3ccccc3c2c1] Intermediate B3 | 86%/ $C_{18}H_{11}IO_2$/ 386.18 |
| 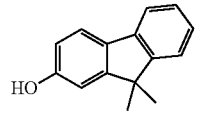 Reactant A4 | 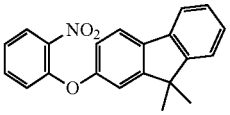 [SMILES: CC1(C)c2ccccc2-c2ccc(Oc3ccccc3[N+](=O)[O-])cc21] Intermediate B4-1 | 93% | 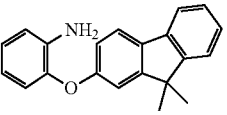 [SMILES: CC1(C)c2ccccc2-c2ccc(Oc3ccccc3N)cc21] Intermediate B4-2 | 94% | 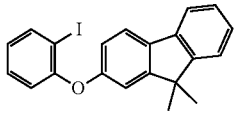 [SMILES: CC1(C)c2ccccc2-c2ccc(Oc3ccccc3I)cc21] Intermediate B4 | 81%/ $C_{21}H_{17}IO$/ 412.26 |

Synthesis of Intermediate B5 and B6

Unlike Intermediates B1 to B4, Intermediates B5 and B6 were synthesized by reacting 2-bromobenzenethiol and aryl iodide. Another general synthesis pathway for Intermediate Bn was summarized in Scheme B-2. In the following Scheme B-2, "Reactant An" may be any one of Reactants A5 and A6 as listed in Table 2-2 or the like, and "Intermediate Bn" may be any one of Intermediates B5 and B6.

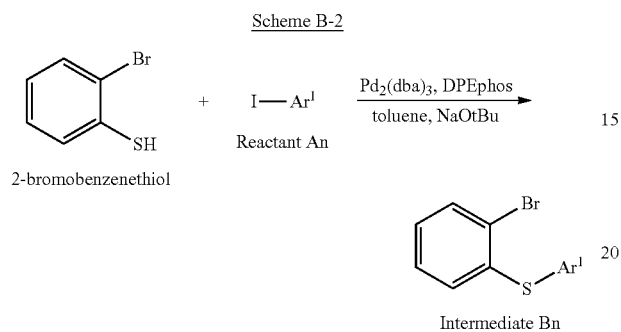

Scheme B-2

According to the Scheme B-2, a mixture of Pd$_2$(dba)$_3$ (0.5% eq), DPEphos (0.01 eq), and NaOt-Bu (1.5 eq) were added to a screw-cap vial followed by toluene and a stir bar. Iodobenzene (1.0 eq) and 2-bromobenzenethiol (1.05 eq) were added. The vial was sealed and the mixture stirred at 100° C. for 1 h. The crude mixture was filtered through a pad of Celite and the filtrate was concentrated. The residue was purified by filtration through a short column of silica gel and eluted with heptane to give Intermediate Bn.

The chemical structure of I—Ar$^1$ used for synthesizing Intermediate Bn, i.e., Intermediates B5 to B6, the chemical structures of the Intermediate Bn, and the yield were listed in Table 2-2. All Intermediate Bn, including Intermediates B5 to B6, were analyzed by FD-MS, and the results were listed in Table 2-2.

TABLE 2-2

Reactant An used for preparing Intermediates B5 and B6, and the chemical structures, yields, formulae, and mass analyzed by FD-MS of Intermediates B5 to B6.

| Reactant An Chemical Structure | Intermediate B Chemical Structure | Yield | Formula/ Mass (M$^+$) |
|---|---|---|---|
| Reactant A5 | Intermediate B5 | 85.6% | C$_{12}$H$_9$BrS/ 265.17 |
| Reactant A6 | Intermediate B6 | 83.7% | C$_{16}$H$_{11}$BrS/ 315.23 |

Modifications of Intermediates B1 to B4

In addition to the Intermediates B1 to B4, one person skilled in the art can adopt any halonitrobenzenes other than 1-fluoro-2-nitrobenzene and any phenol derivative other than Reactants A1 to A4 to successfully synthesize other desired Intermediate Bn through a reaction mechanism similar to Scheme B-1. Applicable modifications of Intermediates B1 to B4 may be, for example, but not limited to, Intermediates B7 to B18 as follows.

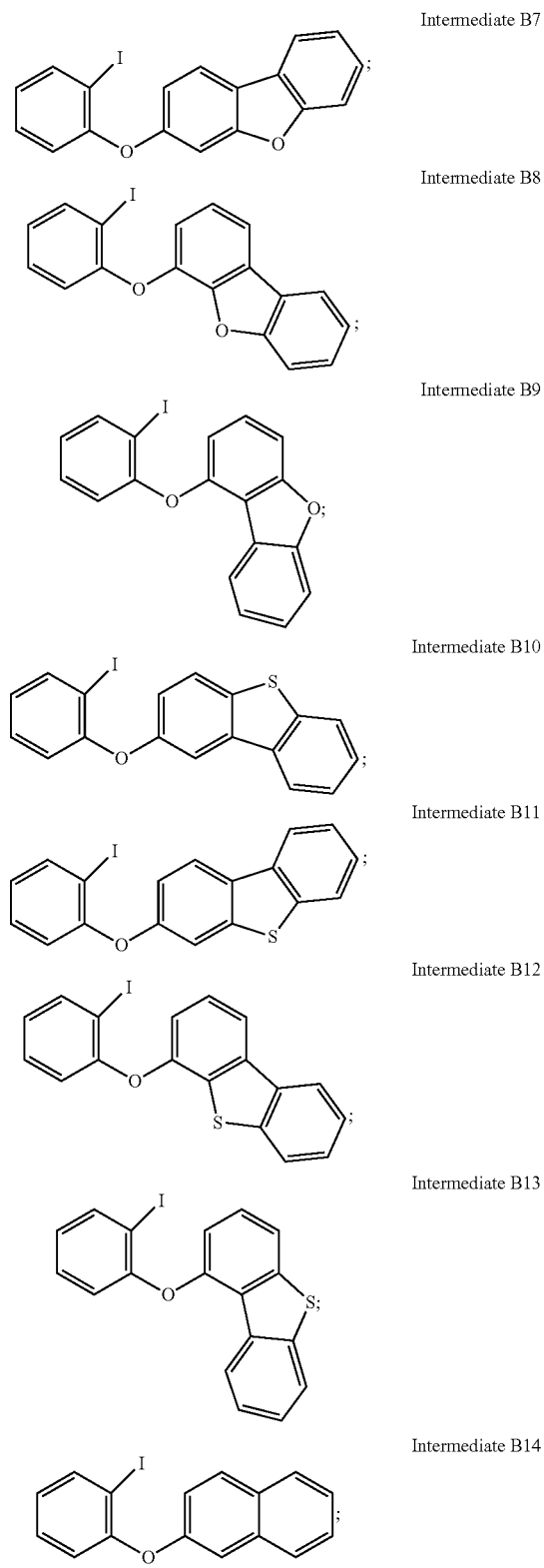

Intermediate B15
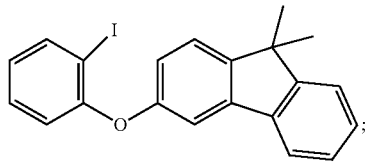

Intermediate B16
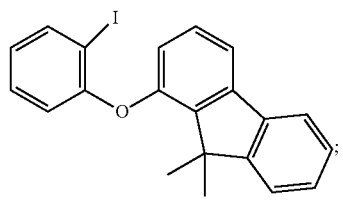

Intermediate B17
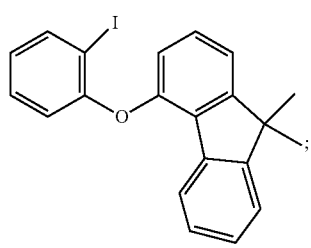

Intermediate B18
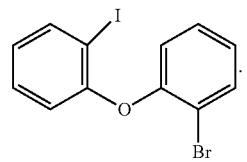

Modifications of Intermediates B5 and B6

In addition to the Intermediates B5 and B6, one person skilled in the art can adopt any halobenzenethiol other than 2-bromonzenethiol and any aryl iodide other than Reactants A5 and A6 to successfully synthesize other desired Intermediate Bn through a reaction mechanism similar to Scheme B-2. Applicable modifications of Intermediates B5 and B6 may be, for example, but not limited to, Intermediates B19 to B34 as follows.

Intermediate B19
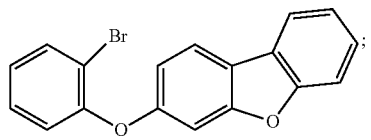

Intermediate B20
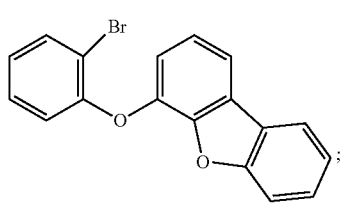

Intermediate B21
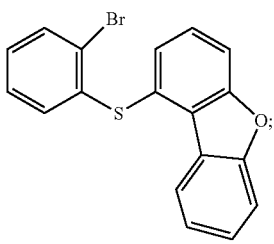

Intermediate B22
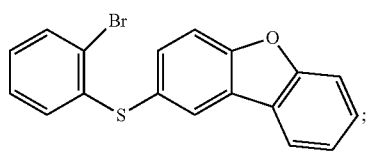

Intermediate B23
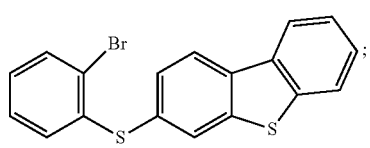

Intermediate B24
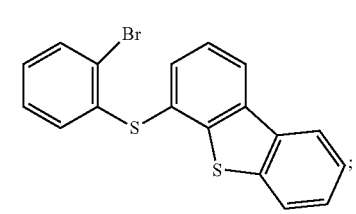

Intermediate B25
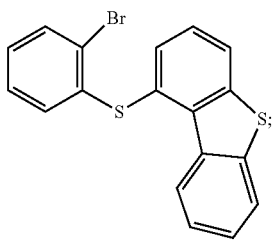

Intermediate B26
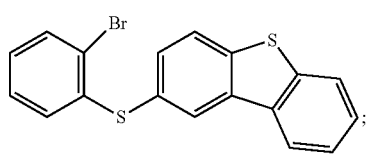

Intermediate B27
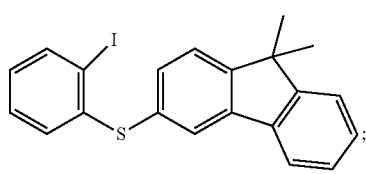

-continued

Intermediate B28
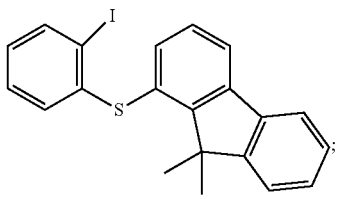

Intermediate B29
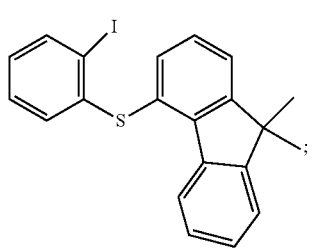

Intermediate B30
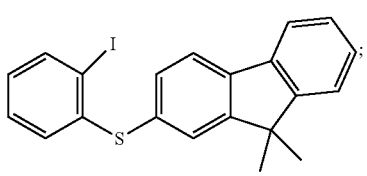

Intermediate B31
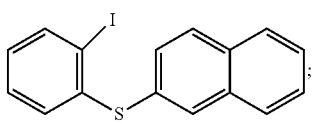

Intermediate B32
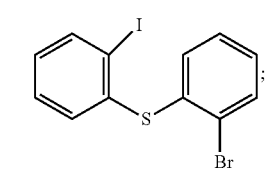

Intermediate B33
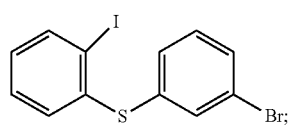

Intermediate B34
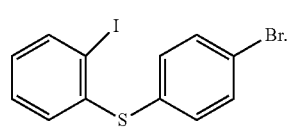

Synthesis of Intermediate Cn

The foresaid Intermediates B1 to B34, especially Intermediates B1 to B6, could be further adopted to synthesize Intermediate Cn. A general synthesis pathway for Intermediate Cn was summarized in Scheme C-1. In the following Scheme C-1, "Intermediate An" may be any one of foresaid Intermediates A1 to A15 or the like, "Intermediate Bn" may be any one of foresaid Intermediates B1 to B34 or the like, and "Intermediate Cn" may be any one of Intermediates C1 to C12 as listed in Table 3-1 or the like. Intermediates C1 to C12 were each synthesized by the following steps.

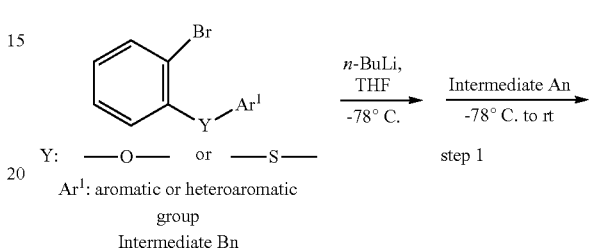

Y: —O— or —S—
Ar¹: aromatic or heteroaromatic group
Intermediate Bn

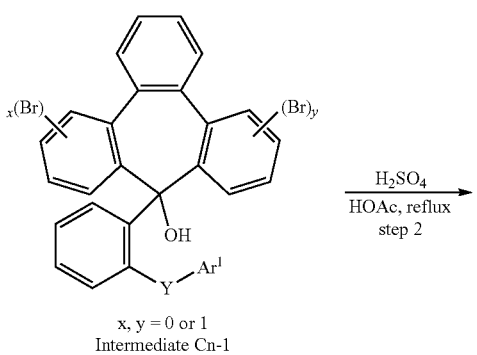

x, y = 0 or 1
Intermediate Cn-1

Intermediate Cn

Step 1: Synthesis of Alcohol Intermediate

Intermediate Bn (1.0 eq) was dissolved in 120 mL of anhydrous THF (0.4M), and cooled to −78° C. n-Butyllithium (n-BuLi)(2.5 M, 1.0 eq) was slowly added to the above cooled solution, and the reaction mass was stirred for 1 h. After 1 h of stirring, Intermediate An (0.7 eq) was added to the reaction solution and stirred for additional 3 h at normal temperature. After the completion of the reaction, it was quenched by saturated solution of ammonium chloride, and extracted with organic solvent. The organic layer was separated, concentrated, and recrystallized with petroleum ether to obtain a white solid product.

The white solid product was analyzed by FD-MS, and the result was listed in Table 3-1. The chemical structures of Intermediates Cn-1 were listed in Table 3-1.

Step 2: Synthesis of Intermediate Cn

The foresaid Intermediate Cn-1 (1.0 eq), acetic acid (w/v=1/3 to the reactant) and $H_2SO_4$ (5 drops) were mixed, and then stirred at 110° C. for 6 h. The solvent was then removed under reduced pressure, and the residue was purified with column chromatography. The residual mass was recrystallized with toluene to obtain a white solid product.

The solid product was identified by FD-MS analysis. The chemical structures, yields, formulae, and mass analyzed by FD-MS of Intermediates C1 to C12 were listed in Table 3-1.

TABLE 3-1

Intermediates An and Bn used for preparing Intermediates C1 to C12, chemical structures of alcohol intermediates, and chemical structures, yields, formulae, and mass analyzed by FD-MS of Intermediates C1 to C12.

| Intermediate An | Intermediate Bn | Alcohol intermediate Chemical Structure | Yield (%) | Intermediate Cn Chemical Structure/ Formula/ Mass (M+) | Yield (%) |
|---|---|---|---|---|---|
| A1 | B1 | Intermediate C1-1/ $C_{31}H_{21}BrO_2$/ 505.40 | 86 | Intermediate C1/ $C_{31}H_{19}BrO$/ 487.39 | 86 |
| A2 | B1 | Intermediate C2-1 | 90 | Intermediate C2 | 93 |
| A3 | B1 | Intermediate C3-1 | 72 | Intermediate C3/ $C_{31}H_{18}Br_2O$/ 566.28 | 84 |

TABLE 3-1-continued

Intermediates An and Bn used for preparing Intermediates C1 to C12, chemical structures of alcohol intermediates, and chemical structures, yields, formulae, and mass analyzed by FD-MS of Intermediates C1 to C12.

| Intermediate An | Intermediate Bn | Alcohol intermediate Chemical Structure | Yield (%) | Intermediate Cn Chemical Structure/ Formula/ Mass (M⁺) | Yield (%) |
|---|---|---|---|---|---|
| A1 | B2 | Intermediate C4-1 | 84 | Intermediate C4 | 82 |
| A3 | B2 | Intermediate C5-1 | 76 | Intermediate C5/ $C_{35}H_{20}Br_2O$/ 616.34 | 84 |
| A1 | B3 | Intermediate C6-1 | 82 | Intermediate C6 | 89 |

TABLE 3-1-continued

Intermediates An and Bn used for preparing Intermediates C1 to C12, chemical structures of alcohol intermediates, and chemical structures, yields, formulae, and mass analyzed by FD-MS of Intermediates C1 to C12.

| Intermediate An | Intermediate Bn | Alcohol intermediate Chemical Structure | Yield (%) | Intermediate Cn Chemical Structure/ Formula/ Mass (M+) | Yield (%) |
|---|---|---|---|---|---|
| A1 | B4 | Intermediate C7-1 | 78 | Intermediate C7<br>C$_{40}$H$_{27}$BrO/<br>603.55 | 85 |
| A3 | B4 | Intermediate C8-1 | 73 | Intermediate C8<br>C$_{40}$H$_{26}$Br$_2$O/<br>682.44 | 81 |
| A1 | B5 | Intermediate C9-1 | 81 | Intermediate C9/<br>C$_{31}$H$_{19}$BrS/<br>503.45 | 87 |

TABLE 3-1-continued

Intermediates An and Bn used for preparing Intermediates C1 to C12, chemical structures of alcohol intermediates, and chemical structures, yields, formulae, and mass analyzed by FD-MS of Intermediates C1 to C12.

| Intermediate An | Intermediate Bn | Alcohol intermediate Chemical Structure | Yield (%) | Intermediate Cn Chemical Structure/ Formula/ Mass (M⁺) | Yield (%) |
|---|---|---|---|---|---|
| A2 | B5 | Intermediate C10-1 | 85 | Intermediate C10 | 78 |
| A1 | B6 | Intermediate C11-1 | 77 | Intermediate C11 | 71 |
| A3 | B6 | Intermediate C12-1 | 79 | Intermediate C12/ $C_{35}H_{20}Br_2S$/ 632.41 | 75 |

Synthesis of Intermediate C13

The foresaid Intermediates C9 to C12 could be further oxidized to synthesize other Intermediate Cn. Take Intermediate C9 as an example, the Intermediate C9 could be oxidized into Intermediate C13 by a method of Scheme C-2.

Scheme C-2

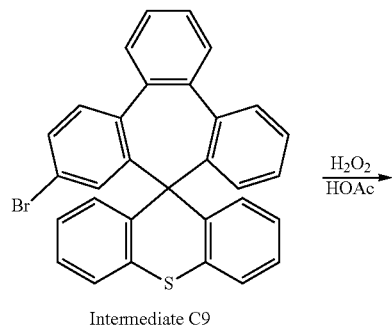

Intermediate C9

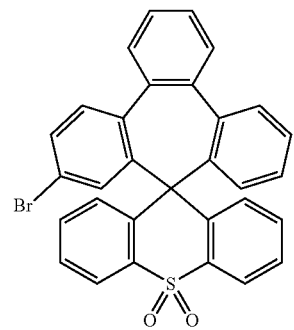

Intermediate C13

A mixture of Intermediate C9 (20 g, 1.0 eq) and 30% aqueous hydrogen peroxide (7.0 eq) in HOAc (250 ml) was heated at 100° C. for 8 h under nitrogen atmosphere. After the completion of the reaction, the reaction mixture was washed with water, followed by filtered to get solid crude mixture. The crude mixture was purified by silica-gel column chromatography to obtain Intermediate C13 in a yield of 85.3%.

The solid product was identified as intermediate C13 by FD-MS analysis. FD-MS analysis: $C_{31}H_{19}BrO_2S$: theoretical value of 535.45 and observed value of 535.45

Synthesis of Intermediate C14

Scheme C-3

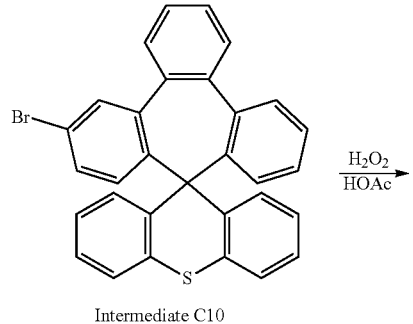

Intermediate C10

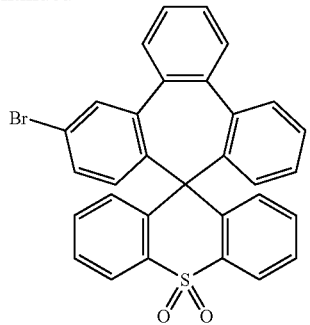

Intermediate C14

Intermediates C14 was synthesized in a similar manner as Intermediate C13, except that the Intermediate C9 was replaced by Intermediate C10.

Modifications of Intermediates C1 to C12

In addition to the Intermediates C1 to C12, one person skilled in the art can adopt any intermediate An other than Intermediates A1 to A3 and any Intermediate Bn other than Intermediates B1 to B6 to successfully synthesize other desired Intermediate Cn through a reaction mechanism similar to Scheme C-1. Applicable modifications of Intermediates C1 to C12 may be, for example, but not limited to, Intermediates C15 to C46 as follows.

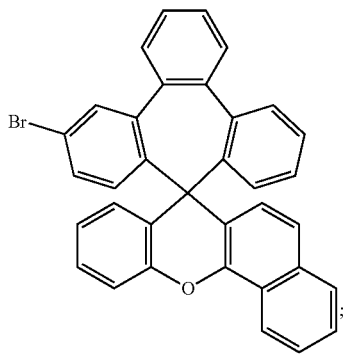

Intermediate C15

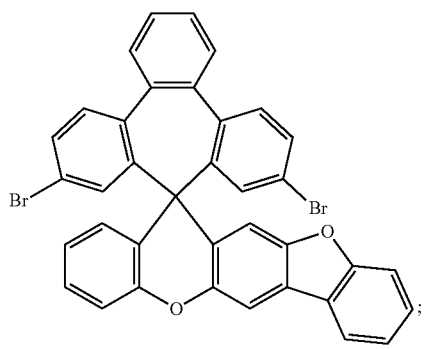

Intermediate C16

Intermediate C17
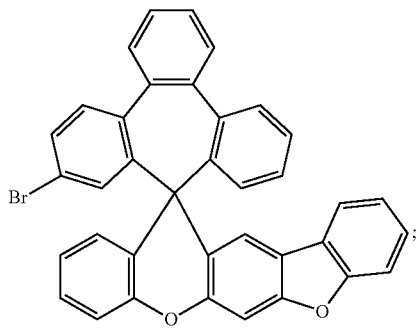
Intermediate C18
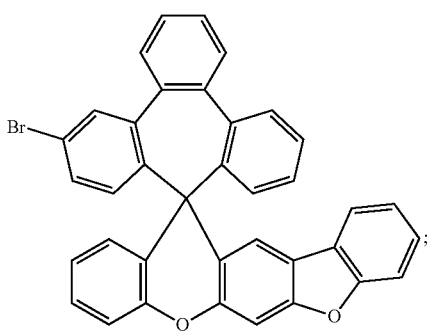
Intermediate C19
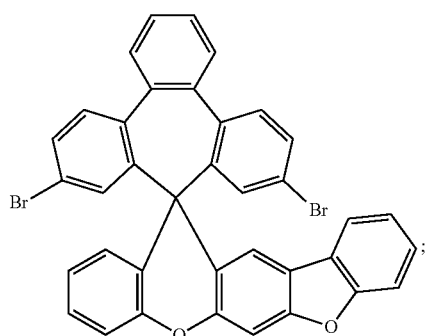
Intermediate C20
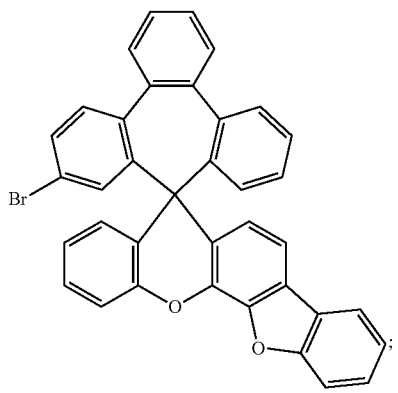
Intermediate C21
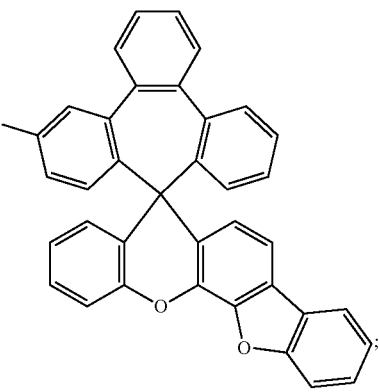
Intermediate C22
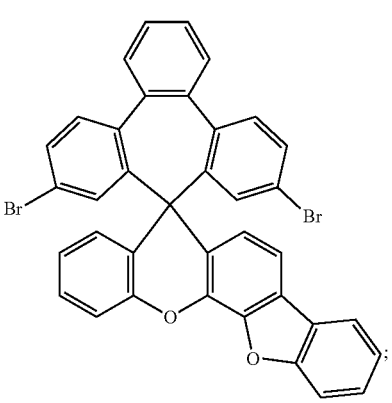
Intermediate C23
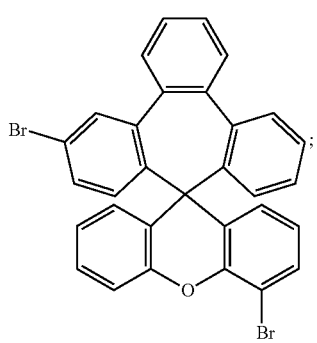
Intermediate C24
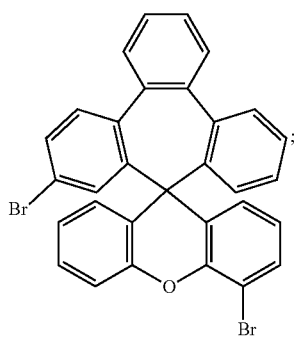

Intermediate C25
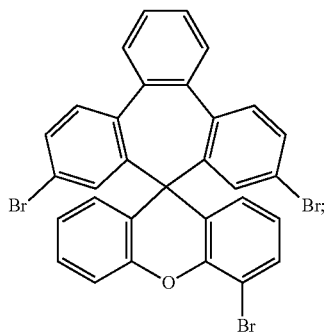
Intermediate C26
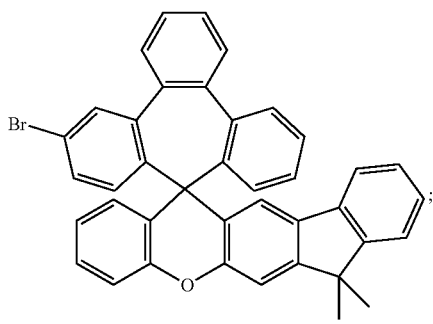
Intermediate C27
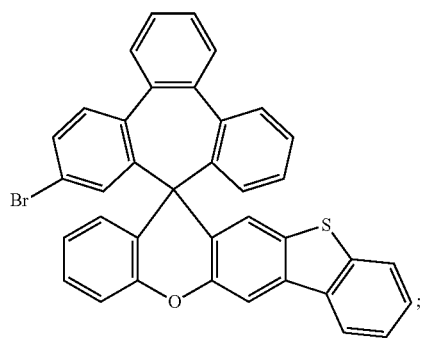
Intermediate C28
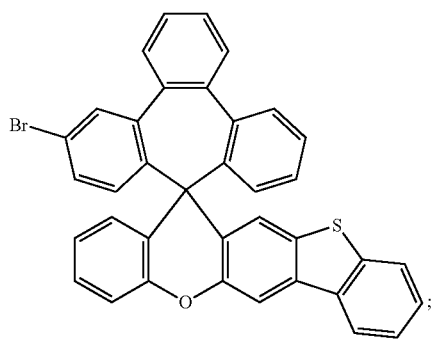
Intermediate C29
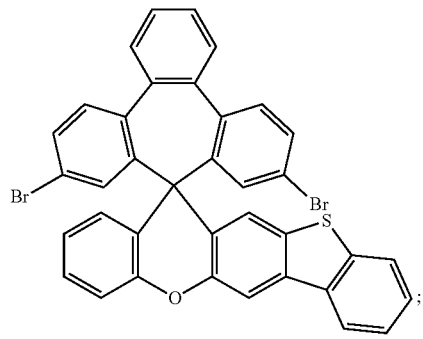
Intermediate C30
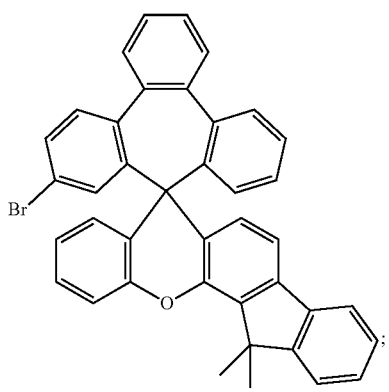
Intermediate C31
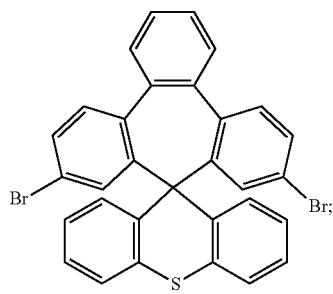
Intermediate C32
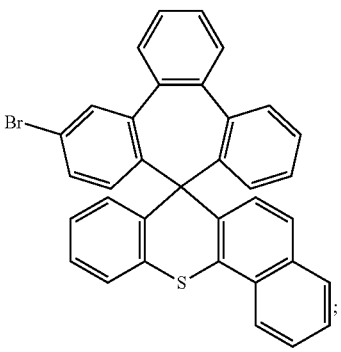

Intermediate C33
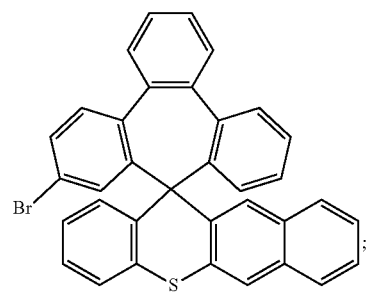
Intermediate C34
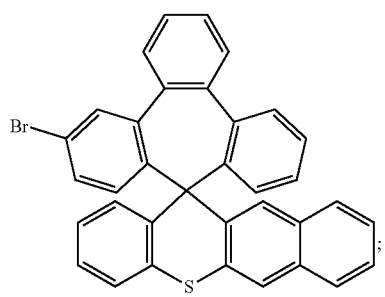
Intermediate C35
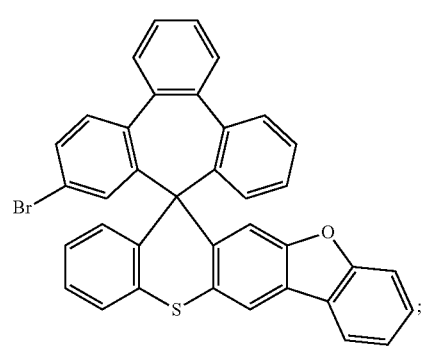
Intermediate C36
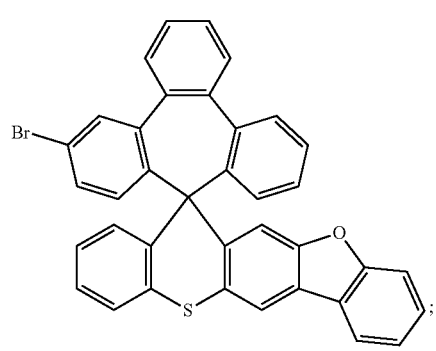
Intermediate C37
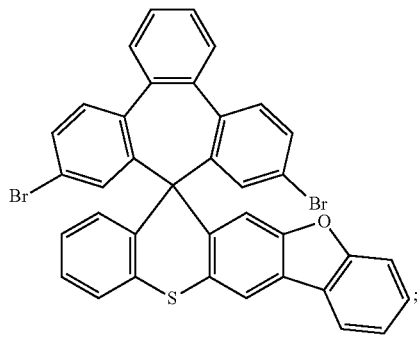
Intermediate C38
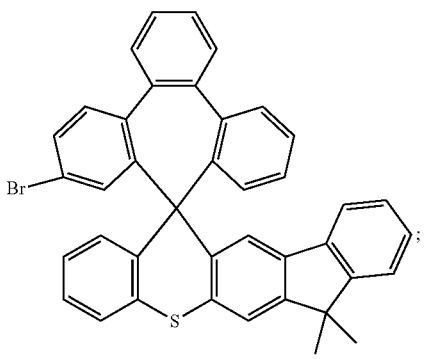
Intermediate C39
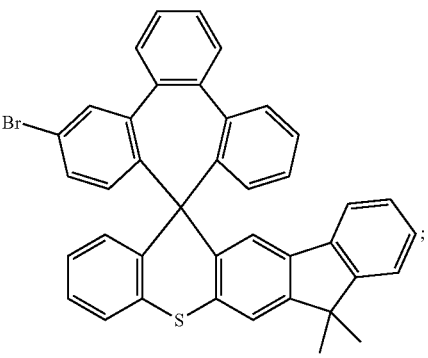
Intermediate 40
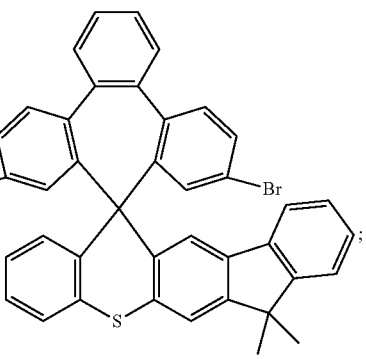

Intermediate C41

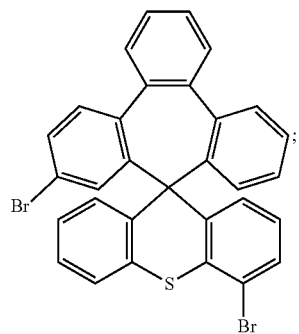

Intermediate C42

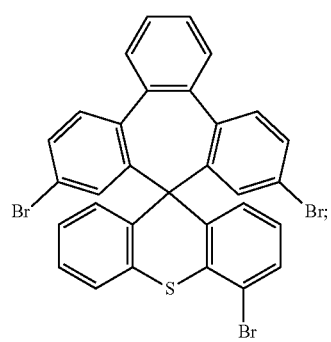

Intermediate C43

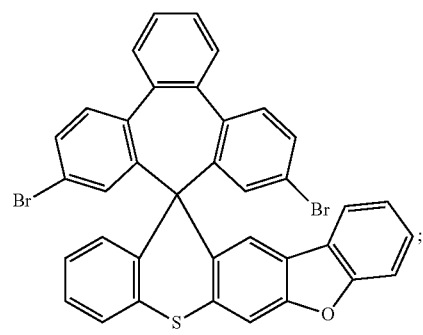

Intermediate C44

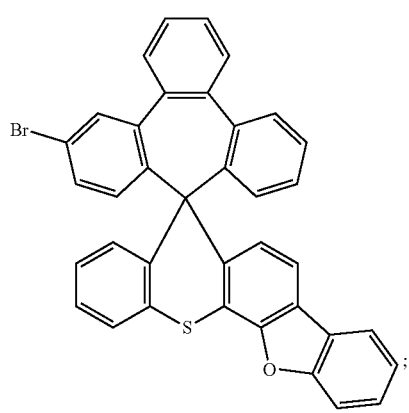

Intermediate C45

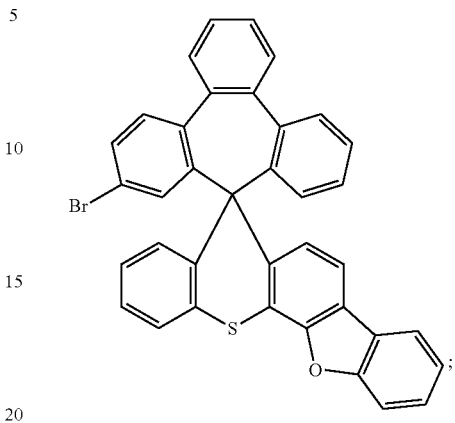

Intermediate C46

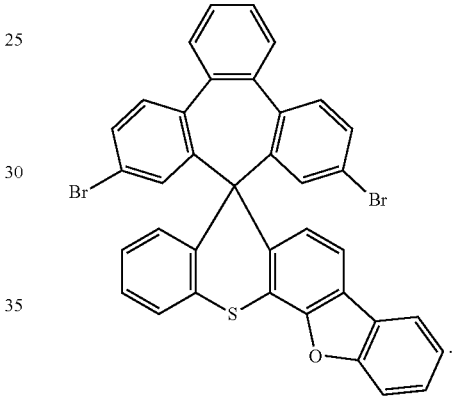

Modifications of Intermediates C13 and C14

In addition to the Intermediates C13 and C14, one person skilled in the art can adopt other Intermediate Cn, such as Intermediates C9 to C12, C31 to C46 to synthesize other desired Intermediate Cn through a reaction mechanism similar to Scheme C-2 or Scheme C-3. Applicable modifications of Intermediates C13 and C14 may be, for example, but not limited to, Intermediates C47 to C58 as follows.

Intermediate C47

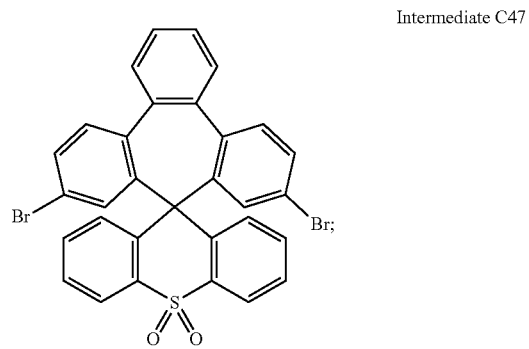

Intermediate C48
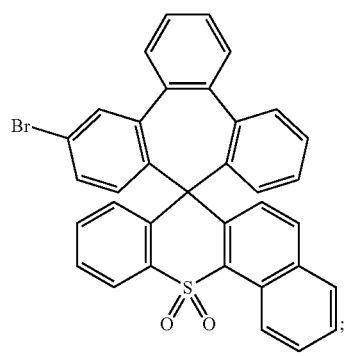
Intermediate C49
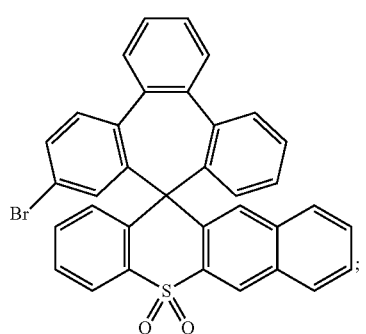
Intermediate C50
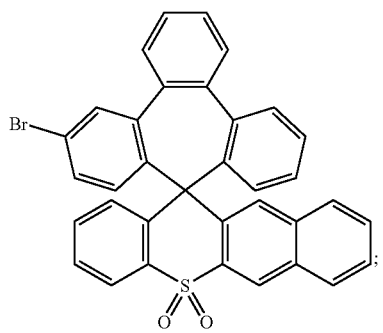
Intermediate C51
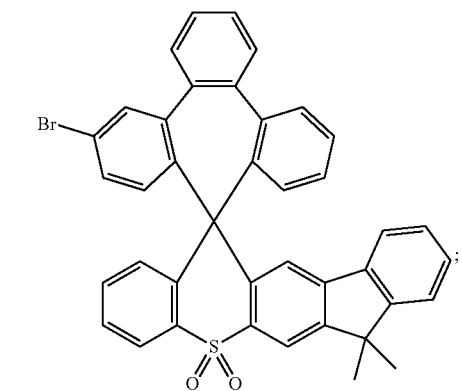
Intermediate C52
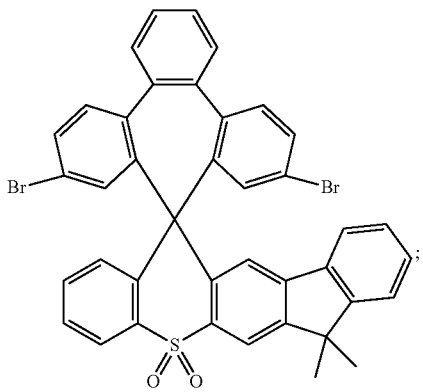
Intermediate C53
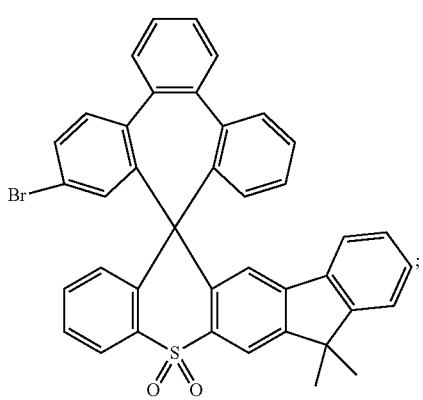
Intermediate C54
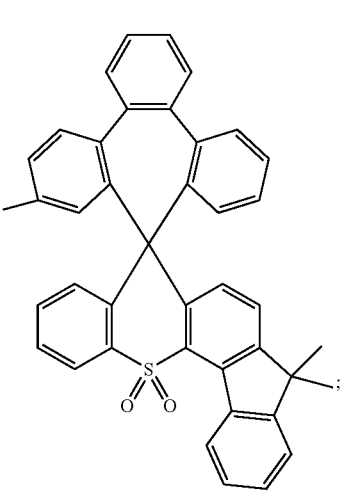

Intermediate C55

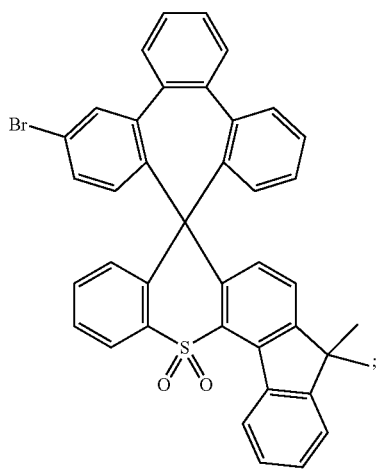

Intermediate C56

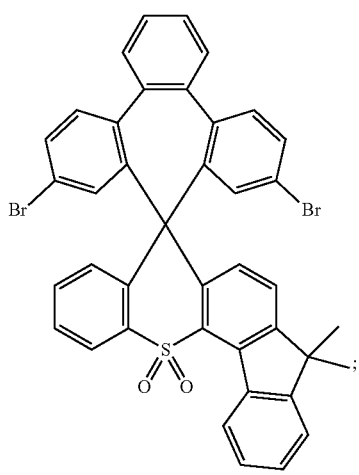

Intermediate C57

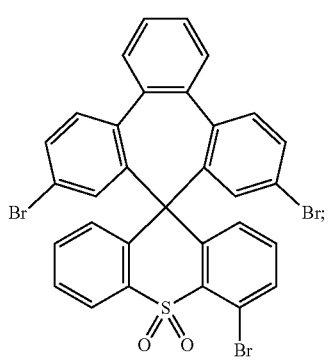

Intermediate C58

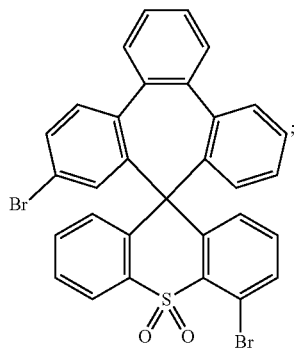

Synthesis of Intermediate Cn-B

The foresaid Intermediate Cn could be further modified into an Intermediate Cn-B through Miyaura borylation reaction. "Intermediate Cn-B" was directed to a compound derived from Intermediate Cn whose bromo group was replaced by (pinacolato)boron group. A synthesis pathway of Intermediate Cn-B was summarized in Scheme C1-B. Intermediate Cn-B was synthesized by the following steps.

Scheme C1-B

Intermediate Cn +

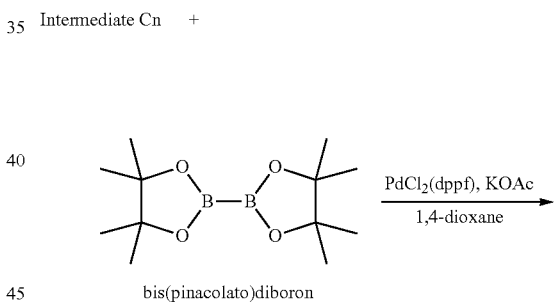

bis(pinacolato)diboron

Intermediate Cn-B

A mixture of bis(pinacolato)diboron (1.2 eq), Intermediate Cn (1.0 eq), 1,1-bis(diphenylphosphino)-ferrocene dichloropalladium (II) (PdCl$_2$(dppf)) (0.015 eq), and potassium acetate (KOAc) (3.0 eq) in 1,4-dioxane (0.3 M) was stirred at 110° C. for 8 hours under nitrogen atmosphere. After cooling to room temperature, the solvent was then removed under reduced pressure, and the residue was purified via column chromatography to obtain a pale yellow solid product.

The pale yellow solid product was identified by FD-MS analysis. The chemical structures, yields, formulae, and mass analyzed by FD-MS of Intermediates Cn-B were listed in Table 3-2.

TABLE 3-2

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| Intermediate C1 | 86 | Intermediate C1-B | 96 | $C_{37}H_{31}BO_3$/ 534.45 |
| Intermediate C2 | 93 | Intermediate C2-B | 93 | $C_{37}H_{31}BO_3$/ 534.45 |
| Intermediate C4 | 82 | Intermediate C4-B | 98 | $C_{41}H_{33}BO_3$/ 584.51 |
| Intermediate C6 | 89 | Intermediate C6-B | 92 | $C_{43}H_{33}BO_4$/ 624.53 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| 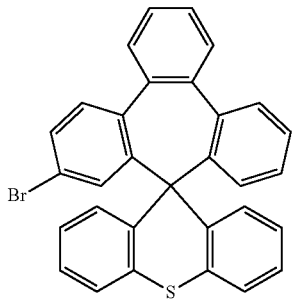 Intermediate C9 | 87 | 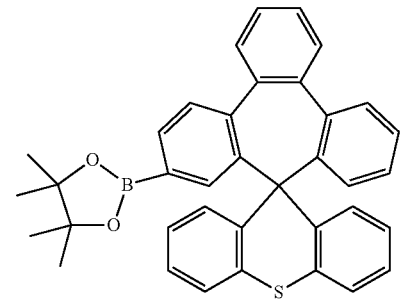 [SMILES: CC1(C)OB(c2ccc3c(c2)C2(c4ccccc4Sc4ccccc42)c2ccccc2-c2ccccc2-3)OC1(C)C] Intermediate C9-B | 92 | $C_{37}H_{31}BO_2S$/ 550.52 |
| 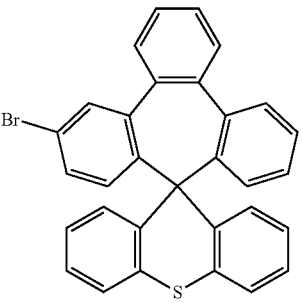 Intermediate C10 | 78 | 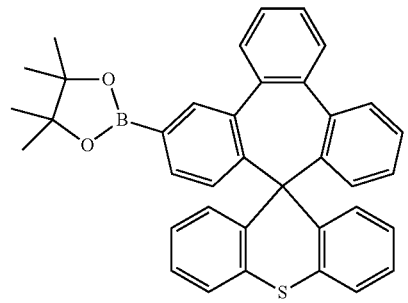 [SMILES: CC1(C)OB(c2ccc3c(c2)-c2ccccc2-c2ccccc2C32c3ccccc3Sc3ccccc32)OC1(C)C] Intermediate C10-B | 96 | $C_{37}H_{31}BO_2S$/ 550.52 |
| 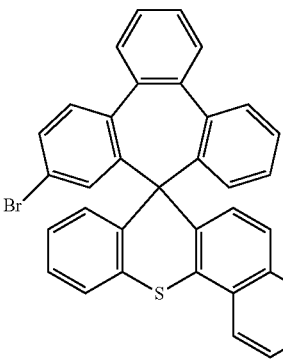 Intermediate C11 | 71 | 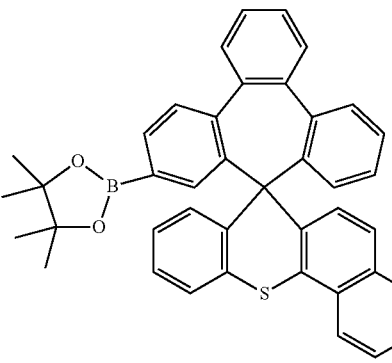 Intermediate C11-B | 96 | $C_{41}H_{33}BO_2S$/ 600.58 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| Intermediate C13 | 85.3 | Intermediate C13-B | 87 | $C_{37}H_{31}BO_4S$/ 582.52 |
| Intermediate C14 | NA | Intermediate C14-B | 88 | $C_{37}H_{31}BO_4S$/ 582.52 |

Modifications of Intermediate Cn-B

In addition to the Intermediate Cn-B, one person skilled in the art can adopt any one of foresaid Intermediates Cn to undergo a Miyaura borylation reaction to successfully synthesize other desired Intermediate Cn-B.

Synthesis of Novel Compounds

Each of the foresaid Intermediates Cn and Cn-B could be reacted with various reactants to synthesis various claimed novel compounds. The general synthesis pathway of the claimed novel compound was summarized in Scheme I. In the following Scheme I, "Reactant B" may be any one of Reactants B1 to B11 as listed in Table 4, and "Intermediate C" may be any one of the foresaid Intermediates Cn and Cn-B or the like. The compounds were each synthesized by the following steps.

Scheme I

Reactant B + Intermediate C $\xrightarrow[\text{K}_2\text{CO}_3,\text{ toluene/EtOH}]{\text{Pd(OAc)}_2,\text{ P(Cy}_2)(2\text{-biPh})}$ Claimed Compound

TABLE 4 chemical structure and CAS No. of Reactants B1 to B34.

| Reactant No. | Reactant B1 | Reactant B2 | Reactant B3 | Reactant B4 |
|---|---|---|---|---|
| Chemical Structure | (HO)₂B—⌬—CN | | | |
| CAS No. | [126747-14-6] | [1319255-85-0] | [181219-01-2] | [1260106-29-3] |

TABLE 4-continued chemical structure and CAS No. of Reactants B1 to B34.

| Reactant No. | Reactant B5 | Reactant B6 | Reactant B7 | Reactant B8 |
|---|---|---|---|---|
| Chemical Structure | | | | |
| CAS No. | [6484-25-9] | [29874-83-7] | [29509-91-9] | [3842-55-5] |
| Reactant No. | Reactant B9 | Reactant B10 | | Reactant B11 |
| Chemical Structure | | | | |
| CAS No. | [3114-52-1] | [867044-33-5] | | [916653-46-8] |
| Reactant No. | Reactant B12 | Reactant B13 | | Reactant B14 |
| Chemical Structure | | | | |
| CAS No. | [1300115-09-6] | [329214-79-1] | | [406482-73-3] |
| Reactant No. | Reactant B15 | Reactant B16 | | Reactant B17 |
| Chemical Structure | | | | |
| CAS No. | [150255-96-2] | [7089-68-1] | | [1616231-57-2] |

TABLE 4-continued chemical structure and CAS No. of Reactants B1 to B34.

| Reactant No. | Reactant B18 | Reactant B19 | Reactant B20 |
|---|---|---|---|
| Chemical Structure | (structure) | (structure) | (structure) |
| CAS No. | [952514-79-3] | [1588407-97-9] | [1421599-34-9] |
| Reactant No. | Reactant B21 | | Reactant B22 |
| Chemical Structure | (structure) | | (structure) |
| CAS No. | [99682-89-0] | | [170230-28-1] |
| Reactant No. | Reactant B23 | Reactant B24 | Reactant B25 | Reactant B26 |
| Chemical Structure | (structure) | (structure) | (structure) | (structure) |
| Reactant No. | | Reactant B27 | | Reactant B28 |
| Chemical Structure | | (structure) | | (structure) |

TABLE 4-continued chemical structure and CAS No. of Reactants B1 to B34.

| Reactant No. | Reactant B29 | Reactant B30 |
|---|---|---|
| Chemical Structure | 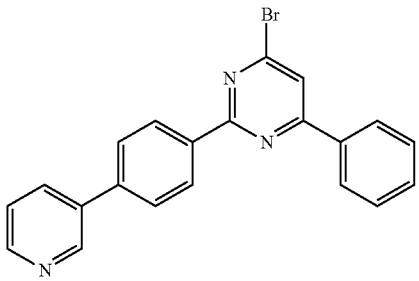 [SMILES: Brc1cc(-c2ccccc2)nc(-c2ccc(-c3cccnc3)cc2)n1] | 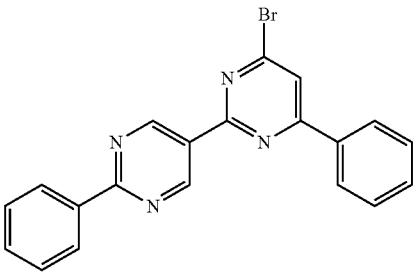 [SMILES: Brc1cc(-c2ccccc2)nc(-c2cnc(-c3ccccc3)nc2)n1] |
| Reactant No. | Reactant B31 | Reactant B32 |
| Chemical Structure | 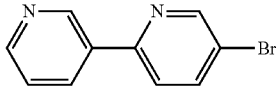 [SMILES: Brc1ccc(-c2cccnc2)nc1] | 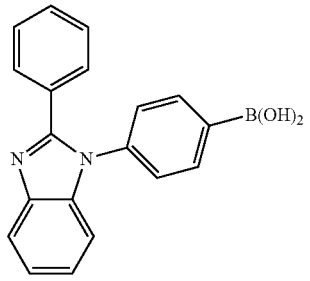 [SMILES: OB(O)c1ccc(-n2c(-c3ccccc3)nc3ccccc32)cc1] |
| CAS No. | [774-53-8] | [867044-33-5] |
| Reactant No. | Reactant B33 | Reactant B34 |
| Chemical Structure | 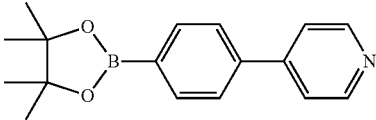 [SMILES: CC1(C)OB(c2ccc(-c3ccncc3)cc2)OC1(C)C] | 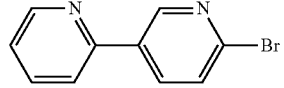 |
| CAS No. | [1009033-87-7] | — |

A mixture of Intermediate Cn or CnB (1.0 eq), Pd(OAc)$_2$(0.01 eq), P(Cy)$_2$(2-biphenyl) 0.04 eq), toluene/ethanol (0.5M, v/v=10/1), 3.0 M potassium carbonate solution, and Reactant B (2.1 eq) was stirred at 100° C. for 12 h under nitrogen atmosphere. After the completion of the reaction, water and toluene were added to the reaction mass. Subsequently, the organic layer was recovered by solvent extraction operation and dried over sodium sulfate. The solvent was then removed from the organic layer under reduced pressure, and the resulting residue was purified by silica gel column chromatography. The obtained residue was recrystallized with toluene to obtain white solid as claimed novel compound.

Figure 2:
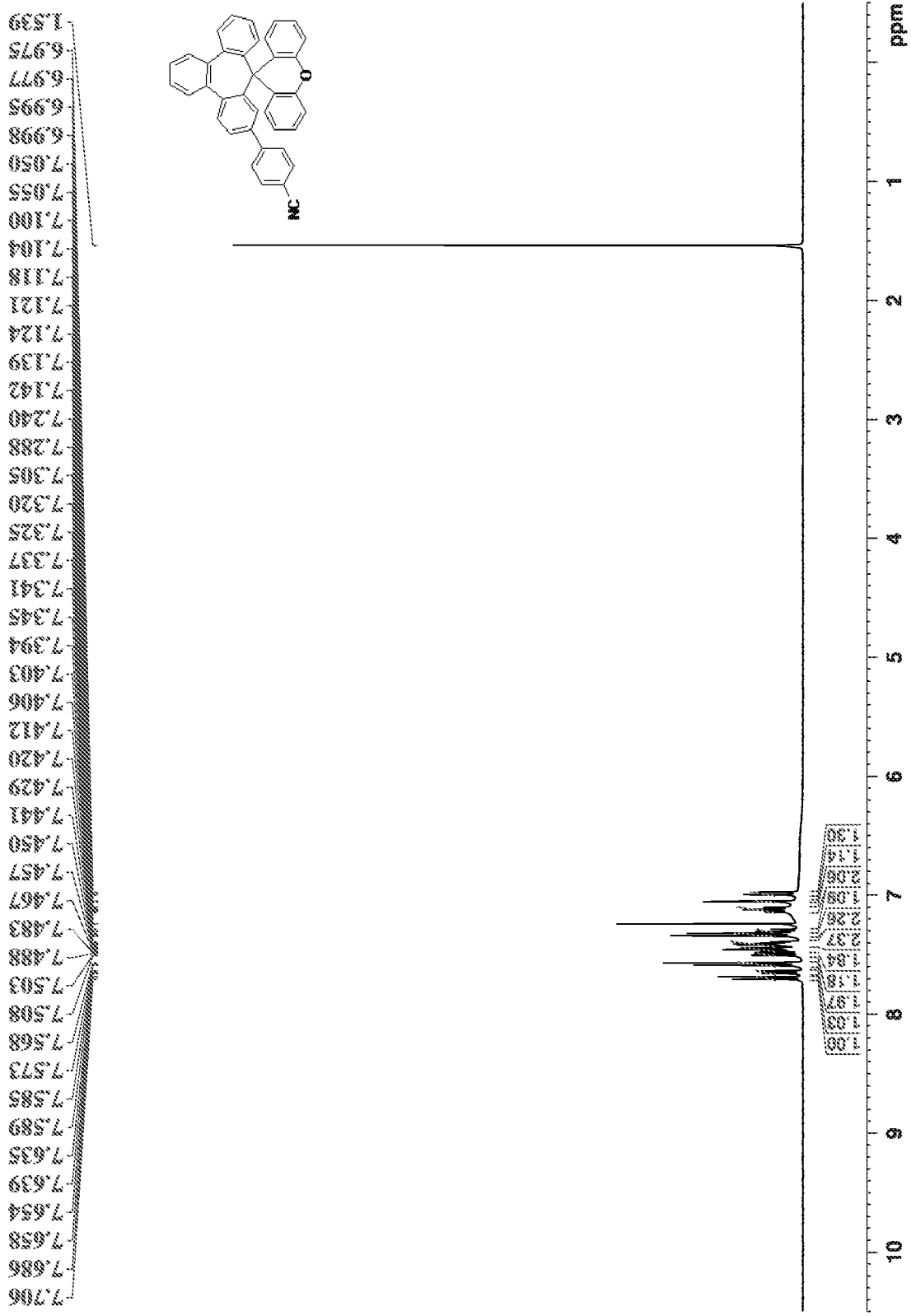
FIGS. 2 to 27 are respectively $^1$H nuclear magnetic resonance (NMR) spectra of Compounds I to XXVI.
Figure 3:
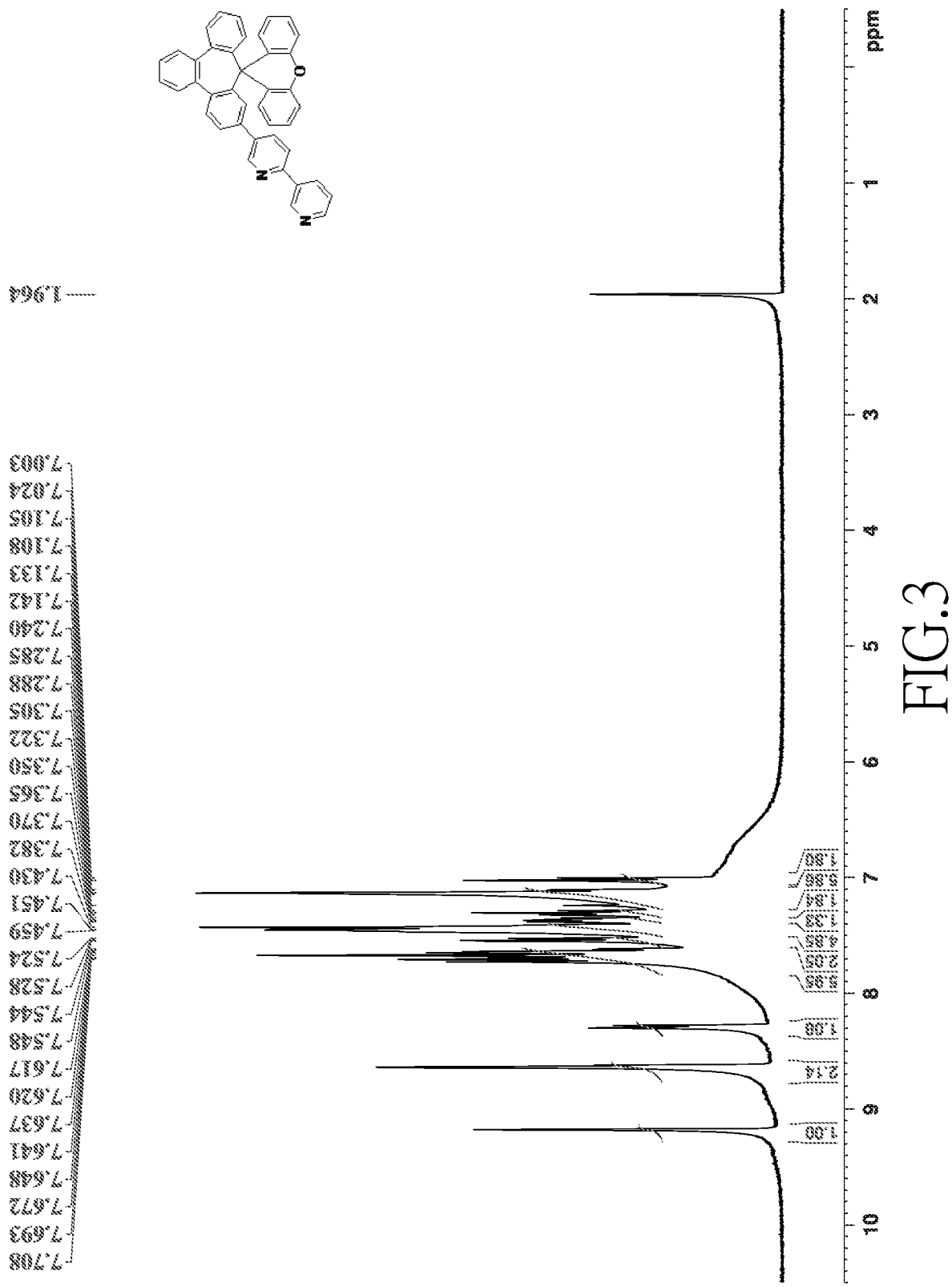
Figure 4:
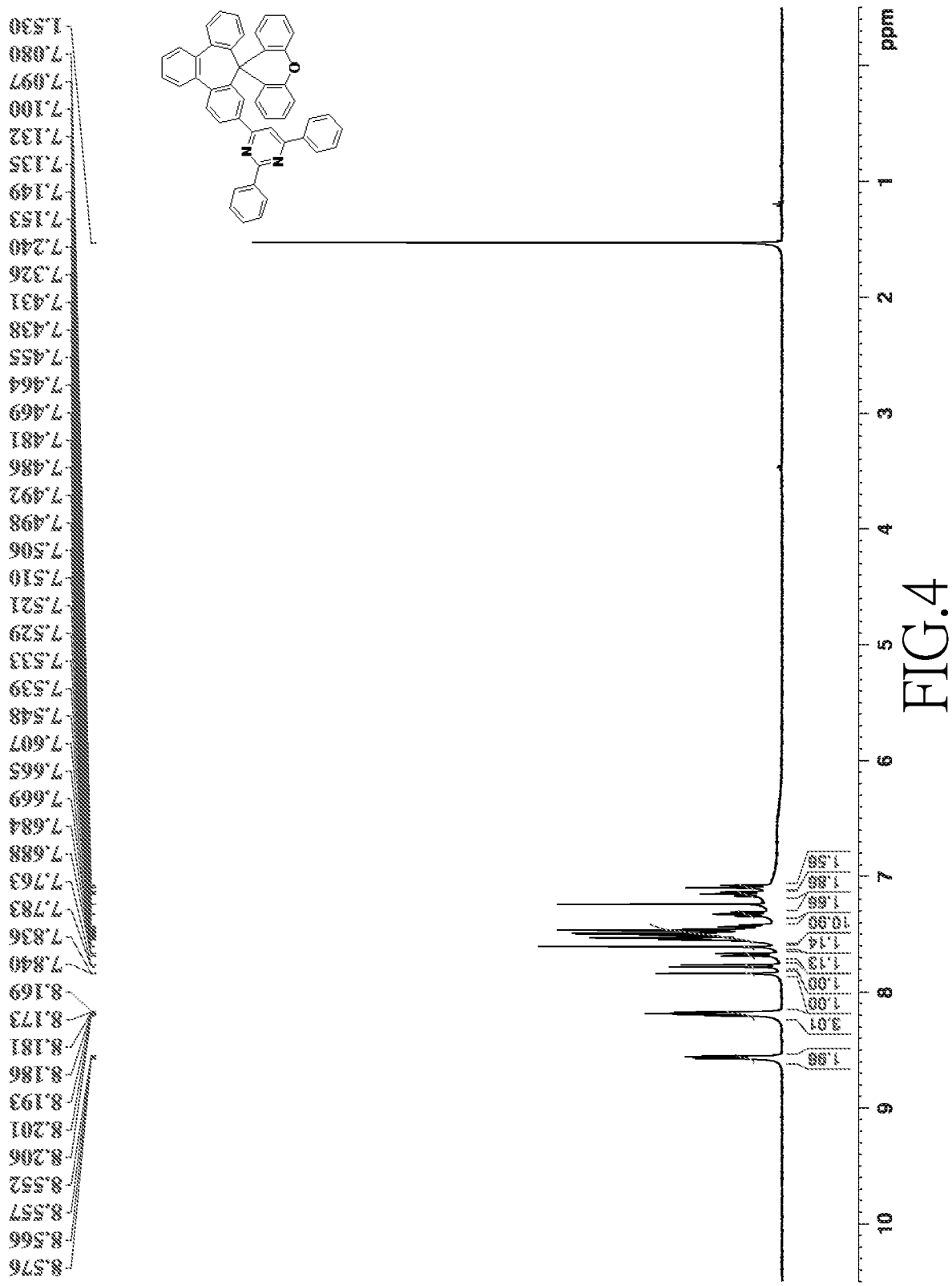
Figure 5:
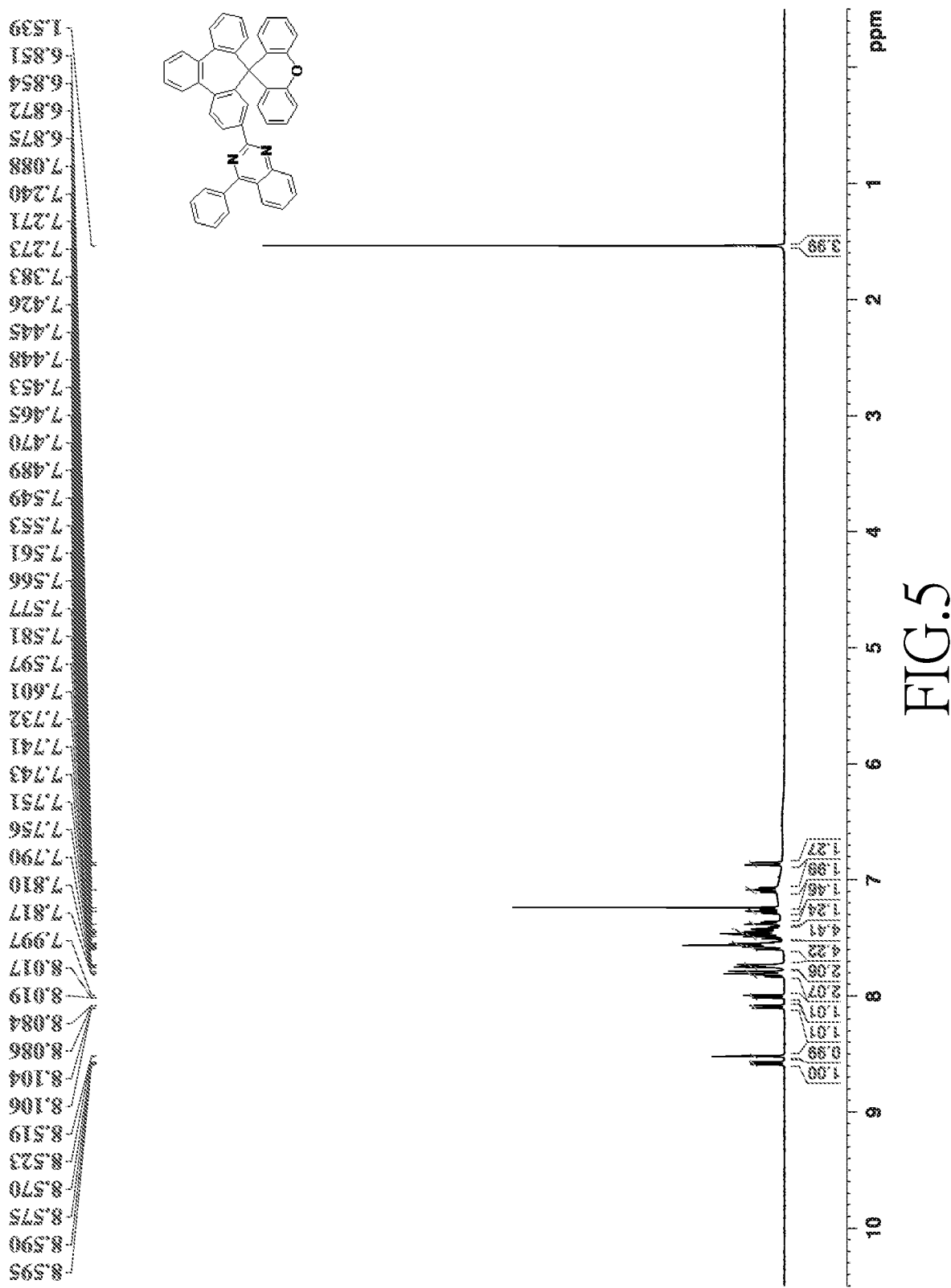
Figure 6:
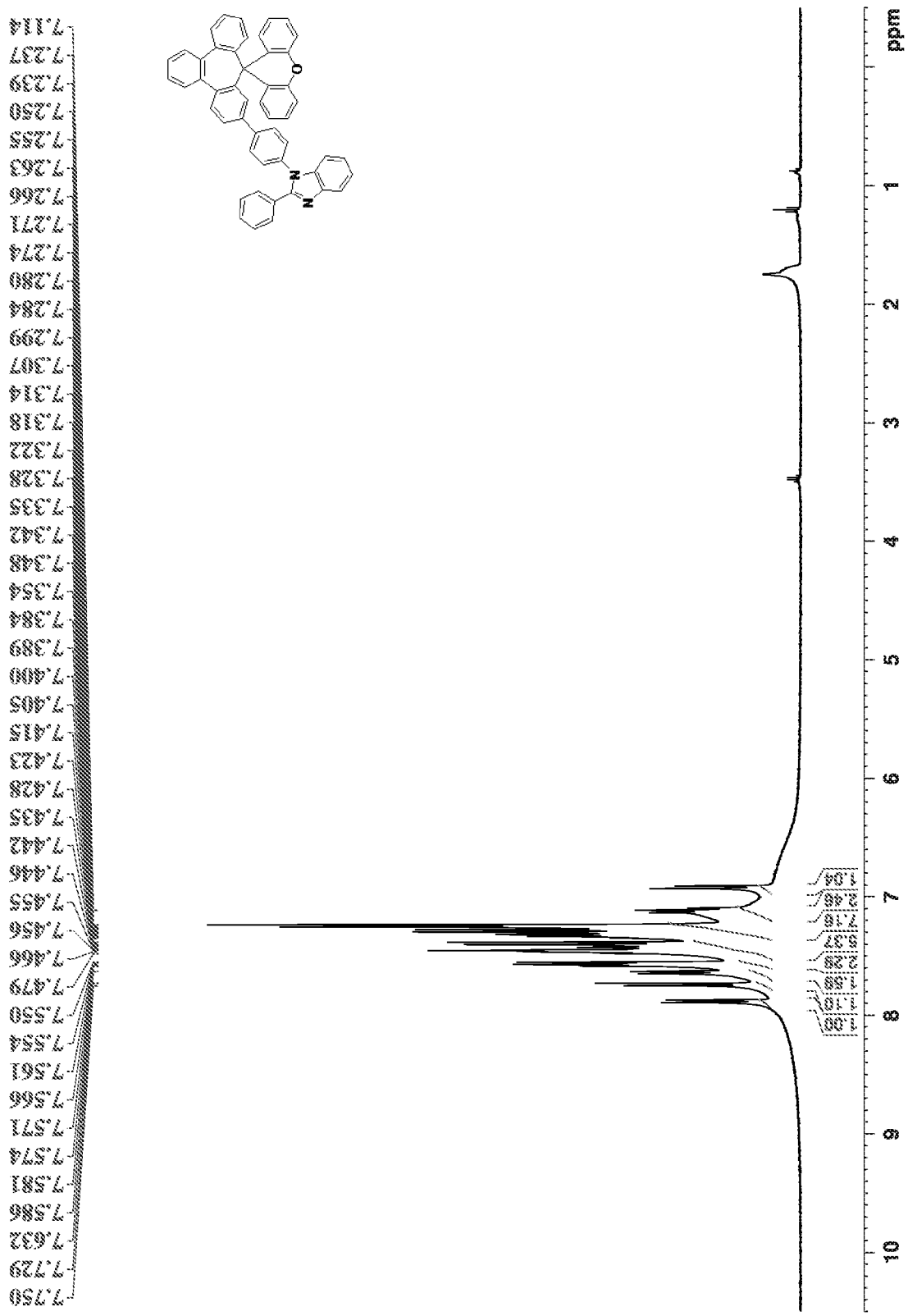
Figure 7:
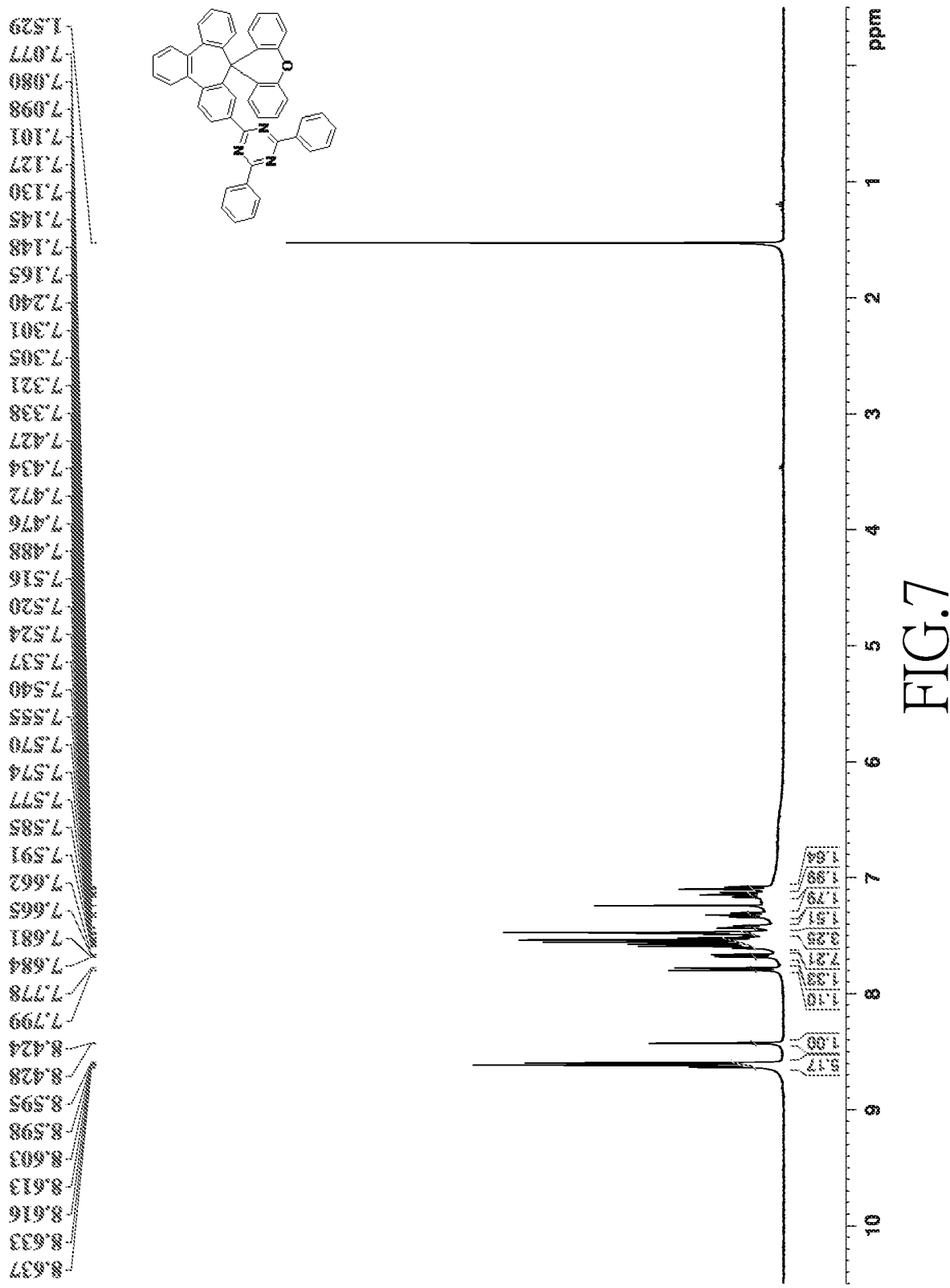
Figure 8:
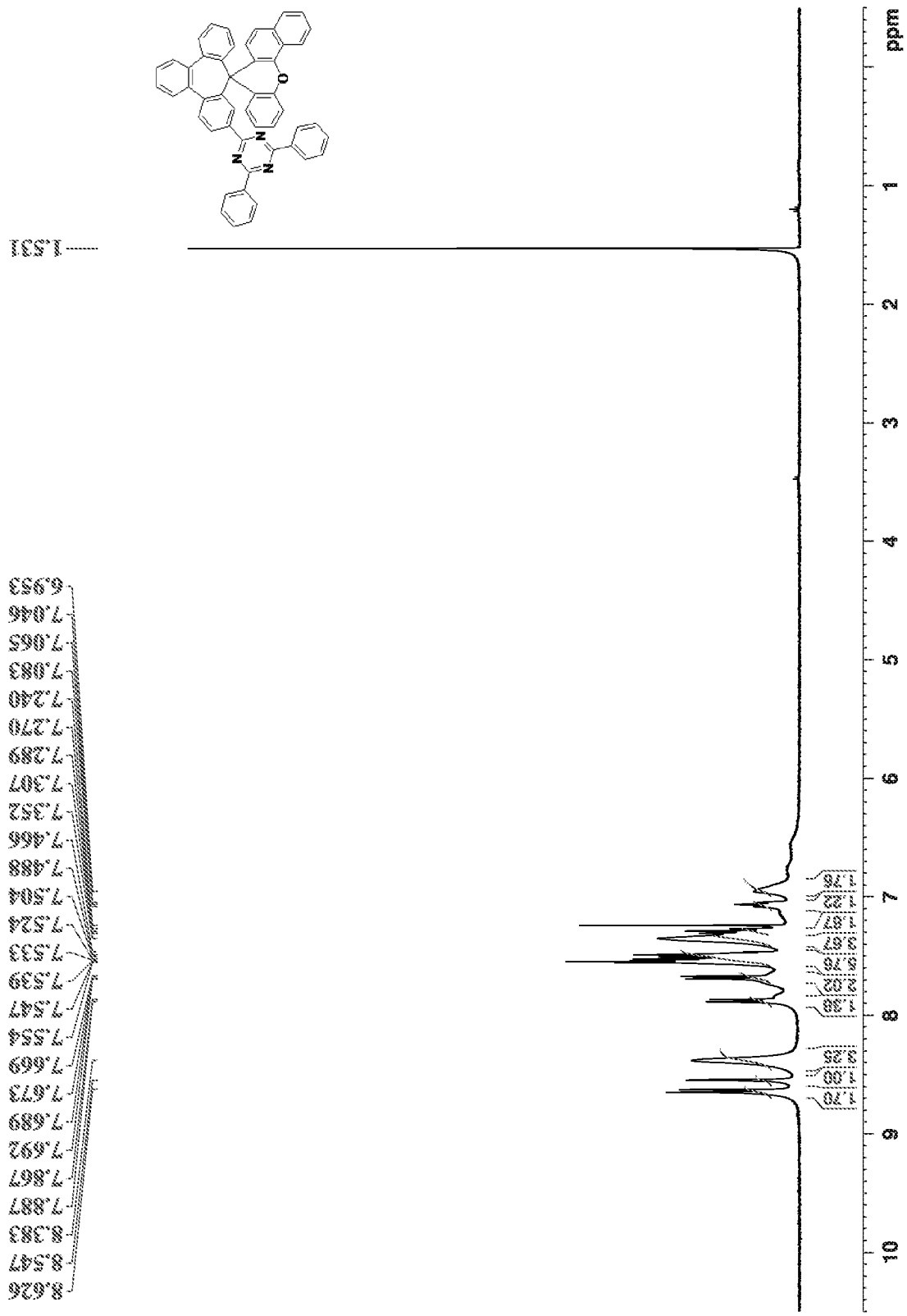
Figure 9:
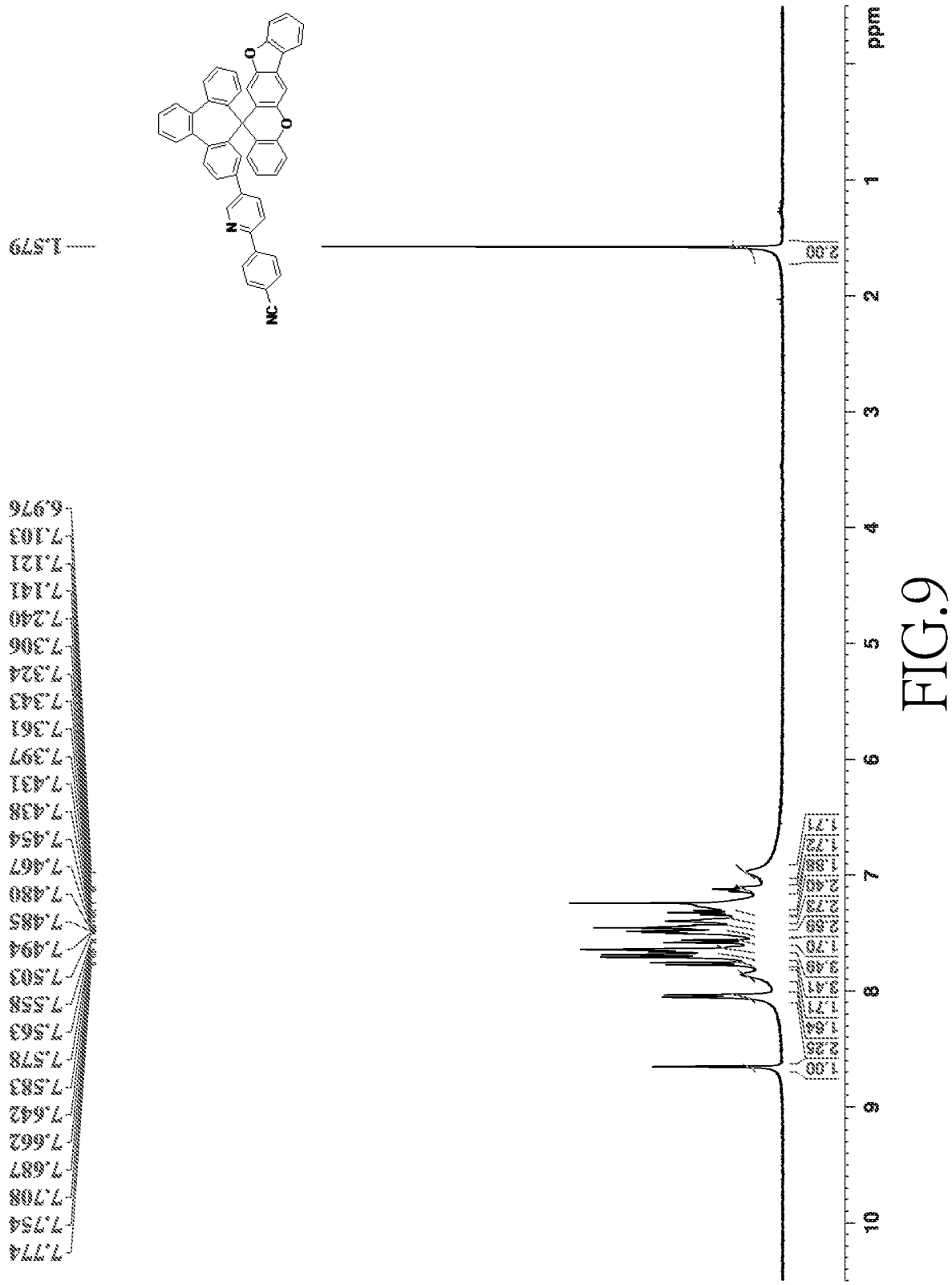
Figure 10:
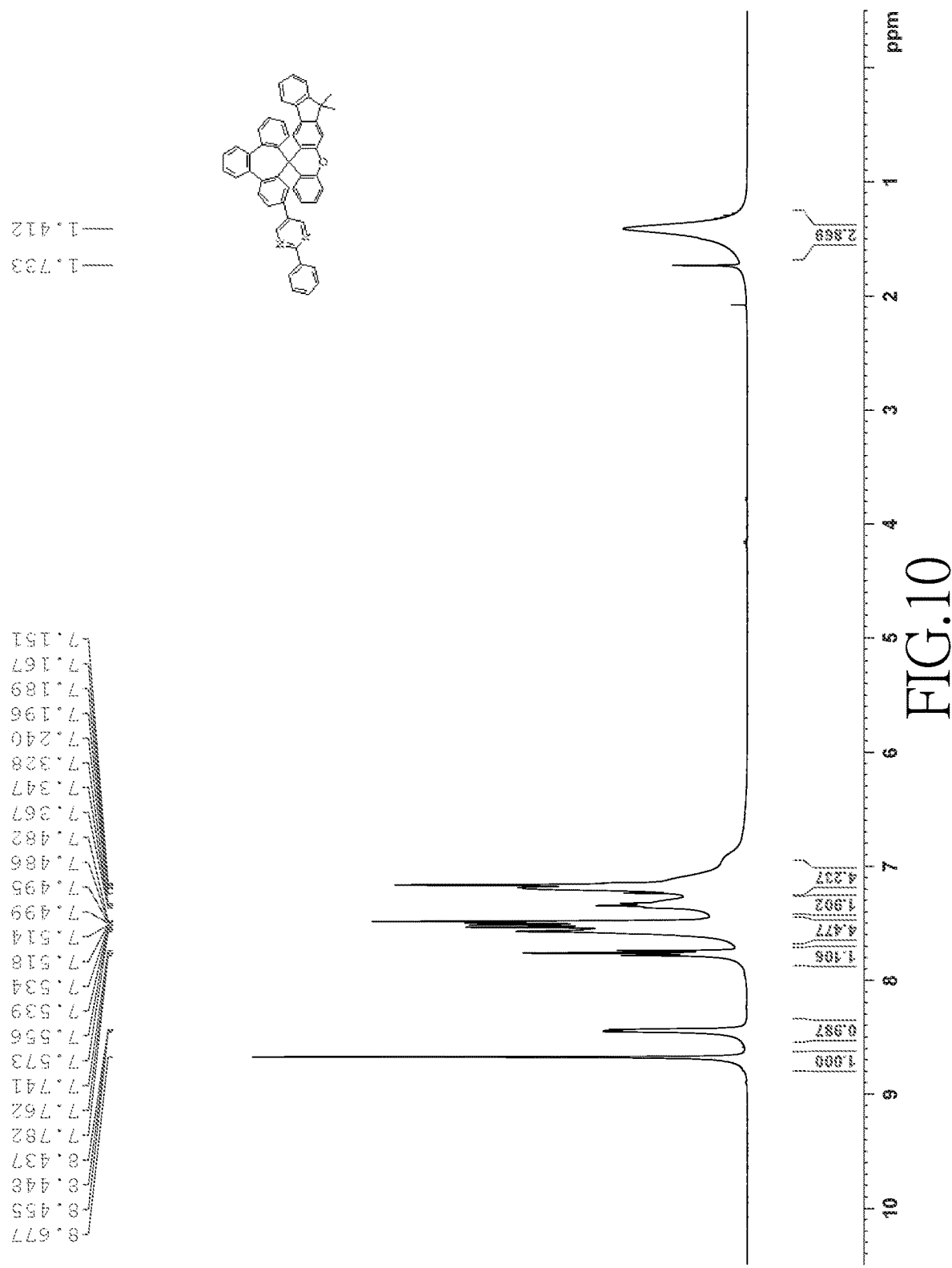
Figure 11:
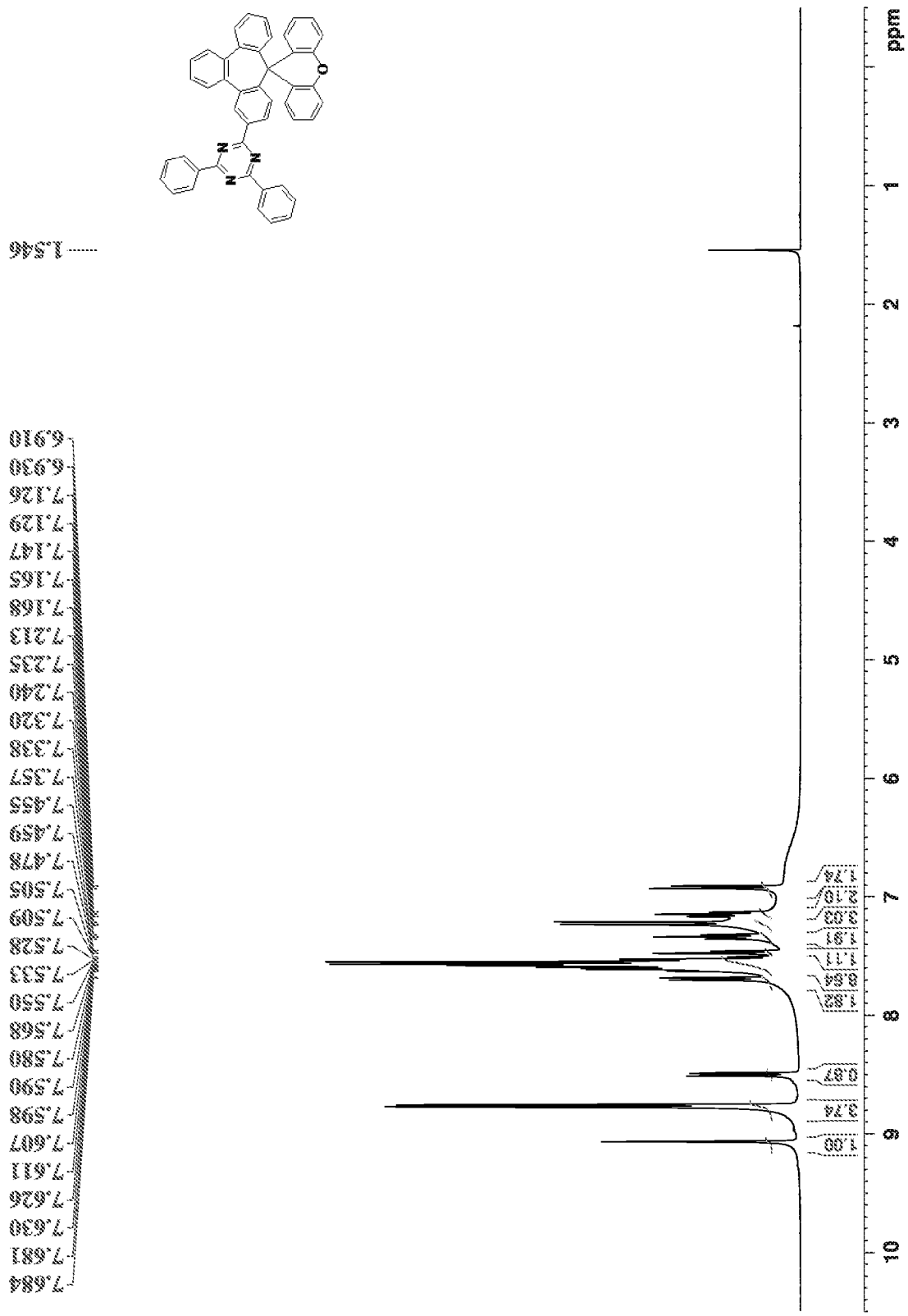
Figure 12:
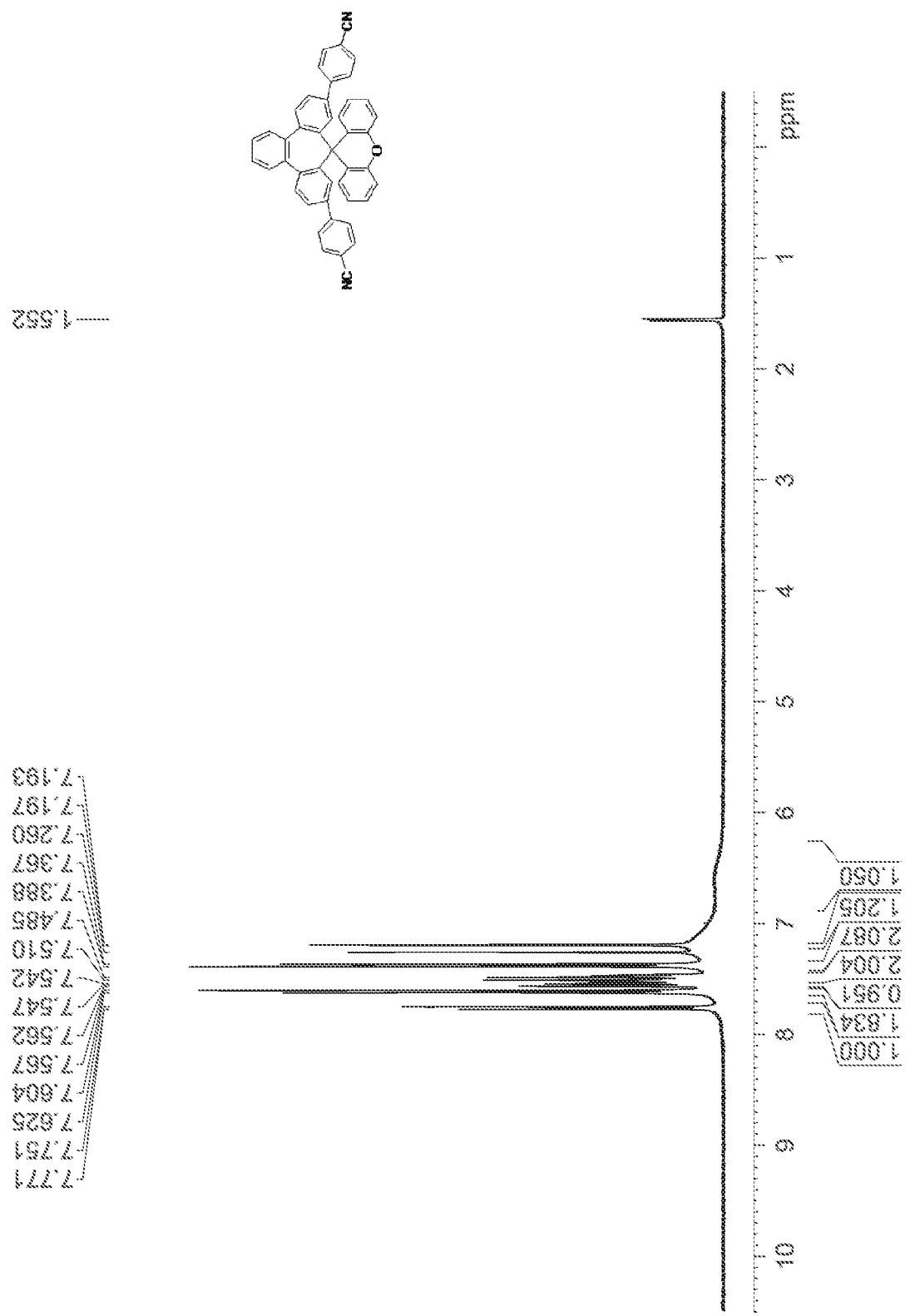
Figure 13:
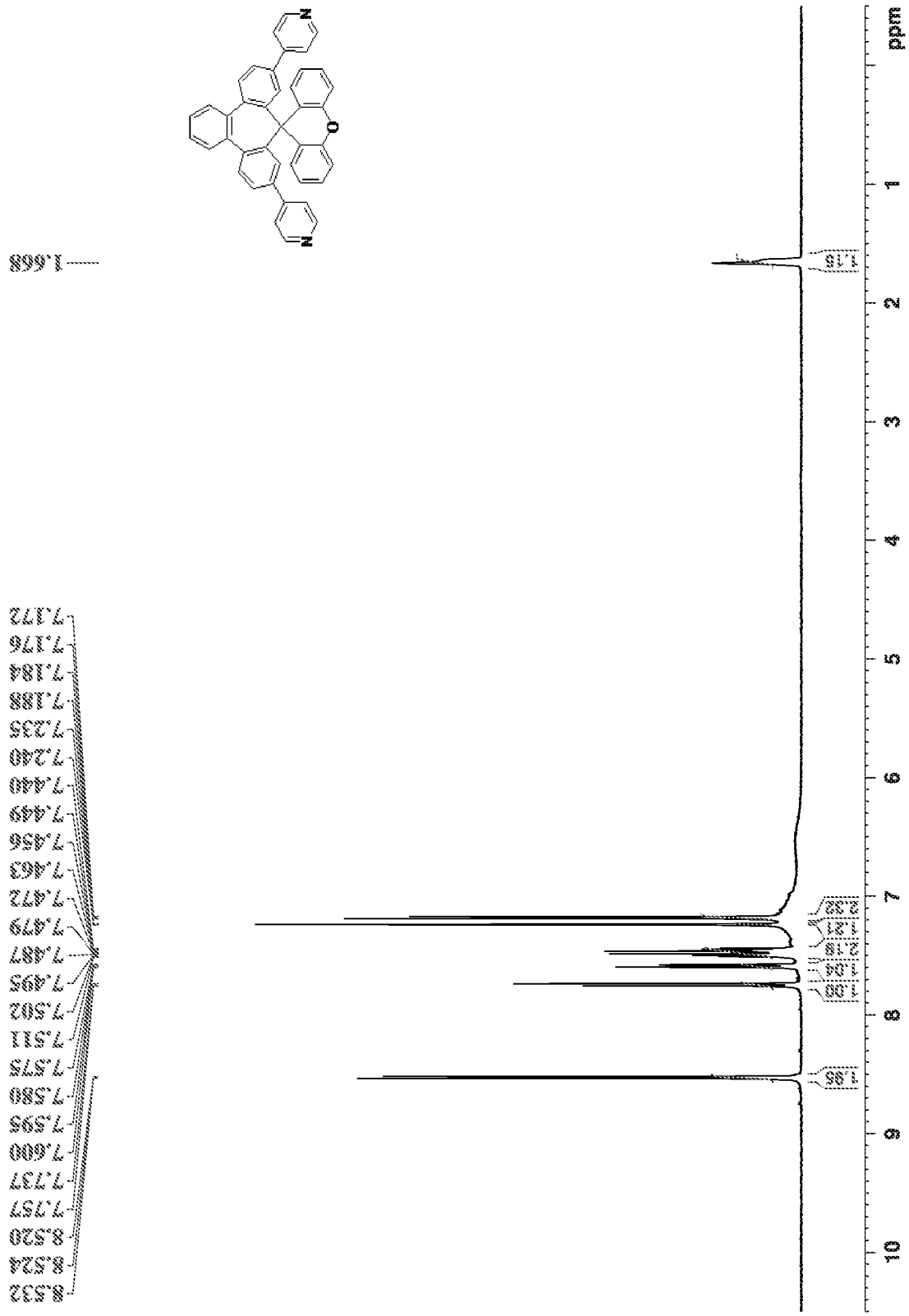
Figure 14:
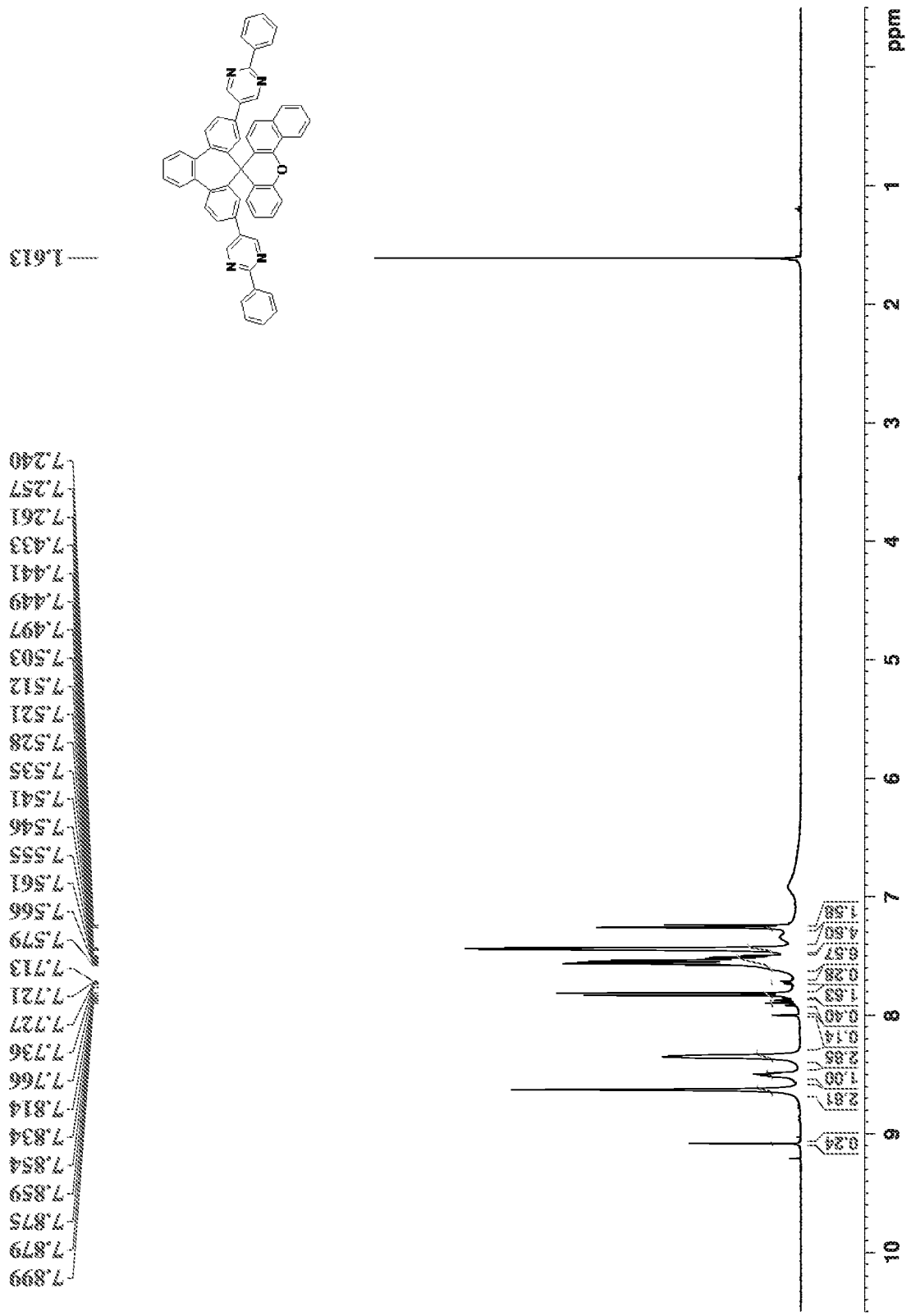
Figure 15:
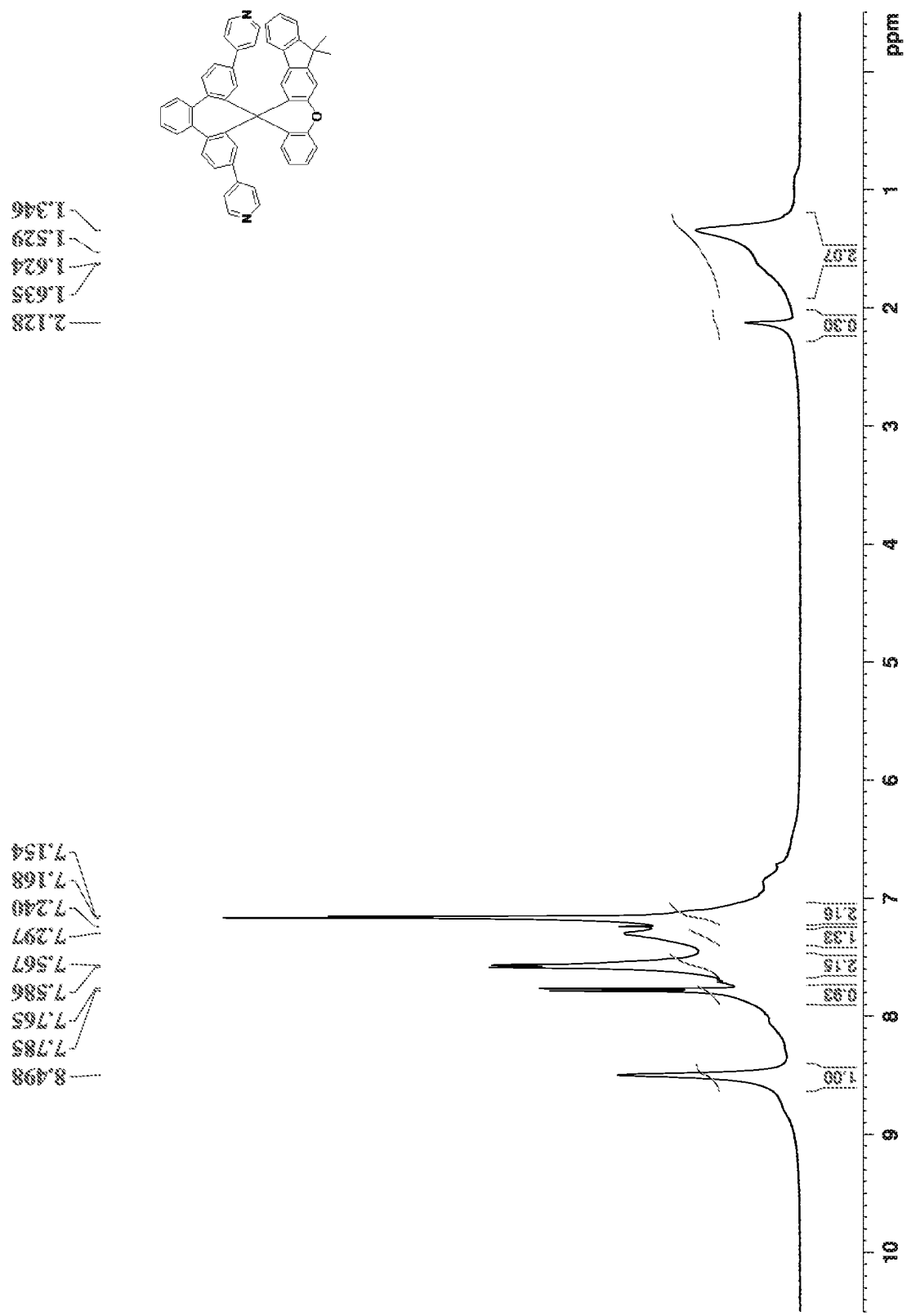
Figure 16:
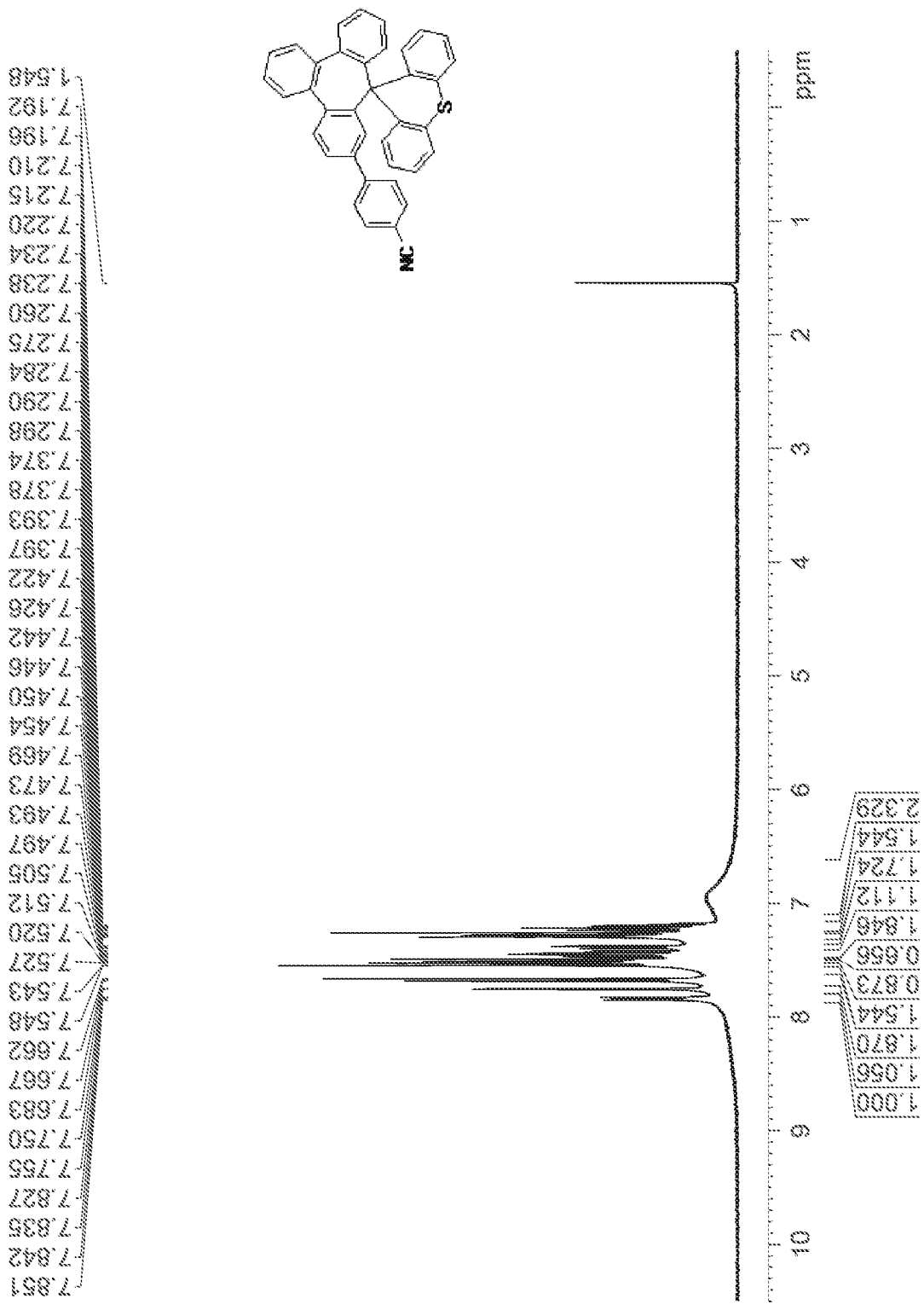
Figure 17:
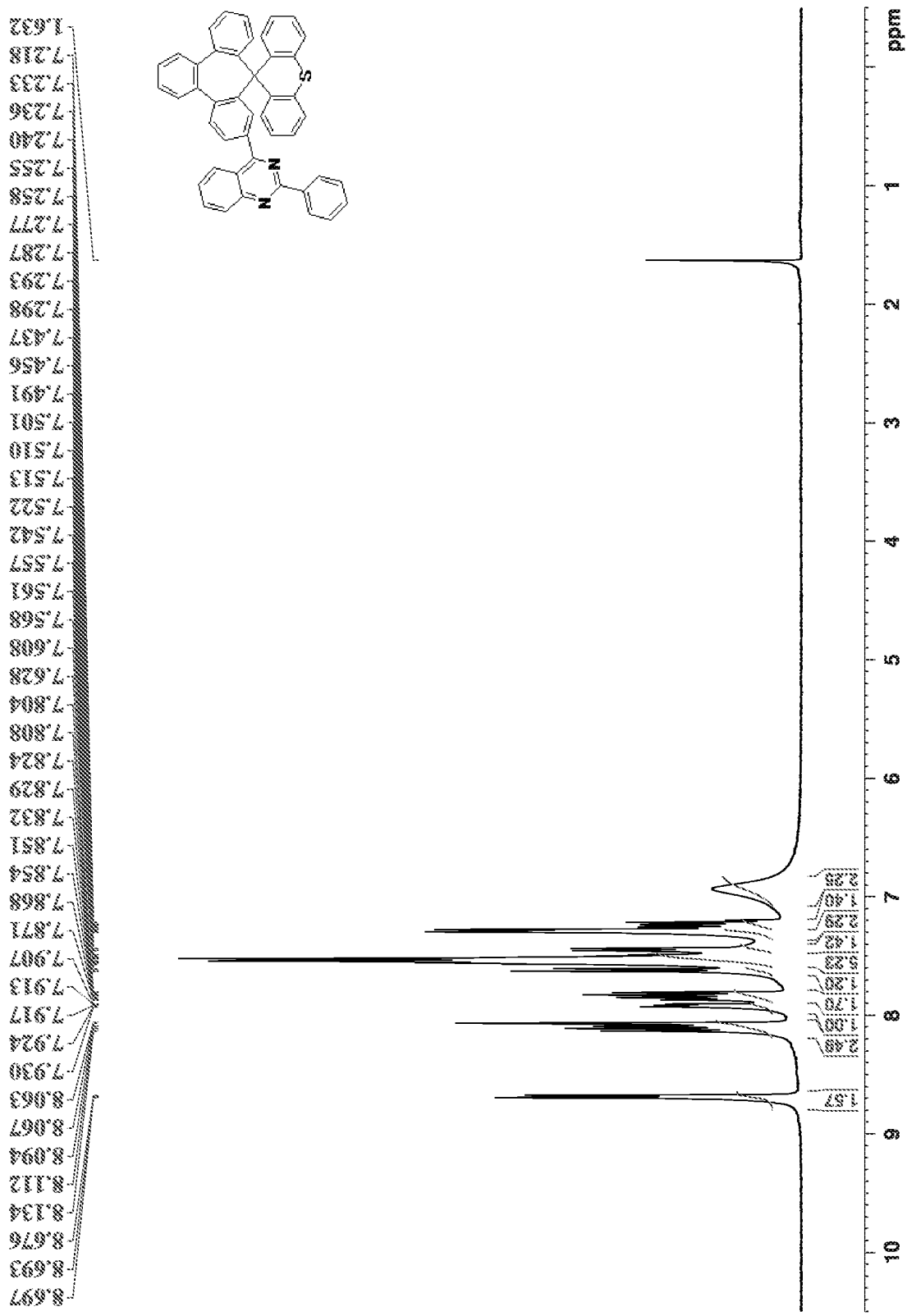
Figure 18:
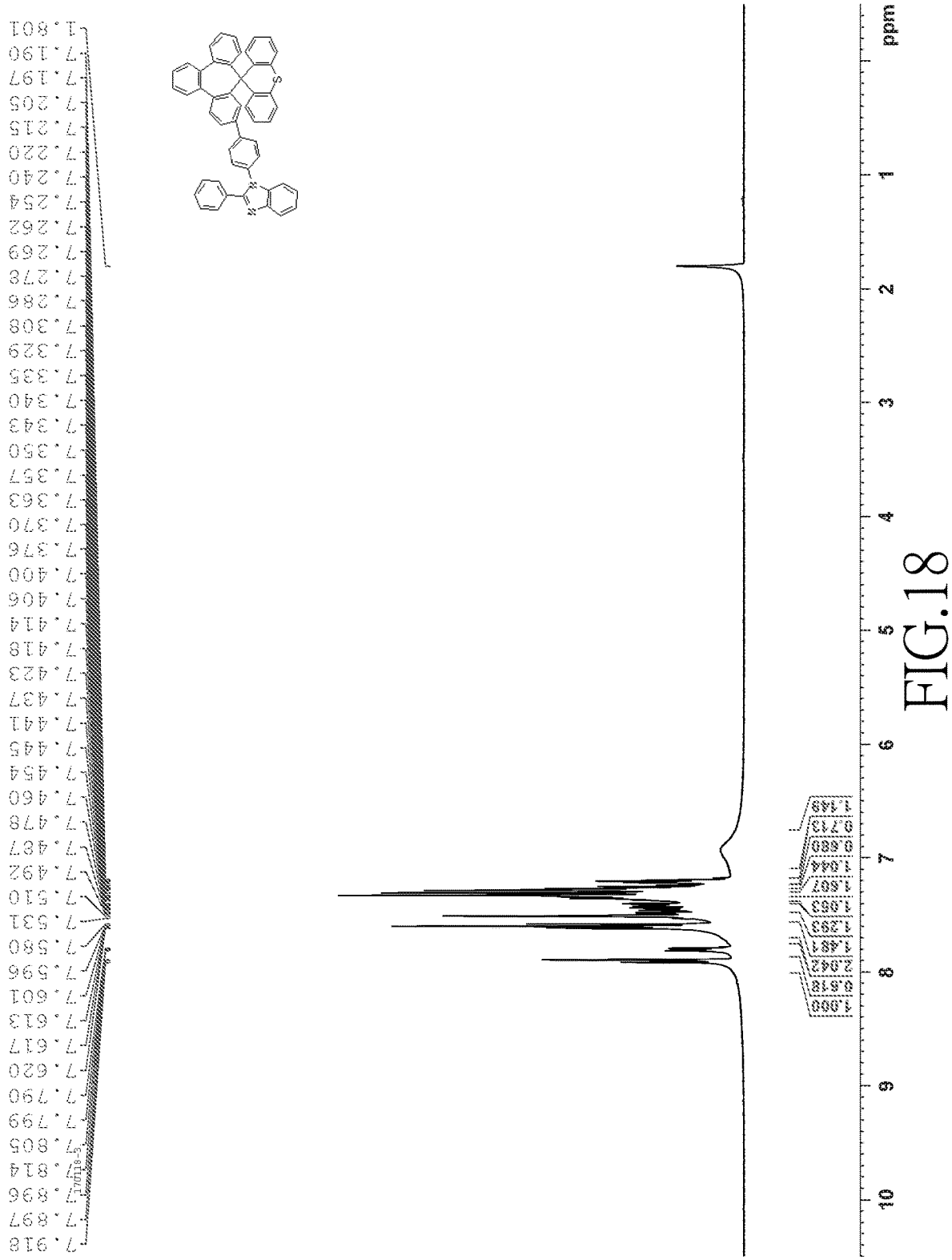
Figure 19:
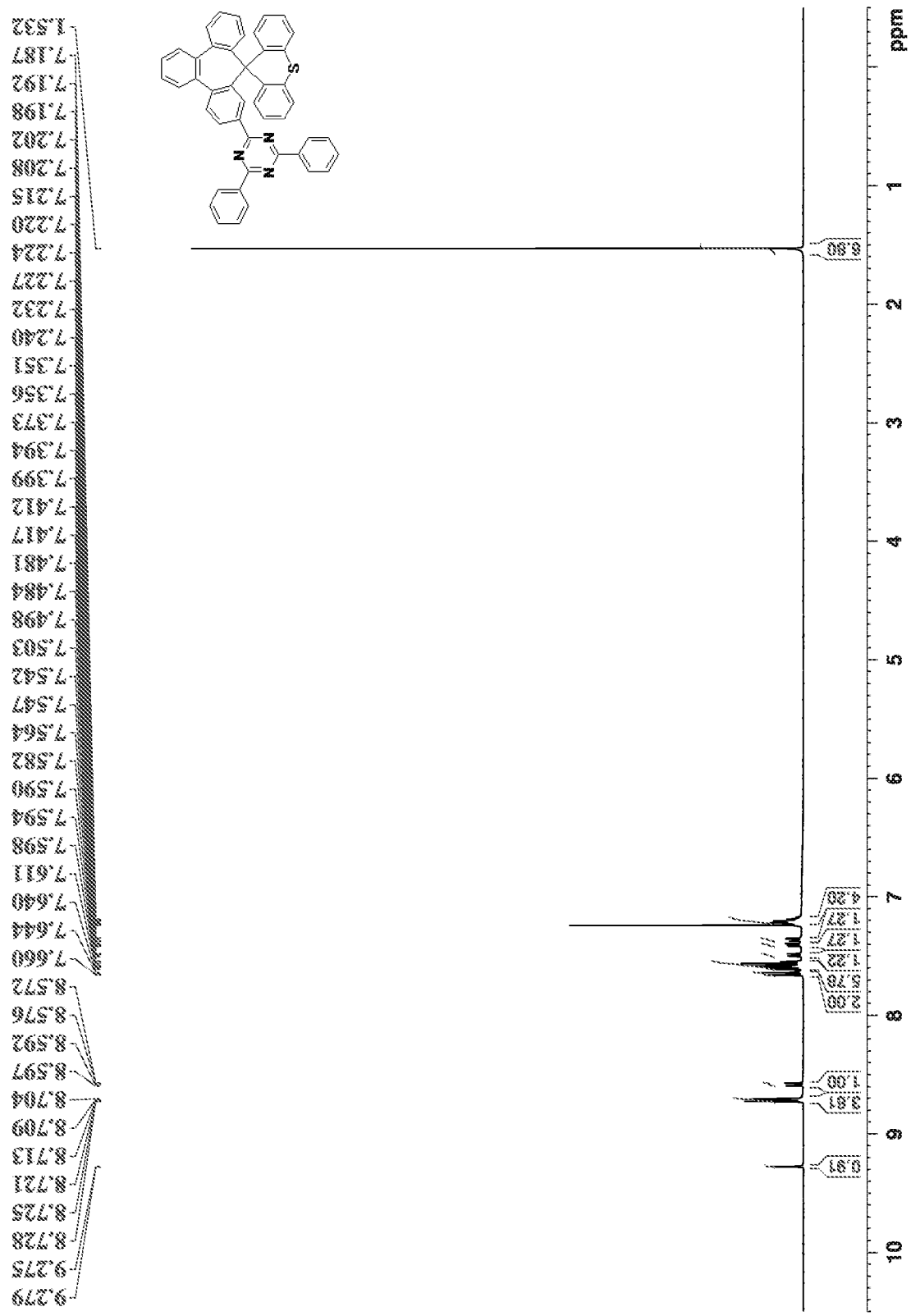
Figure 20:
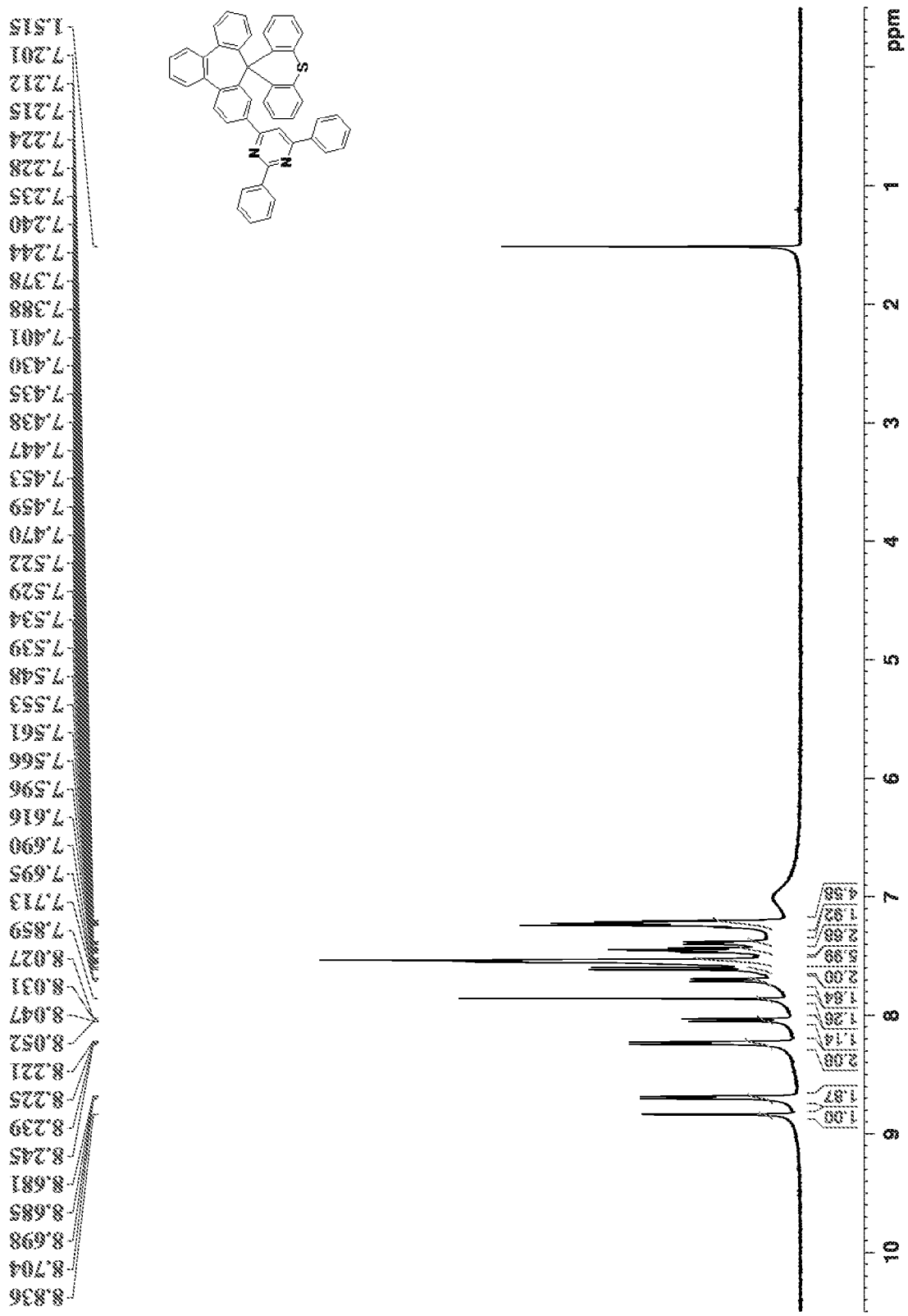
Figure 21:
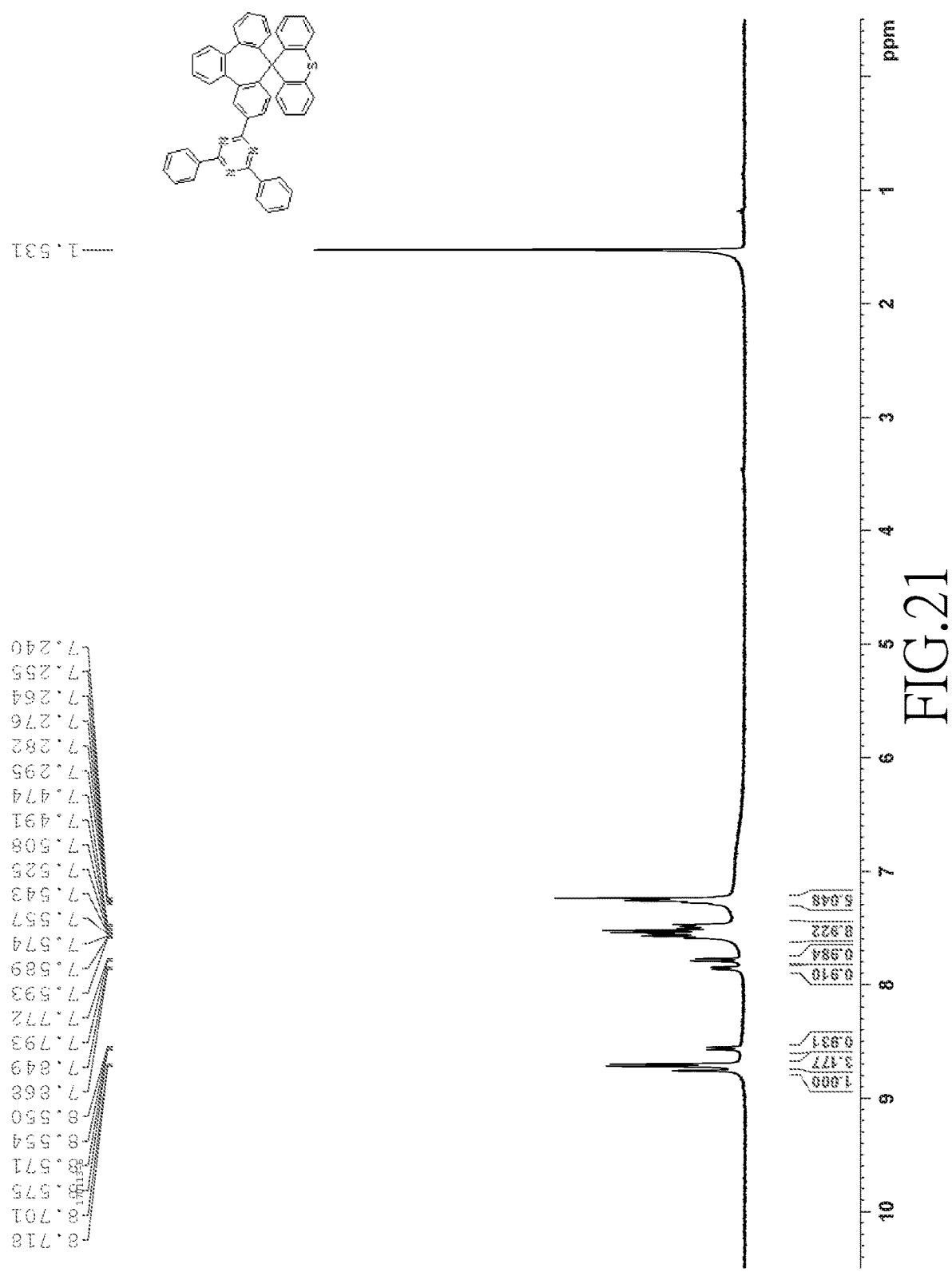
Figure 22:
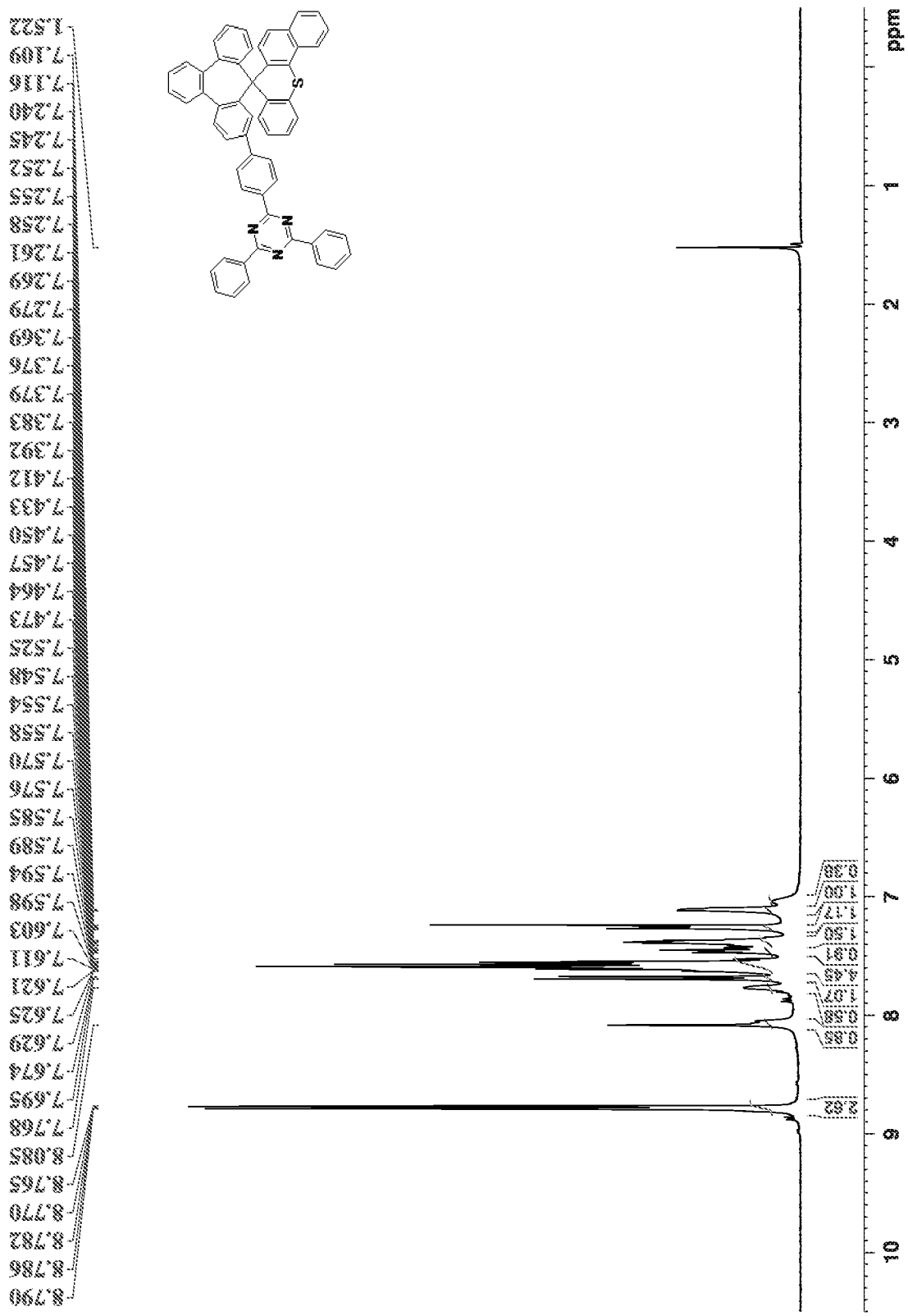
Figure 23:
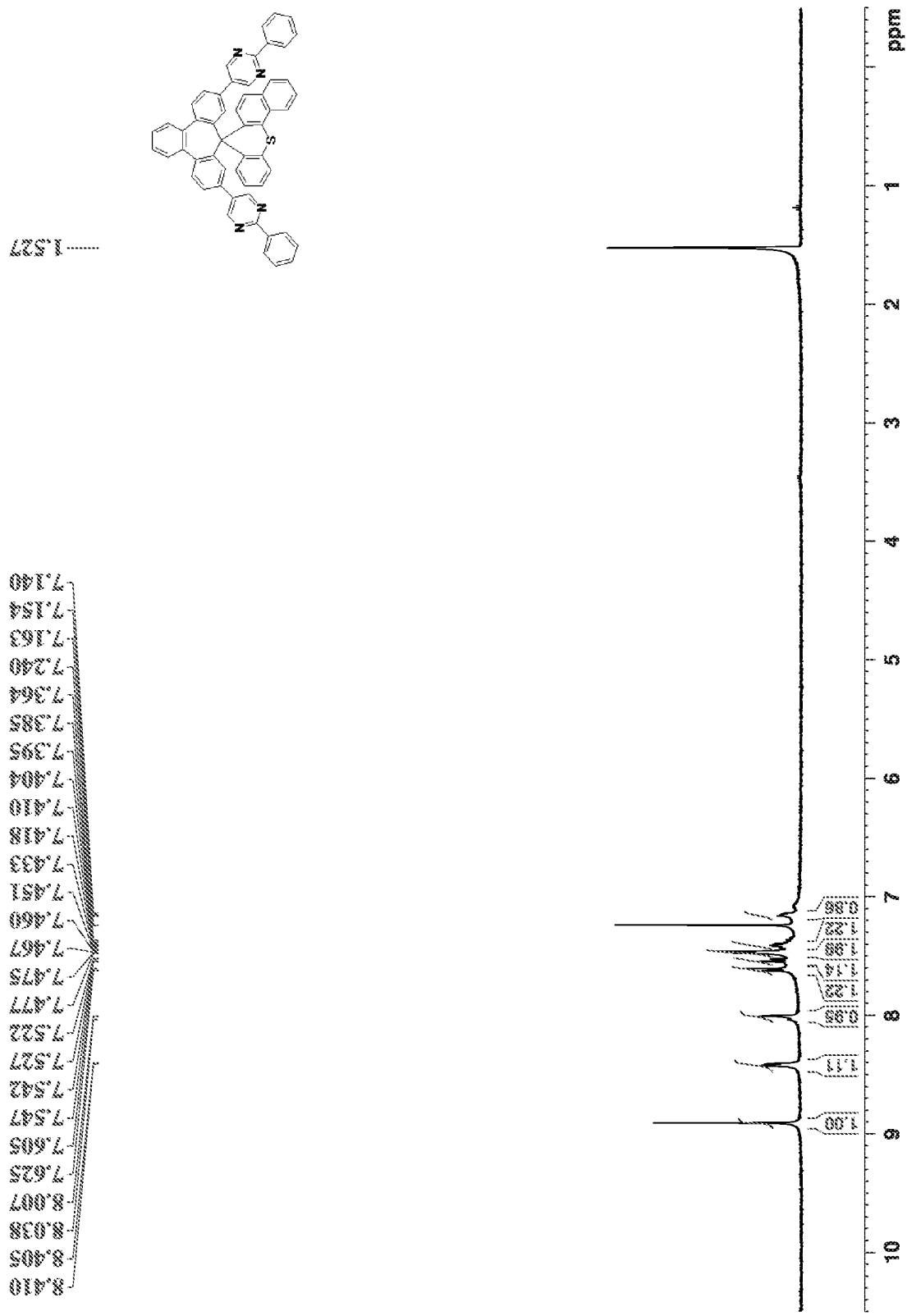
Figure 24:
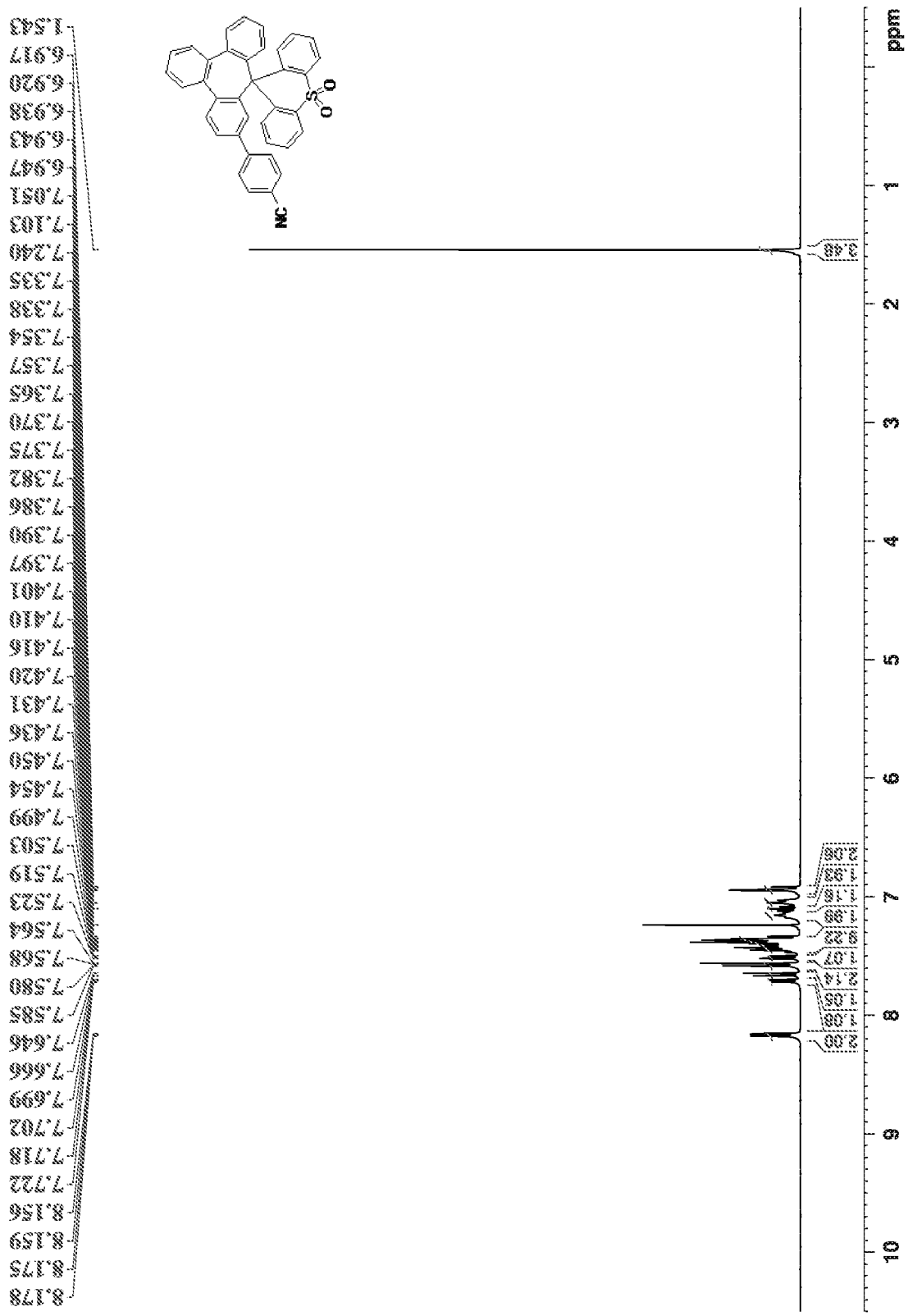
Figure 25:
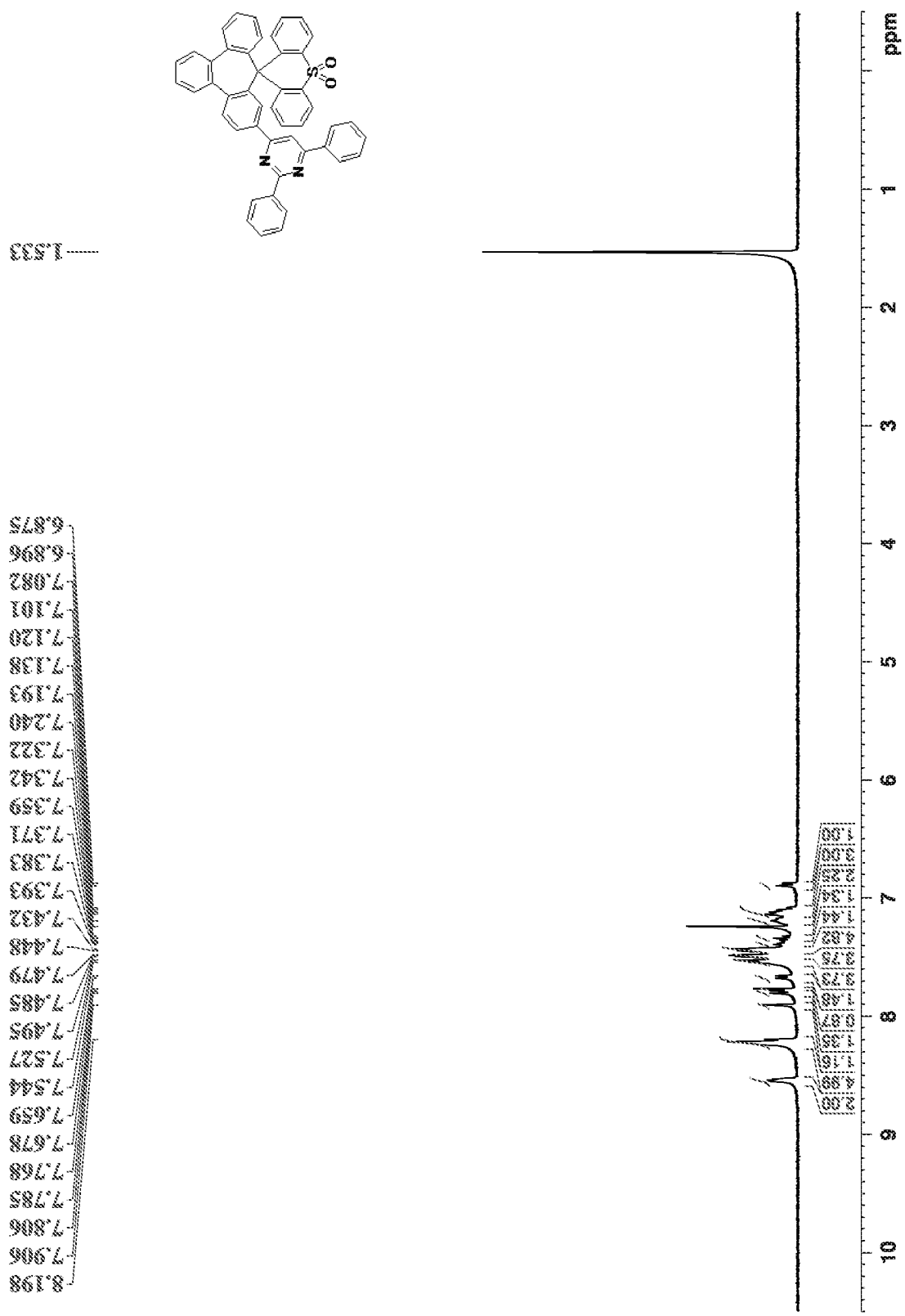
Figure 26:
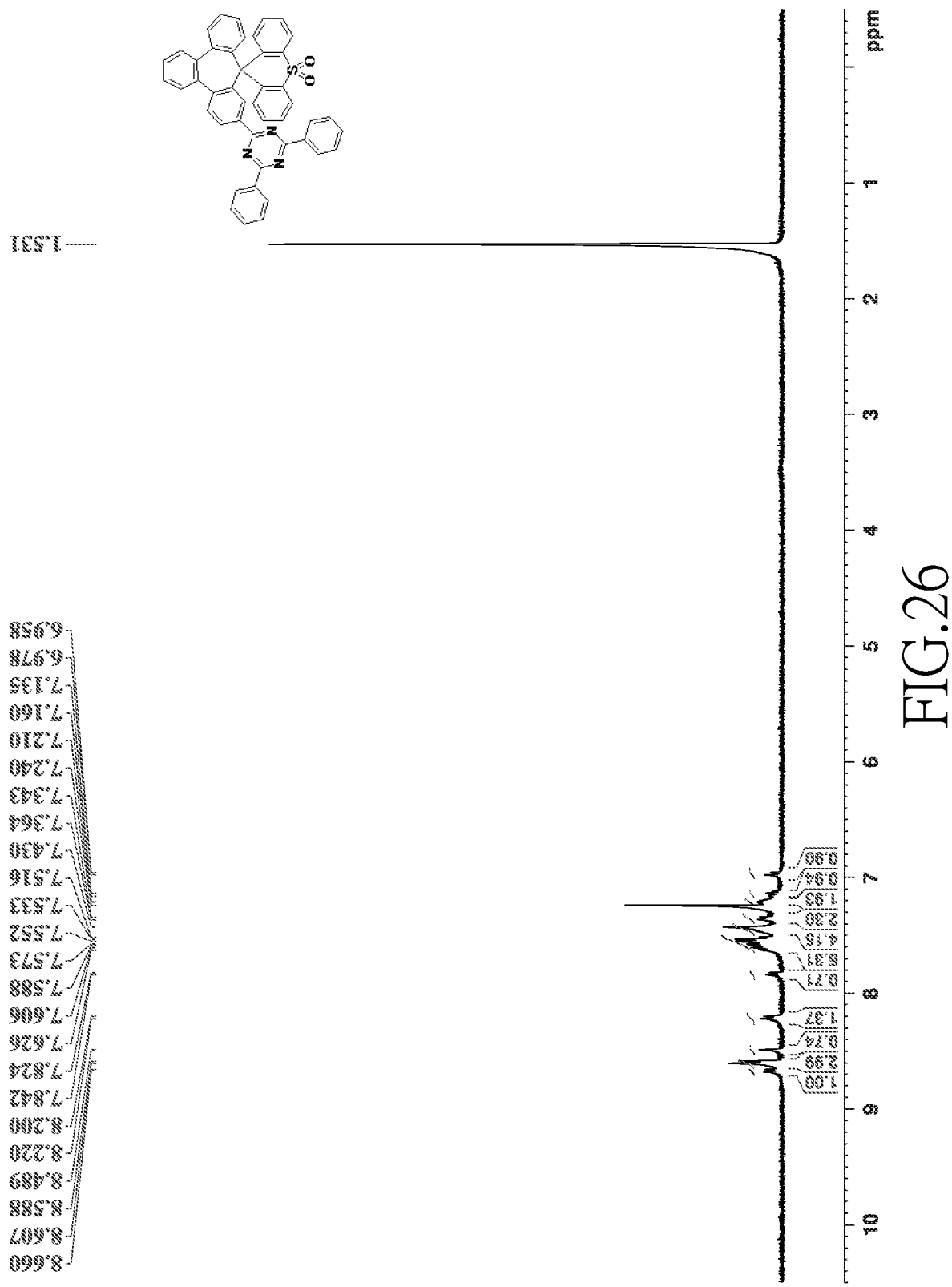
Figure 27:
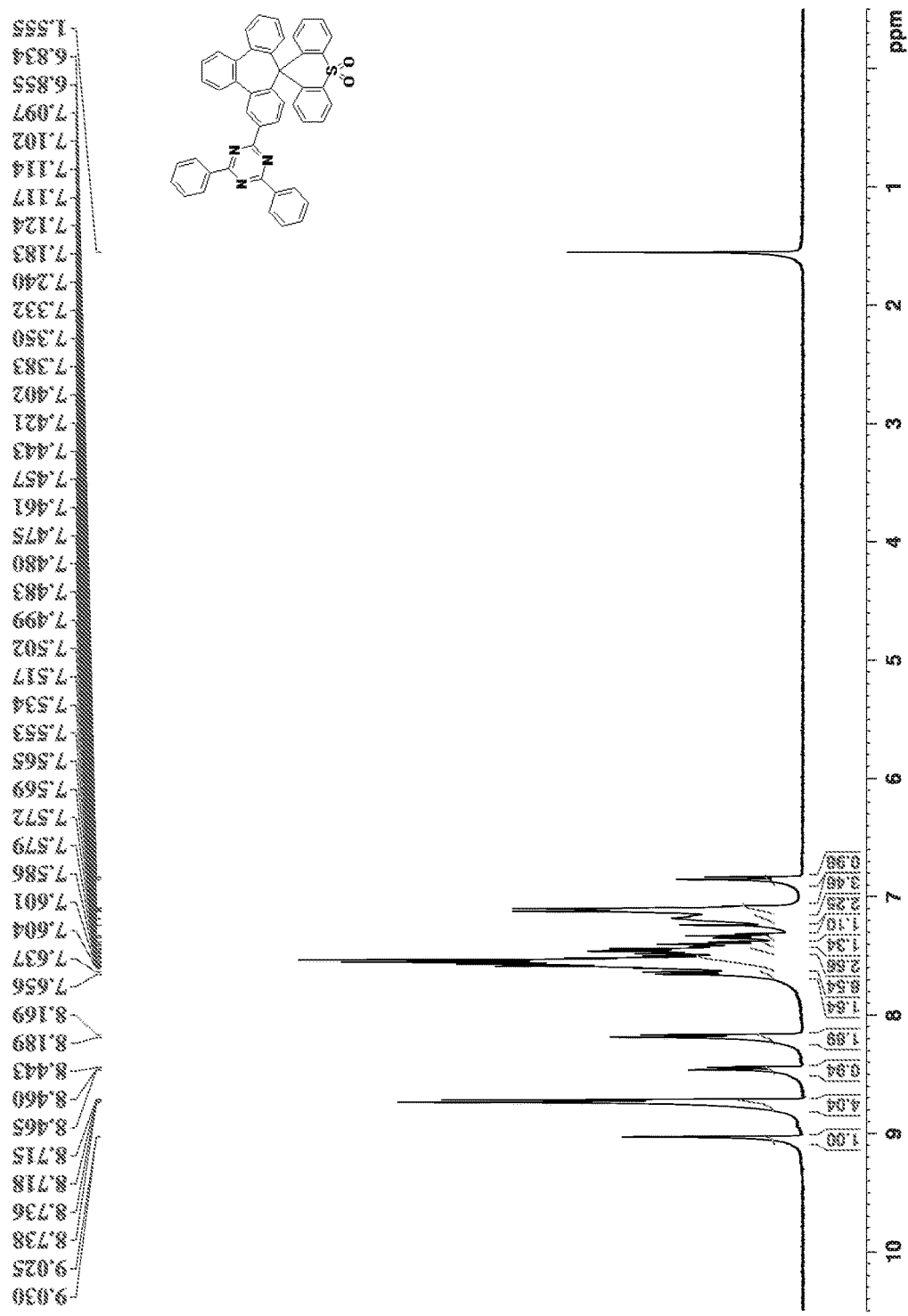

Reactant B and Intermediate Cn or CnB adopted to synthesize Compounds I to XXVI were listed in Table 5. Compounds I to XXVI were identified by H$^1$-NMR and FD-MS, and the chemical structure, yield, formula and mass of each of Compounds I to XXVI were also listed in Table 5. According to FIGS. 2 to 27 and the results of FD-MS, the chemical structure of Compounds I to XXVI were identified as follows.

TABLE 5 reactants and intermediates adopted to prepare Compounds I to XXVI
and their yields, formulae, and FD-MS data.

| Intermediate No. | Reactant No. | Chemical Structure of Claimed Compound | Yield (%) | Formula/ Mass (M+) |
|---|---|---|---|---|
| C1 | B1 | Compound I | 75 | $C_{38}H_{23}NO$/ 509.6 |
| C1 | B4 | Compound II | 80 | $C_{41}H_{26}N_2O$/ 562.66 |
| C1-B | B7 | Compound III | 82 | $C_{47}H_{30}N_2O$ 638.75 |
| C1-B | B6 | Compound IV | 72 | $C_{45}H_{28}N_2O$/ 612.72 |

TABLE 5-continued reactants and intermediates adopted to prepare Compounds I to XXVI and their yields, formulae, and FD-MS data.

| Intermediate No. | Reactant No. | Chemical Structure of Claimed Compound | Yield (%) | Formula/ Mass (M+) |
|---|---|---|---|---|
| C1-B | B10 | Compound V | 87 | $C_{50}H_{32}N_2O$/ 676.80 |
| C1-B | B8 | Compound VI | 93 | $C_{46}H_{29}N_3O$/ 639.74 |
| C4-B | B8 | Compound VII | 79 | $C_{50}H_{31}N_3O$/ 689.80 |

TABLE 5-continued reactants and intermediates adopted to prepare Compounds I to XXVI
and their yields, formulae, and FD-MS data.

| Intermediate No. | Reactant No. | Chemical Structure of Claimed Compound | Yield (%) | Formula/ Mass (M+) |
|---|---|---|---|---|
| C6-B | B11 | Compound VIII | 78 | $C_{49}H_{28}N_2O_2$/ 676.76 |
| C7 | B2 | Compound IX | 88 | $C_{50}H_{34}N_2O$/ 678.82 |
| C2-B | B8 | Compound X | 83 | $C_{46}H_{29}N_3O$/ 639.74 |

TABLE 5-continued
reactants and intermediates adopted to prepare Compounds I to XXVI and their yields, formulae, and FD-MS data.
| | | Claimed Compound | | |
|---|---|---|---|---|
| Intermediate No. | Reactant No. | Chemical Structure of Claimed Compound | Yield (%) | Formula/ Mass (M+) |
| C3 | B1 | 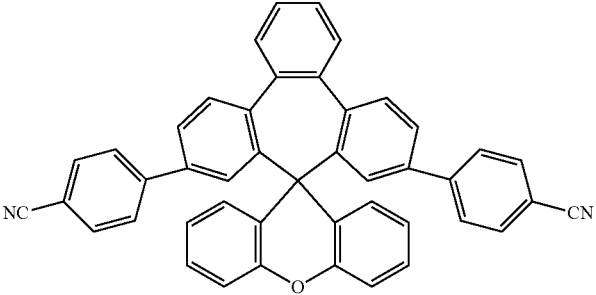 [SMILES: N#Cc1ccc(-c2ccc3c(c2)C2(c4ccccc4Oc4ccccc42)c2cc(-c4ccc(C#N)cc4)ccc2-c2ccccc2-3)cc1]      Compound XI | 82 | $C_{45}H_{26}N_2O$/ 610.70 |
| C3 | B3 | 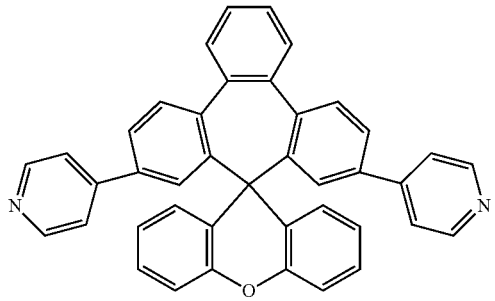 [SMILES: c1ccc2c(c1)Oc1ccccc1C21c2cc(-c3ccncc3)ccc2-c2ccccc2-c2ccc(-c3ccncc3)cc21]      Compound XII | 80 | $C_{41}H_{26}N_2O$/ 562.66 |
| C5 | B2 | 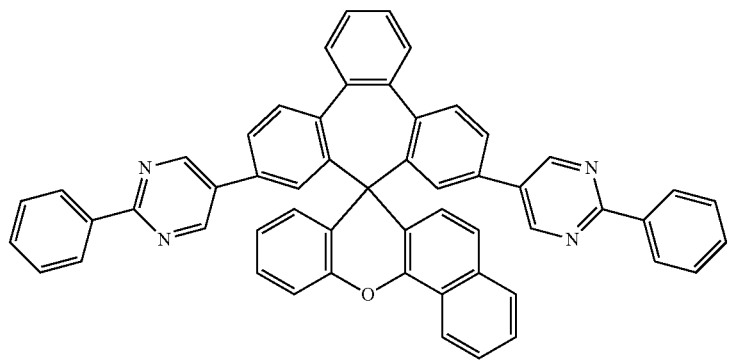 [SMILES: c1ccc(-c2ncc(-c3ccc4c(c3)C3(c5ccccc5Oc5c3ccc3ccccc53)c3cc(-c5cnc(-c6ccccc6)nc5)ccc3-c3ccccc3-4)cn2)cc1]      Compound XIII | 62 | $C_{55}H_{34}N_4O$/ 766.88 |

TABLE 5-continued reactants and intermediates adopted to prepare Compounds I to XXVI
and their yields, formulae, and FD-MS data.

| | | Claimed Compound | | |
|---|---|---|---|---|
| Intermediate No. | Reactant No. | Chemical Structure of Claimed Compound | Yield (%) | Formula/ Mass (M+) |
| C8 | B3 | Compound XIV | 80 | $C_{50}H_{34}N_2O$/ 678.82 |
| C9 | B1 | Compound XV | 86 | $C_{38}H_{23}NS$/ 525.66 |
| C9-B | B5 | Compound XVI | 91 | $C_{45}H_{28}N_2S$/ 628.78 |

TABLE 5-continued reactants and intermediates adopted to prepare Compounds I to XXVI
and their yields, formulae, and FD-MS data.

| Intermediate No. | Reactant No. | Chemical Structure of Claimed Compound | Yield (%) | Formula/ Mass (M+) |
|---|---|---|---|---|
| C9-B | B10 | Compound XVII | 71 | $C_{50}H_{32}N_2S$/ 692.87 |
| C9-B | B8 | Compound XVIII | 62 | $C_{46}H_{29}N_3S$/ 655.81 |
| C9-B | B7 | Compound XIX | 76 | $C_{47}H_{30}N_2S$/ 654.82 |

TABLE 5-continued reactants and intermediates adopted to prepare Compounds I to XXVI
and their yields, formulae, and FD-MS data.

| Intermediate No. | Reactant No. | Chemical Structure of Claimed Compound | Yield (%) | Formula/ Mass (M+) |
|---|---|---|---|---|
| C10-B | B8 | Compound XX | 92 | $C_{46}H_{29}N_3S$/ 655.81 |
| C11-B | B9 | Compound XXI | 83 | $C_{56}H_{35}N_3S$/ 781.96 |
| C12 | B2 | Compound XXII | 58 | $C_{55}H_{34}N_4S$/ 782.95 |

TABLE 5-continued reactants and intermediates adopted to prepare Compounds I to XXVI
and their yields, formulae, and FD-MS data.

| Intermediate No. | Reactant No. | Chemical Structure of Claimed Compound | Yield (%) | Formula/ Mass (M+) |
|---|---|---|---|---|
| C13 | B1 | Compound XXIII | 80 | $C_{38}H_{23}NO_2S$ / 557.66 |
| C13-B | B7 | Compound XXIV | 76 | $C_{47}H_{30}N_2O_2S$ / 686.82 |
| C13-B | B8 | Compound XXV | 77 | $C_{46}H_{29}N_3O_2S$ / 687.81 |

TABLE 5-continued reactants and intermediates adopted to prepare Compounds I to XXVI
and their yields, formulae, and FD-MS data.

| Intermediate No. | Reactant No. | Chemical Structure of Claimed Compound | Yield (%) | Formula/ Mass (M+) |
|---|---|---|---|---|
| C14-B | B8 | 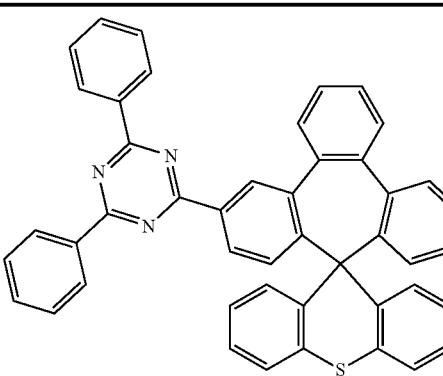<br>Compound XXVI | 86 | $C_{46}H_{29}N_3O_2S$/ 687.81 |

Modifications of Compounds I to XXVI

In addition to the Compounds I to XXVI, one person skilled in the art can react any Intermediate C, i.e., the foresaid Intermediate Cn or Cn-B, with any Reactant B through a reaction mechanism similar to Scheme I to synthesize other desired claimed novel compounds.

Preparation of OLED Devices

A glass substrate coated with an ITO layer (abbreviated as ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 33. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and was a dopant for forming HIL-2; HI-2 was a material for forming HIL-2; HT-1 and HT-2 were materials for forming HTL-1 and HTL-2; conventional ET and novel compounds of the present invention were materials for forming ETL; Liq was a dopant for forming ETL and a material for forming EIL. RH/GH/BH were host material for forming REL/GEL/BEL, and RD/GD/BD were dopants for forming REL/GEL/BEL. The main difference of the OLEDs between Example and Comparative Example was that the ETL of OLED in following comparative examples was made of BCP but the ETL of OLED in following examples was made of the novel compounds of the present invention were listed in Table 5. The detailed chemical structures of foresaid commercial materials were listed in Table 6.

TABLE 6 chemical structures of commercial materials for OLED devices.

HAT

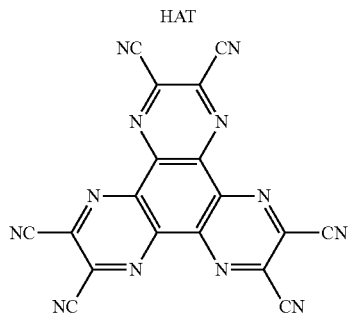

TABLE 6-continued
chemical structures of commercial materials for OLED devices.
HI-2
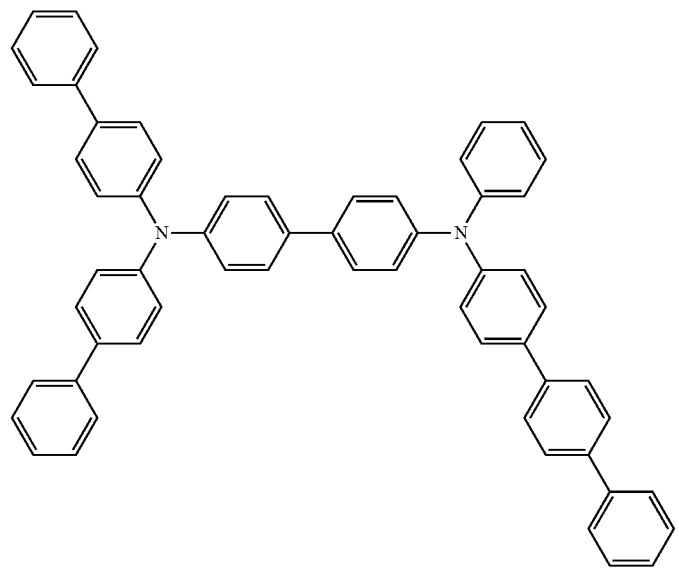 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
HT-1
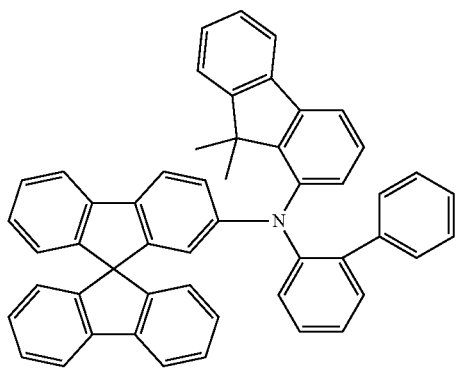 [SMILES: CC1(C)c2ccccc2-c2cccc(N(c3ccc4c(c3)C3(c5ccccc5-c5ccccc53)c3ccccc3-4)c3ccccc3-c3ccccc3)c21]
HT-2
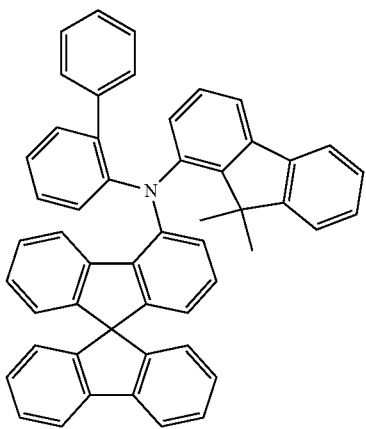 [SMILES: CC1(C)c2ccccc2-c2cccc(N(c3ccccc3-c3ccccc3)c3cccc4c3-c3ccccc3C43c4ccccc4-c4ccccc43)c21]

TABLE 6-continued
chemical structures of commercial materials for OLED devices.
BH
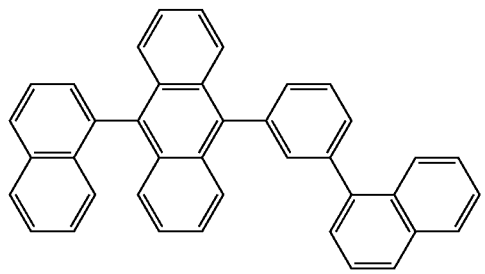 [SMILES: c1cc(-c2cccc3ccccc23)cc(-c2c3ccccc3c(-c3cccc4ccccc34)c3ccccc23)c1]
BD
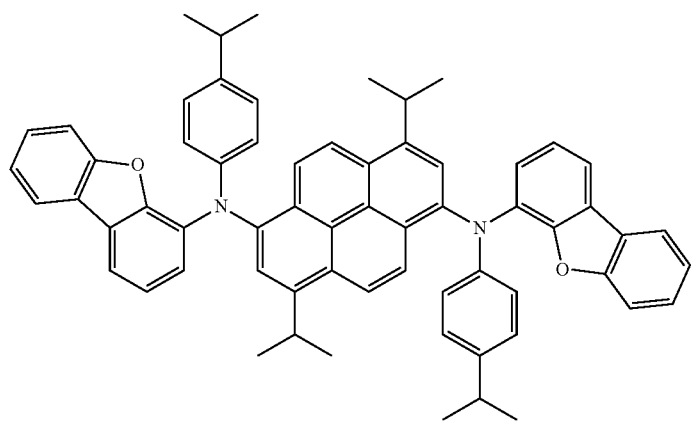 [SMILES: CC(C)c1ccc(N(c2cc(C(C)C)c3ccc4c(N(c5ccc(C(C)C)cc5)c5cccc6c5oc5ccccc56)cc(C(C)C)c5ccc2c3c54)c2cccc3c2oc2ccccc23)cc1]
GH
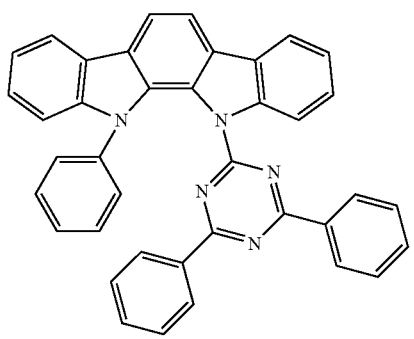 [SMILES: c1ccc(-c2nc(-c3ccccc3)nc(-n3c4ccccc4c4ccc5c6ccccc6n(-c6ccccc6)c5c43)n2)cc1]
GD
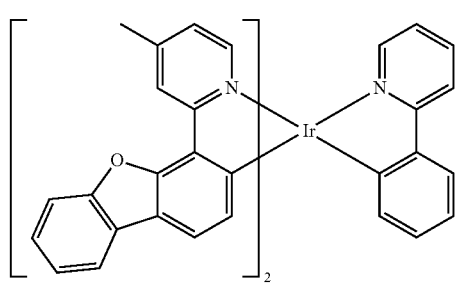

TABLE 6-continued
chemical structures of commercial materials for OLED devices.
RH
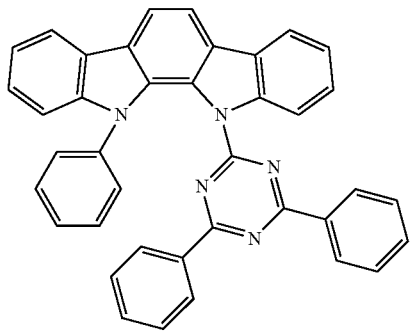 [SMILES: c1ccc(-c2nc(-c3ccccc3)nc(-n3c4ccccc4c4ccc5c6ccccc6n(-c6ccccc6)c5c43)n2)cc1]
RD
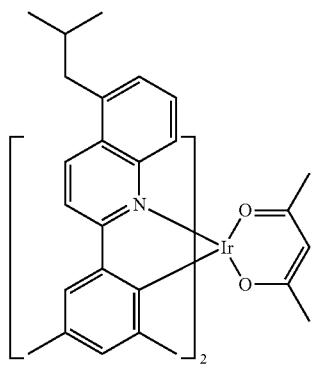
Liq
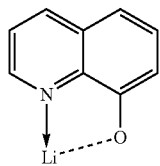
BCP
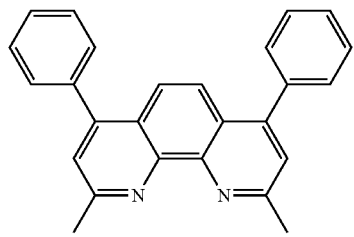 [SMILES: Cc1cc(-c2ccccc2)c2ccc3c(-c4ccccc4)cc(C)nc3c2n1]

Preparation of Red OLED Devices

To prepare the red OLED device, multiple organic layers were respectively deposited on the ITO substrate according to the sequence as listed in Table 7, and the materials and the thicknesses of the organic layers in red OLED devices were also listed in Table 7.

TABLE 7 coating sequence, materials and thickness of the organic layers in red OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 2100 Å |
| 3 | HTL-1 | HT-1 | 100 Å |
| 4 | HTL-2 | HT-2 | 100 Å |
| 5 | REL | RH doped with 3.5 wt % of RD | 300 Å |
| 6 | ETL | Commercial ET/novel compounds doped with 35.0 wt % of Liq | 350 Å |
| 7 | EIL | Liq | 15 Å |
| 8 | Cthd | Al | 1500 Å |

Preparation of Green OLED Devices

To prepare the green OLED device, multiple organic layers were respectively deposited on the ITO substrate according to the sequence as listed in Table 8, and the materials and the thicknesses of the organic layers in green OLED devices were also listed in Table 8.

TABLE 8 coating sequence, materials and thickness of the layers in green OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 1300 Å |
| 3 | HTL-1 | HT-1 | 100 Å |
| 4 | HTL-2 | HT-2 | 100 Å |
| 5 | GEL | GH doped with 10.0 wt % of GD | 400 Å |
| 6 | ETL | Commercial ET/novel compounds doped with 35.0 wt % of Liq | 350 Å |
| 7 | EIL | Liq | 15 Å |
| 8 | Cthd | Al | 1500 Å |

Preparation of Blue OLED Devices

To prepare the blue OLED device, multiple organic layers were respectively deposited on the ITO substrate according to the sequence as listed in Table 9, and the materials and the thicknesses of the organic layers in blue OLED devices were also listed in Table 9.

TABLE 9 coating sequence, materials and thickness of the layers in blue OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 750 Å |
| 3 | HTL-1 | HT-1 | 100 Å |
| 4 | HTL-2 | HT-2 | 100 Å |
| 5 | BEL | BH doped with 3.5 wt % of BD | 250 Å |
| 6 | ETL | Commercial ET/novel compounds doped with 35.0 wt % of Liq | 250 Å |
| 7 | EIL | Liq | 15 Å |
| 8 | Cthd | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 10. For the blue and red OLED devices, the data were collected at 1000 nits. For the green OLED devices, the data were collected at 3000 nits.

The materials of ETL, color and data of CIE, driving voltage, current efficiency, and external quantum efficiency (EQE) of Examples 1 to 33 and Comparative Examples 1 to 3 were listed in Table 10.

TABLE 10 materials of ETL, colors, CIEs, voltages, current efficiencies, and EQE of OLED devices of Examples 1 to 33 and Comparative Examples 1 to 3.

| Example No. | Compound No. | Color CIE (x, y) | Voltage (V) | Efficiency (cd/A) | EQE (%) |
|---|---|---|---|---|---|
| Example 1 | I | B (0.130, 0.150) | 4.32 | 11.70 | 7.99 |
| Example 2 | II | B (0.129, 0.162) | 4.53 | 11.30 | 7.93 |
| Example 3 | IV | B (0.130, 0.144) | 4.84 | 9.96 | 7.39 |
| Example 4 | VII | B (0.130, 0.151) | 3.91 | 11.20 | 7.37 |
| Example 5 | VIII | B (0.129, 0.158) | 4.94 | 10.10 | 7.16 |
| Example 6 | XI | B (0.129, 0.155) | 4.10 | 7.71 | 5.78 |
| Example 7 | XII | B (0.130, 0.151) | 4.14 | 11.10 | 7.78 |
| Example 8 | XIII | B (0.129, 0.164) | 5.74 | 10.50 | 7.22 |
| Example 9 | XV | B (0.129, 0.157) | 5.55 | 8.56 | 6.23 |
| Example 10 | XVI | B (0.129, 0.155) | 5.09 | 10.50 | 7.20 |
| Example 11 | XVIII | B (0.129, 0.153) | 4.21 | 11.40 | 8.20 |
| Example 12 | XIX | B (0.130, 0.151) | 5.39 | 10.20 | 6.82 |
| Example 13 | XX | B (0.129, 0.154) | 5.76 | 7.64 | 5.47 |
| Example 14 | XXII | B (0.129, 0.166) | 4.57 | 11.10 | 7.62 |
| Example 15 | XXIII | B (0.130, 0.148) | 5.91 | 7.64 | 5.54 |
| Example 16 | XXIV | B (0.130, 0.146) | 4.80 | 10.50 | 6.89 |
| Example 17 | XXV | B (0.129, 0.150) | 5.14 | 7.93 | 4.96 |
| Comparative Example 1 | BCP | B (0.130, 0.142) | 6.71 | 6.98 | 4.88 |
| Example 18 | I | G (0.311, 0.640) | 3.20 | 70.90 | 17.75 |
| Example 19 | IV | G (0.311, 0.639) | 3.33 | 74.70 | 17.82 |
| Example 20 | IX | G (0.315, 0.638) | 4.56 | 77.20 | 19.43 |
| Example 21 | XI | G (0.309, 0.641) | 2.75 | 72.00 | 17.01 |
| Example 22 | XII | G (0.315, 0.638) | 3.10 | 73.40 | 17.13 |
| Example 23 | XV | G (0.319, 0.636) | 3.84 | 77.30 | 18.87 |
| Example 24 | XVI | G (0.312, 0.640) | 3.46 | 71.80 | 17.17 |
| Example 25 | XVIII | G (0.316, 0.638) | 2.96 | 74.70 | 17.75 |
| Example 26 | XX | G (0.318, 0.636) | 3.30 | 74.70 | 18.32 |
| Example 27 | XXIII | G (0.319, 0.636) | 4.58 | 78.60 | 19.16 |
| Example 28 | XXIV | G (0.314, 0.638) | 3.87 | 70.40 | 18.12 |
| Example 29 | XXV | G (0.312, 0.639) | 3.36 | 72.30 | 17.38 |
| Example 30 | XXVI | G (0.310, 0.641) | 3.62 | 72.60 | 18.07 |
| Comparative Example 2 | BCP | G (0.313, 0.638) | 4.67 | 70.3 | 16.95 |
| Example 31 | XVI | R (0.659, 0.339) | 4.07 | 24.8 | 16.69 |
| Example 32 | XVIII | R (0.658, 0.340) | 3.43 | 24.30 | 16.16 |
| Example 33 | XX | R (0.662, 0.337) | 3.94 | 24.50 | 16.29 |
| Comparative Example 3 | BCP | R (0.659, 0.340) | 4.16 | 24.1 | 16.05 |

Based on the results, in comparison with the commercial electron transport material, adopting Compounds I to XXVI as the electron transport material can reduce the driving voltage and improve the current efficiency and the external quantum efficiency of the red, green, or blue OLEDs. It demonstrated that the novel compound of the present invention is suitable as an electron transport material for any color OLEDs, and allows the OLEDs using the same to have low driving voltage and improved current efficiency as well as improved external quantum efficiency.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:
1. A compound represented by any one of the following Formulae (I-I) to (I-XXXIII):
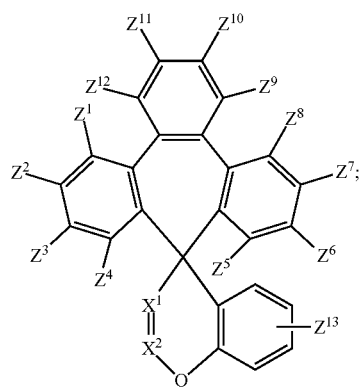
Formula (I-I)
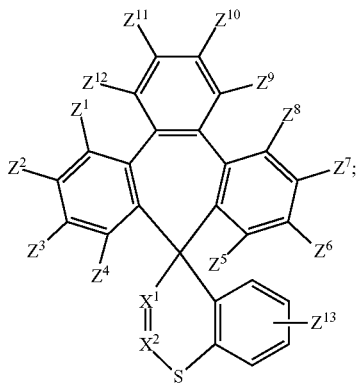
Formula (I-II)
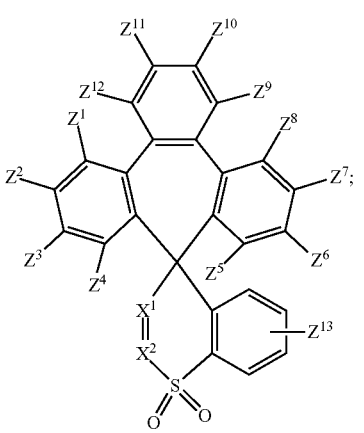
Formula (I-III)
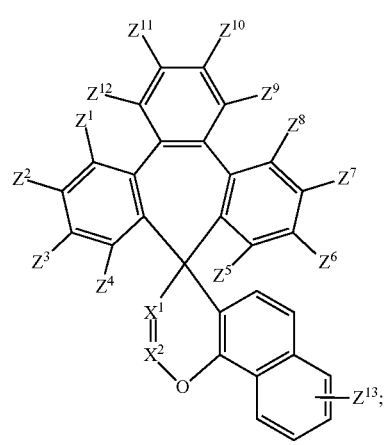
Formula (I-IV)
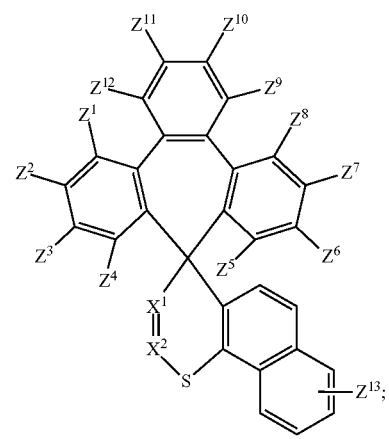
Formula (I-V)
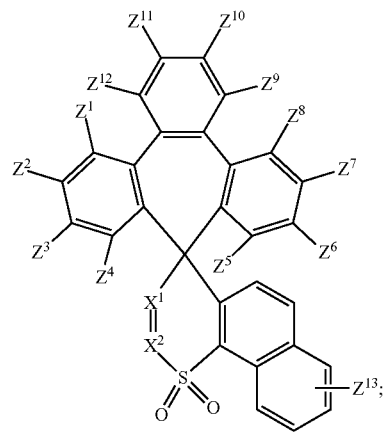
Formula (I-VI)

-continued
Formula (I-VII)
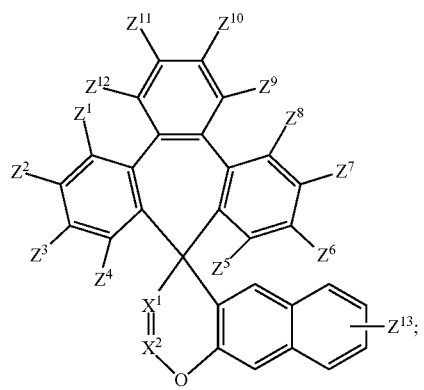
Formula (I-VIII)
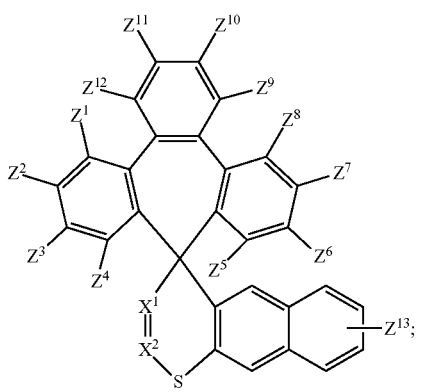
Formula (I-IX)
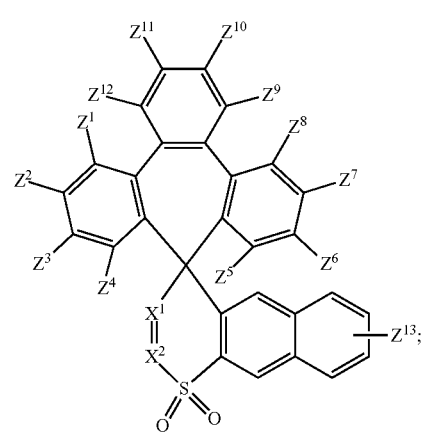
Formula (I-X)
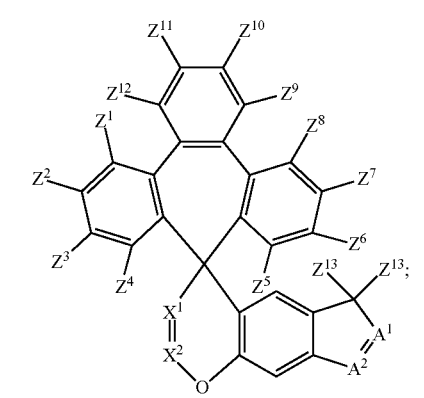
-continued
Formula (I-XI)
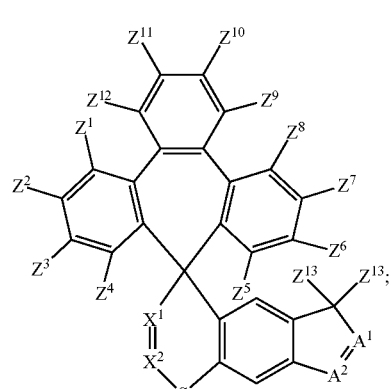
Formula (I-XII)
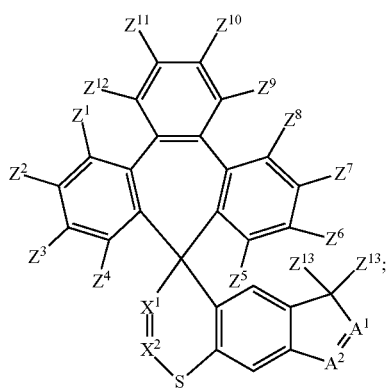
Formula (I-XIII)
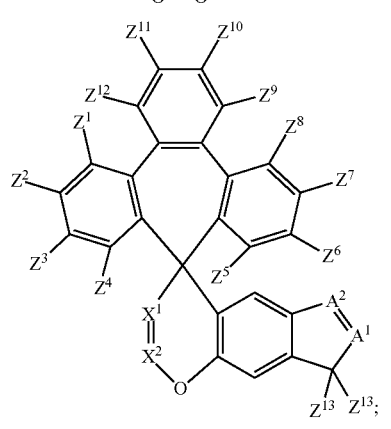
Formula (I-XIV)
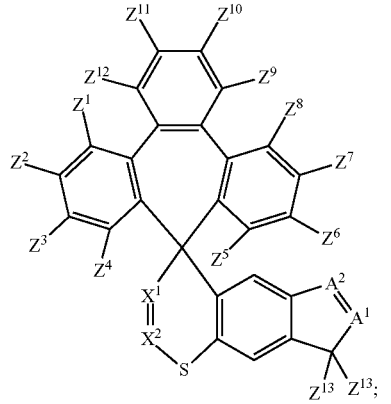

Formula (I-XV)
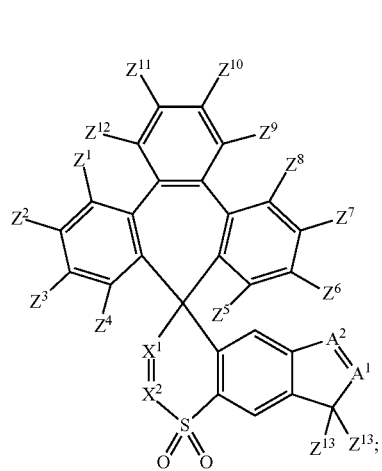
Formula (I-XVIII)
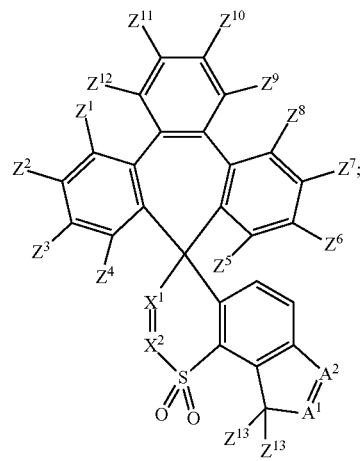
Formula (I-XVI)
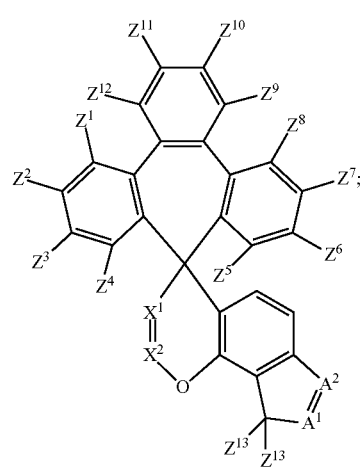
Formula (I-XIX)
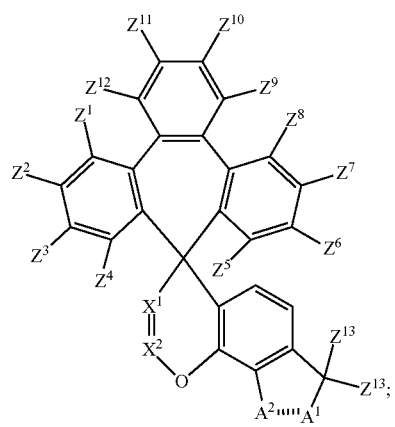
Formula (I-XVII)
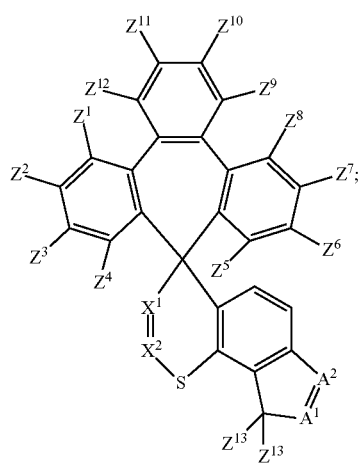
Formula (I-XX)
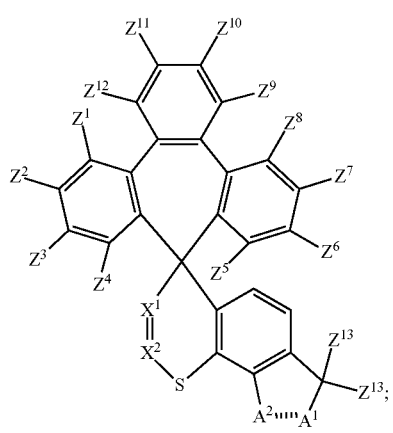

Formula (I-XXI)
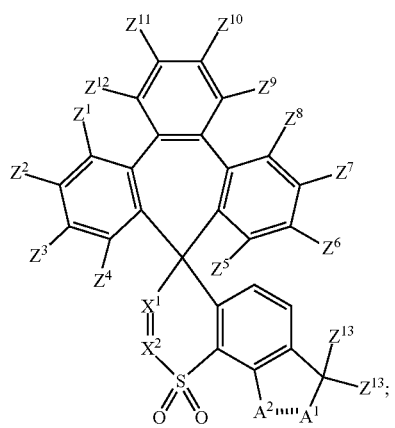
Formula (I-XXII)
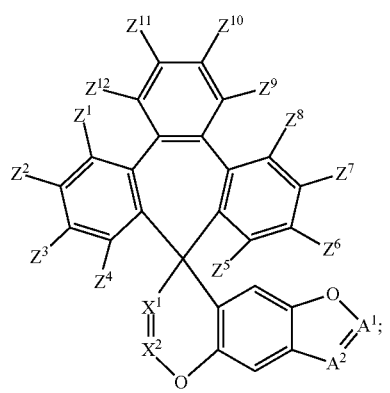
Formula (I-XXIII)
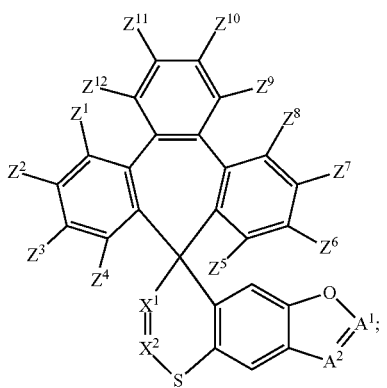
Formula (I-XXIV)
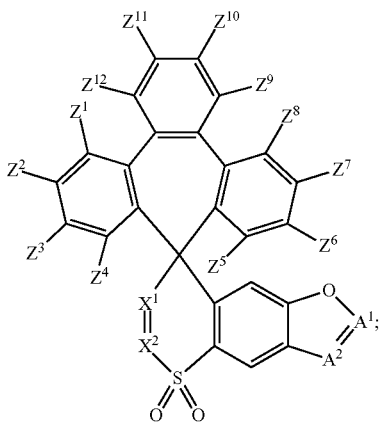
Formula (I-XXV)
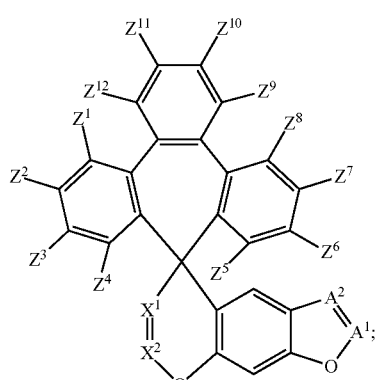
Formula (I-XXVI)
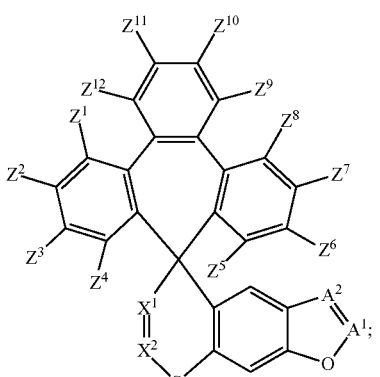
Formula (I-XXVII)
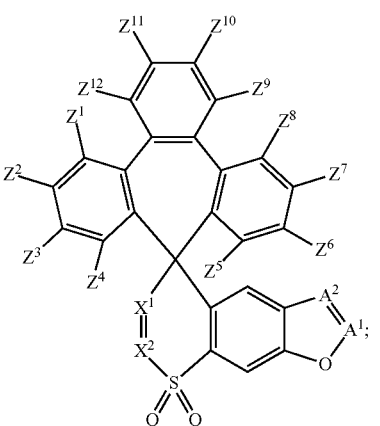
Formula (I-XXVIII)
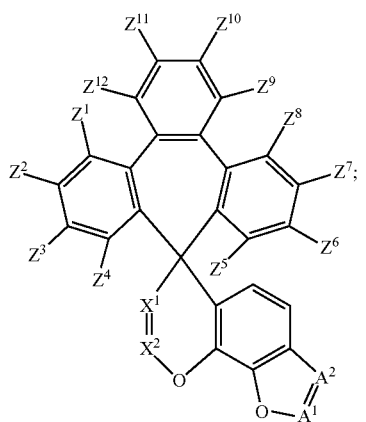

-continued

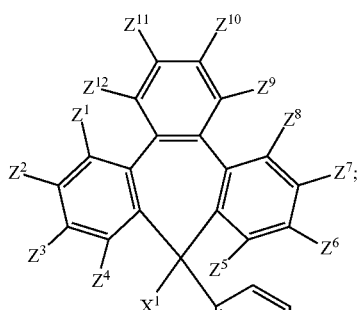
Formula (I-XXIX)

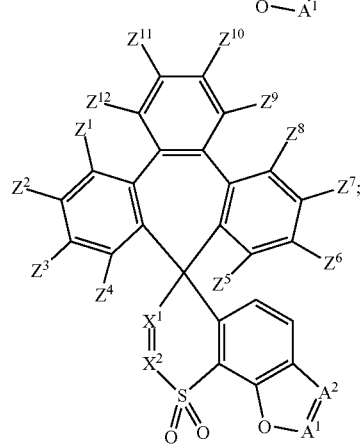
Formula (I-XXX)

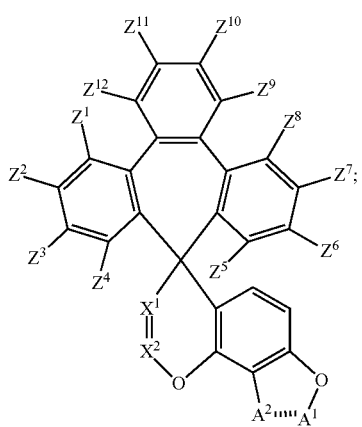
Formula (I-XXXI)

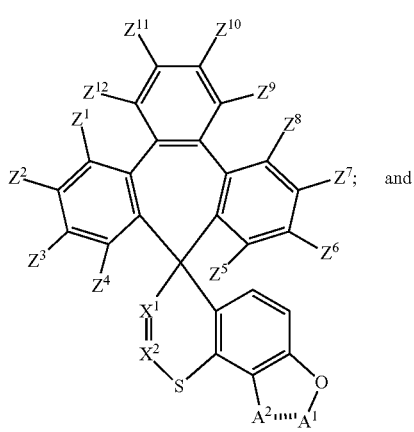
Formula (I-XXXII) and

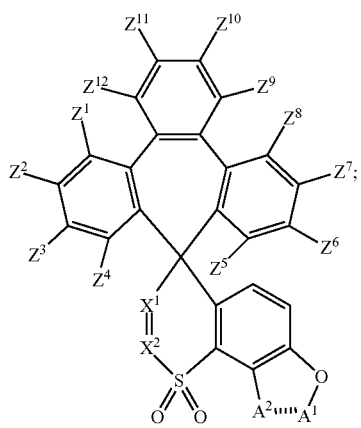
Formula (I-XXXIII)

wherein in Formulae (I-I) to (I-XXXIII), $X^1$ and $X^2$ are each independently $C(R^a)$, multiple $(R^a)$s are the same or different, and the two $(R^a)$s are joined together to form a first aryl ring;

wherein in Formulae (I-I) to (I-XXXIII), $A^1$ and $A^2$ are each independently $C(R^c)$, multiple $(R^c)$s are the same or different, and the two $(R^c)$s are joined together to form an aromatic structure;

wherein in Formulae (I-I) to (I-XXXIII), $Z^1$ to $Z^{12}$ are each independently selected from the group consisting of: a hydrogen atom, a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms;

wherein in Formulae (I-I) to (I-XXXIII), each of $Z^{13}$ is selected from the group consisting of: a hydrogen atom, a methyl group, an ethyl group, a propyl group, a butyl group, a pentyl group, a hexyl group, and a phenyl group.

2. The compound as claimed in claim 1, wherein the aromatic structure extended from $A^1$ and $A^2$ is a substituted or unsubstituted 6 to 20-membered carbon aromatic cyclic structure.

3. The compound as claimed in claim 2, wherein the substituted or unsubstituted 6 to 20-membered carbon aromatic cyclic structure is selected from the group consisting of: a substituted or unsubstituted benzene structure, a substituted or unsubstituted naphthalene structure, a substituted or unsubstituted anthracene structure, a substituted or unsubstituted phenanthrene structure, a substituted or unsubstituted pyrene structure, a substituted or unsubstituted fluoranthene structure, a substituted or unsubstituted benzofluoranthene structure, and a substituted or unsubstituted fluorene structure.

4. The compound as claimed in claim 1, wherein the first aryl ring extended from $X^1$ and $X^2$ is a substituted or unsubstituted 6 to 60-membered carbon ring.

5. The compound as claimed in claim 4, wherein the substituted or unsubstituted 6 to 60-membered carbon ring is selected from the group consisting of: a substituted or unsubstituted benzene ring, a substituted or unsubstituted naphthalene ring, a substituted or unsubstituted anthracene ring, a substituted or unsubstituted phenanthrene ring, a substituted or unsubstituted pyrene ring, a substituted or unsubstituted fluoranthene ring, a substituted or unsubstituted benzofluoranthene ring, and a substituted or unsubstituted fluorene structure.

6. The compound as claimed in claim 5, wherein the substituted or unsubstituted 6 to 60-membered carbon ring is a substituted or unsubstituted benzene structure.

7. The compound as claimed in claim 1, wherein at least one of $Z^1$ to $Z^8$ in Formulae (I-I) to (I-XXXIII) is selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 ring carbon atoms and substituted with at least one functional group, and a phosphine oxide group having 1 to 40 carbon atoms and substituted with at least one functional group, wherein said functional group is selected from the group consisting of: a cyano group, a nitro group, a fluoro group, and a chloro group.

8. The compound as claimed in claim 1, wherein at least one of $Z^1$ to $Z^8$ in Formulae (I-I) to (I-XXXIII) is selected from the group consisting of:

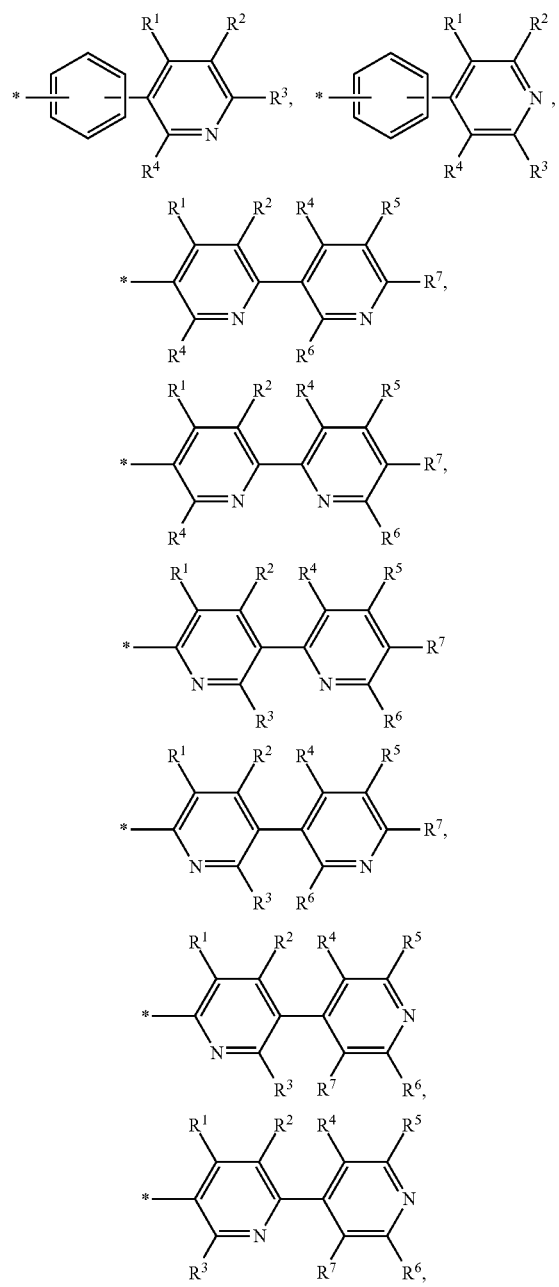

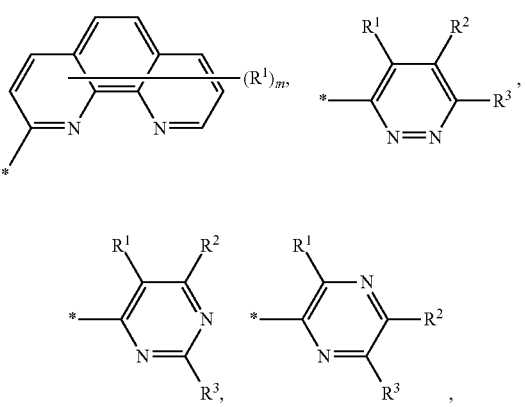

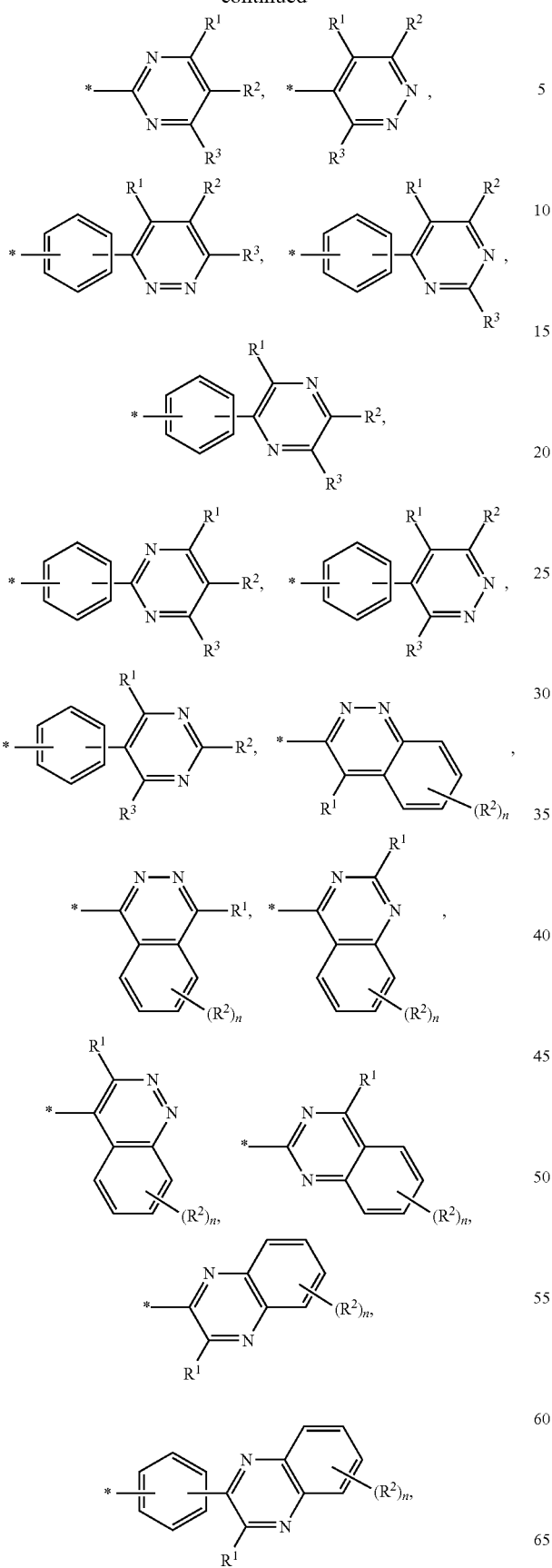
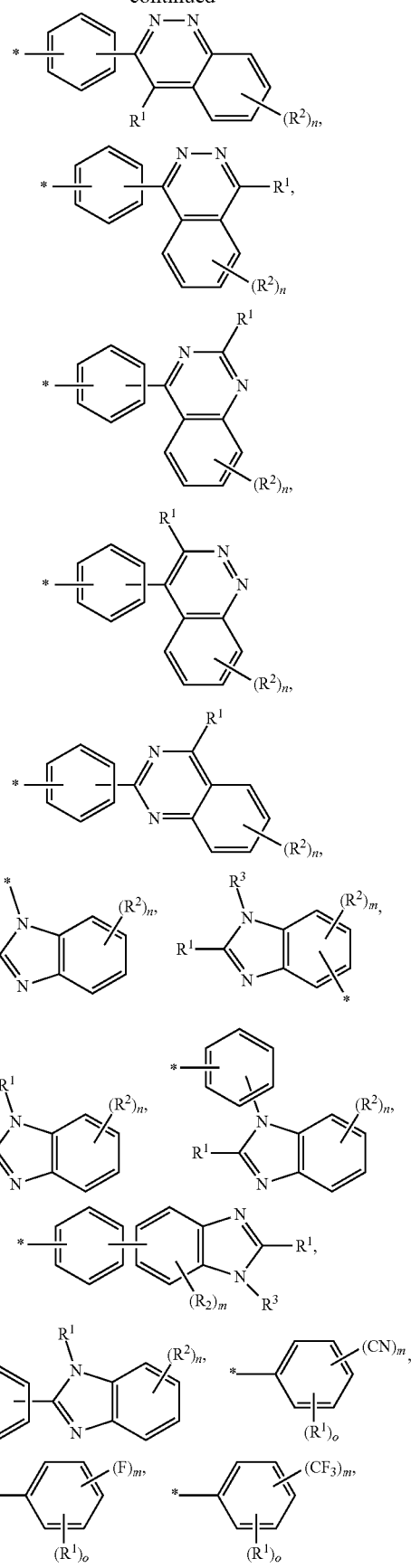

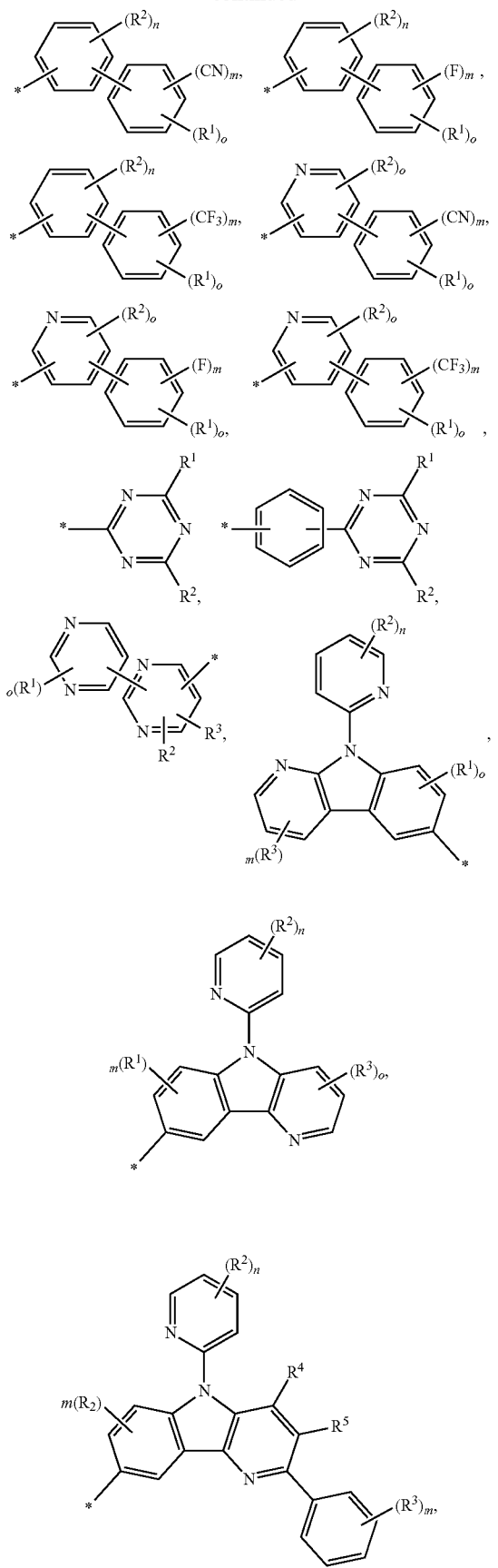
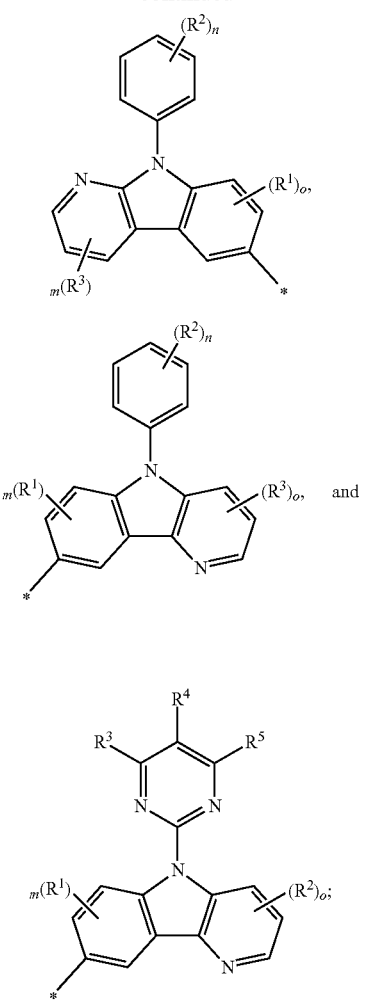

wherein R[1] to R[7] are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 ring carbon atoms, an arylboron group having 6 to 30 ring carbon atoms, a phosphine group having 1 to 30 carbon atoms, and a phosphine oxide group having 1 to 30 carbon atoms;

wherein n is a positive integral from 0 to 4, m is a positive integral from 0 to 3, o is a positive integral from 0 to 3, and the total of m and o is not more than 5.

9. The compound as claimed in claim 1, wherein at least one of $Z^2$, $Z^3$, $Z^6$, and $Z^7$ in Formulae (I-I) to (I-XXXIII) is selected from the group consisting of:

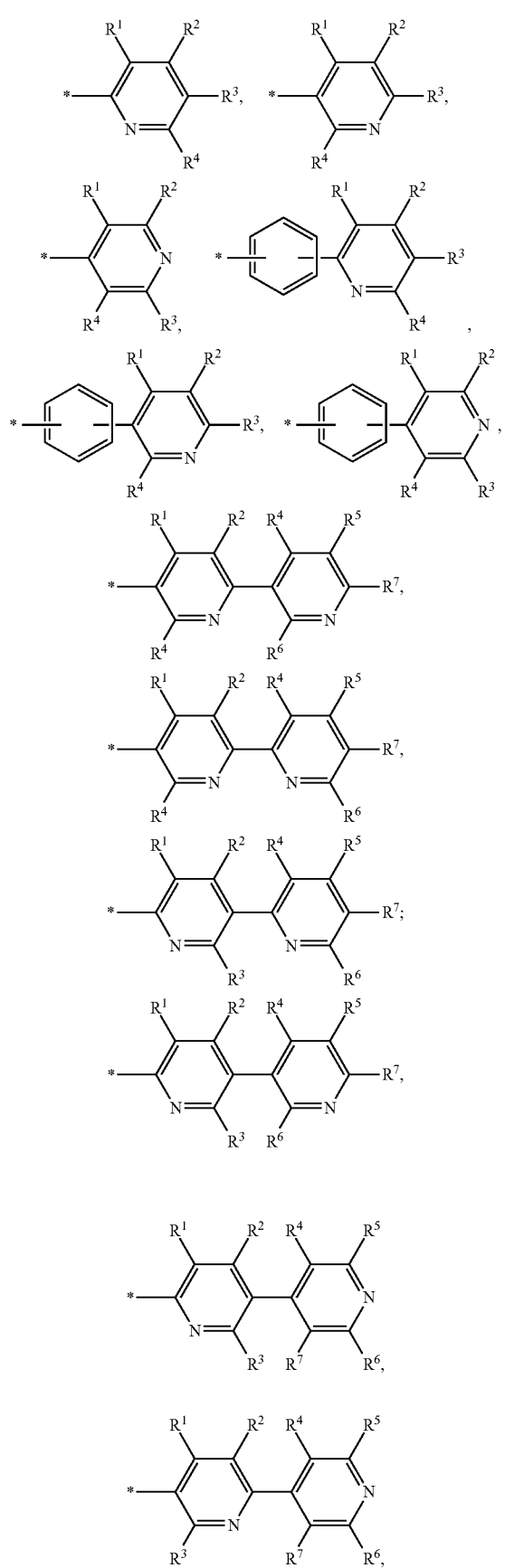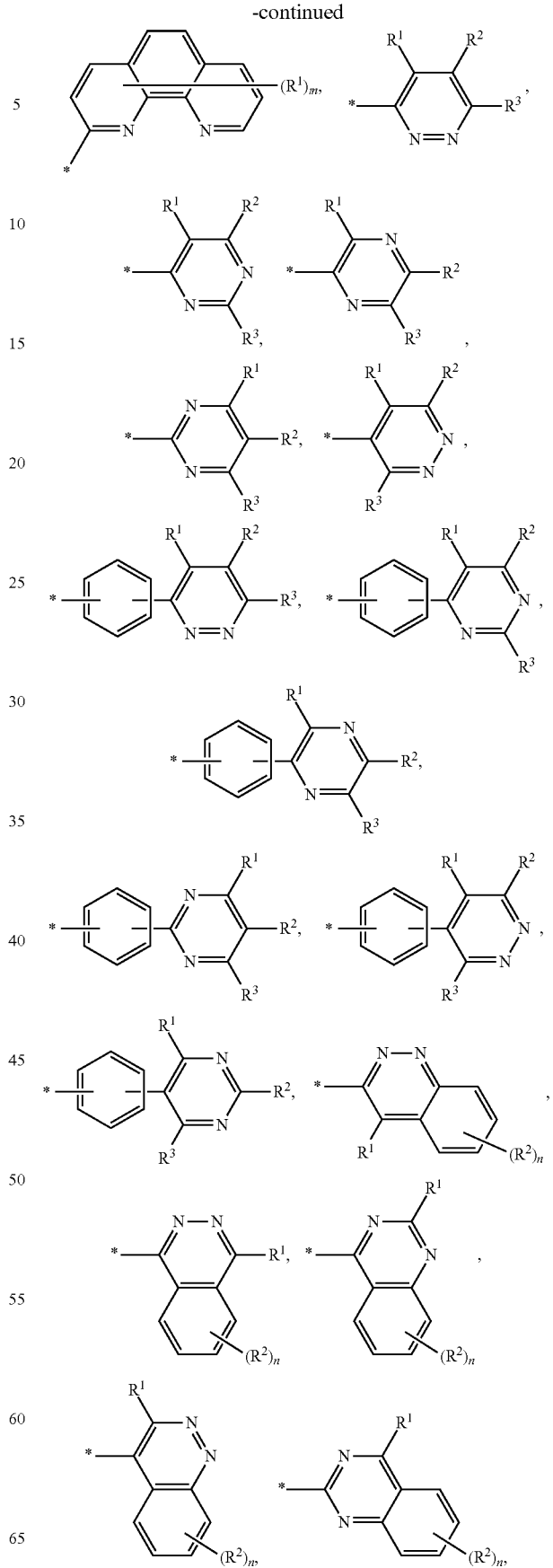

-continued
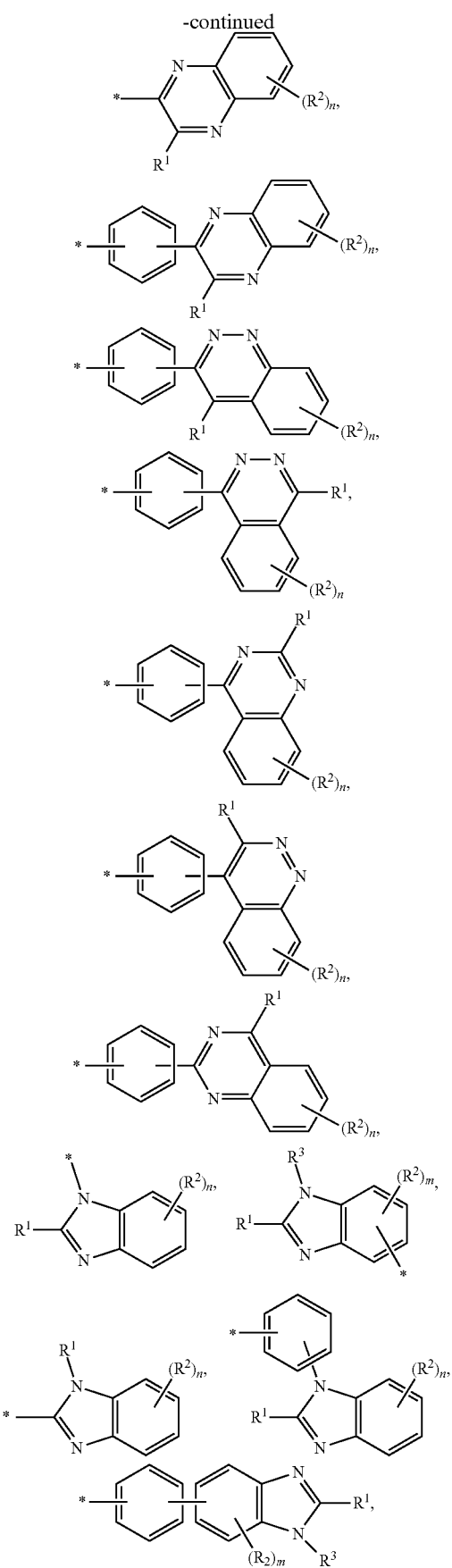
-continued
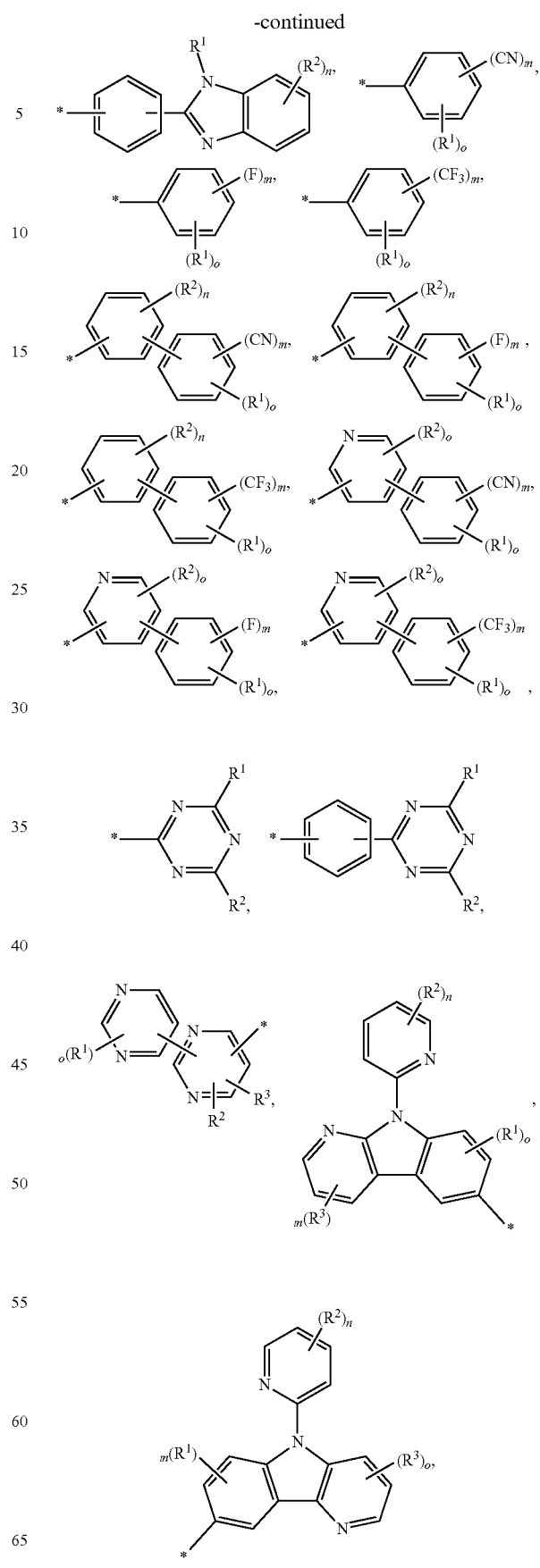

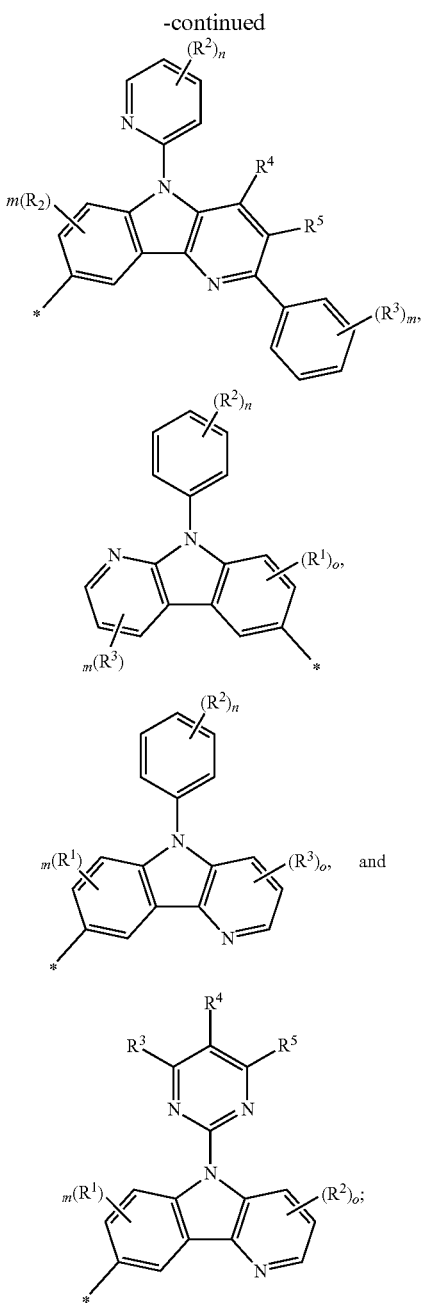

wherein $R^1$ to $R^7$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

n is a positive integral from 0 to 4, m is a positive integral from 0 to 3, o is a positive integral from 0 to 3, and the total of m and o is not more than 5;

wherein $Z^1$, $Z^4$, $Z^5$, $Z^8$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

10. The compound as claimed in claim 1, wherein at least one of $Z^2$, $Z^3$, $Z^6$, and $Z^7$ in Formulae (I-I) to (I-XXXIII) is selected from the group consisting of:

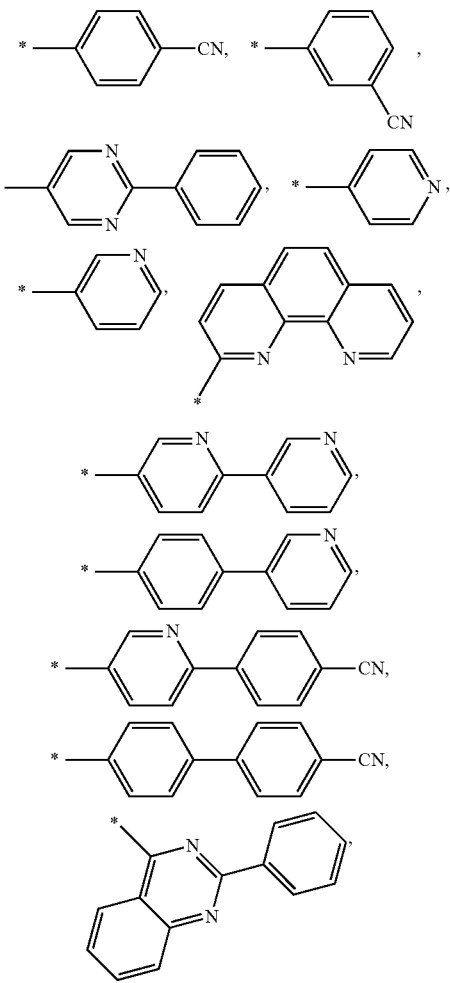

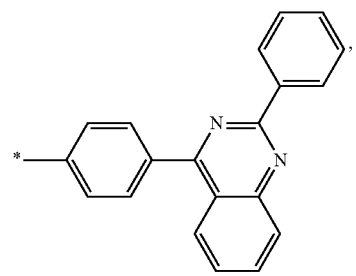

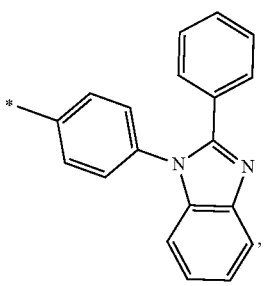
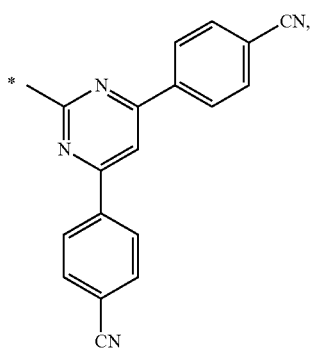
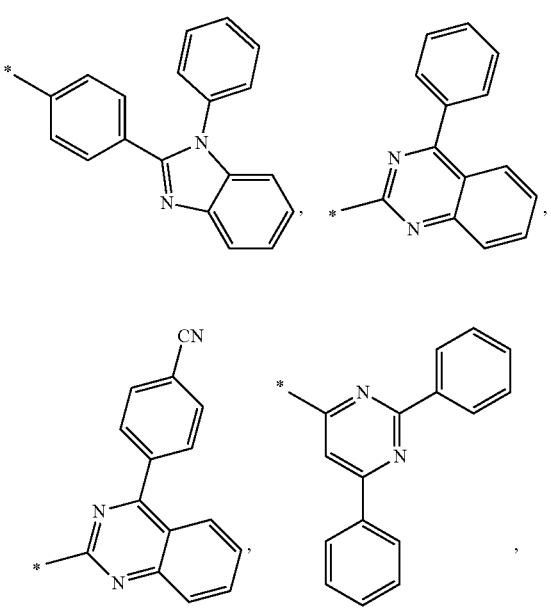
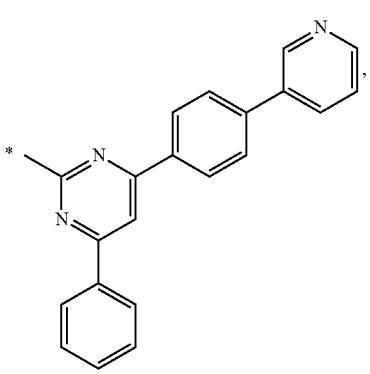
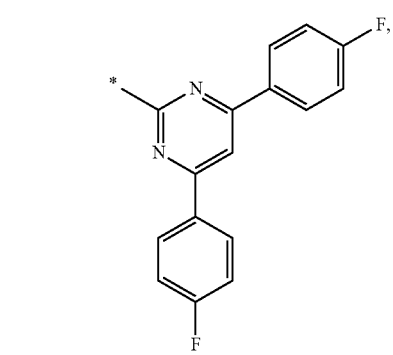
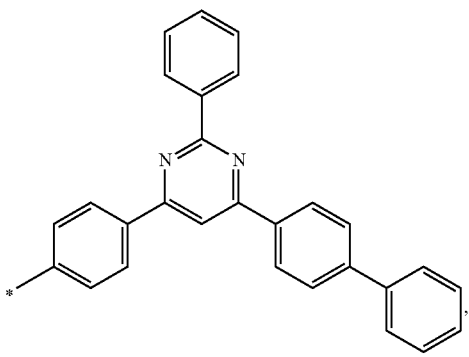
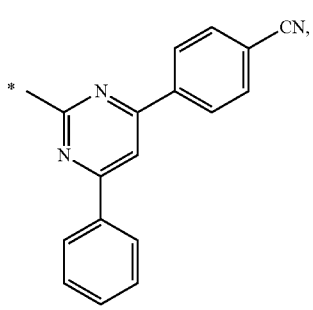
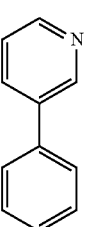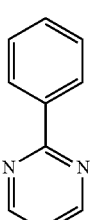
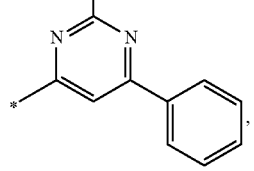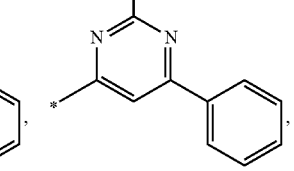

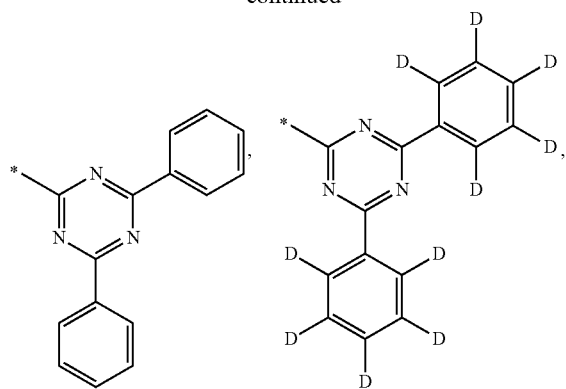
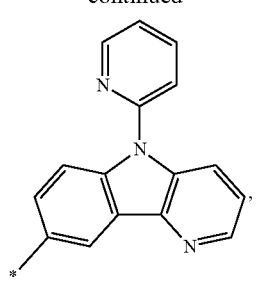
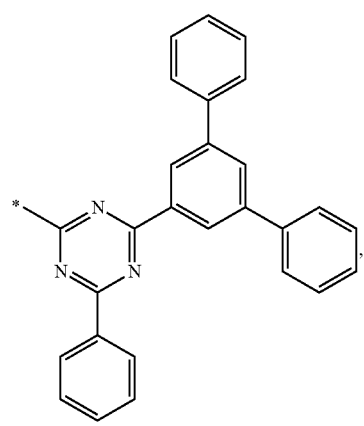
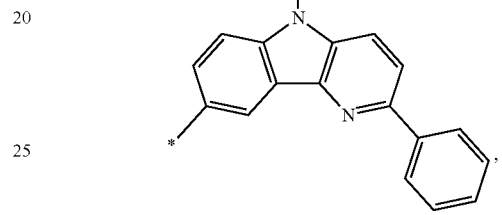
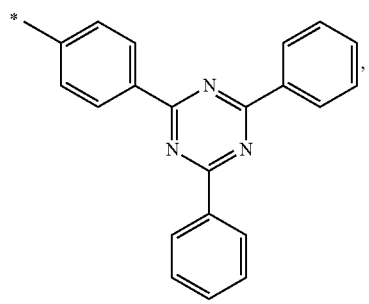
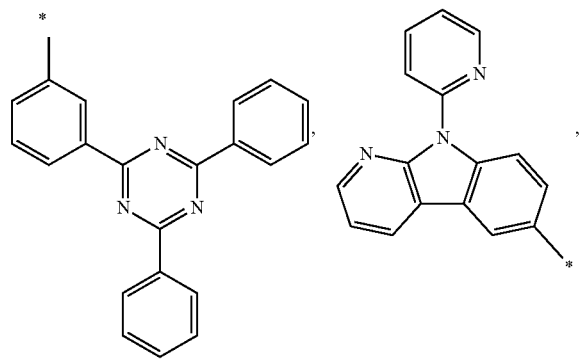
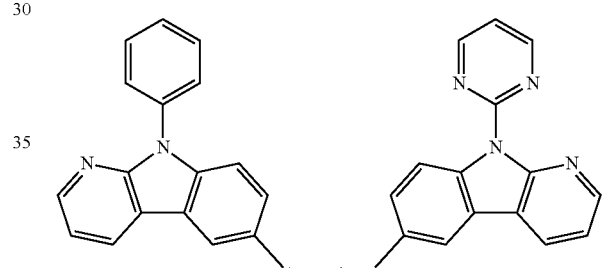

11. The compound as claimed in claim 1, wherein $Z^9$ to $Z^{12}$ in Formulae (I-I) to (I-XXXIII) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

12. The compound as claimed in claim 1, wherein the compound is selected from the group consisting of:

Compound I

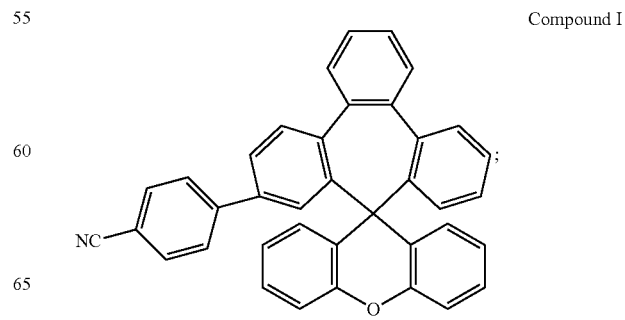

Compound II
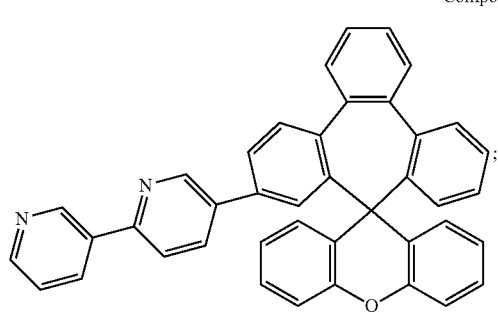
Compound III
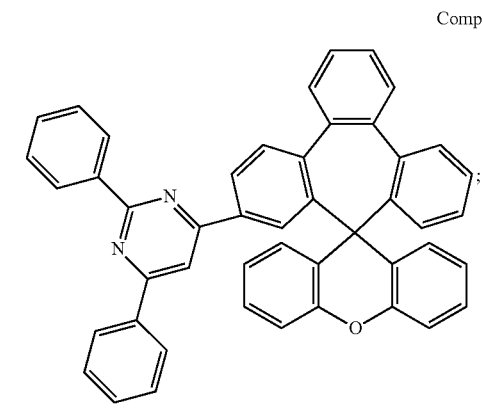
Compound IV
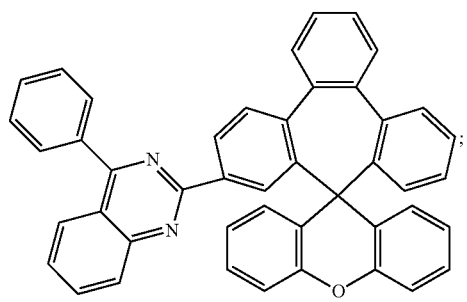
Compound V
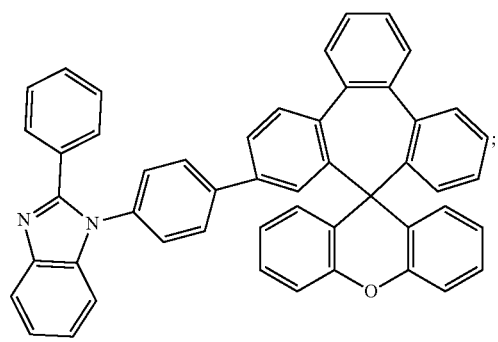
Compound VI
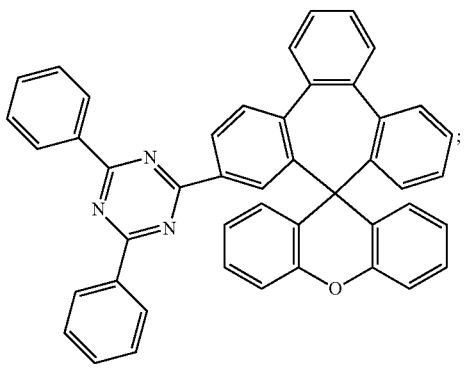
Compound VII
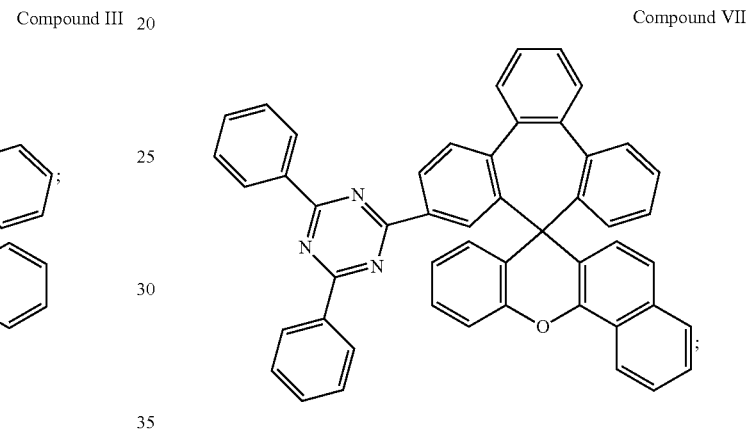
Compound VIII
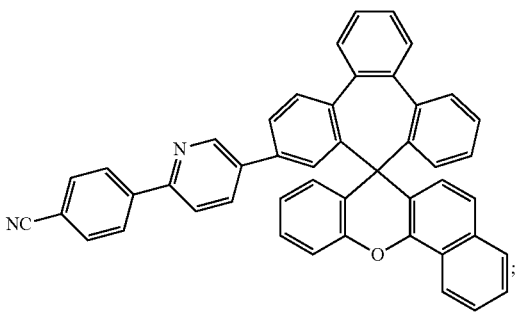
Compound IX
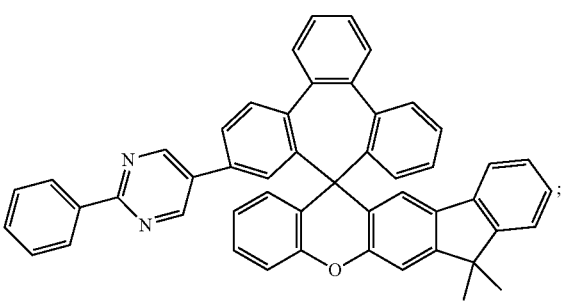

Compound X
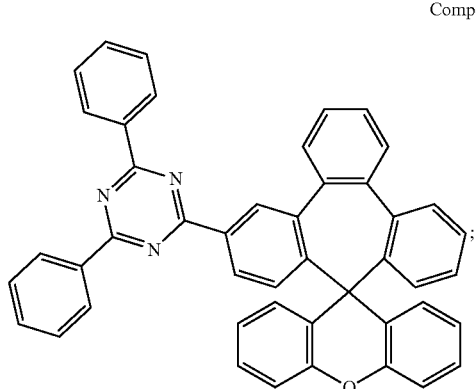
Compound XI
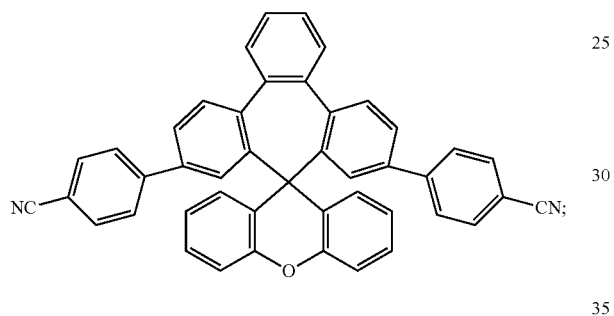
Compound XII
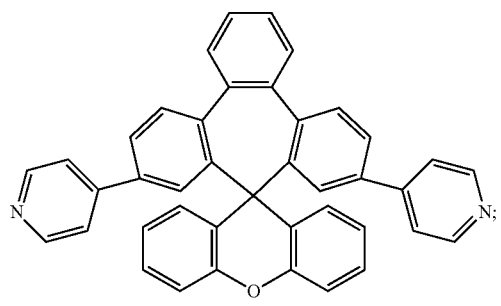
Compound XIII
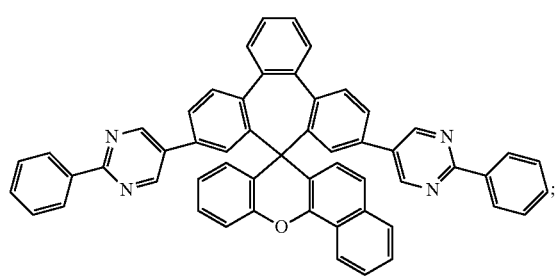
Compound XIV
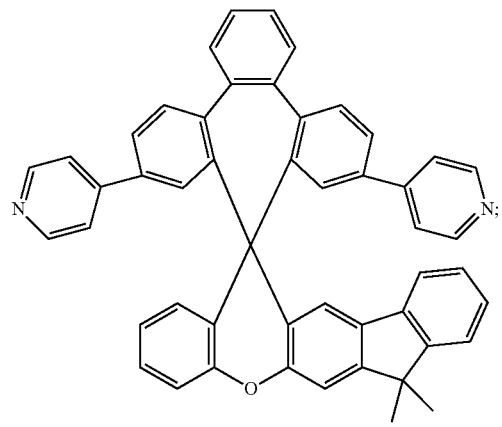
Compound XV
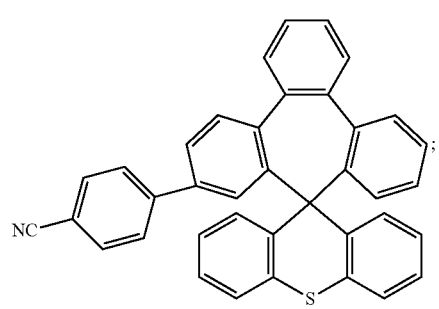
Compound XVI
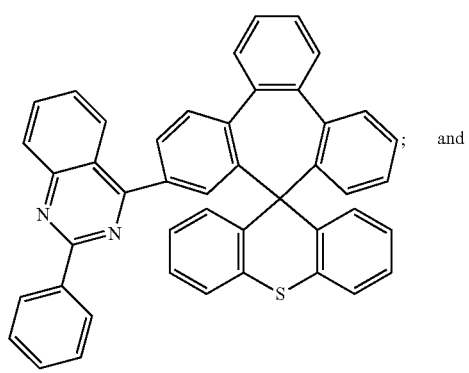; and
Compound XVII
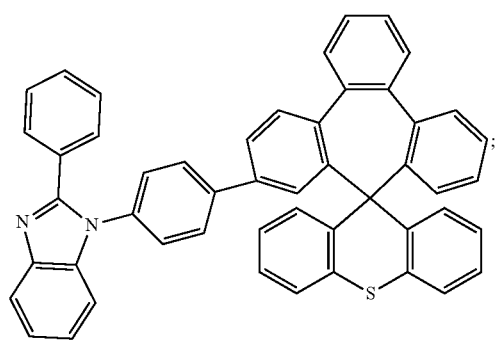;

Compound XVIII
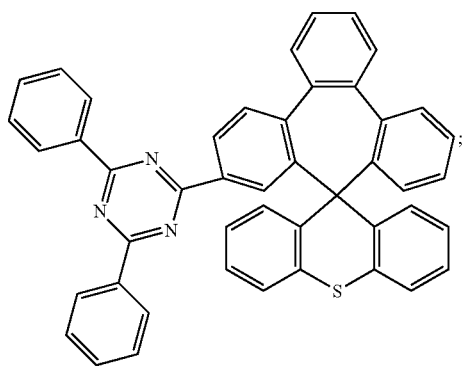
Compound XXII
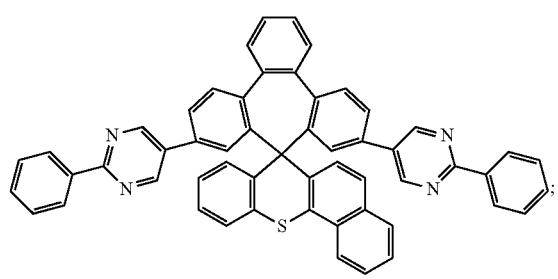
Compound XIX
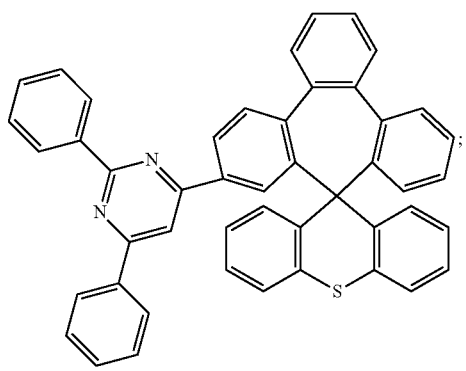
Compound XXIII
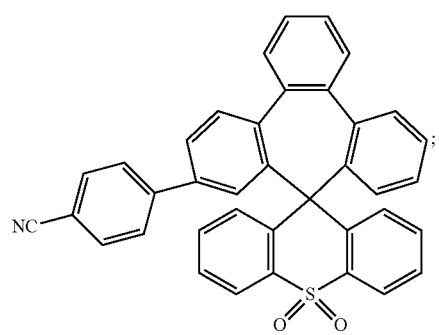
Compound XX
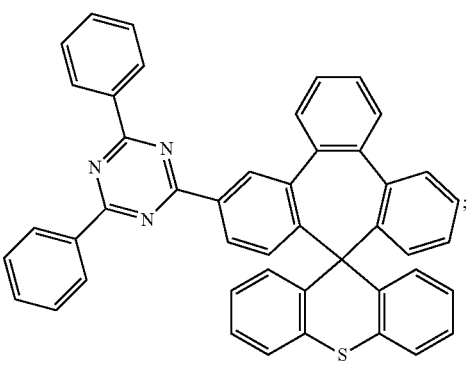
Compound XXIV
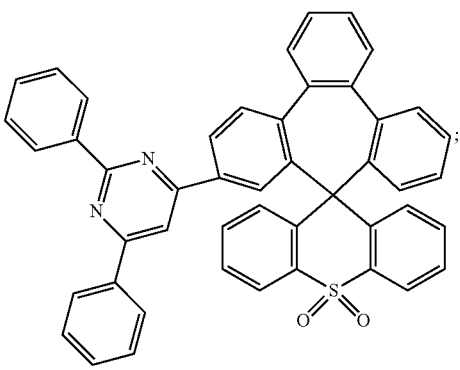
Compound XXI
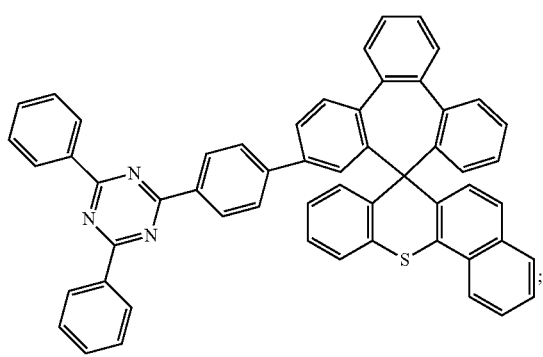
Compound XXV
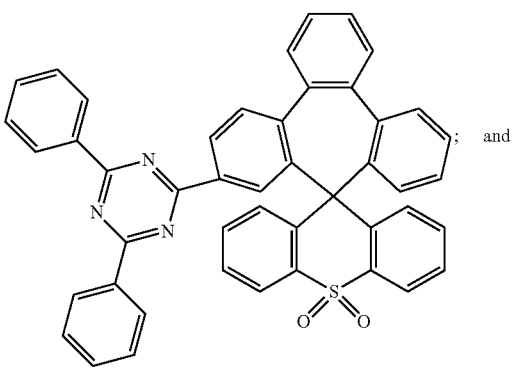
and Compound XXVI

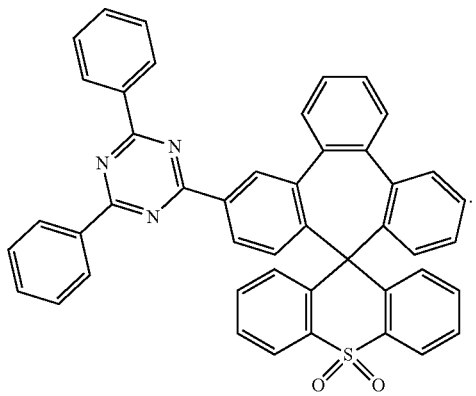

Compound II

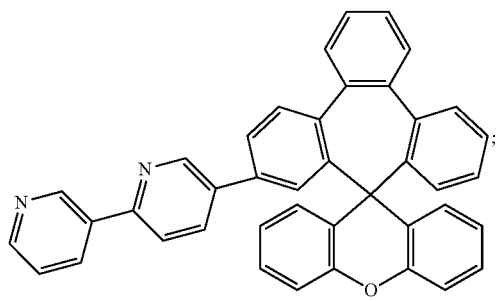

Compound III

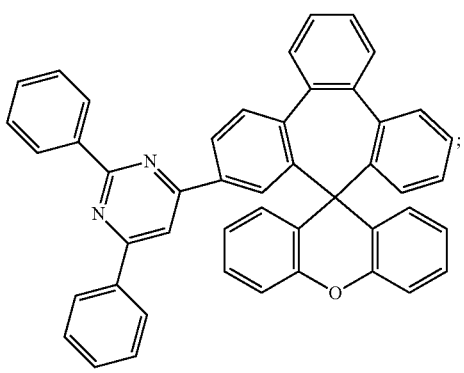

Compound IV

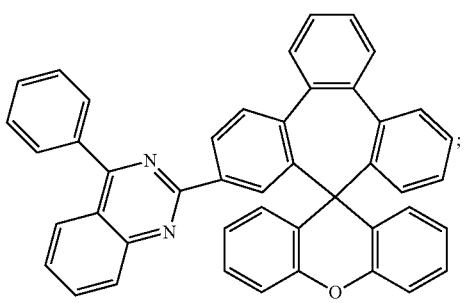

13. An organic electronic device, comprising a first electrode, a second electrode, and an organic layer disposed between the first electrode and the second electrode, wherein the organic layer comprises the compound as claimed in claim 1.

14. The organic electronic device as claimed in claim 13, wherein the organic electronic device is an organic light emitting device.

15. The organic electronic device as claimed in claim 14, wherein the organic light emitting device comprises:
   a hole injection layer formed on the first electrode;
   a hole transport layer formed on the hole injection layer;
   an emission layer formed on the hole transport layer;
   an electron transport layer formed on the emission layer, wherein the organic layer is the electron transport layer; and
   an electron injection layer formed between the electron transport layer and the second electrode.

16. The organic electronic device as claimed in claim 14, wherein the organic light emitting device comprises:
   a hole injection layer formed on the first electrode;
   a hole transport layer formed on the hole injection layer;
   an emission layer formed on the hole transport layer;
   a hole blocking layer formed on the emission layer, wherein the organic layer is the hole blocking layer;
   an electron transport layer formed on the hole blocking layer; and
   an electron injection layer formed between the electron transport layer and the second electrode.

17. The organic electronic device as claimed in claim 13, wherein the compound is selected from the group consisting of:

Compound I

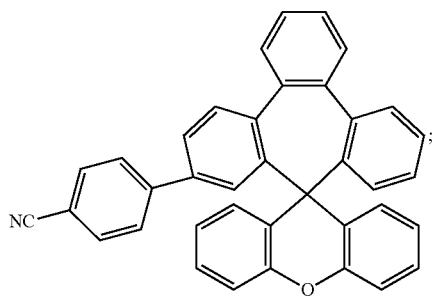

Compound V

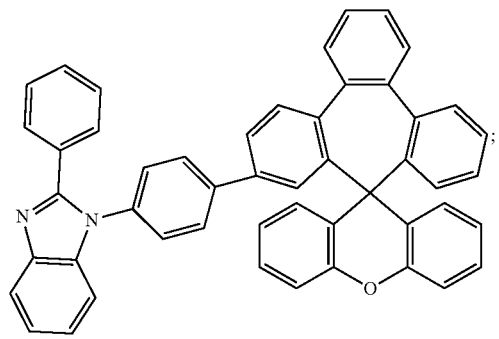

Compound VI
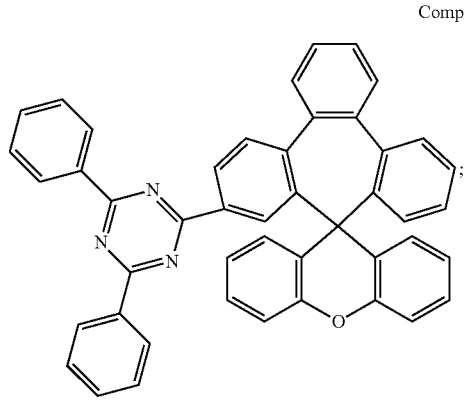
Compound X
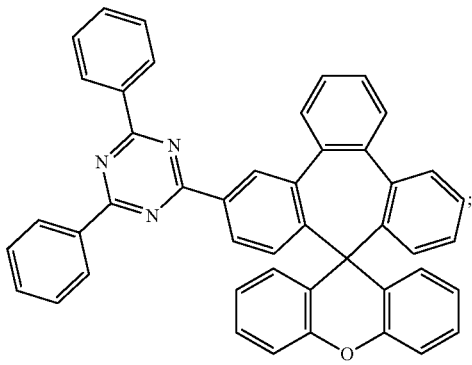
Compound VII
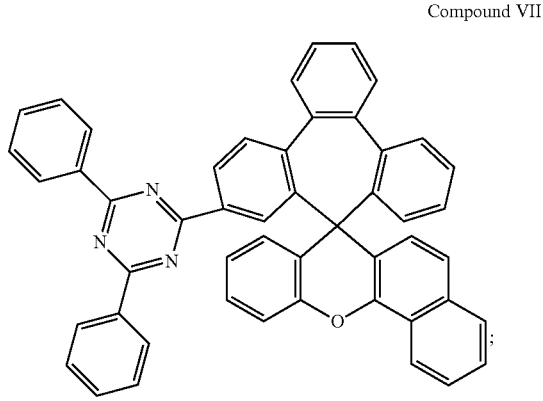
Compound XI
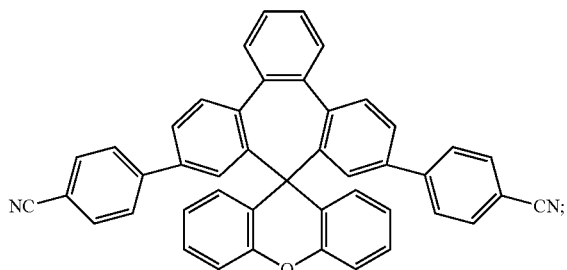
Compound VIII
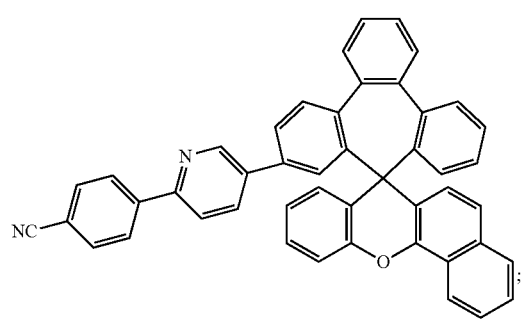
Compound XII
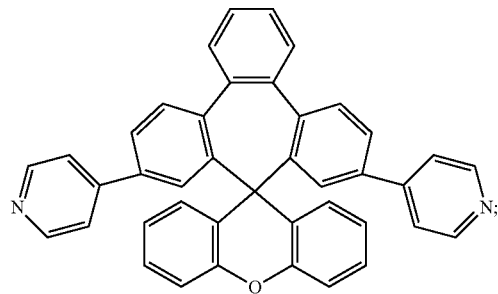
Compound IX
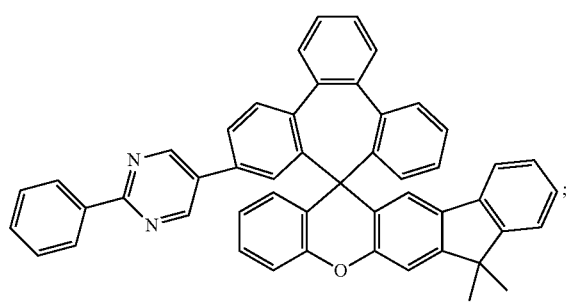
Compound XIII
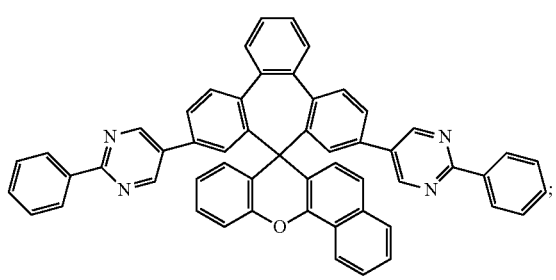

Compound XIV
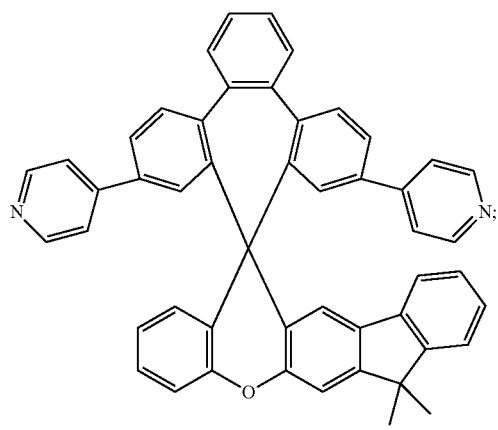
Compound XV
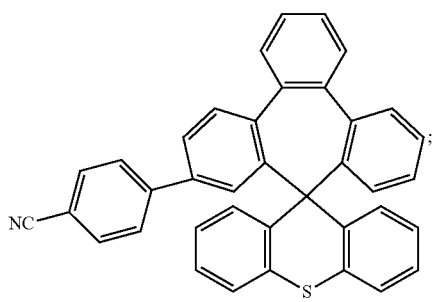
Compound XVI
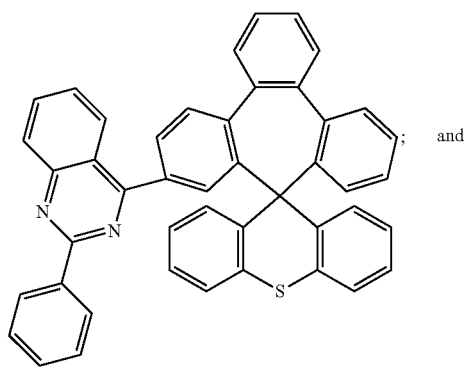
Compound XVII
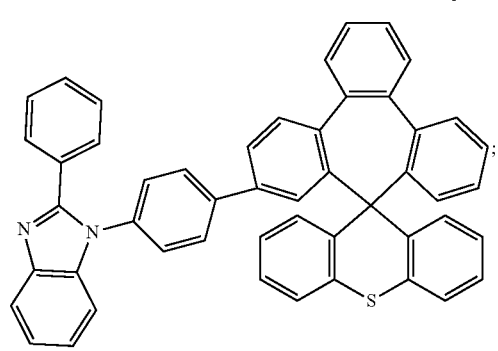
Compound XVIII
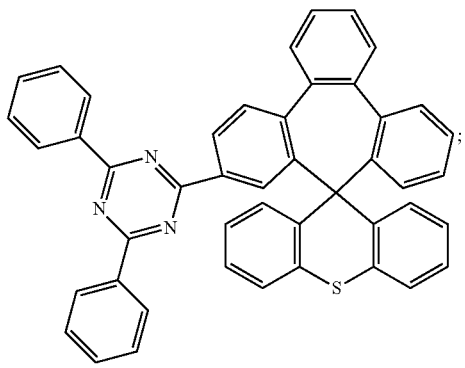
Compound XIX
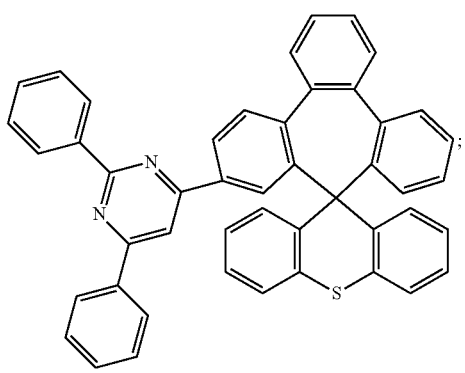
Compound XX
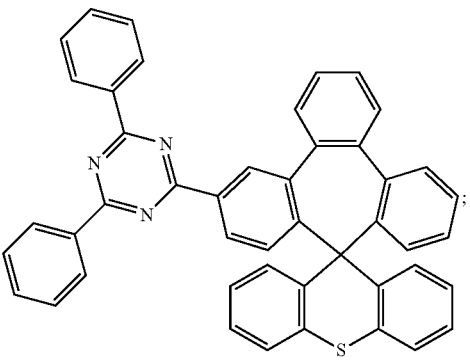
Compound XXI
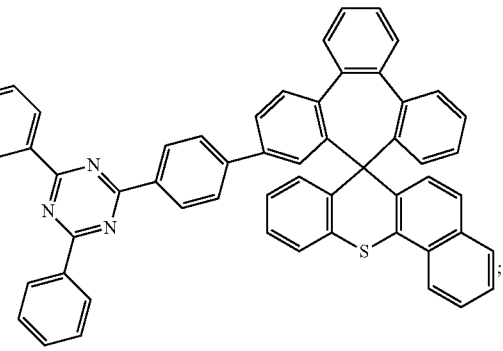
and -continued
Compound XXII
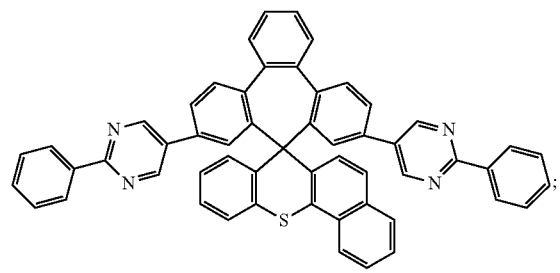
Compound XXIII
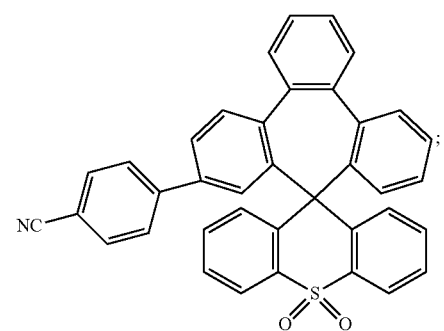
Compound XXIV
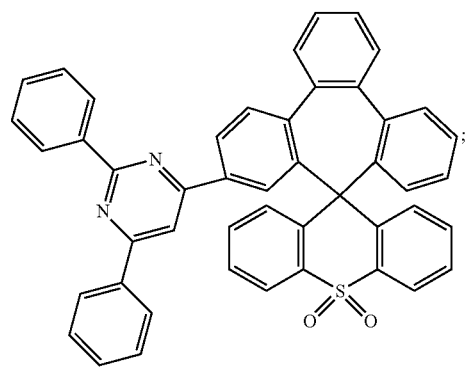
-continued
Compound XXV
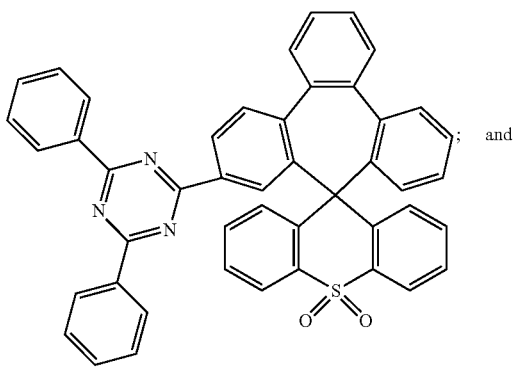
and
Compound XXVI
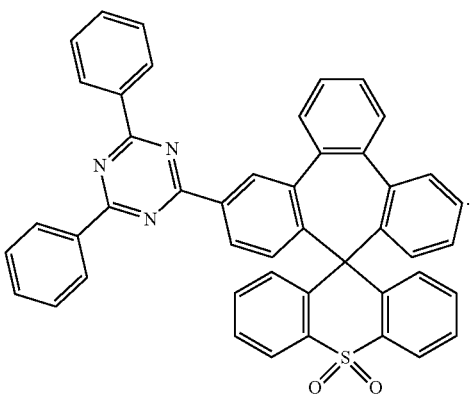
* * * * *